(12) United States Patent
Steele et al.

(10) Patent No.: US 11,999,987 B2
(45) Date of Patent: Jun. 4, 2024

(54) BACTERIAL COCULTURES EXPRESSING A BACTERIOCIN SYSTEM

(71) Applicant: Lallemand Hungary Liquidity Management LLC, Budapest (HU)

(72) Inventors: James L. Steele, Lebanon, NH (US); Brooks Henningsen, Salisbury, NH (US); Jeffery R. Broadbent, North Amalga, UT (US); Ekkarat Phrommao, Lebanon, NH (US); Fernanda Cristina Firmino, Lebanon, NH (US)

(73) Assignee: Lallemand Hungary Liquidity Management LLC, Budapest (HU)

( * ) Notice: Subject to any disclaimer, the term of this patent is extended or adjusted under 35 U.S.C. 154(b) by 33 days.

(21) Appl. No.: 17/206,943

(22) Filed: Mar. 19, 2021

(65) Prior Publication Data
US 2021/0292803 A1    Sep. 23, 2021

Related U.S. Application Data

(60) Provisional application No. 62/991,850, filed on Mar. 19, 2020.

(51) Int. Cl.
| | |
|---|---|
| C12P 39/00 | (2006.01) |
| C07K 14/335 | (2006.01) |
| C12N 1/20 | (2006.01) |
| C12P 7/06 | (2006.01) |

(52) U.S. Cl.
CPC .......... C12P 39/00 (2013.01); C07K 14/335 (2013.01); C12N 1/20 (2013.01); C12P 7/06 (2013.01); C12Y 101/01001 (2013.01); C12Y 401/01001 (2013.01)

(58) Field of Classification Search
CPC .. C12P 39/00; C12P 7/06; C12P 21/02; C07K 14/335; C12N 1/20; C12N 9/0006; C12N 9/88; C12Y 101/01001; C12Y 401/01001
See application file for complete search history.

(56) References Cited

U.S. PATENT DOCUMENTS 8,956,851 B2    2/2015    Argyros et al.

FOREIGN PATENT DOCUMENTS

| WO | 2011/153516 A2 | 12/2011 | |
|---|---|---|---|
| WO | WO 2013141905 A2 * | 9/2013 | |
| WO | 2015/023989 A1 | 2/2015 | |
| WO | WO 2015097686 A1 * | 7/2015 | |
| WO | 2017/037614 A1 | 3/2017 | |
| WO | 2018/013791 A1 | 1/2018 | |
| WO | 2018/167670 A1 | 9/2018 | |

OTHER PUBLICATIONS

Whisstock et al. Quaterly Reviews of Biophysics, 2003, "Prediction of protein function from protein sequence and structure", 36(3):307-340. (Year: 2003).*
Witkowski et al. Conversion of a beta-ketoacyl synthase to a malonyl decarboxylase by replacement of the active-site cysteine with glutamine, Biochemistry. Sep. 7, 1999;38(36):11643-50. (Year: 1999).*
Kisselev L., Polypeptide release factors in prokaryotes and eukaryotes: same function, different structure. Structure, 2002, vol. 10:8-9. (Year: 2002).*
Siegers et al. Genes Involved in Immunity to the Lantibiotic Nisin Produced by Lactococcus lactis 6F3. Applied and Environmental Microbiology, Mar. 1995, 61(3): 1082-1089. (Year: 1995).*
Engelke et al. Regulation of Nisin Biosynthesis and Immunity in Lactococcus lactis 6F3. Applied and Environmental Microbiology, Mar. 1994, 60(3): 814-825. (Year: 1994).*
Desmond et al. Improved stress tolerance of GroESL-overproducing Lactococcus lactis and Probiotic Lactobacillus paracasei NFBC 338. Applied and Environmental Microbiology, Oct. 2004, 70(10): 5929-5936. (Year: 2004).*
Fukao et al., "Complete Covalent Structure of Nisin Q, New Natural Nisin Variant, Containing Post-Translationally Modified Amino Acids," *Biosci. Biotechnol. Biochem.* 72(7):1750-1755, 2008.
O'Connor et al., "Nisin H Is a New Nisin Variant Produced by the Gut-Derived Strain *Streptococcus hyointestinalis* DPC6484," *Appl Environ Microbiol* 81:3953-3960, 2015.
O'Sullivan et al., "Nisin J, a Novel Natural Nisin Variant, Is Produced by *Staphylococcus capitis* Sourced from the Human Skin Microbiota," *Journal of Bacteriology* 202(3):e00639-19, 2020, 15 pages.
Wirawan et al., "Molecular and Genetic Characterization of a Novel Nisin Variant Produced by *Streptococcus uberis*," *Applied and Environmental Microbiology* 72(2):1148-1156, 2006.

* cited by examiner

*Primary Examiner* — Iqbal H Chowdhury
(74) *Attorney, Agent, or Firm* — Seed IP Law Group LLP

(57) ABSTRACT

The present disclosure concerns a co-culture of bacterial cells for making a fermented product from a biomass. The co-culture comprising a first recombinant lactic acid bacteria (LAB) cell expressing at least one bacteriocin and a second recombinant lactic acid bacteria (LAB) cell capable of converting, at least in part, the biomass into the fermented product. The second recombinant LAB cell is immune to the bacteriocin produced by the first recombinant LAB cell. The co-culture can be used, optionally in combination with a yeast host cell, to make a fermented product. The present disclosure also provides processes for making the fermented product by using the co-culture as wells kits and media comprising the co-culture.

22 Claims, 3 Drawing Sheets
Specification includes a Sequence Listing.

BACTERIAL COCULTURES EXPRESSING A BACTERIOCIN SYSTEM

CROSS-REFERENCE TO RELATED APPLICATION AND SEQUENCE LISTING

The present application claims priority from U.S. provisional application 62/991,850 filed on Mar. 19, 2020 and herewith incorporated in its entirety. The Sequence Listing associated with this application is provided in text format in lieu of a paper copy, and is hereby incorporated by reference into the specification. The name of the text file containing the Sequence Listing is 580127_429_SEQUENCE_LISTING.txt. The text file is 183 KB, was created on Mar. 18, 2021, and is being submitted electronically via EFS-Web.

TECHNOLOGICAL FIELD

The present disclosure relates to cocultures of bacterial cells expressing a bacteriocin system for limiting contamination during the fermentation of a biomass to make a fermentation product (such as ethanol).

BACKGROUND

Bacterial contamination in commercial ethanol facilities is a chronic problem that has led to a heavy reliance on the addition of antibiotics. However, this practice raises concerns related to the emergence of resistant bacterial strains and the presence of antibiotics in fermentation residuals that are sold as animal feed. Several species of Lactic Acid Bacteria (LAB) natively produce bacteriocins, which are small peptides exhibiting potent antimicrobial properties. These compounds have several advantages over the use of conventional antibiotics, including broad pH and temperature ranges, and a few are already used within the food industry.

One of the most well studied bacteriocins is nisin, a molecule that has been used commercially as a food preservative for over 50 years. Its long history of safe use without the emergence of widespread resistance, has led the FDA to grant nisin the classification of generally regarded as safe (GRAS). Nisin's bactericidal effects occur through binding of the peptidoglycan precursor molecule, lipid II. This inhibits cell wall synthesis and generates pores in the cytoplasmic membrane which cause a loss of membrane potential, leaking of cellular contents, and eventual cell death. Nisin-producing strains of *Lactococcus lactis* generate autoimmunity through the expression of a lipoprotein, NisI, which obstructs nisin from binding lipid II, and a three component ABC transporter encoded by the genes nisE, nisF, and nisG. Although the heterologous expression of nisin production has proven difficult, it is possible to engineer the immunity phenotype into other LAB species through expression of the nisIEFG components.

There is thus a need for limiting contamination during fermentation while limiting the use of antibiotics.

BRIEF SUMMARY

The present disclosure concerns a co-culture of two distinct lactic acid bacteria cells, one of which being capable of expressing a bacteriocin. Both lactic acid bacteria cells are immune to the bacteriocin and are capable of making a fermented product (from a biomass). The co-culture can be used, optionally in combination with a yeast host cell, to make the fermented product and limit microbial contamination during the process for making the fermented product.

According to a first aspect, the present disclosure provides a co-culture of lactic acid bacterial cells for making a fermented product from a biomass. The co-culture comprises a first recombinant lactic acid bacteria (LAB) cell expressing at least one bacteriocin and optionally a further bacteriocin. The first recombinant LAB cell and a second recombinant LAB cell capable of converting, at least in part, the biomass into the fermented product. The first LAB comprises (i) one or more first heterologous nucleic acid molecule encoding one or more polypeptide for converting, at least in part, the biomass into the fermented product and (ii) optionally one or more second heterologous nucleic acid molecules encoding the at least one bacteriocin and/or the further bacteriocin and one or more polypeptide for conferring immunity against the at least one bacteriocin and/or the further bacteriocin. The second recombinant LAB comprises (i) one or more third heterologous nucleic acid molecule encoding one or more polypeptide for converting, at least in part, the biomass into the fermented product and (ii) one or more fourth heterologous nucleic acid molecule encoding one or more polypeptide for conferring immunity against the at least one bacteriocin and/or the further bacteriocin expressed by the first recombinant LAB cell. In an embodiment, the first recombinant LAB lacks the one or more second heterologous nucleic acid molecule. In another embodiment, the first recombinant LAB cell comprises the one or more second heterologous nucleic acid molecule.

In some embodiments, the at least one bacteriocin and/or the further bacteriocin comprises a lantibiotic. For example, the lantibiotic can be nisin and the second and/or the fourth heterologous nucleic acid molecule can encode NisI. For example, nisin has the amino acid sequence of any one of SEQ ID NO: 7 to 10, is a variant of the amino acid sequence of any one of SEQ ID NO: 7 to 10 having nisin bacteriocin activity or is a fragment of the amino acid sequence of any one of SEQ ID NO: 7 to 10 having nisin bacteriocin activity. In an embodiment, the second and/or the fourth heterologous nucleic acid molecule comprises a nucleic acid sequence of SEQ ID NO: 53 or a degenerate sequence encoding SEQ ID NO: 7. In some additional embodiments, the second and/or the fourth heterologous nucleic acid molecule comprises a nucleic acid sequence of SEQ ID NO: 54 or a degenerate sequence encoding SEQ ID NO: 8. In some embodiments, NisI has the amino acid sequence of SEQ ID NO: 11, is a variant of the amino acid sequence of SEQ ID NO: 11 conferring immunity against nisin or is a fragment of the amino acid sequence of SEQ ID NO: 11 conferring immunity against nisin. In some embodiments, the second and/or the fourth heterologous nucleic acid molecule comprises a nucleic acid sequence of SEQ ID NO: 55, 56 or a degenerate sequence encoding SEQ ID NO: 11. In an embodiment, the second and/or the fourth heterologous nucleic acid molecule further encodes NisE, NisF and/or NisG. In a further embodiment, NisE has the amino acid sequence of SEQ ID NO: 13, is a variant of the amino acid sequence of SEQ ID NO: 13 having nisin transporter activity or is a fragment of the amino acid sequence of SEQ ID NO: 13 having nisin transporter activity. In some embodiments, the second and/or the fourth heterologous nucleic acid molecule comprises a nucleic acid sequence of SEQ ID NO: 59, 60 or a degenerate sequence encoding SEQ ID NO: 13. In yet another embodiment, NisF has the amino acid sequence of SEQ ID NO: 12, is a variant of the amino acid sequence of SEQ ID NO: 12 having nisin transporter activity or is a fragment of the amino acid sequence of SEQ ID NO: 12 having nisin transporter activity. In some embodiments, the second and/or the fourth heterologous nucleic acid molecule comprises a nucleic acid sequence of SEQ ID NO: 57, 58 or a degenerate sequence encoding SEQ ID NO: 12. In still a further embodiment, NisG has the amino acid sequence of SEQ ID NO: 14, is a variant of the amino acid sequence of SEQ ID NO: 14 having nisin permease activity or is a fragment of the amino acid sequence of SEQ ID NO: 14 having nisin permease activity. In some embodiments, the second and/or the fourth heterologous nucleic acid molecule comprises a nucleic acid sequence of SEQ ID NO: 61, 62 or a degenerate sequence encoding SEQ ID NO: 14.

In some embodiments, the at least one bacteriocin and/or the further bacteriocin comprises a cyclic bacteriocin. For example, the cyclic bacteriocin can be gassericin and the second and/or the fourth heterologous nucleic acid molecule can encode GaaI. In another embodiment, gassericin has the amino acid sequence of SEQ ID NO: 15 or 16, is a variant of the amino acid sequence of SEQ ID NO: 15 or 16 having gassericin bacteriocin activity or is a fragment of the amino acid sequence of SEQ ID NO: 15 or 16 having gassericin bacteriocin activity. In some embodiments, the second and/or the fourth heterologous nucleic acid molecule comprises a nucleic acid sequence of SEQ ID NO: 63, 64 or a degenerate sequence encoding SEQ ID NO: 15. In still a further embodiment, GaaI has the amino acid sequence of SEQ ID NO: 17, is a variant of the amino acid sequence of SEQ ID NO: 17 conferring immunity against gassericin or is a fragment of the amino acid sequence of SEQ ID NO: 17 conferring immunity against gassericin. In some embodiments, the second and/or the fourth heterologous nucleic acid molecule comprises a nucleic acid sequence of SEQ ID NO: 65, 66, 67 or a degenerate sequence encoding SEQ ID NO: 17. In still a further embodiment, the second heterologous nucleic acid molecule further encodes GaaT and/or GaaE. In embodiments, GaaT has the amino acid sequence of SEQ ID NO: 18, is a variant of the amino acid sequence of SEQ ID NO: 18 having gassericin transporter activity or is a fragment of the amino acid sequence of SEQ ID NO: 18 having gassericin transporter activity. In an embodiment, the second and/or the fourth heterologous nucleic acid molecule comprises a nucleic acid sequence of SEQ ID NO: 68, 69 or a degenerate sequence encoding SEQ ID NO: 18. In embodiments, GaaE has the amino acid sequence of SEQ ID NO: 19, is a variant of the amino acid sequence of SEQ ID NO: 19 having gassericin permease activity or is a fragment of the amino acid sequence of SEQ ID NO: 19 having gassrin permease activity. In an embodiment, the second and/or the fourth heterologous nucleic acid molecule comprises a nucleic acid sequence of SEQ ID NO: 70, 71 or a degenerate sequence encoding SEQ ID NO: 19. In yet another embodiment, the cyclic bacteriocin is plantaricyclin A and the second and/or the fourth heterologous nucleic acid molecule encodes PlcD and/or PlcI. In an embodiment, plantaricyclin A has the amino acid sequence of SEQ ID NO: 28 or 29, is a variant of the amino acid sequence of SEQ ID NO: 28 or 29 having plantaricyclin A bacteriocin activity or is a fragment of the amino acid sequence of SEQ ID NO: 28 or 29 having plantaricyclin A bacteriocin activity. In yet another embodiment, the second and/or the fourth heterologous nucleic acid molecule comprises a nucleic acid sequence of SEQ ID NO: 94, 95 or a degenerate sequence encoding SEQ ID NO: 28. In another embodiment, PlcD has the amino acid sequence of SEQ ID NO: 30, is a variant of the amino acid sequence of SEQ ID NO: 30 conferring, in the presence of PlcI, immunity against plantaricyclin A or is a fragment of the amino acid sequence of SEQ ID NO: 30 conferring, in the presence of PlcI, immunity against plantaricyclin A. In a further embodiment, the second and/or the fourth heterologous nucleic acid molecule comprises a nucleic acid sequence of SEQ ID NO: 96, 97, 98 or a degenerate sequence encoding SEQ ID NO: 30. In some embodiments, PlcI has the amino acid sequence of SEQ ID NO: 31, is a variant of the amino acid sequence of SEQ ID NO: 31 conferring, in the presence of PlcD, immunity against plantaricyclin A or is a fragment of the amino acid sequence of SEQ ID NO: 31 conferring, in the presence of PlcD, immunity against plantaricyclin A. In some embodiments, the second and/or the fourth heterologous nucleic acid molecule comprises a nucleic acid sequence of SEQ ID NO: 99, 100, 101 or a degenerate sequence encoding SEQ ID NO: 31. In some embodiments, the second and/or the fourth heterologous nucleic acid molecule further encodes PlcT, PlcE, and/or PlcB. In another embodiment, PlcT has the amino acid sequence of SEQ ID NO: 32, is a variant of the amino acid sequence of SEQ ID NO: 32 having ATP binding activity or is a fragment of the amino acid sequence of SEQ ID NO: 32 having ATP binding activity. In yet another embodiment, the second and/or the fourth heterologous nucleic acid molecule comprises a nucleic acid sequence of SEQ ID NO: 102, 103 or a degenerate sequence encoding SEQ ID NO: 32. In some embodiments, PlcE has the amino acid sequence of SEQ ID NO: 33, is a variant of the amino acid sequence of SEQ ID NO: 33 having plantaricyclin A transporter activity or is a fragment of the amino acid sequence of SEQ ID NO: 33 having plantaricyclin A transporter activity. In a further embodiment, the second and/or the fourth heterologous nucleic acid molecule comprises a nucleic acid sequence of SEQ ID NO: 104, 105 or a degenerate sequence encoding SEQ ID NO: 33. In another embodiment, PlcB has the amino acid sequence of SEQ ID NO: 34, is a variant of the amino acid sequence of SEQ ID NO: 34 or is a fragment of the amino acid sequence of SEQ ID NO: 34. In a further embodiment, the second and/or the fourth heterologous nucleic acid molecule comprises a nucleic acid sequence of SEQ ID NO: 106, 107 or a degenerate sequence encoding SEQ ID NO: 34.

In yet another embodiment, the at least one bacteriocin and/or the further bacteriocin comprises a Class IIA bacteriocin. For example, the Class II A bacteriocin can be plantaricin 423 and the second and/or the fourth heterologous nucleic acid molecule encodes PlaB. In some embodiments, plantaricin 423 has the amino acid sequence of SEQ ID NO: 35, 36, 111 or 113, is a variant of the amino acid sequence of SEQ ID NO: 35, 36, 111 or 113 having plantaricin 423 bacteriocin activity or is a fragment of the amino acid sequence of SEQ ID NO: 35, 36, 111 or 113 having plantaricin 423 bacteriocin activity. In a further embodiment, the second and/or the fourth heterologous nucleic acid molecule comprises a nucleic acid sequence of SEQ ID NO: 108, 109 or a degenerate sequence encoding SEQ ID NO: 35. In a further embodiment, the second and/or the fourth heterologous nucleic acid molecule comprises a nucleic acid sequence of SEQ ID NO: 110 or a degenerate sequence encoding SEQ ID NO: 111. In yet a further embodiment, the second and/or the fourth heterologous nucleic acid molecule comprises a nucleic acid sequence of SEQ ID NO: 112 or a degenerate sequence encoding SEQ ID NO: 113. In some embodiments, PlaB has the amino acid sequence of SEQ ID NO: 37, is a variant of the amino acid sequence of SEQ ID NO: 37 conferring immunity against plantaricin 423 or is a fragment of the amino acid sequence of SEQ ID NO: 37 conferring immunity against plantaricin 423. In a further embodiment, the second and/or the fourth heterologous nucleic acid molecule comprises a nucleic acid sequence of SEQ ID NO: 114, 115, 116 or a degenerate sequence encoding SEQ ID NO: 37. In some embodiments, the second and/or the fourth heterologous nucleic acid molecule further encodes PlaC and/or PlaD. In an embodiment, PlaC has the amino acid sequence of SEQ ID NO: 38, is a variant of the amino acid sequence of SEQ ID NO: 38 or is a fragment of the amino acid sequence of SEQ ID NO: 38. In a further embodiment, the second and/or the fourth heterologous nucleic acid molecule comprises a nucleic acid sequence of SEQ ID NO: 117, 118 or a degenerate sequence encoding SEQ ID NO: 38. In some embodiments, PlaD has the amino acid sequence of SEQ ID NO: 39, is a variant of the amino acid sequence of SEQ ID NO: 39 having plantaricin 423 transporter activity or is a fragment of the amino acid sequence of SEQ ID NO: 39 having plantaricin 423 transporter activity. In a further embodiment, the second and/or the fourth heterologous nucleic acid molecule comprises a nucleic acid sequence of SEQ ID NO: 119, 120 or a degenerate sequence encoding SEQ ID NO: 39. For example, the Class IIA bacteriocin can be pediocin and the second and/or fourth heterologous nucleic acid molecule can encode PedB. In embodiments, pediocin has the amino acid sequence of SEQ ID NO: 20, 21, 51, 52, 75 or 144, is a variant of the amino acid sequence of SEQ ID NO: 20, 21, 51, 52, 75 or 144 having pediocin bacteriocin activity or is a fragment of the amino acid sequence of SEQ ID NO: 20, 21, 51, 52, 75 or 144 having pediocin bacteriocin activity. In a further embodiment, the second and/or the fourth heterologous nucleic acid molecule comprises a nucleic acid sequence of SEQ ID NO: 72, 73 or a degenerate sequence encoding SEQ ID NO: 20. In yet another embodiment, the second and/or the fourth heterologous nucleic acid molecule comprises a nucleic acid sequence of SEQ ID NO: 141, 142 or a degenerate sequence encoding SEQ ID NO: 51. In yet another embodiment, the second and/or the fourth heterologous nucleic acid molecule comprises a nucleic acid sequence of SEQ ID NO: 74 or a degenerate sequence encoding SEQ ID NO: 75. In yet a further embodiment, the second and/or the fourth heterologous nucleic acid molecule comprises a nucleic acid sequence of SEQ ID NO: 143 or a degenerate sequence encoding SEQ ID NO: 144. In specific embodiments, PedB has the amino acid sequence of SEQ ID NO: 22, is a variant of the amino acid sequence of SEQ ID NO: 22 conferring immunity against pediocin or is a fragment of the amino acid sequence of SEQ ID NO: 22 conferring immunity against pediocin. In yet a further embodiment, the second and/or the fourth heterologous nucleic acid molecule comprises a nucleic acid sequence of SEQ ID NO: 76, 77 or 78 or a degenerate sequence encoding SEQ ID NO: 22. In some embodiments, the second and/or the fourth heterologous nucleic acid molecule further encode PlaC and/or PlaD. In some embodiments, PedC has the amino acid sequence of SEQ ID NO: 146, is a variant of the amino acid sequence of SEQ ID NO: 146 having, in the presence of PedD, accessory pediocin transporter activity or is a fragment of the amino acid sequence of SEQ ID NO: 146 having, in the presence of PedD, accessory pediocin transporter activity. In a further embodiment, the second and/or the fourth heterologous nucleic acid molecule comprises a nucleic acid sequence of SEQ ID NO: 147, 148 or a degenerate sequence encoding SEQ ID NO: 146. In some embodiments, PedD has the amino acid sequence of SEQ ID NO: 149, is a variant of the amino acid sequence of SEQ ID NO: 149 having pediocin transporter activity or is a fragment of the amino acid sequence of SEQ ID NO: 149 having pediocin transporter activity. In a further embodiment, the second and/or the fourth heterologous nucleic acid molecule comprises a nucleic acid sequence of SEQ ID NO: 150, 151 or a degenerate sequence encoding SEQ ID NO: 149. In another embodiment, the Class IIA bacteriocin is lactoccin A and the second and/or fourth heterologous nucleic acid molecule encodes LciA. In an embodiment, the lactoccin A has the amino acid sequence of SEQ ID NO: 40 or 41, is a variant of the amino acid sequence of SEQ ID NO: 40 or 41 having lactoccin A bacteriocin activity or is a fragment of the amino acid sequence of SEQ ID NO: 40 or 41 having lactoccin A bacteriocin activity. In a further embodiment, the second and/or the fourth heterologous nucleic acid molecule comprises a nucleic acid sequence of SEQ ID NO: 121 or a degenerate sequence encoding SEQ ID NO: 40. In some embodiments, LciA has the amino acid sequence of SEQ ID NO: 42, is a variant of the amino acid sequence of SEQ ID NO: 42 conferring immunity against lactoccin A or is a fragment of the amino acid sequence of SEQ ID NO: 42 conferring immunity against lactoccin A. In a further embodiment, the second and/or the fourth heterologous nucleic acid molecule comprises a nucleic acid sequence of SEQ ID NO: 122, 123, or a degenerate sequence encoding SEQ ID NO: 42. In another embodiment, the second and/or the fourth heterologous nucleic acid molecule further encodes LcmA and/or LceA. In an embodiment, LcmA has the amino acid sequence of SEQ ID NO: 43, is a variant of the amino acid sequence of SEQ ID NO: 43 having lactoccin A export/processing activity or is a fragment of the amino acid sequence of SEQ ID NO: 43 having lactoccin A export/processing activity. In a further embodiment, the second and/or the fourth heterologous nucleic acid molecule comprises a nucleic acid sequence of SEQ ID NO: 124 or a degenerate sequence encoding SEQ ID NO: 43. In some embodiments, LceA has the amino acid sequence of SEQ ID NO: 44, is a variant of the amino acid sequence of SEQ ID NO: 44 having ATP binding activity or is a fragment of the amino acid sequence of SEQ ID NO: 44 having ATP binding activity. In a further embodiment, the second and/or the fourth heterologous nucleic acid molecule comprises a nucleic acid sequence of SEQ ID NO: 125 or a degenerate sequence encoding SEQ ID NO: 44. In another embodiment, the Class IA bacteriocin is horediocin A and the second and/or the fourth heterologous nucleic acid molecule encodes HdrI. In some embodiments, horediocin A has the amino acid sequence of SEQ ID NO: 45, 46, 129 or 131, is a variant of the amino acid sequence of SEQ ID NO: 45, 46, 129 or 131 having horediocin A bacteriocin activity or is a fragment of the amino acid sequence of SEQ ID NO: 45, 46, 129 or 131 having horediocin A bacteriocin activity. In a further embodiment, the second and/or the fourth heterologous nucleic acid molecule comprises a nucleic acid sequence of SEQ ID NO: 126, 127 or a degenerate sequence encoding SEQ ID NO: 45. In a further embodiment, the second and/or the fourth heterologous nucleic acid molecule comprises a nucleic acid sequence of SEQ ID NO: 128 or a degenerate sequence encoding SEQ ID NO: 129. In a further embodiment, the second and/or the fourth heterologous nucleic acid molecule comprises a nucleic acid sequence of SEQ ID NO: 130 or a degenerate sequence encoding SEQ ID NO: 131. In some embodiments, HdrI has the amino acid sequence of SEQ ID NO: 47, is a variant of the amino acid sequence of SEQ ID NO: 47 conferring immunity against horediocin A or is a fragment of the amino acid sequence of SEQ ID NO: 47 conferring immunity against horediocin A. In a further embodiment, the second and/or the fourth heterologous nucleic acid molecule comprises a nucleic acid sequence of SEQ ID NO: 132, 133, 134 or a degenerate sequence encoding SEQ ID NO: 47. In some embodiments, the second and/or the fourth heterologous nucleic acid molecule further encodes HdrM, HdrD and/or HdrC. In some embodiments, HdrM has the amino acid sequence of SEQ ID NO: 48, is a variant of the amino acid sequence of SEQ ID NO: 48 having horediocin A disulfide isomerase activity or is a fragment of the amino acid sequence of SEQ ID NO: 48 having horediocin A disulfide isomerase activity. In a further embodiment, the second and/or the fourth heterologous nucleic acid molecule comprises a nucleic acid sequence of SEQ ID NO: 135, 136 or a degenerate sequence encoding SEQ ID NO: 48. In some embodiments, HdrD has the amino acid sequence of SEQ ID NO: 49, is a variant of the amino acid sequence of SEQ ID NO: 49 having horediocin A cleavage and transporter activity or is a fragment of the amino acid sequence of SEQ ID NO: 49 having having horediocin A cleavage and transporter activity. In a further embodiment, the second and/or the fourth heterologous nucleic acid molecule comprises a nucleic acid sequence of SEQ ID NO: 137, 138 or a degenerate sequence encoding SEQ ID NO: 49. In some embodiments, HdrC has the amino acid sequence of SEQ ID NO: 50, is a variant of the amino acid sequence of SEQ ID NO: 50 having, in the presence of HdrD, accessory horediocin A transporter activity or is a fragment of the amino acid sequence of SEQ ID NO: 50 having, in the presence of HdrD, accessory horediocin A transporter activity. In a further embodiment, the second and/or the fourth heterologous nucleic acid molecule comprises a nucleic acid sequence of SEQ ID NO: 139, 140 or a degenerate sequence encoding SEQ ID NO: 50.

In some embodiments, the at least one bacteriocin and/or the further bacteriocin comprises a Class IIB bacteriocin. For example, the Class IIB bacteriocin can be brochocin and the second and/or fourth heterologous nucleic acid molecule can encode BrcI. Brochocin is a dimer comprising BrcA and BrcB. In some embodiments, BrcA has the amino acid sequence of SEQ ID NO: 23, 24, 82 or 84, is a variant of the amino acid sequence of SEQ ID NO: 23, 24, 82 or 84 having, in combination with BrcB, brochocin bacteriocin activity or is a fragment of the amino acid sequence of SEQ ID NO: 23, 24, 82 or 84 having, in combination with BrcB, brochocin bacteriocin activity. In a further embodiment, the second and/or the fourth heterologous nucleic acid molecule comprises a nucleic acid sequence of SEQ ID NO: 79 or 80 or a degenerate sequence encoding SEQ ID NO: 23. In a further embodiment, the second and/or the fourth heterologous nucleic acid molecule comprises a nucleic acid sequence of SEQ ID NO: 81 or a degenerate sequence encoding SEQ ID NO: 82. In a further embodiment, the second and/or the fourth heterologous nucleic acid molecule comprises a nucleic acid sequence of SEQ ID NO: 83 or a degenerate sequence encoding SEQ ID NO: 84. In additional embodiments, BrcB has the amino acid sequence of SEQ ID NO: 25, 26, 88 or 90, is a variant of the amino acid sequence of SEQ ID NO: 25, 26, 88 or 90 having, in combination with BrcA, brochocin bacteriocin activity or is a fragment of the amino acid sequence of SEQ ID NO: 25, 26, 88 or 90 having, in combination with BrcA, brochocin bacteriocin activity. In a further embodiment, the second and/or the fourth heterologous nucleic acid molecule comprises a nucleic acid sequence of SEQ ID NO: 85 or 86 or a degenerate sequence encoding SEQ ID NO: 25. In a further embodiment, the second and/or the fourth heterologous nucleic acid molecule comprises a nucleic acid sequence of SEQ ID NO: 87 or a degenerate sequence encoding SEQ ID NO: 88. In a further embodiment, the second and/or the fourth heterologous nucleic acid molecule comprises a nucleic acid sequence of SEQ ID NO: 89 or a degenerate sequence encoding SEQ ID NO: 90. In some embodiments, BrcI has the amino acid sequence of SEQ ID NO: 27, is a variant of the amino acid sequence of SEQ ID NO: 27 conferring immunity against brochocin or is a fragment of the amino acid sequence of SEQ ID NO: 27 conferring immunity against brochocin. In a further embodiment, the second and/or the fourth heterologous nucleic acid molecule comprises a nucleic acid sequence of SEQ ID NO: 91, 92 or 93 or a degenerate sequence encoding SEQ ID NO: 27.

In some embodiments, when the at least one bacteriocin and/or the further bacteriocin is the Class IIA or the Class IIB bacteriocin, the at least one bacteriocin comprises, prior to secretion, a signal sequence having the amino acid sequence of SEQ ID NO: 145, being a variant of the amino acid sequence of SEQ ID NO: 145 having signal sequence activity or being a fragment of the amino acid sequence of SEQ ID NO: 145 having signal sequence activity. In some embodiments, the second and/or fourth heterologous nucleic acid sequence can comprise a nucleic acid sequence of SEQ ID NO: 152 or a degenerate sequence encoding SEQ ID NO: 145.

In yet another embodiment, the first LAB expresses a plurality of bacteriocins. In some embodiments, the first and/or third heterologous nucleic acid molecule encodes a pyruvate decarboxylase.

In specific embodiments, the pyruvate decarboxylase has the amino acid sequence of SEQ ID NO: 1, is a variant of the amino acid sequence of SEQ ID NO: 1 having pyruvate decarboxylase activity or is a fragment of the amino acid sequence of SEQ ID NO: 1 having pyruvate decarboxylase activity. In a further embodiment, the first and/or third heterologous nucleic acid molecule comprises a nucleic acid sequence of SEQ ID NO: 2, 5 or 153 or a degenerate sequence encoding SEQ ID NO: 1. In some embodiments, the first and/or third heterologous nucleic acid molecule encodes an alcohol dehydrogenase. In a specific embodiment, the alcohol dehydrogenase has the amino acid sequence of SEQ ID NO: 3, is a variant of the amino acid sequence of SEQ ID NO: 3 having alcohol dehydrogenase activity or is a fragment of the amino acid sequence of SEQ ID NO: 3 having alcohol dehydrogenase activity. In a further embodiment, the first and/or third heterologous nucleic acid molecule comprises a nucleic acid sequence of SEQ ID NO: 4, 6 or 154 or a degenerate sequence encoding SEQ ID NO: 3. In embodiments, the first recombinant LAB cell and/or the second recombinant LAB cell has a decreased lactate dehydrogenase activity when compared to a corresponding native LAB cell. In another embodiment, the first recombinant LAB cell and/or the second recombinant LAB cell comprises at least one inactivated or deleted native gene coding for a lactate dehydrogenase. In a further embodiment, the at least one native gene coding for the lactate dehydrogenase is ldh1, ldh2, ldh3, ldh4 or dhic. In some additional embodiments, the first recombinant LAB cell and/or the second recombinant LAB cell comprises inactivated or deleted native ldh1, ldh2, ldh3, ldh4 and dhic genes. In a further embodiment, the first recombinant LAB cell and/or the second recombinant LAB cell has a decreased mannitol dehydrogenase activity compared to a corresponding native LAB cell. In some embodiments, the first recombinant LAB cell and/or the second recombinant LAB cell comprises at least one inactivated or deleted native gene coding for a mannitol-1-phosphate 5-dehydrogenase. In specific embodiments, the at least one native gene coding for the mannitol-1-phosphate 5-dehydrogenase is mltD1 or mltD2. In some additional embodiments, the first recombinant LAB cell and/or the second recombinant LAB cell comprises inactivated or deleted native mltD1 and mltD2 genes. In another embodiment, at least one of the first, second, third and/or fourth heterologous nucleic acid molecule is on an extrachromosomal vector. In yet another embodiment, at least one of the first, second, third and/or fourth heterologous nucleic acid molecule is integrated in a bacterial chromosome. In some embodiments, the first recombinant LAB cell is from the genus *Lactococcus*, and, in additional embodiments, from the species *Lactococcus lactis*. In some embodiments, the second recombinant LAB cell is from the genus *Lactobacillus*, and, for example, from the species *Lactobacillus paracasei*.

According to a second aspect, the present disclosure comprises combination comprising the co-culture described herein and a yeast cell. In an embodiment, the yeast cell is a recombinant yeast cell. In some embodiments, the yeast cell is from the genus *Saccharomyces* sp., and, in some further embodiments, from the species *Saccharomyces cerevisiae*.

According to a third aspect, the present disclosure provides a process for converting a biomass into a fermentation product. The process comprises contacting the biomass with the co-culture described herein or the combination described herein under condition to allow the conversion of at least a part of the biomass into the fermentation product. In an embodiment, the biomass comprises corn, which can be provided as a mash. In some embodiments, the fermentation product is ethanol. In some embodiments, the process is for preventing the contamination of the biomass by a contaminating microorganism.

According to a fourth aspect, the present disclosure provides a kit comprising the first recombinant lactic acid bacteria (LAB) cell described herein and the second recombinant lactic acid bacteria (LAB) cell described herein. In an embodiment, the kit further comprises the yeast cell described herein. In additional embodiments, the kit further comprises instructions to perform the process described herein.

According to a fifth aspect, the present disclosure provides a medium comprising the first recombinant lactic acid bacteria (LAB) cell described herein, the second recombinant lactic acid bacteria (LAB) cell described herein and optionally the yeast cell described herein. In an embodiment, the medium is a propagation medium. In another embodiment, the medium is a fermentation medium. In yet a further embodiment, the medium further comprises a fermentation product such as, for example, ethanol.

BRIEF DESCRIPTION OF THE DRAWINGS

Having thus generally described the nature of the invention, reference will now be made to the accompanying drawings, showing by way of illustration, a preferred embodiment thereof, and in which:

(FIG. 3A) A nisin-producing *L. lactis* strain was transformed with an empty vector. In the mass spectrum provided on FIG. 3A, nisin was the sole bacteriocin detected.

(FIG. 3B) A nisin-producing *L. lactis* strain was transformed with a vector encoding genes for pediocin production. In the mass spectrum provided on FIG. 3B, nisin and pediocin were detected.

(FIG. 3C) A nisin-producing *L. lactis* strain was transformed with a vector encoding genes for brochocin production. In the mass spectrum provided on FIG. 3C, nisin and brochocin were detected.

(FIG. 3D) Mass spectrum of an uninoculated growth medium free of bacteriocin.

DETAILED DESCRIPTION

Figure 1:
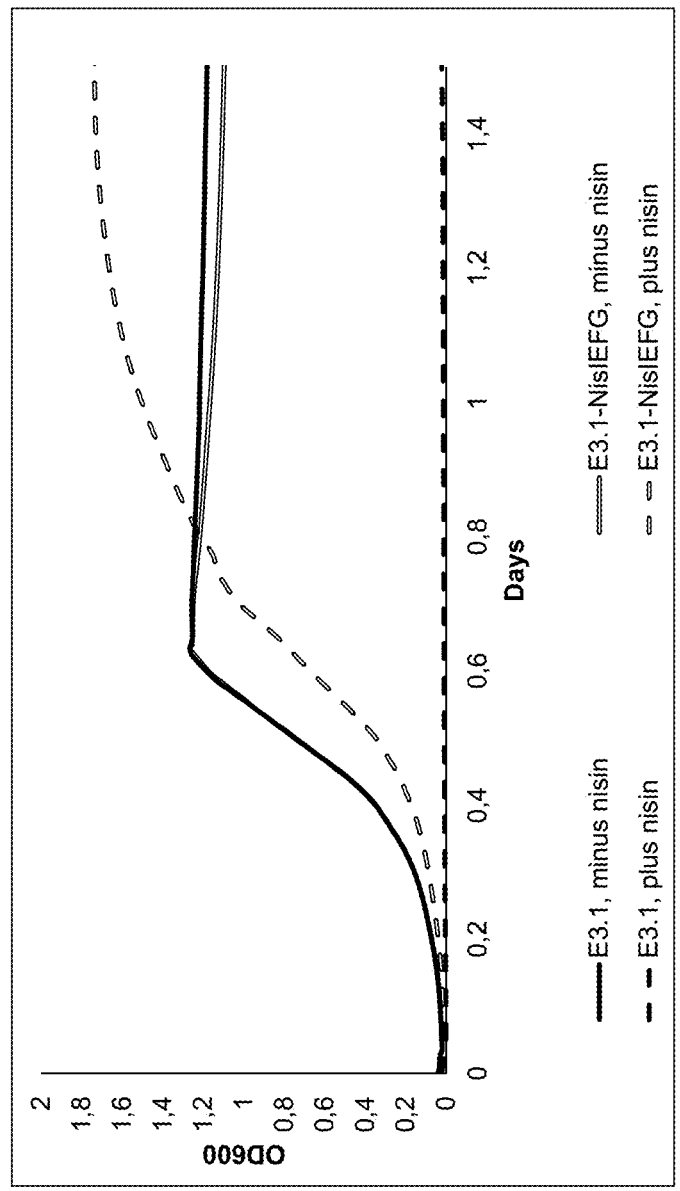
FIG. 1 illustrates the growth of *Lb. paracasei* E3.1 bearing the pDW2 empty vector (black lines) or the pDW2-PS-NisIEFG (grey lines) in MRS plus (dashed lines) and minus (solid lines) the inclusion of nisin. Results are shown as the OD at 600 nm in function of days.

The present disclosure concerns a co-culture of two distinct lactic acid bacteria cells, one of which being capable of expressing a bacteriocin (or a plurality of bacteriocins). Both lactic acid bacteria cells are capable of making a fermented product (from a biomass) as well as immune to the bacteriocin. The co-culture can be used, optionally in combination with a yeast cell, to limit microbial contamination during a process for making the fermented product. In some embodiments, the co-culture of the present disclosure can limit the use of antibiotic(s) during the fermentation of a biomass to make a fermented product (e.g., an alcohol, such as, for example, ethanol).

The co-cultures of the present disclosure comprise one or more recombinant LAB cells and can be used in combination with a recombinant yeast cell. These recombinant (bacterial and yeast) cells can be obtained by introducing one or more genetic modifications in a corresponding native (parental) microbial host cell. When the genetic modification is aimed at reducing or inhibiting the expression of a specific targeted gene (which is endogenous to the host cell), the genetic modifications can be made in one or both copies of the targeted gene(s). When the genetic modification is aimed at increasing the expression of a specific targeted gene, the genetic modification can be made in one or multiple genetic locations. In the context of the present disclosure, when recombinant microbial cells are qualified as being "genetically engineered", it is understood to mean that they have been manipulated to either add at least one or more heterologous or exogenous nucleic acid residue and/or removed at least one endogenous (or native) nucleic acid residue. In some embodiments, the one or more nucleic acid residues that are added can be derived from an heterologous cell or the recombinant cell itself. In the latter scenario, the nucleic acid residue(s) is (are) added at a genomic location which is different than the native genomic location. The genetic manipulations did not occur in nature and are the results of in vitro manipulations of the native host cell.

When expressed in recombinant microbial cells, the heterologous polypeptides described herein are encoded on one or more heterologous nucleic acid molecule. The term "heterologous" when used in reference to a nucleic acid molecule (such as a promoter or a coding sequence) refers to a nucleic acid molecule that is not natively found in the microbial cell. "Heterologous" also includes a native coding region, or portion thereof, that is removed from the source organism and subsequently reintroduced into the source organism in a form that is different from the corresponding native gene, e.g., not in its natural location in the organism's genome. The heterologous nucleic acid molecule is purposively introduced into the recombinant microbial cell. The term "heterologous" as used herein also refers to an element (nucleic acid or protein) that is derived from a source other than the endogenous source. Thus, for example, a heterologous element could be derived from a different strain of host cell, or from an organism of a different taxonomic group (e.g., different kingdom, phylum, class, order, family genus, or species, or any subgroup within one of these classifications). The term "heterologous" is also used synonymously herein with the term "exogenous".

When an heterologous nucleic acid molecule is present in the recombinant microbial cell, it can be integrated in the host cell's chromosome. The term "integrated" as used herein refers to genetic elements that are placed, through molecular biology techniques, into the chromosome of a host cell. For example, genetic elements can be placed into the chromosomes of the microbial cell as opposed to in a vector such as a plasmid carried by the host cell. Methods for integrating genetic elements into the chromosome of a host cell are well known in the art and include homologous recombination. The heterologous nucleic acid molecule can be present in one or more copies in the microbial host cell's chromosome(s). Alternatively, the heterologous nucleic acid molecule can be independently replicating from the microbial cell's chromosome. In such embodiment, the nucleic acid molecule can be stable and self-replicating.

In some embodiments, heterologous nucleic acid molecules which can be introduced into the recombinant microbial cells are codon-optimized with respect to the intended recipient recombinant microbial host cell (e.g., bacterial or yeast for example). As used herein the term "codon-optimized coding region" means a nucleic acid coding region that has been adapted for expression in the cells of a given organism by replacing at least one, or more than one, codons with one or more codons that are more frequently used in the genes of that organism. In general, highly expressed genes in an organism are biased towards codons that are recognized by the most abundant tRNA species in that organism. One measure of this bias is the "codon adaptation index" or "CAI," which measures the extent to which the codons used to encode each amino acid in a particular gene are those which occur most frequently in a reference set of highly expressed genes from an organism. The CAI of codon optimized heterologous nucleic acid molecule described herein corresponds to between about 0.8 and 1.0, between about 0.8 and 0.9, or about 1.0. In some embodiments, heterologous nucleic acid molecules which can be introduced into the recombinant microbial cells are codon-optimized with respect to the intended recipient recombinant microbial cell so as to limit or prevent homologous recombination with the corresponding native gene.

The heterologous nucleic acid molecules of the present disclosure comprise a coding region for the one or more polypeptides to be expressed by the recombinant microbial cell. A DNA or RNA "coding region" is a DNA or RNA molecule which is transcribed and/or translated into a polypeptide in a cell in vitro or in vivo when placed under the control of appropriate regulatory sequences. "Suitable regulatory regions" refer to nucleic acid regions located upstream (5' non-coding sequences), within, or downstream (3' non-coding sequences) of a coding region, and which influence the transcription, RNA processing or stability, or translation of the associated coding region. Regulatory regions may include promoters, translation leader sequences, RNA processing sites, effector binding sites and stem-loop structures. The boundaries of the coding region are determined by a start codon at the 5' (amino) terminus and a translation stop codon at the 3' (carboxyl) terminus. A coding region can include, but is not limited to, prokaryotic regions, cDNA from mRNA, genomic DNA molecules, synthetic DNA molecules, or RNA molecules. If the coding region is intended for expression in a eukaryotic cell, a polyadenylation signal and transcription termination sequence will usually be located 3' to the coding region. In an embodiment, the coding region can be referred to as an open reading frame. "Open reading frame" is abbreviated ORF and means a length of nucleic acid, either DNA, cDNA or RNA, that comprises a translation start signal or initiation codon, such as an ATG or AUG, and a termination codon and can be potentially translated into a polypeptide sequence.

The nucleic acid molecules described herein can comprise a non-coding region, for example a transcriptional and/or translational control regions. "Transcriptional and translational control regions" are DNA regulatory regions, such as promoters, enhancers, terminators, and the like, that provide for the expression of a coding region in a microbial cell. In eukaryotic cells, polyadenylation signals are control regions.

The heterologous nucleic acid molecule can be introduced in the host cell using a vector. A "vector," e.g., a "plasmid", "cosmid" or "artificial chromosome" (such as, for example, a bacterial or yeast artificial chromosome) refers to an extra chromosomal element and is usually in the form of a circular double-stranded DNA molecule. Such vectors may be autonomously replicating sequences, genome integrating sequences, phage or nucleotide sequences, linear, circular, or supercoiled, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a microbial cell.

In the heterologous nucleic acid molecule described herein, the promoter and the nucleic acid molecule coding for the one or more polypeptides can be operatively linked to one another. In the context of the present disclosure, the expressions "operatively linked" or "operatively associated" refers to fact that the promoter is physically associated to the nucleotide acid molecule coding for the one or more polypeptide in a manner that allows, under certain conditions, for expression of the one or more polypeptide from the nucleic acid molecule. In an embodiment, the promoter can be located upstream (5') of the nucleic acid sequence coding for the one or more polypeptide. In still another embodiment, the promoter can be located downstream (3') of the nucleic acid sequence coding for the one or more polypeptide. In the context of the present disclosure, one or more than one promoter can be included in the heterologous nucleic acid molecule. When more than one promoter is included in the heterologous nucleic acid molecule, each of the promoters is operatively linked to the nucleic acid sequence coding for the one or more polypeptide. The promoters can be located, in view of the nucleic acid molecule coding for the one or more polypeptide, upstream, downstream as well as both upstream and downstream.

"Promoter" refers to a DNA fragment capable of controlling the expression of a coding sequence or functional RNA. The term "expression," as used herein, refers to the transcription and stable accumulation of sense (mRNA) from the heterologous nucleic acid molecule described herein. Expression may also refer to translation of mRNA into a polypeptide. Promoters may be derived in their entirety from a native gene, or be composed of different elements derived from different promoters found in nature, or even comprise synthetic DNA segments. It is understood by those skilled in the art that different promoters may direct the expression at different stages of development, or in response to different environmental or physiological conditions. Promoters which cause a gene to be expressed in most cells at most times at a substantial similar level are commonly referred to as "constitutive promoters". It is further recognized that since in most cases the exact boundaries of regulatory sequences have not been completely defined, DNA fragments of different lengths may have identical promoter activity. A promoter is generally bounded at its 3' terminus by the transcription initiation site and extends upstream (5' direction) to include the minimum number of bases or elements necessary to initiate transcription at levels detectable above background. Within the promoter will be found a transcription initiation site (conveniently defined for example, by mapping with nuclease S1), as well as protein binding domains (consensus sequences) responsible for the binding of the polymerase.

The promoter can be heterologous to the nucleic acid molecule encoding the one or more polypeptide. The promoter can be heterologous or derived from a strain being from the same genus or species as the microbial cell. In an embodiment, the promoter is derived from the same genus or species of the microbial cell and the heterologous polypeptide is derived from different genus.

In some embodiments, the present disclosure concerns the expression of one or more heterologous polypeptide, a variant thereof or a fragment thereof in a host cell. A variant comprises at least one amino acid difference when compared to the amino acid sequence of the native (wild-type) polypeptide. The polypeptide "variants" have at least 50%, 55%, 60%, 65%, 70%, 75%, 80%, 85%, 90%, 95%, 96%, 97%, 98% or 99% identity to the heterologous polypeptide described herein and exhibits the biological activity associated with the heterologous polypeptide. In some embodiments, the variant polypeptide exhibits more activity that the corresponding wild-type polypeptide. In the embodiment in which the polypeptide is a bacteriocin, the biological activity of the polypeptide is its anti-bacterial (e.g., bacteriostatic and/or cytotoxic) activity. In the embodiment in which the polypeptide is a bacteriocin transporter or a permease or otherwise involved in bacteriocin secretion (such as, for example, an accessory protein involved in transport), the biological activity of the polypeptide is its ability to translocate the bacteriocin inside or outside the cell. In the embodiment in which the polypeptide confers immunity against the bacteriocin, the biological activity of the polypeptide is immunity. In the embodiment in which the polypeptide confers bacteriocin processing activity (e.g., such as disulfide isomerase activity), the biological activity of the polypeptide is its ability to modify the bacteriocin (e.g., exhibit isomerase activity towards the bacteriocin). In the embodiment in which the polypeptide confers ATP binding activity, the biological activity of the polypeptide is its ability to bind to ATP. In an embodiment, the variant polypeptide exhibits at least 50%, 55%, 60%, 65%, 70%, 75%, 80%, 85%, 90%, 95%, 96%, 97%, 98% or 99% of the biological identity with respect to the wild-type polypeptide. The term "percent identity", as known in the art, is a relationship between two or more polypeptide sequences or two or more polynucleotide sequences, as determined by comparing the sequences. The level of identity can be determined conventionally using known computer programs. Identity can be readily calculated by known methods, including but not limited to those described in: Computational Molecular Biology (Lesk, A. M., ed.) Oxford University Press, NY (1988); Biocomputing: Informatics and Genome Projects (Smith, D. W., ed.) Academic Press, NY (1993); Computer Analysis of Sequence Data, Part I (Griffin, A. M., and Griffin, H. G., eds.) Humana Press, NJ (1994); Sequence Analysis in Molecular Biology (von Heinje, G., ed.) Academic Press (1987); and Sequence Analysis Primer (Gribskov, M. and Devereux, J., eds.) Stockton Press, NY (1991). Preferred methods to determine identity are designed to give the best match between the sequences tested. Methods to determine identity and similarity are codified in publicly available computer programs. Sequence alignments and percent identity calculations may be performed using the Megalign program of the LASERGENE bioinformatics computing suite (DNASTAR Inc., Madison, Wis.). Multiple alignments of the sequences disclosed herein were performed using the Clustal method of alignment (Higgins and Sharp (1989) CABIOS. 5:151-153) with the default parameters (GAP PENALTY=10, GAP LENGTH PEN ALT Y=10). Default parameters for pairwise alignments using the Clustal method were KTUPLB 1, GAP PENALTY=3, WINDOW=5 and DIAGONALS SAVED=5.

The variant heterologous polypeptides described herein may be (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues includes a substituent group, or (iii) one in which the mature polypeptide is fused with another compound, such as a compound to increase the half-life of the polypeptide (for example, polyethylene glycol), or (iv) one in which the additional amino acids are fused to the mature polypeptide for purification of the polypeptide.

A "variant" of the polypeptide can be a conservative variant or an allelic variant. As used herein, a conservative variant refers to alterations in the amino acid sequence that do not adversely affect the biological functions of the polypeptide. A substitution, insertion or deletion is said to adversely affect the polypeptide when the altered sequence prevents or disrupts a biological function associated with the polypeptide. For example, the overall charge, structure or hydrophobic-hydrophilic properties of the polypeptide can be altered without adversely affecting its biological activity. Accordingly, the amino acid sequence can be altered, for example to render the polypeptide more hydrophobic or hydrophilic, without adversely affecting the biological activities of the polypeptide.

The heterologous polypeptide can be a fragment of the native (wild-type) polypeptide or fragment of a variant of the polypeptide which exhibits the biological activity of the polypeptide or the variant. In an embodiment, the fragment exhibits at least 50%, 55%, 60%, 65%, 70%, 75%, 80%, 85%, 90%, 95%, 96%, 97%, 98% or 99% of the biological activity of the heterologous polypeptides or variant thereof. In some embodiments, the variant polypeptide exhibits more activity that the corresponding wild-type polypeptide. In the embodiment in which the polypeptide is a bacteriocin, the biological activity of the polypeptide is its anti-bacterial (e.g., bacteriostatic and/or cytotoxic) activity. In the embodiment in which the polypeptide is a bacteriocin transporter or a permease or otherwise involved in bacteriocin secretion (such as, for example, an accessory protein involved in transport), the biological activity of the polypeptide is its ability to translocate the bacteriocin inside or outside the cell. In the embodiment in which the polypeptide confers immunity against the bacteriocin, the biological activity of the polypeptide is immunity. In the embodiment in which the polypeptide confers bacteriocin processing activity (e.g., such as disulfide isomerase activity), the biological activity of the polypeptide is its ability to modify the bacteriocin (e.g., exhibit isomerase activity towards the bacteriocin). In the embodiment in which the polypeptide confers ATP binding activity, the biological activity of the polypeptide is its ability to bind to ATP. In some embodiments, the "fragments" have at least 50%, 55%, 60%, 65%, 70%, 75%, 80%, 85%, 90%, 95%, 96%, 97%, 98% or 99% identity to the wild-type polypeptides described herein.

In some additional embodiments, the present disclosure also provides expressing a polypeptide encoded by a gene ortholog of a gene known to encode the polypeptide. A "gene ortholog" is understood to be a gene in a different species that evolved from a common ancestral gene by speciation. In the context of the present disclosure, a gene ortholog encodes a polypeptide exhibiting the same biological function than the native polypeptide.

In some further embodiments, the present disclosure also provides expressing a protein encoded by a gene paralog of a gene known to encode the polypeptide. A "gene paralog" is understood to be a gene related by duplication within the genome. In the context of the present disclosure, a gene paralog encodes a polypeptide that could exhibit additional biological function than the native polypeptide.

First Recombinant Lactic Acid Bacteria (LAB) Cell

In the context of the present disclosure, the first bacterial cell of the co-culture is a lactic acid bacterium (LAB). The first recombinant LAB cells can be provided as a pure culture to the fermentation or as a blend with the second recombinant LAB cells. As it is known in the art, LAB are a group of Gram-positive bacteria, non-respiring non-spore-forming, cocci or rods, which produce lactic acid as the major end product of the fermentation of carbohydrates. Bacterial genus of LAB include, but are not limited to, *Lactobacillus, Leuconostoc, Pediococcus, Lactococcus, Streptococcus, Aerococcus, Carnobacterium, Enterococcus, Oenococcus, Sporolactobacillus, Tetragenococcus, Vagococcus*, and Weissella. Bacterial species of LAB include, but are not limited to, *Lactococcus lactis, Lactococcus garviae, Lactococcus raffinolactis, Lactococcus plantarum, Oenococcus oeni, Pediococcus pentosaceus, Pediococcus acidilactici, Carnococcus allantoicus, Carnobacterium gallinarum, Vagococcus fessus, Streptococcus thermophilus, Enterococcus phoeniculicola, Enterococcus plantarum, Enterococcus raffinosus, Enterococcus avium, Enterococcus pallens Enterococcus hermanniensis, Enterococcus faecalis*, and *Enterococcus faecium*. In an embodiment, the LAB is a *Lactobacillus* and, in some additional embodiment, the *Lactobacillus* species is *L. acetotolerans, L. acidifarinae, L. acidipiscis, L. acidophilus, L. agilis, L. algidus, L. alimentarius, L. amylolyticus, L. amylophilus, L. amylotrophicus, L. amylovorus, L. animalis, L. antri, L. apodemi, L. aviarius, L. bifermentans, L. brevis, L. buchneri, L. camelliae, L. casei, L. catenaformis, L. ceti, L. coleohominis, L. collinoides, L. composti, L. concavus, L. coryniformis, L. crispatus, L. crustorum, L. curvatus, L. delbrueckii* (including *L. delbrueckii* subsp. *bulgaricus, L. delbrueckii* subsp. *delbrueckii, L. delbrueckii* subsp. *lactis*), *L. dextrinicus, L. diolivorans, L. equi, L. equigenerosi, L. farraginis, L. farciminis, L. fermentum, L. fornicalis, L. fructivorans, L. frumenti, L. fuchuensis, L. gallinarum, L. gasseri, L. gastricus, L. ghanensis, L. graminis, L. ammesii, L. hamsteri, L. harbinensis, L. hayakitensis, L. helveticus, L. hilgardii, L. omohiochii, L. iners, L. ingluviei, L. intestinalis, L. jensenii, L. johnsonii, L. kalixensis, L. efiranofaciens, L. kefiri, L. kimchii, L. kitasatonis, L. kunkeei, L. leichmannii, L. lindneri, L. alefermentans, L. mali, L. manihotivorans, L. mindensis, L. mucosae, L. murinus, L. nagelii, L. namurensis, L. nantensis, L. oligofermentans, L. oris, L. panis, L. pantheris, L. parabrevis, L. parabuchneri, L. paracasei, L. paracollinoides, L. parafarraginis, L. parakefiri, L. aralimentarius, L. paraplantarum, L. pentosus, L. perolens, L. plantarum, L. pontis, L. protectus, L. psittaci, L. rennini, L. reuteri, L. rhamnosus, L. rimae, L. rogosae, L. rossiae, L. ruminis, L. saerimneri, L. sakei, L. salivarius, L. sanfranciscensis, L. satsumensis, L. secaliphilus, L. sharpeae, L. siliginis, L. spicheri, L. suebicus, L. thailandensis, L. ultunensis, L. vaccinostercus, L. vaginalis, L. versmoldensis, L. vini, L. vitulinus, L. zeae* or *L. zymae*.

In a specific embodiment, the first recombinant LAB cell is from the genus *Lactococcus* sp. and can be, in a further embodiment, from the species *Lactococcus lactis*. The first recombinant LAB cell is a recombinant LAB cell because it comprises a first heterologous nucleic acid molecule encoding a polypeptide for converting, at least in part, a biomass (such as corn for example) into a fermented product. In some embodiments, more than one first heterologous nucleic acid molecules can be provided to encode a plurality of polypeptides for converting, at least in part, a biomass (such as corn for example) into a fermented product. In such embodiments, each first heterologous nucleic acid molecules can include one or more coding sequences corresponding to one or more polypeptides. In another embodiment, a single first heterologous nucleic acid molecule can encode the one or more polypeptides. The one or more polypeptide included on the first heterologous nucleic acid molecule(s) can be made to improve the fermentation yield and allow the first recombinant LAB cell to make a fermented product, such as, for example, ethanol. Without wishing to be bound to theory, the presence of the one or more first nucleic acid molecules and the expression of the one or more polypeptide in the first recombinant LAB cell favors the production of the fermented product instead of organic acids which may be detrimental to the growth or viability of other microbial cells (yeasts for example) during fermentation.

In an embodiment, one or more first heterologous nucleic acid molecule encodes a pyruvate decarboxylase and/or an alcohol dehydrogenase. When the first recombinant LAB cell has an intrinsic ability of expressing a pyruvate decarboxylase, the first heterologous nucleic acid molecule can encode an heterologous alcohol dehydrogenase. In such embodiment, it is possible that the first heterologous nucleic acid molecule (same or different molecule) encodes an heterologous pyruvate decarboxylase (to increase the overall pyruvate decarboxylase activity of the first recombinant LAB cell). When the first recombinant LAB cell has an intrinsic ability of expressing an alcohol dehydrogenase, the first heterologous nucleic acid molecule can encode a pyruvate decarboxylase. In such embodiment, it is possible that the first heterologous nucleic acid molecule further encodes an heterologous alcohol dehydrogenase (to increase the overall alcohol dehydrogenase activity of the first recombinant LAB cell). If the first recombinant LAB does not have an intrinsic ability of expressing a pyruvate decarboxylase and an alcohol dehydrogenase, the first heterologous nucleic acid molecule can encode an alcohol dehydrogenase and a pyruvate decarboxylase (on the same or different molecules). The one or more first heterologous nucleic acid molecules can be integrated in the bacterial genome or be independently replicating from the bacterial genome. The nucleic acid sequences encoding the pyruvate decarboxylase and the alcohol dehydrogenase can be on the same or distinct first heterologous nucleic acid molecules.

In an embodiment, the one or more polypeptide for converting a biomass includes an heterologous pyruvate decarboxylase. In such embodiment, the first recombinant LAB cell includes on a first heterologous nucleic acid molecule a coding sequence for an heterologous pyruvate decarboxylase. As used herein, the term "pyruvate decarboxylase" refers to an enzyme catalyzing the decarboxylation of pyruvic acid to acetaldehyde and carbon dioxide. In *Zymonas mobilis*, the pyruvate decarboxylase gene is referred to as PDC (Gene ID: 33073732) and could be used in the first recombinant LAB cell of the present disclosure. In some additional embodiments, the pyruvate decarboxylase polypeptide can be from *Lactobacillus florum* (Accession Number WP_009166425.1), *Lactobacillus fructivorans* (Accession Number WP_039145143.1), *Lactobacillus lindneri* (Accession Number WP_065866149.1), *Lactococcus lactis* (Accession Number WP_104141789.1), *Carnobacterium gallinarum* (Accession Number WP_034563038.1), *Enterococcus plantarum* (Accession Number WP_069654378.1), *Clostridium acetobutylicum* (Accession Number NP_149189.1), *Bacillus megaterium* (Accession Number WP_075420723.1) or *Bacillus thuringiensis* (Accession Number WP_052587756.1). In the first recombinant LAB cell of the present disclosure, the pyruvate decarboxylase can have the amino acid of SEQ ID NO: 1, be a variant of SEQ ID NO: 1 (having pyruvate carboxylase activity) or be a fragment of SEQ ID NO: 1 having pyruvate carboxylase activity). In some specific embodiments, the first recombinant LAB cell of the present disclosure can express an heterologous nucleic acid molecule comprising the nucleic acid sequence of SEQ ID NO: 2, 5 or 153, a variant thereof (encoding a polypeptide having pyruvate carboxylase activity) or a fragment thereof (encoding a polypeptide having pyruvate carboxylase activity). In yet a further specific embodiment, the first heterologous nucleic acid molecule can comprise the nucleic acid sequence of SEQ ID NO: 2, 5 or 153 or a degenerate sequence encoding SEQ ID NO: 1.

In an embodiment, the one or more polypeptide for converting a biomass includes an heterologous alcohol dehydrogenase. In such embodiment, the first recombinant LAB cell includes on a first heterologous nucleic acid molecule a coding sequence for an heterologous alcohol dehydrogenase. The nucleic acid sequence encoding the heterologous alcohol dehydrogenase can physically be located on the same or on a distinct nucleic acid molecule as the nucleic acid sequence encoding the pyruvate decarboxylase. As used herein, the term "alcohol dehydrogenase" refers to an enzyme of the EC 1.1.1.1 class. In some embodiments, the alcohol dehydrogenase is an iron-containing alcohol dehydrogenase. The alcohol dehydrogenase that can be expressed in the first recombinant LAB cell includes, but is not limited to, ADH4 from *Saccharomyces cerevisiae*, ADHB from *Zymonas mobilis*, FUCO from *Escherichia coli*, ADHE from *Escherichia coli*, ADH1 from *Clostridium acetobutylicum*, ADH1 from *Entamoeba nuttalli*, BDHA from *Clostridium acetobutylicum*, BDHB from *Clostridium acetobutylicum*, 4HBD from *Clostridium kluyveri*, DHAT from *Citrobacter freundii* or DHAT from *Klebsiella pneumoniae*. In an embodiment, the alcohol dehydrogenase can be ADHB from *Zymonas mobilis* (Gene ID: AHJ71151.1), *Lactobacillus reuteri* (Accession Number: KRK51011.1), *Lactobacillus mucosae* (Accession Number WP_048345394.1), *Lactobacillus brevis* (Accession Number WP_003553163.1) or *Streptococcus* thermophiles (Accession Number WP_113870363.1). In the first recombinant LAB cell of the present disclosure, the alcohol dehydrogenase can have the amino acid of SEQ ID NO: 3, be a variant of SEQ ID NO: 3 (having alcohol dehydrogenase activity) or a fragment of SEQ ID NO: 3 (having alcohol dehydrogenase activity). In some specific embodiments, the first recombinant LAB cell of the present disclosure can express an heterologous nucleic acid molecule comprising the nucleic acid sequence of SEQ ID NO: 4, 6 or 154, be a variant of the nucleic acid sequence of SEQ ID NO: 4, 6 or 154 (encoding a polypeptide having alcohol dehydrogenase activity) or be a fragment of the nucleic acid sequence of SEQ ID NO: 4, 6 or 154 (encoding a polypeptide having alcohol dehydrogenase activity). In yet another embodiment, the first heterologous nucleic acid molecule can comprise the nucleic acid sequence of SEQ ID NO: 4, 6 or 154 or a degenerate sequence encoding SEQ ID NO: 3.

In some embodiments, it may be advantageous to reduce the lactate dehydrogenase activity in the first recombinant LAB cell. In such embodiment, the first recombinant LAB cell can be genetically modified to as to decrease its lactate dehydrogenase activity. As used in the context of the present disclosure, the expression "lactate dehydrogenase" refers to an enzyme of the E.C. 1.1.1.27 class which is capable of catalyzing the conversion of pyruvic acid into lactate. The first recombinant LAB cell can thus have one or more gene coding for a protein having lactate dehydrogenase activity which is inactivated (via partial or total deletion of the gene). In bacteria, the ldh1, ldh2, ldh3 and ldh4 genes encode proteins having lactate dehydrogenase activity. Some bacteria may contain as many as six or more such genes (i.e., ldh5, ldh6, etc.). The enzyme encoded by the ldh3 gene is a protein having lactate dehydrogenase activity and is sometimes referred to as a l-hydroxyisocaproic acid dehydrogenase (encoded by the lhic gene). Another enzyme having lactate dehydrogenase activity is d-hydroxyisocaproic acid dehydrogenase (encoded by the dhic gene). In an embodiment, at least one of the ldh1, ldh2, ldh3, ldh4 or dhic genes, their corresponding orthologs and paralogs is inactivated or deleted in the first recombinant LAB cell. In an embodiment, only one of the ldh gene is inactivated or deleted in the first recombinant LAB cell. In another embodiment, at least two of the ldh genes are inactivated or deleted in the first recombinant LAB cell. In another embodiment, only two of the ldh genes are inactivated or deleted in the first recombinant LAB cell. In a further embodiment, at least three of the ldh genes are inactivated or deleted in the first recombinant LAB cell. In a further embodiment, only three of the ldh genes are inactivated or deleted in the first recombinant LAB cell. In a further embodiment, at least four of the ldh genes are inactivated or deleted in the first recombinant LAB cell. In a further embodiment, only four of the ldh genes are inactivated or deleted in the first recombinant LAB cell. For example, in the first recombinant LAB cell of the present disclosure, the ldh1, ldh2, ldh3 and ldh4 genes are inactivated or deleted. In a further embodiment, at least five of the ldh genes are inactivated or deleted in the first recombinant LAB cell. In a further embodiment, only five of the ldh genes are inactivated or deleted in the first recombinant LAB cell. For example, in the first recombinant LAB cell of the present disclosure, the ldh1, ldh2, ldh3, ldh4 and dhic genes are inactivated or deleted. In a further embodiment, at least six of the ldh genes are inactivated or deleted in the first recombinant LAB cell. In a further embodiment, only six of the ldh genes are inactivated in the first recombinant LAB cell. In still another embodiment, all of the ldh genes are inactivated in the first recombinant LAB cell.

In some embodiments, it may be advantageous to reduce mannitol dehydrogenase activity, such as the mannitol-1-phosphate 5-dehydrogenase activity, in the first recombinant LAB cell. In such embodiment, the first recombinant LAB cell can be genetically engineered to decrease its mannitol-1-phosphate 5-dehydrogenase activity. As used in the context of the present disclosure, the expression "mannitol-1-P 5-dehydrogenase" refer to an enzyme of the E.C. 1.1.1.17 class which is capable of catalyzing the conversion of mannitol into fructose-6-phosphate. The first recombinant LAB cell can thus have one or more gene coding for a protein having mannitol dehydrogenase activity which is inactivated (via partial or total deletion of the gene). In bacteria, the mltd1 and mltd2 genes encode proteins having mannitol-1-P 5-dehydrogenase activity. In an embodiment, at least one of the mltd1 and mltd2 genes, their corresponding orthologs and paralogs is inactivated in the first recombinant LAB cell. In an embodiment, only one of the mltd1 and mltd2 genes is inactivated in the first recombinant LAB cell. In another embodiment, both of the mltd1 and mltd2 genes are inactivated in the first recombinant LAB cell.

The first recombinant LAB cell expresses a bacteriocin. In some embodiments, the first recombinant LAB cell can have the intrinsic ability (e.g., an ability that is not conferred by the introduction of an heterologous nucleic acid molecule) to express and produce at least one bacteriocin (e.g., a native bacteriocin, such as, for example, at least one lantibiotic) as well as being immune to the bacteriocin it expresses. In some embodiments, the first recombinant LAB cell can be genetically modified to express and produce one or more further bacteriocin (which may be in addition to the one it already expresses). In such embodiment, the first recombinant LAB cell will include one or more second heterologous nucleic acid molecule encoding the further bacteriocin and/or the polypeptide(s) associated with the immunity to the further bacteriocin. The coding sequence for the further bacteriocin and for the polypeptide(s) associated with the immunity to the further bacteriocin can be provided on the same or distinct second nucleic acid molecules. The second heterologous nucleic acid molecule(s) can be integrated in the bacterial genome or be independently replicating from the bacterial genome.

In other embodiments, the first recombinant LAB cell can also lack the intrinsic ability to express one or more bacteriocin and can be genetically modified to express and produce one or more bacteriocin (e.g., a recombinant bacteriocin). In such embodiment, the first recombinant LAB cell will include one or more second heterologous nucleic acid molecule encoding the recombinant bacteriocin. The coding sequence for the recombinant bacteriocin and for the polypeptide(s) associated with the immunity to the recombinant bacteriocin can be provided on the same or distinct second nucleic acid molecules. In some embodiments, the first recombinant LAB cell can be genetically modified to express and produce a further recombinant bacteriocin (in addition to the one it already expresses). In such embodiment, the first recombinant LAB cell will include one or more second heterologous nucleic acid molecule encoding the further recombinant bacteriocin and/or the polypeptide(s) associated with the immunity to the further recombinant bacteriocin. The coding sequence for the further recombinant bacteriocin and for the polypeptide(s) associated with the immunity to the further recombinant bacteriocin can be provided on the same or distinct second nucleic acid molecules. The second heterologous nucleic acid molecule(s) can be integrated in the bacterial genome or be independently replicating from the bacterial genome.

Bacteriocins are known as a class of peptides and polypeptides exhibiting, as their biological activity, anti-bacterial properties. Bacteriocins can exhibit bacteriostatic or cytotoxic activity. Bacteriocin can be provided as a monomeric polypeptide, a dimer polypeptide (homo- and heterodimers) as well as a circular polypeptide. Since bacteriocin are usually expressed to be exported outside of the cell, they are usually synthesized as pro-polypeptides including a signal sequence, the latter being cleaved upon secretion. The bacteriocin of the present disclosure can be expressed using their native signal sequence or an heterologous signal sequence. The bacteriocin of the present disclosure can be expressed using a signal sequence which may be heterologous to the bacteriocin (such as, for example, the usp45TM8 signal sequence which can have, in some embodiments, the amino acid sequence of SEQ ID NO: 145, be a variant or a fragment thereof or encoded by the nucleic acid sequence of SEQ ID NO: 152 or a related degenerate sequence). It is known in the art that some bacteriocins are modified after being translated to include uncommon amino acids (such as lanthionine, methyllanthionine, didehydroalanine, and/or didehydroaminobutyric acid). The amino acid sequences provided herein for the different bacteriocins do not include such post-translational modifications, but it is understood that a first recombinant LAB cell expressing a bacteriocin from a second nucleic acid molecule can produce a polypeptide which does not exactly match the amino acid sequence of the different SEQ ID NOs, but the exported bacteriocin can be derived from such amino acid sequences (by post-translational modification or proteolytic cleavage of the signal sequence).

In some embodiments, the at least one bacteriocin comprises one or more bacteriocin from Gram-negative bacteria. The bacteriocin from Gram-negative bacteria which can be used also or in combination with one or more additional bacteriocin. Bacteriocins from Gram-negative bacteria include, but are not limited to, microcins, colicin-like bacteriocins and tailocins. In some embodiments, the at least one bacteriocin comprises one or more bacteriocin from Gram-positive bacteria. The bacteriocin from Gram-positive bacteria which can be used also or in combination with one or more additional bacteriocin. Bacteriocins from Gram-positive bacteria include, but are not limited to, class I bacteriocins (such as, for example nisin A and/or nisin Z), class II bacteriocins, including class IIa (such as, for example, plantaricin 423, pediocin, lactoccin A and/or horediocin A) and IIb (such as, for example, brochocin for example) bacteriocins, class III bacteriocins, class IV bacteriocins and circular bacteriocins (such as, for example, gassericin and/or plantaricyclin A). Known bacteriocins include, but are not limited to, acidocin, actagardine, agrocin, alveicin, aureocin, aureocin A53, aureocin A70, bisin, carnocin, carnocyclin, caseicin, cerein, circularin A, colicin, curvaticin, divercin, duramycin, enterocin, enterolysin, epidermin/gallidermin, erwiniocin, gardimycin, gassericin A, glycinecin, halocin, haloduracin, klebicin, lactocin S, lactococcin, lacticin, leucoccin, lysostaphin, macedocin, mersacidin, mesentericin, microbisporicin, microcin S, mutacin, nisin A, nisin Z, paenibacillin, planosporicin, pediocin, pentocin, plantaricin, pneumocyclicin, pyocin, reutericin 6, sakaci, salivaricin, sublancin, subtilin, sulfolobicin, tasmancin, thuricin 17, trifolitoxin, variacin, vibriocin, warnericin and warnerin.

In a specific embodiment, the bacteriocin natively expressed by the first recombinant LAB cell or encoded by the second nucleic acid molecule can be a Gram-positive class I bacteriocin. The Gram-positive class I bacteriocin can be the only bacteriocin expressed in the first recombinant LAB cell or it can be expressed with one or more further bacteriocin. For example, nisin can be the only bacteriocin produced by the first recombinant LAB cell. In another example, nisin can be produced in combination with pediocin and brochocin in the first recombinant LAB cell. In some embodiments, the Gram-positive class I bacteriocin can be nisin A, nisin Z, nisin J (as described in O'Sullivan et al., 2020), nisin H (as described in O'Conner et al., 2015), nisin Q (as described in Fukao et al., 2008) and/or nisin U (as described in Wirawan et al., 2006). Nisin is a bacteriocin natively produced by some strains of *Lactococcus lactis*. Nisin is a relatively broad-spectrum bacteriocin effective against many Gram-positive organisms as well as spores. In an embodiment, nisin A has the amino acid sequence of SEQ ID NO: 9 (including its native signal sequence), is a variant of the amino acid sequence of SEQ ID NO: 9 (retaining, at least in part, the biological activity of nisin A) or is a fragment of the amino acid sequence of SEQ ID NO: 9 (retaining, at least in part, the biological activity of nisin A). In an embodiment, nisin A has the amino acid sequence of SEQ ID NO: 10 (excluding its native signal sequence), is a variant of the amino acid sequence of SEQ ID NO: 10 (retaining, at least in part, the biological activity of nisin A) or is a fragment of the amino acid sequence of SEQ ID NO: 10 (retaining, at least in part, the biological activity of nisin A). In an embodiment, nisin Z has the amino acid sequence of SEQ ID NO: 7 (including its native signal sequence), is a variant of the amino acid sequence of SEQ ID NO: 7 (retaining, at least in part, the biological activity of nisin Z) or is a fragment of the amino acid sequence of SEQ ID NO: 7 (retaining, at least in part, the biological activity of nisin Z). In some embodiments, the first recombinant LAB call can include a (native or heterologous) nucleic acid molecule comprises the nucleic acid sequence of SEQ ID NO: 53 or a degenerate sequence encoding SEQ ID NO: 7. In an embodiment, nisin A has the amino acid sequence of SEQ ID NO: 8 (excluding its native signal sequence), is a variant of the amino acid sequence of SEQ ID NO: 8 (retaining, at least in part, the biological activity of nisin Z) or is a fragment of the amino acid sequence of SEQ ID NO: 8 (retaining, at least in part, the biological activity of nisin Z). In some embodiments, the first recombinant LAB call can include a (native or heterologous) nucleic acid molecule comprises the nucleic acid sequence of SEQ ID NO: 54 or a degenerate sequence encoding SEQ ID NO: 8.

In embodiments in which the first recombinant LAB cell produces nisin as the bacteriocin, the first recombinant LAB cell can possess the machinery for making nisin or can be genetically engineered to express the machinery for making nisin. Polypeptides involved in the production and/or the regulation of production of nisin include, but are not limited to NisB, NisT, NisC, NisP, NisR and/or NisK. The one or more polypeptides involved in the production and/or the regulation of production of nisin can be located on the same or a distinct nucleic acid molecule as the one encoding nisin.

In embodiments in which the first recombinant LAB cell produces nisin as the bacteriocin, the first recombinant LAB cell possess immunity against nisin or can be genetically engineered to gain immunity against nisin. A polypeptide known to confer immunity or resistance against nisin is NisI. In an embodiment, NisI has the amino acid sequence of SEQ ID NO: 11 (as well as functional variants and fragments thereof retaining at least on part their ability to confer immunity against nisin). As such, the first recombinant LAB cell can comprise a (native or heterologous) nucleic acid molecule further encoding NisI. In such embodiment, the first recombinant LAB cell can comprise the nucleic acid sequence of SEQ ID NO: 55, 56 or a degenerate sequence encoding SEQ ID NO: 11. Additional polypeptides involved in conferring immunity against nisin include, without limitation, NisE (which is a nisin transporter), NisF (which is a nisin transporter) and NisG (which is a nisin permease). As such, the second heterologous nucleic acid molecule can further encode NisE, NisF and/or NisG. In an embodiment, NisE has the amino acid sequence of SEQ ID NO: 13 (as well as functional variants and fragments thereof retaining, at least in part, their ability to transport nisin). In an embodiment, the first recombinant LAB cell can comprise a (native or heterologous) nucleic acid molecule having the nucleic acid sequence of SEQ ID NO: 59, 60 or a degenerate sequence encoding SEQ ID NO: 13. In an embodiment, NisF has the amino acid sequence of SEQ ID NO: 12 (as well as functional variants and fragments thereof retaining, at least in part, their ability to transport nisin). In such embodiment, the first recombinant LAB cell can comprise a (native or heterologous) nucleic acid sequence of SEQ ID NO: 57, 58 or a degenerate sequence encoding SEQ ID NO: 12. In an embodiment, NisG has the amino acid sequence of SEQ ID NO: 14 (as well as functional variants and fragments thereof retaining, at least in part, their ability to transport nisin). The one or more polypeptides involved in the conferring immunity against nisin can be located on the same or on a distinct nucleic acid molecule as the one encoding nisin and/or the polypeptides involved in the production and/or the regulation of production of nisin. In an embodiment, the first recombinant LAB cell can comprise a (native or heterologous) nucleic acid molecule having the nucleic acid sequence of SEQ ID NO: 61, 62 or a degenerate sequence encoding SEQ ID NO: 14.

In a specific embodiment, the bacteriocin natively expressed by the first recombinant LAB cell or encoded by the second heterologous nucleic acid molecule can be a Gram-positive class II bacteriocin. The Gram-positive class II bacteriocin can be the only bacteriocin expressed in the first recombinant LAB cell or it can be expressed with one or more further bacteriocin. Gram-positive class II bacteriocins include two subgroups: class IA and class IIB bacteriocins. In a specific example, the Gram-positive class IIA bacteriocin can be, without limitation, pediocin (also referred to as the PedA polypeptide), lactoccin A and horedicin A.

In an embodiment, pediocin has the amino acid sequence of SEQ ID NO: 20 (including its native signal sequence), is a variant of the amino acid sequence of SEQ ID NO: 20 (retaining, at least in part, the biological activity of pediocin) or is a fragment of the amino acid sequence of SEQ ID NO: 20 (retaining, at least in part, the biological activity of pediocin). In an embodiment, the first recombinant LAB cell can comprise a (native or heterologous) nucleic acid molecule having the nucleic acid sequence of SEQ ID NO: 72, 73 or a degenerate sequence encoding SEQ ID NO: 20. In an embodiment, pediocin has the amino acid sequence of SEQ ID NO: 21 (excluding its native signal sequence), is a variant of the amino acid sequence of SEQ ID NO: 21 (retaining, at least in part, the biological activity of pediocin) or is a fragment of the amino acid sequence of SEQ ID NO: 21 (retaining, at least in part, the biological activity of pediocin). In an embodiment, pediocin has the amino acid sequence of SEQ ID NO: 51 (including its native signal sequence), is a variant of the amino acid sequence of SEQ ID NO: 51 (retaining, at least in part, the biological activity of pediocin) or is a fragment of the amino acid sequence of SEQ ID NO: 51 (retaining, at least in part, the biological activity of pediocin). In an embodiment, the first recombinant LAB cell can comprise a (native or heterologous) nucleic acid molecule having the nucleic acid sequence of SEQ ID NO: 141, 142 or a degenerate sequence encoding SEQ ID NO: 51. In an embodiment, pediocin has the amino acid sequence of SEQ ID NO: 52 (excluding its native signal sequence), is a variant of the amino acid sequence of SEQ ID NO: 52 (retaining, at least in part, the biological activity of pediocin) or is a fragment of the amino acid sequence of SEQ ID NO: 52 (retaining, at least in part, the biological activity of pediocin). In an embodiment, pediocin has the amino acid sequence of SEQ ID NO: 75 (including an heterologous signal sequence), is a variant of the amino acid sequence of SEQ ID NO: 75 (retaining, at least in part, the biological activity of pediocin) or is a fragment of the amino acid sequence of SEQ ID NO: 75 (retaining, at least in part, the biological activity of pediocin). In an embodiment, the first recombinant LAB cell can comprise a (native or heterologous) nucleic acid molecule having the nucleic acid sequence of SEQ ID NO: 74 or a degenerate sequence encoding SEQ ID NO: 75. In an embodiment, pediocin has the amino acid sequence of SEQ ID NO: 144 (including an heterologous signal sequence), is a variant of the amino acid sequence of SEQ ID NO: 144 (retaining, at least in part, the biological activity of pediocin) or is a fragment of the amino acid sequence of SEQ ID NO: 144 (retaining, at least in part, the biological activity of pediocin). In an embodiment, the first recombinant LAB cell can comprise a (native or heterologous) nucleic acid molecule having the nucleic acid sequence of SEQ ID NO: 143 or a degenerate sequence encoding SEQ ID NO: 144.

In embodiments in which the first recombinant LAB cell produces pediocin as the bacteriocin, the first recombinant LAB cell can possess the machinery for making and regulating pediocin production or can be genetically engineered to express the machinery for making and regulating pediocin production. One of the polypeptide involved in the production and regulation of pediocin production is PedC, an ABC transporter accessory factor for pediocin. In an embodiment, PedC has the amino acid sequence of SEQ ID NO: 146, is a variant of the amino acid sequence of SEQ ID NO: 146 (having, in the presence of PedD, accessory pediocin transporter activity) or is a fragment of the amino acid sequence of SEQ ID NO: 146 (having, in the presence of PedD, accessory pediocin transporter activity). In an embodiment, the first recombinant LAB cell can comprise a (native or heterologous) nucleic acid molecule having the nucleic acid sequence of SEQ ID NO: 147, 148 or a degenerate sequence encoding SEQ ID NO: 146. Another polypeptide involved in the production and regulation of pediocin production is PedD, a pediocin transporter. In an embodiment, PedD has the amino acid sequence of SEQ ID NO: 149, is a variant of the amino acid sequence of SEQ ID NO: 149 (having pediocin transporter activity) or is a fragment of the amino acid sequence of SEQ ID NO: 149 (having pediocin transporter activity). In an embodiment, the first recombinant LAB cell can comprise a (native or heterologous) nucleic acid molecule having the nucleic acid sequence of SEQ ID NO: 150, 151 or a degenerate sequence encoding SEQ ID NO: 149.

In embodiments in which the first recombinant LAB cell produces pediocin as the bacteriocin, the first recombinant LAB cell can possess immunity against pediocin or can be genetically engineered to gain immunity against pediocin. A polypeptide known to confer immunity or resistance against pediocin is PedB. In an embodiment, PedB has the amino acid sequence of SEQ ID NO: 22 (as well as functional variants and fragments thereof retaining at least on part their ability to confer immunity against pediocin). In an embodiment, the first recombinant LAB cell can comprise a (native or heterologous) nucleic acid molecule having the nucleic acid sequence of SEQ ID NO: 76, 77 or 78 or a degenerate sequence encoding SEQ ID NO: 22. As such, the first recombinant LAB cell can express PedB or be genetically engineered to express PedB. In some embodiments, the second heterologous nucleic acid molecule can further encode PedB (which can be present on the same nucleic acid molecule encoding pediocin or a distinct one).

In an embodiment, lactoccin A has the amino acid sequence of SEQ ID NO: 40 (including its native signal sequence), is a variant of the amino acid sequence of SEQ ID NO: 40 (retaining, at least in part, the biological activity of lactoccin A) or is a fragment of the amino acid sequence of SEQ ID NO: 40 (retaining, at least in part, the biological activity of lactoccin A). In an embodiment, the first recombinant LAB cell can comprise a (native or heterologous) nucleic acid molecule having the nucleic acid sequence of SEQ ID NO: 121 or a degenerate sequence encoding SEQ ID NO: 40. In an embodiment, lactoccin A has the amino acid sequence of SEQ ID NO: 41 (excluding its native signal sequence), is a variant of the amino acid sequence of SEQ ID NO: 41 (retaining, at least in part, the biological activity of lactoccin A) or is a fragment of the amino acid sequence of SEQ ID NO: 41 (retaining, at least in part, the biological activity of lactoccin A).

In embodiments in which the first recombinant LAB cell produces lactoccin A as the bacteriocin, the first recombinant LAB cell can possess the machinery for making and regulating lactoccin A production or can be genetically engineered to express the machinery for making and regulating lactoccin A production. Polypeptides involved in the production and regulation of lactoccin A production include LcmA (which is involved in the export and the processing of lactoccin A) and LceA (which is an ATP-binding protein). In an embodiment, LcmA has the amino acid sequence of SEQ ID NO: 43, is a variant of the amino acid sequence of SEQ ID NO: 43 (having lactoccin A processing and transporter activity) or is a fragment of the amino acid sequence of SEQ ID NO: 43 (having lactoccin A processing and transporter activity). In an embodiment, the first recombinant LAB cell can comprise a (native or heterologous) nucleic acid molecule having the nucleic acid sequence of SEQ ID NO: 124 or a degenerate sequence encoding SEQ ID NO: 43. In an embodiment, LceA has the amino acid sequence of SEQ ID NO: 44, is a variant of the amino acid sequence of SEQ ID NO: 4 (having ATP-binding activity) or is a fragment of the amino acid sequence of SEQ ID NO: 44 (having ATP-binding activity). In an embodiment, the first recombinant LAB cell can comprise a (native or heterologous) nucleic acid molecule having the nucleic acid sequence of SEQ ID NO: 125 or a degenerate sequence encoding SEQ ID NO: 44.

In embodiments in which the first recombinant LAB cell produces lactoccin A as the bacteriocin, the first recombinant LAB cell can possess immunity against lactoccin A or can be genetically engineered to gain immunity against lactoccin A. A polypeptide known to confer immunity or resistance against pediocin is LciA. In an embodiment, LciA has the amino acid sequence of SEQ ID NO: 42 (as well as functional variants and fragments thereof retaining at least on part their ability to confer immunity against lactoccin A). In an embodiment, the first recombinant LAB cell can comprise a (native or heterologous) nucleic acid molecule having the nucleic acid sequence of SEQ ID NO: 122, 123 or a degenerate sequence encoding SEQ ID NO: 42. As such, the first recombinant LAB cell can express LciA or be genetically engineered to express LciA. In some embodiments, the second heterologous nucleic acid molecule can further encode LciA (which can be present on the same nucleic acid molecule encoding lactoccin A or a distinct one).

In an embodiment, horediocin A has the amino acid sequence of SEQ ID NO: 45 (including its native signal sequence), is a variant of the amino acid sequence of SEQ ID NO: 45 (retaining, at least in part, the biological activity of horediocin A) or is a fragment of the amino acid sequence of SEQ ID NO: 45 (retaining, at least in part, the biological activity of horediocin A). In an embodiment, the first recombinant LAB cell can comprise a (native or heterologous) nucleic acid molecule having the nucleic acid sequence of SEQ ID NO: 126, 127 or a degenerate sequence encoding SEQ ID NO: 45. In an embodiment, horediocin A has the amino acid sequence of SEQ ID NO: 46 (excluding its native signal sequence), is a variant of the amino acid sequence of SEQ ID NO: 46 (retaining, at least in part, the biological activity of horediocin A) or is a fragment of the amino acid sequence of SEQ ID NO: 46 (retaining, at least in part, the biological activity of horediocin A). In an embodiment, horediocin A has the amino acid sequence of SEQ ID NO: 129 (including a pediocin signal sequence), is a variant of the amino acid sequence of SEQ ID NO: 129 (retaining, at least in part, the biological activity of horediocin A) or is a fragment of the amino acid sequence of SEQ ID NO: 129 (retaining, at least in part, the biological activity of horediocin A). In an embodiment, the first recombinant LAB cell can comprise a (native or heterologous) nucleic acid molecule having the nucleic acid sequence of SEQ ID NO: 128 or a degenerate sequence encoding SEQ ID NO: 129. In an embodiment, horediocin A has the amino acid sequence of SEQ ID NO: 131 (including a heterologous signal sequence sequence), is a variant of the amino acid sequence of SEQ ID NO: 131 (retaining, at least in part, the biological activity of horediocin A) or is a fragment of the amino acid sequence of SEQ ID NO: 131 (retaining, at least in part, the biological activity of horediocin A). In an embodiment, the first recombinant LAB cell can comprise a (native or heterologous) nucleic acid molecule having the nucleic acid sequence of SEQ ID NO: 130 or a degenerate sequence encoding SEQ ID NO: 131.

In embodiments in which the first recombinant LAB cell produces horediocin A as the bacteriocin, the first recombinant LAB cell can possess the machinery for making and regulating horediocin A production or can be genetically engineered to express the machinery for making and regulating horediocin A production. Polypeptides involved in the production and regulation of horediocin A production include HdrM (which is involved in the processing of horediocin A), HdrD (which is involved in the cleavage and the transport of horediocin A) and HdrC (which is involved in the transport of horediocin A). In an embodiment, HdrM has the amino acid sequence of SEQ ID NO: 48, is a variant of the amino acid sequence of SEQ ID NO: 48 (having horediocin A disulfide isomerase activity) or is a fragment of the amino acid sequence of SEQ ID NO: 48 (having horediocin A disulfide isomerase activity). In an embodiment, the first recombinant LAB cell can comprise a (native or heterologous) nucleic acid molecule having the nucleic acid sequence of SEQ ID NO: 135, 136 or a degenerate sequence encoding SEQ ID NO: 48. In an embodiment, HdrD has the amino acid sequence of SEQ ID NO: 49, is a variant of the amino acid sequence of SEQ ID NO: 49 (having horediocin A cleavage and transporter activity) or is a fragment of the amino acid sequence of SEQ ID NO: 49 (having horediocin A cleavage and transporter activity). In an embodiment, the first recombinant LAB cell can comprise a (native or heterologous) nucleic acid molecule having the nucleic acid sequence of SEQ ID NO: 137, 138 or a degenerate sequence encoding SEQ ID NO: 49. In an embodiment, HdrC has the amino acid sequence of SEQ ID NO: 50, is a variant of the amino acid sequence of SEQ ID NO: 50 (having, in the presence of HdrD, accessory horediocin A transporter activity) or is a fragment of the amino acid sequence of SEQ ID NO: 50 (having, in the presence of HdrD, accessory horediocin A transporter activity). In an embodiment, the first recombinant LAB cell can comprise a (native or heterologous) nucleic acid molecule having the nucleic acid sequence of SEQ ID NO: 139, 140 or a degenerate sequence encoding SEQ ID NO: 50.

In embodiments in which the first recombinant LAB cell produces horediocin A as the bacteriocin, the first recombinant LAB cell can possess immunity against horediocin A or can be genetically engineered to gain immunity against horediocin A. A polypeptide known to confer immunity or resistance against pediocin is HdrI. In an embodiment, HdrI has the amino acid sequence of SEQ ID NO: 47 (as well as functional variants and fragments thereof retaining at least on part their ability to confer immunity against horediocin A). In an embodiment, the first recombinant LAB cell can comprise a (native or heterologous) nucleic acid molecule having the nucleic acid sequence of SEQ ID NO: 132, 133, 134 or a degenerate sequence encoding SEQ ID NO: 47. As such, the first recombinant LAB cell can express HdrI or be genetically engineered to express HdrI. In some embodiments, the second heterologous nucleic acid molecule can further encode HdrI (which can be present on the same nucleic acid molecule encoding horediocin A or a distinct one).

In a specific example, the Gram-positive class IIB bacteriocin can be, without limitation, bronchocin. Brochocin is an heterodimer comprising a BrcA polypeptide and a BrcB polypeptide. In an embodiment, BrcA has the amino acid sequence of SEQ ID NO: 23 (including the pediocin signal sequence), is a variant of the amino acid sequence of SEQ ID NO: 23 (retaining, at least in part, the biological activity of bronchocin when forming an heterodimer with BrcB) or is a fragment of the amino acid sequence of SEQ ID NO: 23 (retaining, at least in part, the biological activity of bronchocin when forming an heterodimer with BrcB). In an embodiment, the first recombinant LAB cell can comprise a (native or heterologous) nucleic acid molecule having the nucleic acid sequence of SEQ ID NO: 79 or 80 or a degenerate sequence encoding SEQ ID NO: 23. In an embodiment, BrcA has the amino acid sequence of SEQ ID NO: 24 (excluding its native signal sequence), is a variant of the amino acid sequence of SEQ ID NO: 24 (retaining, at least in part, the biological activity of bronchocin when forming an heterodimer with BrcB) or is a fragment of the amino acid sequence of SEQ ID NO: 24 (retaining, at least in part, the biological activity of bronchocin when forming an heterodimer with BrcB). In an embodiment, BrcA has the amino acid sequence of SEQ ID NO: 82 (including a pediocin signal sequence), is a variant of the amino acid sequence of SEQ ID NO: 82 (retaining, at least in part, the biological activity of bronchocin when forming an heterodimer with BrcB) or is a fragment of the amino acid sequence of SEQ ID NO: 82 (retaining, at least in part, the biological activity of bronchocin when forming an heterodimer with BrcB). In an embodiment, the first recombinant LAB cell can comprise a (native or heterologous) nucleic acid molecule having the nucleic acid sequence of SEQ ID NO: 81 or a degenerate sequence encoding SEQ ID NO: 82. In an embodiment, BrcA has the amino acid sequence of SEQ ID NO: 84 (including a heterologous signal sequence), is a variant of the amino acid sequence of SEQ ID NO: 84 (retaining, at least in part, the biological activity of bronchocin when forming an heterodimer with BrcB) or is a fragment of the amino acid sequence of SEQ ID NO: 84 (retaining, at least in part, the biological activity of bronchocin when forming an heterodimer with BrcB). In an embodiment, the first recombinant LAB cell can comprise a (native or heterologous) nucleic acid molecule having the nucleic acid sequence of SEQ ID NO: 83 or a degenerate sequence encoding SEQ ID NO: 84.

In an embodiment, BrcB has the amino acid sequence of SEQ ID NO: 25 (including the pediocin signal sequence), is a variant of the amino acid sequence of SEQ ID NO: 25 (retaining, at least in part, the biological activity of bronchocin when forming an heterodimer with BrcA) or is a fragment of the amino acid sequence of SEQ ID NO: 25 (retaining, at least in part, the biological activity of bronchocin when forming an heterodimer with BrcA). In an embodiment, the first recombinant LAB cell can comprise a (native or heterologous) nucleic acid molecule having the nucleic acid sequence of SEQ ID NO: 85 or 86 or a degenerate sequence encoding SEQ ID NO: 25. In an embodiment, BrcB has the amino acid sequence of SEQ ID NO: 26 (excluding its native signal sequence), is a variant of the amino acid sequence of SEQ ID NO: 26 (retaining, at least in part, the biological activity of bronchocin when forming an heterodimer with BrcA) or is a fragment of the amino acid sequence of SEQ ID NO: 26 (retaining, at least in part, the biological activity of bronchocin when forming an heterodimer with BrcA). In an embodiment, BrcB has the amino acid sequence of SEQ ID NO: 88 (including the pediocin signal sequence), is a variant of the amino acid sequence of SEQ ID NO: 88 (retaining, at least in part, the biological activity of bronchocin when forming an heterodimer with BrcA) or is a fragment of the amino acid sequence of SEQ ID NO: 88 (retaining, at least in part, the biological activity of bronchocin when forming an heterodimer with BrcA). In an embodiment, the first recombinant LAB cell can comprise a (native or heterologous) nucleic acid molecule having the nucleic acid sequence of SEQ ID NO: 87 or a degenerate sequence encoding SEQ ID NO: 88. In an embodiment, BrcB has the amino acid sequence of SEQ ID NO: 90 (including a heterologous signal sequence), is a variant of the amino acid sequence of SEQ ID NO: 90 (retaining, at least in part, the biological activity of bronchocin when forming an heterodimer with BrcA) or is a fragment of the amino acid sequence of SEQ ID NO: 90 (retaining, at least in part, the biological activity of bronchocin when forming an heterodimer with BrcA). In an embodiment, the first recombinant LAB cell can comprise a (native or heterologous) nucleic acid molecule having the nucleic acid sequence of SEQ ID NO: 89 or a degenerate sequence encoding SEQ ID NO: 90.

In embodiments in which the first recombinant LAB cell produces brochocin as the bacteriocin, the first recombinant LAB cell can possess the machinery for making or regulating the production of brochocin or can be genetically engineered to express the machinery for making or regulating the production of brochocin.

In embodiments in which the first recombinant LAB cell produces brochocin as the bacteriocin, the first recombinant LAB cell can possess immunity against the brochocin or can be genetically engineered to gain immunity against brochocin. A polypeptide known to confer immunity or resistance against pediocin is BrcI. In an embodiment, BrcI has the amino acid sequence of SEQ ID NO: 27 (as well as functional variants and fragments thereof retaining at least on part their ability to confer immunity against brochocin). In an embodiment, the first recombinant LAB cell can comprise a (native or heterologous) nucleic acid molecule having the nucleic acid sequence of SEQ ID NO: 91, 92 or 93 or a degenerate sequence encoding SEQ ID NO: 27. As such, the first recombinant LAB cell can express BrcI or be genetically engineered to express BrcI. In some embodiments, the second heterologous nucleic acid molecule can further encode BrcI (which can be present on the same nucleic acid molecule encoding BrcA/BrcB or a distinct one).

In a specific example, the Class IIA bacteriocin can be plantaricin 423. In an embodiment, plantaricin 423 has the amino acid sequence of SEQ ID NO: 35 (including its native signal sequence), is a variant of the amino acid sequence of SEQ ID NO: 35 (retaining, at least in part, the biological activity of plantaricin 423) or is a fragment of the amino acid sequence of SEQ ID NO: 35 (retaining, at least in part, the biological activity of plantaricin 423). In an embodiment, the first recombinant LAB cell can comprise a (native or heterologous) nucleic acid molecule having the nucleic acid sequence of SEQ ID NO: 108, 109 or a degenerate sequence encoding SEQ ID NO: 35. In an embodiment, plantaricyclin A has the amino acid sequence of SEQ ID NO: 36 (excluding its native signal sequence), is a variant of the amino acid sequence of SEQ ID NO: 36 (retaining, at least in part, the biological activity of plantaricyclin A) or is a fragment of the amino acid sequence of SEQ ID NO: 36 (retaining, at least in part, the biological activity of plantaricyclin A). In such embodiment, the first recombinant LAB cell includes plantaricyclin A which can be expressed from the second heterologous nucleic acid molecule. In an embodiment, plantaricin 423 has the amino acid sequence of SEQ ID NO: 111 (including a pediocin signal sequence), is a variant of the amino acid sequence of SEQ ID NO: 111 (retaining, at least in part, the biological activity of plantaricin 423) or is a fragment of the amino acid sequence of SEQ ID NO: 111 (retaining, at least in part, the biological activity of plantaricin 423). In an embodiment, the first recombinant LAB cell can comprise a (native or heterologous) nucleic acid molecule having the nucleic acid sequence of SEQ ID NO: 110 or a degenerate sequence encoding SEQ ID NO: 111. In an embodiment, plantaricin 423 has the amino acid sequence of SEQ ID NO: 113 (including a heterologous signal sequence signal sequence), is a variant of the amino acid sequence of SEQ ID NO: 113 (retaining, at least in part, the biological activity of plantaricin 423) or is a fragment of the amino acid sequence of SEQ ID NO: 113 (retaining, at least in part, the biological activity of plantaricin 423). In an embodiment, the first recombinant LAB cell can comprise a (native or heterologous) nucleic acid molecule having the nucleic acid sequence of SEQ ID NO: 112 or a degenerate sequence encoding SEQ ID NO: 113.

In embodiments in which the first recombinant LAB cell produces plantaricin 423 as the bacteriocin, the first recombinant LAB cell can possess the machinery for making or for regulating the production of plantaricin 423 or can be genetically engineered to express the machinery for making or for regulating the production of plantaricin 423. Polypeptides involved in the machinery for making plantaricyclin A include, without limitations, PlaC (which is plantaricin 423 accessory protein) and PlaD (which is an ABC plantaricin 423 transporter). As such, the second heterologous nucleic acid molecule can further encode PlaC and/or PlaD (which can be on the same or on a different nucleic acid molecule than the one encoding plantaricin 423). In an embodiment, PlaC has the amino acid sequence of SEQ ID NO: 38 (as well as functional variants and fragments thereof). In an embodiment, the first recombinant LAB cell can comprise a (native or heterologous) nucleic acid molecule having the nucleic acid sequence of SEQ ID NO: 117, 118 or a degenerate sequence encoding SEQ ID NO: 38. In an embodiment, PlaD has the amino acid sequence of SEQ ID NO: 39 (as well as functional variants and fragments thereof retaining, at least in part, their ability to transport plantaricin 423). In an embodiment, the first recombinant LAB cell can comprise a (native or heterologous) nucleic acid molecule having the nucleic acid sequence of SEQ ID NO: 119, 120 or a degenerate sequence encoding SEQ ID NO: 39.

In embodiments in which the first recombinant LAB cell produces plantaricin 423 as the bacteriocin, the first recombinant LAB cell can possess immunity against plantaricin 423 or can be genetically engineered to gain immunity against plantaricin 423. A polypeptide known to confer immunity or resistance against plantaricyclin A is PlaB. In an embodiment, PlaB has the amino acid sequence of SEQ ID NO: 37 (as well as functional variants and fragments thereof retaining at least on part their ability to confer immunity against plantaricin 423). In an embodiment, the first recombinant LAB cell can comprise a (native or heterologous) nucleic acid molecule having the nucleic acid sequence of SEQ ID NO: 114, 115, 116 or a degenerate sequence encoding SEQ ID NO: 37. As such, the second heterologous nucleic acid molecule can further encode PlaB (which can be on the same or on a different nucleic acid molecule than the one encoding plantaricin 423, PlaC and/or PlaD).

In embodiments in which the at least one bacteriocin comprises a Class IIA or a Class IIB bacteriocin, it is possible to engineer the first recombinant LAB cell to use its native secretory system to export the bacteriocin outside the cell. In such embodiments, it may be useful to include a heterologous signal sequence (in frame with the open reading frame encoding bacteriocin) which is recognized by the native secretory system of the first recombinant LAB cell. In one embodiment, this heterologous signal sequence can be the usp45TM8 signal sequence. In some specific embodiments, the usp45TM8 signal sequence can have the amino acid sequence of SEQ ID NO: 145, be a variant of the amino acid sequence of SEQ ID NO: 145 (having signal sequence activity) or be a fragment of the amino acid sequence of SEQ ID NO: 145 (having signal sequence activity). In a further embodiment, the second nucleic acid molecule can comprise the nucleic acid sequence of SEQ ID NO: 152 or a degenerate sequence encoding SEQ ID NO: 145.

In a specific example, the Gram-positive cyclic bacteriocin can be gasserin. In an embodiment, gasserin has the amino acid sequence of SEQ ID NO: 15 (including its native signal sequence), is a variant of the amino acid sequence of SEQ ID NO: 15 (retaining, at least in part, the biological activity of gasserin) or is a fragment of the amino acid sequence of SEQ ID NO: 15 (retaining, at least in part, the biological activity of gasserin). In an embodiment, the first recombinant LAB cell can comprise a (native or heterologous) nucleic acid molecule having the nucleic acid sequence of SEQ ID NO: 63, 64 or a degenerate sequence encoding SEQ ID NO: 15. In an embodiment, gasserin has the amino acid sequence of SEQ ID NO: 16 (excluding its native signal sequence), is a variant of the amino acid sequence of SEQ ID NO: 16 (retaining, at least in part, the biological activity of gasserin) or is a fragment of the amino acid sequence of SEQ ID NO: 16 (retaining, at least in part, the biological activity of gasserin). In such embodiment, the first recombinant LAB cell includes gasserin which can be expressed from the second heterologous nucleic acid molecule.

In embodiments in which the first recombinant LAB cell produces gasserin as the bacteriocin, the first recombinant LAB cell can possess the machinery for making or for regulating the production of gasserin or can be genetically engineered to express the machinery for making or for regulating the production of gasserin. Polypeptides involved in the machinery for making gasserin include, without limitations, GaaT (which is a gasserin transporter) and GaaE (which is a gasserin permease). As such, the second heterologous nucleic acid molecule can further encode GaaT and/or GaaE (which can be on the same or on a different nucleic acid molecule than the one encoding gasserin). In an embodiment, GaaT has the amino acid sequence of SEQ ID NO: 18 (as well as functional variants and fragments thereof retaining, at least in part, their ability to transport gasserin). In an embodiment, the first recombinant LAB cell can comprise a (native or heterologous) nucleic acid molecule having the nucleic acid sequence of SEQ ID NO: 68, 69 or a degenerate sequence encoding SEQ ID NO: 18. In an embodiment, GaaE has the amino acid sequence of SEQ ID NO: 19 (as well as functional variants and fragments thereof retaining, at least in part, their ability to transport gasserin). In an embodiment, the first recombinant LAB cell can comprise a (native or heterologous) nucleic acid molecule having the nucleic acid sequence of SEQ ID NO: 70, 71 or a degenerate sequence encoding SEQ ID NO: 19.

In embodiments in which the first recombinant LAB cell produces gasserin as the bacteriocin, the first recombinant LAB cell can possess immunity against gasserin or can be genetically engineered to gain immunity against gasserin. A polypeptide known to confer immunity or resistance against gasserin is GaaI. In an embodiment, GaaI has the amino acid sequence of SEQ ID NO: 17 (as well as functional variants and fragments thereof retaining at least on part their ability to confer immunity against gasserin). In an embodiment, the first recombinant LAB cell can comprise a (native or heterologous) nucleic acid molecule having the nucleic acid sequence of SEQ ID NO: 65, 66, 67 or a degenerate sequence encoding SEQ ID NO: 17. As such, the second heterologous nucleic acid molecule can further encode GaaI (which can be on the same or on a different nucleic acid molecule than the one encoding gasserin, GaaT or GaaE).

In a specific example, the Gram-positive cyclic bacteriocin can be gasserin. In an embodiment, gasserin has the amino acid sequence of SEQ ID NO: 15 (including its native signal sequence), is a variant of the amino acid sequence of SEQ ID NO: 15 (retaining, at least in part, the biological activity of gasserin) or is a fragment of the amino acid sequence of SEQ ID NO: 15 (retaining, at least in part, the biological activity of gasserin). In an embodiment, the first recombinant LAB cell can comprise a (native or heterologous) nucleic acid molecule having the nucleic acid sequence of SEQ ID NO: 63, 64 or a degenerate sequence encoding SEQ ID NO: 15. In an embodiment, gasserin has the amino acid sequence of SEQ ID NO: 16 (excluding its native signal sequence), is a variant of the amino acid sequence of SEQ ID NO: 16 (retaining, at least in part, the biological activity of gasserin) or is a fragment of the amino acid sequence of SEQ ID NO: 16 (retaining, at least in part, the biological activity of gasserin). In such embodiment, the first recombinant LAB cell includes gasserin which can be expressed from the second heterologous nucleic acid molecule.

In a specific example, the Gram-positive cyclic bacteriocin can be plantaricyclin A. In an embodiment, plantaricyclin A has the amino acid sequence of SEQ ID NO: 28 (including its native signal sequence), is a variant of the amino acid sequence of SEQ ID NO: 28 (retaining, at least in part, the biological activity of plantaricyclin A) or is a fragment of the amino acid sequence of SEQ ID NO: 28 (retaining, at least in part, the biological activity of plantaricyclin A). In an embodiment, the first recombinant LAB cell can comprise a (native or heterologous) nucleic acid molecule having the nucleic acid sequence of SEQ ID NO: 94, 95 or a degenerate sequence encoding SEQ ID NO: 28. In an embodiment, plantaricyclin A has the amino acid sequence of SEQ ID NO: 29 (excluding its native signal sequence), is a variant of the amino acid sequence of SEQ ID NO: 29 (retaining, at least in part, the biological activity of plantaricyclin A) or is a fragment of the amino acid sequence of SEQ ID NO: 29 (retaining, at least in part, the biological activity of plantaricyclin A). In such embodiment, the first recombinant LAB cell includes plantaricyclin A which can be expressed from the second heterologous nucleic acid molecule.

In embodiments in which the first recombinant LAB cell produces plantaricyclin A as the bacteriocin, the first recombinant LAB cell can possess the machinery for making or for regulating the production of plantaricyclin A or can be genetically engineered to express the machinery for making or for regulating the production of plantaricyclin A. Polypeptides involved in the machinery for making plantaricyclin A include, without limitations, PlcT (which is an ATP-binding protein), PlcE (which is a plantaricyclin A transporter) and PlcB (which is a plantaricyclin A related protein). As such, the second heterologous nucleic acid molecule can further encode PlcT, PlcE and/or PlcB (which can be on the same or on a different nucleic acid molecule than the one encoding plantaricyclin A). In an embodiment, PlcT has the amino acid sequence of SEQ ID NO: 32 (as well as functional variants and fragments thereof retaining, at least in part, their ability to bind to ATP). In an embodiment, the first recombinant LAB cell can comprise a (native or heterologous) nucleic acid molecule having the nucleic acid sequence of SEQ ID NO: 102, 103 or a degenerate sequence encoding SEQ ID NO: 32. In an embodiment, PlcE has the amino acid sequence of SEQ ID NO: 33 (as well as functional variants and fragments thereof retaining, at least in part, their ability to transport plantaricyclin A). In an embodiment, the first recombinant LAB cell can comprise a (native or heterologous) nucleic acid molecule having the nucleic acid sequence of SEQ ID NO: 104, 105 or a degenerate sequence encoding SEQ ID NO: 33. In an embodiment, PlcB has the amino acid sequence of SEQ ID NO: 34 (as well as functional variants and fragments thereof). In an embodiment, the first recombinant LAB cell can comprise a (native or heterologous) nucleic acid molecule having the nucleic acid sequence of SEQ ID NO: 106, 107 or a degenerate sequence encoding SEQ ID NO: 34.

In embodiments in which the first recombinant LAB cell produces plantaricyclin A as the bacteriocin, the first recombinant LAB cell can possess immunity against plantaricyclin A or can be genetically engineered to gain immunity against plantaricyclin A. Polypeptides known to confer immunity or resistance against plantaricyclin A are PlcD and PlcI. In an embodiment, PlcD has the amino acid sequence of SEQ ID NO: 30 (as well as functional variants and fragments thereof retaining at least on part their ability to confer immunity, in the presence of PlcI, against plantaricyclin A). In an embodiment, the first recombinant LAB cell can comprise a (native or heterologous) nucleic acid molecule having the nucleic acid sequence of SEQ ID NO: 96, 97, 98 or a degenerate sequence encoding SEQ ID NO: 30. In an embodiment, PlcI has the amino acid sequence of SEQ ID NO: 31 (as well as functional variants and fragments thereof retaining at least on part their ability to confer immunity, in the presence of PlcD, against plantaricyclin A). In an embodiment, the first recombinant LAB cell can comprise a (native or heterologous) nucleic acid molecule having the nucleic acid sequence of SEQ ID NO: 99, 100, 101 or a degenerate sequence encoding SEQ ID NO: 30. As such, the second heterologous nucleic acid molecule can further encode PlcD and/or PlcI (which can be on the same or on a different nucleic acid molecule than the one encoding plantaricyclin A, PlcT, PlcE and/or PlcB).

In some embodiments, a population of first recombinant LAB cells is used in the co-culture. The population of first recombinant LAB cells can express the same or different bacteriocins (or combinations of bacteriocins).

Second Recombinant Lactic Acid Bacteria (LAB) Cell

In the context of the present disclosure, the second bacterial cell of the co-culture is a lactic acid bacterium (LAB). The second recombinant LAB cells can be provided as a pure culture during the fermentation or as a blend with the first recombinant LAB cells. As it is known in the art, LAB are a group of Gram-positive bacteria, non-respiring non-spore-forming, cocci or rods, which produce lactic acid as the major end product of the fermentation of carbohydrates. Bacterial genus of LAB include, but are not limited to, *Lactobacillus, Leuconostoc, Pediococcus, Lactococcus, Streptococcus, Aerococcus, Carnobacterium, Enterococcus, Oenococcus, Sporolactobacillus, Tetragenococcus, Vagococcus,* and *Weissella*. Bacterial species of LAB include, but are not limited to, *Lactococcus lactis, Lactococcus garviae, Lactococcus raffinolactis, Lactococcus plantarum, Oenococcus oeni, Pediococcus pentosaceus, Pediococcus acidilactici, Carnococcus allantoicus, Carnobacterium gallinarum, Vagococcus fessus, Streptococcus thermophilus, Enterococcus phoeniculicola, Enterococcus plantarum, Enterococcus raffinosus, Enterococcus avium, Enterococcus pallens Enterococcus hermanniensis, Enterococcus faecalis,* and *Enterococcus faecium*. In an embodiment, the LAB is a *Lactobacillus* and, in some additional embodiment, the *Lactobacillus* species is *L. acetotolerans, L. acidifarinae, L. acidipiscis, L. acidophilus, L. agilis, L. algidus, L. alimentarius, L. amylolyticus, L. amylophilus, L. amylotrophicus, L. amylovorus, L. animalis, L. antri, L. apodemi, L. aviarius, L. bifermentans, L. brevis, L. buchneri, L. camelliae, L. casei, L. catenaformis, L. ceti, L. coleohominis, L. collinoides, L. composti, L. concavus, L. coryniformis, L. crispatus, L. crustorum, L. curvatus, L. delbrueckii* (including *L. delbrueckii* subsp. *bulgaricus, L. delbrueckii* subsp. *delbrueckii, L. delbrueckii* subsp. *lactis*), *L. dextrinicus, L. dioliborans, L. equi, L. equigenerosi, L. farraginis, L. farciminis, L. fermentum, L. fornicalis, L. fructivorans, L. frumenti, L. fuchuensis, L. gallinarum, L. gasseri, L. gastricus, L. ghanensis, L. graminis, L. ammesii, L. hamsteri, L. harbinensis, L. hayakitensis, L. helveticus, L. hilgardii, L. omohiochii, L. iners, L. ingluviei, L. intestinalis, L. jensenii, L. johnsonii, L. kalixensis, L. efiranofaciens, L. kefiri, L. kimchii, L. kitasatonis, L. kunkeei, L. leichmannii, L. lindneri, L. alefermentans, L. mali, L. manihotivorans, L. mindensis, L. mucosae, L. murinus, L. nagelii, L. namurensis, L.*

*nantensis, L. oligofermentans, L. oris, L. panis, L. pantheris, L. parabrevis, L. parabuchneri, L. paracasei, L. paracollinoides, L. parafarraginis, L. parakefiri, L. aralimentarius, L. paraplantarum, L. pentosus, L. perolens, L. plantarum, L. pontis, L. protectus, L. psittaci, L. rennini, L. reuteri, L. rhamnosus, L. rimae, L. rogosae, L. rossiae, L. ruminis, L. saerimneri, L. sakei, L. salivarius, L. sanfranciscensis, L. satsumensis, L. secaliphilus, L. sharpeae, L. siliginis, L. spicheri, L. suebicus, L. thailandensis, L. ultunensis, L. vaccinostercus, L. vaginalis, L. versmoldensis, L. vini, L. vitulinus, L. zeae* or *L. zymae*. In some embodiments, the second recombinant LAB cell is *L. paracasei* and in some embodiments, *L. paracasei* 12A. For example, the second recombinant LAB cell can be one of those described in WO 2018/013791.

The second recombinant LAB cell is a recombinant LAB cell because it comprises a third heterologous nucleic acid molecule encoding a polypeptide for converting, at least in part, a biomass (such as corn for example) into a fermented product. In some embodiments, more than one third heterologous nucleic acid molecules can be provided to encode a plurality of polypeptides for converting, at least in part, a biomass (such as corn for example) into a fermented product. In such embodiments, each third heterologous nucleic acid molecules can include one or more coding sequences corresponding to one or more polypeptides. In another embodiment, a single third heterologous nucleic acid molecule can encode the one or more polypeptides.

The second recombinant LAB cell is a genetically modified LAB cell which includes one or more heterologous nucleic acid molecule (referred to as the one or more third heterologous nucleic acid molecule) encoding one or more polypeptide for converting, at least in part, a biomass into a fermentation product. In an embodiment, the one or more third heterologous nucleic acid molecule encodes a pyruvate decarboxylase and/or an alcohol dehydrogenase. When the second recombinant LAB cell has an intrinsic ability of expressing a pyruvate decarboxylase, the third heterologous nucleic acid molecule can encode an heterologous alcohol dehydrogenase. In such embodiment, it is possible that the third heterologous nucleic acid molecule further encodes an heterologous pyruvate decarboxylase or that a further third heterologous nucleic acid molecule is provided and encodes the heterologous pyruvate decarboxylase (to increase the overall pyruvate decarboxylase activity of the second recombinant LAB cell). When the second recombinant LAB cell has an intrinsic ability of expressing an alcohol dehydrogenase, the third heterologous nucleic acid molecule can encode a pyruvate decarboxylase. In such embodiment, it is possible that the third heterologous nucleic acid molecule further encodes an heterologous alcohol dehydrogenase or that a further third heterologous nucleic acid molecule encode the heterologous alcohol dehydrogenase (to increase the overall alcohol dehydrogenase activity of the second recombinant LAB cell). If the second recombinant LAB does not have an intrinsic ability of expressing a pyruvate decarboxylase and an alcohol dehydrogenase, the third heterologous nucleic acid molecule can encode an alcohol dehydrogenase and a pyruvate decarboxylase (on the same or on different molecules). The third heterologous nucleic acid molecule can be integrated in the bacterial genome or be independently replicating from the bacterial genome. The nucleic acid sequences encoding the pyruvate decarboxylase and the alcohol dehydrogenase can be on the same or distinct nucleic acid molecules.

As used herein, the term "pyruvate decarboxylase" refers to an enzyme catalyzing the decarboxylation of pyruvic acid to acetaldehyde and carbon dioxide. In *Zymonas mobilis*, the pyruvate decarboxylase gene is referred to as PDC (Gene ID: 33073732) and could be used in the second recombinant LAB cell of the present disclosure. In some additional embodiments, the pyruvate decarboxylase polypeptide can be from *Lactobacillus florum* (Accession Number WP_009166425.1), *Lactobacillus fructivorans* (Accession Number WP_039145143.1), *Lactobacillus lindneri* (Accession Number WP_065866149.1), *Lactococcus lactis* (Accession Number WP_104141789.1), *Carnobacterium gallinarum* (Accession Number WP_034563038.1), *Enterococcus plantarum* (Accession Number WP_069654378.1), *Clostridium acetobutylicum* (Accession Number NP_149189.1), *Bacillus megaterium* (Accession Number WP_075420723.1) or *Bacillus thuringiensis* (Accession Number WP_052587756.1). In the second recombinant LAB cell of the present disclosure, the pyruvate decarboxylase can have the amino acid of SEQ ID NO: 1, be a variant of SEQ ID NO: 1 (having pyruvate carboxylase activity) or be a fragment of SEQ ID NO: 1 having pyruvate carboxylase activity). In some specific embodiments, the second recombinant LAB cell of the present disclosure can express an heterologous nucleic acid molecule comprising the nucleic acid sequence of SEQ ID NO: 2, 5 or 153, a variant thereof (encoding a polypeptide having pyruvate carboxylase activity) or a fragment thereof (encoding a polypeptide having pyruvate carboxylase activity). In an additional embodiment, the third heterologous nucleic acid comprises a nucleic acid sequence of SEQ ID NO: 2, 5 or 153 or a degenerate sequence encoding SEQ ID NO: 1.

In an embodiment, the second recombinant LAB cell comprises a further genetic modification allowing the expression of an heterologous alcohol dehydrogenase. In some embodiments, the second recombinant LAB cell comprises a further genetic modification allowing the expression of an heterologous pyruvate carboxylase and an heterologous alcohol dehydrogenase. As used herein, the term "alcohol dehydrogenase" refers to an enzyme of the EC 1.1.1.1 class. In some embodiments, the alcohol dehydrogenase is an iron-containing alcohol dehydrogenase. The alcohol dehydrogenase that can be expressed in the bacterial host cell includes, but is not limited to, ADH4 from *Saccharomyces cerevisiae*, ADHB from *Zymonas mobilis*, FUCO from *Escherichia coli*, ADHE from *Escherichia coli*, ADH1 from *Clostridium acetobutylicum*, ADH1 from *Entamoeba nuttalli*, BDHA from *Clostridium acetobutylicum*, BDHB from *Clostridium acetobutylicum*, 4HBD from *Clostridium kluyveri*, DHAT from *Citrobacter freundii* or DHAT from *Klebsiella pneumoniae*. In an embodiment, the alcohol dehydrogenase can be ADHB from *Zymonas mobilis* (Gene ID: AHJ71151.1), *Lactobacillus reuteri* (Accession Number: KRK51011.1), *Lactobacillus* mucosae (Accession Number WP_048345394.1), *Lactobacillus brevis* (Accession Number WP_003553163.1) or *Streptococcus* thermophiles (Accession Number WP_113870363.1). In the second recombinant LAB cell of the present disclosure, the alcohol dehydrogenase can have the amino acid of SEQ ID NO: 3, be a variant of SEQ ID NO: 3 (having alcohol dehydrogenase activity) or a fragment of SEQ ID NO: 3 (having alcohol dehydrogenase activity). In some specific embodiments, the second recombinant LAB cell of the present disclosure can express an heterologous nucleic acid molecule comprising the nucleic acid sequence of SEQ ID NO: 4, 6 or 154, be a variant of the nucleic acid sequence of SEQ ID NO: 4, 6 or 154 (encoding a polypeptide having alcohol dehydrogenase activity) or be a fragment of the nucleic acid sequence of SEQ ID NO: 4, 6 or 154 (encoding a polypeptide having alcohol dehydrogenase activity). In yet another embodiment, the third heterologous nucleic acid molecule comprises comprises a nucleic acid sequence of SEQ ID NO: 4, 6 or 154 or a degenerate sequence encoding SEQ ID NO: 3.

In some embodiments, it may be advantageous to reduce the lactate dehydrogenase activity in the second recombinant LAB cell. In such embodiment, the second recombinant LAB cell can be genetically modified to as to decrease its lactate dehydrogenase activity. As used in the context of the present disclosure, the expression "lactate dehydrogenase" refer to an enzyme of the E.C. 1.1.1.27 class which is capable of catalyzing the conversion of pyruvic acid into lactate. The second recombinant LAB cell can thus have one or more gene coding for a protein having lactate dehydrogenase activity which is inactivated (via partial or total deletion of the gene). In bacteria, the ldh1, ldh2, ldh3 and ldh4 genes encode proteins having lactate dehydrogenase activity. Some bacteria may contain as many as six or more such genes (i.e., ldh5, ldh6, etc.). The enzyme encoded by the ldh3 gene is a a protein having lactate dehydrogenase activity is sometimes referred to as l-hydroxyisocaproic acid dehydrogenase (encoded by the lhic gene). Another enzyme having lactate dehydrogenase activity is d-hydroxyisocaproic acid dehydrogenase (encoded by the dhic gene). In an embodiment, at least one of the ldh1, ldh2, ldh3, ldh4 or dhic genes, their corresponding orthologs and paralogs is inactivated or deleted in the second recombinant LAB cell. In an embodiment, only one of the ldh gene is inactivated or deleted in the second recombinant LAB cell. In another embodiment, at least two of the ldh genes are inactivated or deleted in the second recombinant LAB cell. In another embodiment, only two of the ldh genes are inactivated or deleted in the second recombinant LAB cell. In a further embodiment, at least three of the ldh genes are inactivated or deleted in the second recombinant LAB cell. In a further embodiment, only three of the ldh genes are inactivated or deleted in the second recombinant LAB cell. In a further embodiment, at least four of the ldh genes are inactivated or deleted in the second recombinant LAB cell. In a further embodiment, only four of the ldh genes are inactivated or deleted in the second recombinant LAB cell. For example, in the second recombinant LAB cell of the present disclosure, the ldh1, ldh2, ldh3 and ldh4 genes are inactivated or deleted. In a further embodiment, at least five of the ldh genes are inactivated or deleted in the second recombinant LAB cell. In a further embodiment, only five of the ldh genes are inactivated or deleted in the second recombinant LAB cell. For example, in the second recombinant LAB cell of the present disclosure, the ldh1, ldh2, ldh3, ldh4 and dhic genes are inactivated or deleted. In a further embodiment, at least six of the ldh genes are inactivated or deleted in the second recombinant LAB cell. In a further embodiment, only six of the ldh genes are inactivated or deleted in the second recombinant LAB cell. In still another embodiment, all of the ldh genes are inactivated in the second recombinant LAB cell.

In some embodiments, it may be advantageous to reduce the mannitol dehydrogenase activity, such as, for example, mannitol-1-phosphate 5-dehydrogenase activity, in the second recombinant LAB cell. In such embodiment, the second recombinant LAB cell can be genetically engineered to decrease its mannitol-1-phosphate 5-dehydrogenase activity. As used in the context of the present disclosure, the expression "mannitol-1-P 5-dehydrogenase" refer to an enzyme of the E.C. 1.1.1.17 class which is capable of catalyzing the conversion of mannitol into fructose-6-phosphate. The second recombinant LAB cell can thus have one or more gene coding for a protein having mannitol dehydrogenase activity which is inactivated (via partial or total deletion of the gene). In bacteria, the mltd1 and mltd2 genes encode proteins having mannitol-1-P 5-dehydrogenase activity. In an embodiment, at least one of the mltd1 and mtld2 genes, their corresponding orthologs and paralogs is inactivated in the second recombinant LAB cell. In an embodiment, only one of the mltd1 and mtld2 genes is inactivated in the second recombinant LAB cell. In another embodiment, both of the mltd1 and mtld2 genes are inactivated in the second recombinant LAB cell.

The second recombinant LAB cell is a genetically modified LAB cell which includes an heterologous nucleic acid molecule (referred to as the fourth heterologous nucleic acid molecule) encoding one or more polypeptide conferring immunity against the bacteriocin expressed by the first recombinant LAB cell. In an embodiment, the second recombinant LAB cell can include one or more fourth heterologous nucleic acid molecule encoding one or more polypeptide(s) associated with the immunity to the bacteriocin(s) expressed by the first LAB. The coding sequences for the polypeptide(s) associated with the immunity to bacteriocin can be provided on the same or distinct fourth heterologous nucleic acid molecules. In some embodiments, the third and the fourth heterologous nucleic acid molecules are present on the same nucleic acid molecule. In alternative embodiments, the third and fourth heterologous nucleic acid molecules are present on distinct nucleic acid molecules. The fourth heterologous nucleic acid molecule can be integrated in the bacterial genome or be independently replicating from the bacterial genome.

In some embodiments, the fourth heterologous nucleic acid molecule encodes a polypeptide conferring immunity/resistance against one or more bacteriocin from Gram-negative bacteria. For example, when the first recombinant LAB cell produces nisin, the second recombinant LAB cell must be genetically modified to be immune to the biological activity of nisin. In another example, when the first recombinant LAB cell produces nisin, pediocin and brochocin, the second recombinant LAB cell must be immune or genetically modified to be immune to the biological activity of nisin, pediocin and brochocin. Bacteriocins from Gram-negative bacteria include, but are not limited to, microcins, colicin-like bacteriocins and tailocins. In some embodiments, the third heterologous nucleic acid molecule encodes a polypeptide conferring immunity/resistance against one or more bacteriocin from Gram-positive bacteria. Bacteriocins from Gram-positive bacteria include, but are not limited to, class I bacteriocins (such as, for example nisin A and/or nisin Z), class II bacteriocins, including class IIa (such as, for example, plantaticin 423, pediocin, lactoccin A and/or horediocin) and IIb (such as, for example, brochocin for example) bacteriocins, class III bacteriocins, class IV bacteriocins and circular bacteriocins (such as, for example, gassericin and/or plantaricyclin A). Known bacteriocins include, but are not limited to, acidocin, actagardine, agrocin, alveicin, aureocin, aureocin A53, aureocin A70, bisin, carnocin, carnocyclin, caseicin, cerein, circularin A, colicin, curvaticin, divercin, duramycin, enterocin, enterolysin, epidermin/gallidermin, erwiniocin, gardimycin, gassericin A, glycinecin, halocin, haloduracin, klebicin, lactocin S, lactococcin, lacticin, leucoccin, lysostaphin, macedocin, mersacidin, mesentericin, microbisporicin, microcin S, mutacin, nisin A, nisin Z, paenibacillin, planosporicin, pediocin, pentocin, plantaricin, pneumocyclicin, pyocin, reutericin 6, sakaci, salivaricin, sublancin, subtilin, sulfolobicin, tasmancin, thuricin 17, trifolitoxin, variacin, vibriocin, warnericin and warnerin.

In embodiments in which the first recombinant LAB cell produces nisin as the bacteriocin, the second recombinant LAB cell is genetically engineered to gain immunity against nisin. A polypeptide known to confer immunity or resistance against nisin is NisI. In an embodiment, NisI has the amino acid sequence of SEQ ID NO: 11 (as well as functional variants and fragments thereof retaining at least on part their ability to confer immunity against nisin). As such, the second recombinant LAB cell can comprise a (native or heterologous) nucleic acid molecule further encoding NisI. In such embodiment, the second recombinant LAB cell can comprise the nucleic acid sequence of SEQ ID NO: 55, 56 or a degenerate sequence encoding SEQ ID NO: 11. Second recombinant LAB cells expressing only NisI or NisEFG are considered to be partially immune against the biological activity of nisin. Second recombinant LAB cells expressing both NisI and NisEFG are considered to be fully immune against the biological activity of nisin. NisE is a nisin transporter, NisF is another nisin transporter and NisG is a nisin permease. The NisE, NisF and NisG polypeptides can be used in combination in the absence of the NisI polypeptide to confer a partial immunity against nisin. The NisI polypeptide can be used in the absence of the NisE, NisF and NisG polypeptides to confer a partial immunity against nisin. The NisI, NisE, NisF and NisG polypeptides can be used in combination to confer a full immunity against nisin (for example full immunity is conferred in the presence of 1000 ppm of nisin). As such, the fourth heterologous nucleic acid molecule can further encode NisE, NisF and/or NisG (optionally in combination with NisI). In an embodiment, NisE has the amino acid sequence of SEQ ID NO: 13 (as well as functional variants and fragments thereof retaining, at least in part, their ability to transport nisin). In an embodiment, the second recombinant LAB cell can comprise a (native or heterologous) nucleic acid molecule having the nucleic acid sequence of SEQ ID NO: 59, 60 or a degenerate sequence encoding SEQ ID NO: 13. In an embodiment, NisF has the amino acid sequence of SEQ ID NO: 12 (as well as functional variants and fragments thereof retaining, at least in part, their ability to transport nisin). In such embodiment, the second recombinant LAB cell can comprise a (native or heterologous) nucleic acid sequence of SEQ ID NO: 57, 58 or a degenerate sequence encoding SEQ ID NO: 12. In an embodiment, NisG has the amino acid sequence of SEQ ID NO: 14 (as well as functional variants and fragments thereof retaining, at least in part, their ability to transport nisin). The one or more polypeptides involved in the conferring immunity against nisin can be located on the same or on a distinct nucleic acid molecule as the one encoding nisin and/or the polypeptides involved in the production and/or the regulation of production of nisin. In an embodiment, the second recombinant LAB cell can comprise a (native or heterologous) nucleic acid molecule having the nucleic acid sequence of SEQ ID NO: 61, 62 or a degenerate sequence encoding SEQ ID NO: 14.

In embodiments in which the first recombinant LAB cell produces pediocin as the bacteriocin, the second recombinant LAB cell can be genetically engineered to gain immunity against pediocin. A polypeptide known to confer immunity or resistance against pediocin is PedB. In an embodiment, PedB has the amino acid sequence of SEQ ID NO: 22 (as well as functional variants and fragments thereof retaining at least on part their ability to confer immunity against pediocin). In an embodiment, the second recombinant LAB cell can comprise a (native or heterologous) nucleic acid molecule having the nucleic acid sequence of SEQ ID NO: 76, 77 or 78 or a degenerate sequence encoding SEQ ID NO: 22. As such, the second recombinant LAB cell can express PedB or be genetically engineered to express PedB. As such, the fourth heterologous nucleic acid molecule can encode PedB.

In embodiments in which the first recombinant LAB cell produces lactoccin A as the bacteriocin, the second recombinant LAB cell can be genetically engineered to gain immunity against lactoccin A. A polypeptide known to confer immunity or resistance against pediocin is LciA. In an embodiment, LciA has the amino acid sequence of SEQ ID NO: 42 (as well as functional variants and fragments thereof retaining at least on part their ability to confer immunity against lactoccin A). In an embodiment, the second recombinant LAB cell can comprise a (native or heterologous) nucleic acid molecule having the nucleic acid sequence of SEQ ID NO: 122, 123 or a degenerate sequence encoding SEQ ID NO: 42. As such, the second recombinant LAB cell can express LciA or be genetically engineered to express LciA. In addition, the fourth heterologous nucleic acid molecule can encode LciA.

In embodiments in which the first recombinant LAB cell produces horediocin A as the bacteriocin, the second recombinant LAB cell can be genetically engineered to gain immunity against horediocin A. A polypeptide known to confer immunity or resistance against pediocin is HdrI. In an embodiment, HdrI has the amino acid sequence of SEQ ID NO: 47 (as well as functional variants and fragments thereof retaining at least on part their ability to confer immunity against horediocin A). In an embodiment, the second recombinant LAB cell can comprise a (native or heterologous) nucleic acid molecule having the nucleic acid sequence of SEQ ID NO: 132, 133, 134 or a degenerate sequence encoding SEQ ID NO: 47. As such, the second recombinant LAB cell can express HdrI or be genetically engineered to express HdrI. In addition, the fourth heterologous nucleic acid molecule can encode HdrI.

In embodiments in which the first recombinant LAB cell produces brochocin as the bacteriocin, the second recombinant LAB cell can be genetically engineered to gain immunity against brochocin. A polypeptide known to confer immunity or resistance against pediocin is BrcI. In an embodiment, BrcI has the amino acid sequence of SEQ ID NO: 27 (as well as functional variants and fragments thereof retaining at least on part their ability to confer immunity against brochocin). In an embodiment, the second recombinant LAB cell can comprise a (native or heterologous) nucleic acid molecule having the nucleic acid sequence of SEQ ID NO: 91, 92 or 93 or a degenerate sequence encoding SEQ ID NO: 27. As such, the second recombinant LAB cell can express BrcI or be genetically engineered to express BrcI. In addition, the fourth heterologous nucleic acid molecule can further encode BrcI.

In embodiments in which the first recombinant LAB cell produces gasserin as the bacteriocin, the second recombinant LAB cell can be genetically engineered to gain immunity against gasserin. A polypeptide known to confer immunity or resistance against gasserin is GaaI. In an embodiment, GaaI has the amino acid sequence of SEQ ID NO: 17 (as well as functional variants and fragments thereof retaining at least on part their ability to confer immunity against gasserin). In an embodiment, the second recombinant LAB cell can comprise a (native or heterologous) nucleic acid molecule having the nucleic acid sequence of SEQ ID NO: 65, 66, 67 or a degenerate sequence encoding SEQ ID NO: 17. In addition, the fourth heterologous nucleic acid molecule can further encode GaaI.

In embodiments in which the first recombinant LAB cell produces plantaricyclin A as the bacteriocin, the second recombinant LAB cell can can be genetically engineered to gain immunity against plantaricyclin A. Polypeptides known to confer immunity or resistance against plantaricyclin A are PlcD and PlcI. In an embodiment, PlcD has the amino acid sequence of SEQ ID NO: 30 (as well as functional variants and fragments thereof retaining at least on part their ability to confer immunity, in the presence of PlcI, against plantaricyclin A). In an embodiment, the second recombinant LAB cell can comprise a (native or heterologous) nucleic acid molecule having the nucleic acid sequence of SEQ ID NO: 96, 97, 98 or a degenerate sequence encoding SEQ ID NO: 30. In an embodiment, PlcI has the amino acid sequence of SEQ ID NO: 31 (as well as functional variants and fragments thereof retaining at least on part their ability to confer immunity, in the presence of PlcD, against plantaricyclin A). In an embodiment, the second recombinant LAB cell can comprise a (native or heterologous) nucleic acid molecule having the nucleic acid sequence of SEQ ID NO: 99, 100, 101 or a degenerate sequence encoding SEQ ID NO: 30. In addition, the fourth heterologous nucleic acid molecule can further encode PlcD and/or PlcI.

In embodiments in which the first recombinant LAB cell produces plantaricin 423 as the bacteriocin, the second recombinant LAB cell can can be genetically engineered to gain immunity against plantaricin 423. A polypeptide known to confer immunity or resistance against plantaricyclin A is PlaB. In an embodiment, PlaB has the amino acid sequence of SEQ ID NO: 37 (as well as functional variants and fragments thereof retaining at least on part their ability to confer immunity against plantaricin 423). In an embodiment, the second recombinant LAB cell can comprise a (native or heterologous) nucleic acid molecule having the nucleic acid sequence of SEQ ID NO: 114, 115, 116 or a degenerate sequence encoding SEQ ID NO: 37. In addition, the fourth heterologous nucleic acid molecule can further encode PlaB.

In embodiments in which a population of first recombinant LAB cells is used in the co-culture and such population of first recombinant LAB cells can express the same or different bacteriocins (or combinations of bacteriocins), a population of second recombinant LAB cells can be used provided that they are immune to the bacteriocin produced by the population of first recombinant LAB cells.

Combinations and Kits

In the context of the present disclosure, the co-cultures of the present disclosure can optionally be used in combination with a yeast cell which can, in some embodiments, be a recombinant yeast cell. Suitable yeast cells can be, for example, from the genus *Saccharomyces, Kluyveromyces, Arxula, Debaryomyces, Candida, Pichia, Phaffia, Schizosaccharomyces, Hansenula, Kloeckera, Schwanniomyces* or *Yarrowia*. Suitable yeast species can include, for example, *S. cerevisiae, S. bulderi, S. barnetti, S. exiguus, S. uvarum, S. diastaticus, K. lactis, K. marxianus* or *K. fragilis*. In some embodiments, the yeast is selected from the group consisting of *Saccharomyces cerevisiae, Schizzosaccharomyces pombe, Candida albicans, Pichia pastoris, Pichia stipitis, Yarrowia lipolytica, Hansenula polymorpha, Phaffia rhodozyma, Candida utilis, Arxula adeninivorans, Debaryomyces hansenii, Debaryomyces polymorphus, Schizosaccharomyces pombe* and *Schwanniomyces occidentalis*. In one particular embodiment, the yeast is *Saccharomyces cerevisiae*. In some embodiments, the host cell can be an oleaginous yeast cell. For example, the oleaginous yeast host cell can be from the genus *Blakeslea, Candida, Cryptococcus, Cunninghamella, Lipomyces, Mortierella, Mucor, Phycomyces, Pythium, Rhodosporidum, Rhodotorula, Trichosporon* or *Yarrowia*. In some alternative embodiments, the host cell can be an oleaginous microalgae host cell (e.g., for example, from the genus Thraustochytrium or Schizochytrium). In an embodiment, the yeast cell is from the genus *Saccharomyces* and, in some embodiments, from the species *Saccharomyces cerevisiae*.

In a specific embodiment, the yeast host cell can have increased biological activity in a polypeptide having acetylating aldehyde dehydrogenase activity. As used in the present disclosure, a polypeptide having acetylating aldehyde dehydrogenase activity has the ability to convert acetyl-coA into an aldehyde. In some embodiments, the polypeptide having acetylating aldehyde dehydrogenase activity is an AADH or is a bifunctional acetylating aldehyde dehydrogenase/alcohol dehydrogenase (ADHE). The bifunctional acetaldehyde/alcohol dehydrogenase is an enzyme capable of converting acetyl-CoA into acetaldehyde as well as acetaldehyde into ethanol. Heterologous bifunctional acetaldehyde/alcohol dehydrogenases (AADH) include but are not limited to those described in U.S. Pat. No. 8,956,851 and WO 2015/023989. Heterologous AADHs of the present disclosure include, but are not limited to, the ADHE polypeptides or a polypeptide encoded by an adhe gene ortholog. In an embodiment, the AADH is from a *Bifidobacterium* sp., such as for example, a *Bifidobacterium adolescentis*. In such embodiment, the genetic modification can comprise introducing an heterologous nucleic acid molecule encoding a polypeptide having acetylating aldehyde dehydrogenase activity in the recombinant yeast cell.

In some embodiments, the yeast cell can also include one or more genetic modifications limiting the production of glycerol. For example, the genetic modification can be a genetic modification leading to the reduction in the production, and in an embodiment to the inhibition in the production, of one or more native enzymes that function to produce glycerol. As used in the context of the present disclosure, the expression "reducing the production of one or more native enzymes that function to produce glycerol" refers to a genetic modification which limits or impedes the expression of genes associated with one or more native polypeptides (in some embodiments enzymes) that function to produce glycerol, when compared to a corresponding yeast strain which does not bear such genetic modification. In some instances, the additional genetic modification reduces but still allows the production of one or more native polypeptides that function to produce glycerol. In other instances, the genetic modification inhibits the production of one or more native enzymes that function to produce glycerol. Polypeptides that function to produce glycerol refer to polypeptides which are endogenously found in the yeast cell. Native enzymes that function to produce glycerol include, but are not limited to, the GPD1 and the GPD2 polypeptide (also referred to as GPD1 and GPD2, respectively) as well as the GPP1 and the GPP2 polypeptides (also referred to as GPP1 and GPP2, respectively). In an embodiment, the yeast cell bears a genetic modification in at least one of the gpd1 gene (encoding the GPD1 polypeptide), the gpd2 gene (encoding the GPD2 polypeptide), the gpp1 gene (encoding the GPP1 polypeptide) or the gpp2 gene (encoding the GPP2 polypeptide). In another embodiment, the yeast cell bears a genetic modification in at least two of the gpd1 gene (encoding the GPD1 polypeptide), the gpd2 gene (encoding the GPD2 polypeptide), the gpp1 gene (encoding the GPP1 polypeptide) or the gpp2 gene (encoding the GPP2 polypeptide). Examples of recombinant yeast cells bearing such genetic modification(s) leading to the reduction in the production of one or more native enzymes that function to produce glycerol are described in WO 2012/138942. In some embodiments, the yeast cell has a genetic modification (such as a genetic deletion or insertion) only in one enzyme that functions to produce glycerol, in the gpd2 gene, which would cause the yeast cell to have a knocked-out gpd2 gene. In some embodiments, the recombinant yeast host cell can have a genetic modification in the gpd1 gene and the gpd2 gene resulting is a recombinant yeast host cell being knock-out for the gpd1 gene and the gpd2 gene. In some specific embodiments, the yeast cell can have be a knock-out for the gpd1 gene and have duplicate copies of the gpd2 gene (in some embodiments, under the control of the gpd1 promoter). In yet another embodiment, the yeast cell does not bear such genetic modification and includes its native genes coding for the GPP/GDP proteins. As such, in some embodiments, there are no genetic modifications leading to the reduction in the production of one or more native enzymes that function to produce glycerol in the yeast cell.

Alternatively or in combination, the yeast cell can also include one or more additional genetic modifications facilitating the transport of glycerol in the yeast cell. For example, the additional genetic modification can be a genetic modification leading to the increase in activity of one or more native enzymes that function to transport glycerol. Native enzymes that function to transport glycerol synthesis include, but are not limited to, the FPS1 polypeptide as well as the STL1 polypeptide. The FPS1 polypeptide is a glycerol exporter and the STL1 polypeptide functions to import glycerol in the recombinant yeast host cell. By either reducing or inhibiting the expression of the FPS1 polypeptide and/or increasing the expression of the STL1 polypeptide, it is possible to control, to some extent, glycerol synthesis.

The STL1 protein is natively expressed in yeasts and fungi, therefore the heterologous protein functioning to import glycerol can be derived from yeasts and fungi. STL1 genes encoding the STL1 protein include, but are not limited to, *Saccharomyces cerevisiae* Gene ID: 852149, *Candida albicans*, *Kluyveromyces lactis* Gene ID: 2896463, *Ashbya gossypii* Gene ID: 4620396, *Eremothecium sinecaudum* Gene ID: 28724161, *Torulaspora delbrueckii* Gene ID: 11505245, *Lachancea thermotolerans* Gene ID: 8290820, *Phialophora attae* Gene ID: 28742143, *Penicillium digitatum* Gene ID: 26229435, *Aspergillus oryzae* Gene ID: 5997623, *Aspergillus fumigatus* Gene ID: 3504696, *Talaromyces atroroseus* Gene ID: 31007540, *Rasamsonia emersonii* Gene ID: 25315795, *Aspergillus flavus* Gene ID: 7910112, *Aspergillus terreus* Gene ID: 4322759, *Penicillium chrysogenum* Gene ID: 8310605, *Alternaria alternata* Gene ID: 29120952, *Paraphaeosphaeria sporulosa* Gene ID: 28767590, *Pyrenophora tritici-repentis* Gene ID: 6350281, *Metarhizium robertsii* Gene ID: 19259252, *Isaria fumosorosea* Gene ID: 30023973, *Cordyceps militaris* Gene ID: 18171218, *Pochonia chlamydosporia* Gene ID: 28856912, *Metarhizium majus* Gene ID: 26274087, *Neofusicoccum parvum* Gene ID:19029314, *Diplodia corticola* Gene ID: 31017281, *Verticillium dahliae* Gene ID: 20711921, *Colletotrichum gloeosporioides* Gene ID: 18740172, *Verticillium albo-atrum* Gene ID: 9537052, *Paracoccidioides lutzii* Gene ID: 9094964, *Trichophyton rubrum* Gene ID: 10373998, *Nannizzia gypsea* Gene ID: 10032882, *Trichophyton verrucosum* Gene ID: 9577427, *Arthroderma benhamiae* Gene ID: 9523991, *Magnaporthe oryzae* Gene ID: 2678012, *Gaeumannomyces graminis* var. *tritici* Gene ID: 20349750, *Togninia minima* Gene ID: 19329524, *Eutypa lata* Gene ID: 19232829, *Scedosporium apiospermum* Gene ID: 27721841, *Aureobasidium namibiae* Gene ID: 25414329, *Sphaerulina musiva* Gene ID: 27905328 as well as *Pachysolen tannophilus* GenBank Accession Numbers JQ481633 and JQ481634, *Saccharomyces paradoxus* STL1 and *Pichia sorbitophilia*. In an embodiment, the STL1 protein is encoded by *Saccharomyces cerevisiae* Gene ID: 852149.

Alternatively or in combination, the yeast cell can have a genetic modification allowing the expression of an heterologous saccharolytic enzyme. As used in the context of the present disclosure, a "saccharolytic enzyme" can be any enzyme involved in carbohydrate digestion, metabolism and/or hydrolysis, including amylases, cellulases, hemicellulases, cellulolytic and amylolytic accessory enzymes, inulinases, levanases, and pentose sugar utilizing enzymes. amylolytic enzyme. In an embodiment, the saccharolytic enzyme is an amylolytic enzyme. As used herein, the expression "amylolytic enzyme" refers to a class of enzymes capable of hydrolyzing starch or hydrolyzed starch. Amylolytic enzymes include, but are not limited to alpha-amylases (EC 3.2.1.1, sometimes referred to fungal alpha-amylase, see below), maltogenic amylase (EC 3.2.1.133), glucoamylase (EC 3.2.1.3), glucan 1,4-alpha-maltotetraohydrolase (EC 3.2.1.60), pullulanase (EC 3.2.1.41), iso-amylase (EC 3.2.1.68) and amylomaltase (EC 2.4.1.25). In an embodiment, the one or more amylolytic enzymes can be an alpha-amylase from *Aspergillus oryzae*, a maltogenic alpha-amylase from *Geobacillus stearothermophilus*, a glucoamylase from *Saccharomycopsis fibuligera*, a glucan 1,4-alpha-maltotetraohydrolase from *Pseudomonas saccharophila*, a pullulanase from *Bacillus naganoensis*, a pullulanase from *Bacillus* acidopullulyticus, an iso-amylase from *Pseudomonas amyloderamosa*, and/or amylomaltase from *Thermus thermophilus*. Some amylolytic enzymes have been described in WO2018/167670 and are incorporated herein by reference.

For example, the yeast cell can bear one or more genetic modifications allowing for the production of an heterologous glucoamylase. Many microbes produce an amylase to degrade extracellular starches. In addition to cleaving the last α(1-4) glycosidic linkages at the non-reducing end of amylose and amylopectin, yielding glucose, γ-amylase will cleave α(1-6) glycosidic linkages. The heterologous glucoamylase can be derived from any organism. In an embodiment, the heterologous protein is derived from a γ-amylase, such as, for example, the glucoamylase of *Saccharomycoces filbuligera* (e.g., encoded by the glu 0111 gene). Examples of yeast cells bearing such genetic modifications are described in WO 2011/153516 as well as in WO 2017/037614 and herewith incorporated in its entirety.

Alternatively or in combination, the yeast cell can bear one or more genetic modifications for increasing formate/acetyl-CoA production. In order to do so, yeast cell can bear one or more genetic modification for increasing its pyruvate formate lyase activity. As used in the context of the present disclosure, "an heterologous enzyme that function to increase formate/acetyl-CoA production" refers to polypeptides which may or may not be endogeneously found in the yeast host cell and that are purposefully introduced into the yeast cells to anabolize formate. In some embodiments, the heterologous enzyme that can be an heterologous pyruvate formate lyase (PFL), such as PFLA or PFLB Heterologous PFL of the present disclosure include, but are not limited to, the PFLA polypeptide, a polypeptide encoded by a pfla gene ortholog, the PFLB polypeptide or a polypeptide encoded by a pflb gene ortholog.

Embodiments of the pyruvate formate lyase activating enzyme and of PFLA can be derived, without limitation, from the following (the number in brackets correspond to the Gene ID number): *Escherichia coli* (MG1655945517), *Shewanella oneidensis* (1706020), *Bifidobacterium longum* (1022452), *Mycobacterium bovis* (32287203), *Haemophilus parasuis* (7277998), *Mannheimia haemolytica* (15341817), *Vibrio vulnificus* (33955434), *Cronobacter sakazakii* (29456271), *Vibrio alginolyticus* (31649536), *Pasteurella multocida* (29388611), *Aggregatibacter actinomycetemcomitans* (31673701), *Actinobacillus suis* (34291363), *Finegoldia magna* (34165045), *Zymomonas mobilis* subsp. *mobilis* (3073423), *Vibrio tubiashii* (23444968), *Gallibacterium anatis* (10563639), *Actinobacillus pleuropneumoniae serovar* (4849949), *Ruminiclostridium thermocellum* (35805539), *Cylindrospermopsis raciborskii* (34474378), *Lactococcus garvieae* (34204939), *Bacillus cytotoxicus* (33895780), *Providencia stuartii* (31518098), *Pantoea ananatis* (31510290), *Teredinibacter turnerae* (29648846), *Morganella morganii* subsp. *morganii* (14670737), *Vibrio anguillarum* (77510775106), *Dickeya dadantii* (39379733484), *Xenorhabdus bovienii* (8830449), *Edwardsiella ictaluri* (7959196), *Proteus mirabilis* (6801040), *Rahnella aquatilis* (34350771), *Bacillus pseudomycoides* (34214771), *Vibrio alginolyticus* (29867350), *Vibrio nigripulchritudo* (29462895), *Vibrio orientalis* (25689084), *Kosakonia sacchari* (23844195), *Serratia marcescens* subsp. *marcescens* (23387394), *Shewanella baltica* (11772864), *Vibrio vulnificus* (2625152), *Streptomyces acidiscabies* (33082227), *Streptomyces davaonensis* (31227069), *Streptomyces scabiei* (24308152), *Volvox carteri* f. *nagariensis* (9616877), *Vibrio breoganii* (35839746), *Vibrio mediterranei* (34766273), *Fibrobacter succinogenes* subsp. *succinogenes* (34755395), *Enterococcus gilvus* (34360882), *Akkermansia muciniphila* (34173806), *Enterobacter hormaechei* subsp. *Steigerwaltii* (34153767), *Dickeya zeae* (33924935), *Enterobacter* sp. (32442159), *Serratia odorifera* (31794665), *Vibrio crassostreae* (31641425), *Selenomonas ruminantium* subsp. *lactilytica* (31522409), *Fusobacterium necrophorum* subsp. *funduliforme* (31520833), *Bacteroides uniformis* (31507008), *Haemophilus somnus* (233631487328), *Rodentibacter pneumotropicus* (31211548), *Pectobacterium carotovorum* subsp. *carotovorum* (29706463), *Eikenella corrodens* (29689753), *Bacillus thuringiensis* (29685036), *Streptomyces rimosus* subsp. *Rimosus* (29531909), *Vibrio fluvialis* (29387180), *Klebsiella oxytoca* (29377541), *Parageobacillus thermoglucosidans* (29237437), *Aeromonas veronii* (28678409), *Clostridium innocuum* (26150741), *Neisseria mucosa* (25047077), *Citrobacter freundii* (23337507), *Clostridium bolteae* (23114831), *Vibrio tasmaniensis* (7160642), *Aeromonas salmonicida* subsp. *salmonicida* (4995006), *Escherichia coli* O157:H7 str. Sakai (917728), *Escherichia coli* O83:H1 str. (12877392), *Yersinia pestis* (11742220), *Clostridioides difficile* (4915332), *Vibrio fischeri* (3278678), *Vibrio parahaemolyticus* (1188496), *Vibrio coralliilyticus* (29561946), *Kosakonia cowanii* (35808238), *Yersinia ruckeri* (29469535), *Gardnerella vaginalis* (99041930), *Listeria fleischmannii* subsp. *Coloradonensis* (34329629), *Photobacterium kishitanii* (31588205), *Aggregatibacter actinomycetemcomitans* (29932581), *Bacteroides caccae* (36116123), *Vibrio toranzoniae* (34373279), *Providencia alcalifaciens* (34346411), *Edwardsiella anguillarum* (33937991), *Lonsdalea quercina* subsp. *Quercina* (33074607), *Pantoea septica* (32455521), *Butyrivibrio proteoclasticus* (31781353), *Photorhabdus temperata* subsp. *Thracensis* (29598129), *Dickeya solani* (23246485), *Aeromonas hydrophila* subsp. *hydrophila* (4489195), *Vibrio cholerae* 01 biovar El Tor str. (2613623), *Serratia rubidaea* (32372861), *Vibrio bivalvicida* (32079218), *Serratia liquefaciens* (29904481), *Gilliamella apicola* (29851437), *Pluralibacter gergoviae* (29488654), *Escherichia coli* O104:H4 (13701423), *Enterobacter aerogenes* (10793245), *Escherichia coli* (7152373), *Vibrio campbellii* (5555486), *Shigella dysenteriae* (3795967), *Bacillus thuringiensis* serovar *konkukian* (2854507), *Salmonella enterica* subsp. *enterica* serovar *Typhimurium* (1252488), *Bacillus anthracis* (1087733), *Shigella flexneri* (1023839), *Streptomyces griseoruber* (32320335), *Ruminococcus gnavus* (35895414), *Aeromonas fluvialis* (35843699), *Streptomyces ossamyceticus* (35815915), *Xenorhabdus doucetiae* (34866557), *Lactococcus piscium* (34864314), *Bacillus glycinifermentans* (34773640), *Photobacterium damselae* subsp. *Damselae* 34509297, *Streptomyces venezuelae* 34035779, *Shewanella algae* (34011413), *Neisseria sicca* (33952518), *Chania multitudinisentens* (32575347), *Kitasatospora purpeofusca* (32375714), *Serratia fonticola* (32345867), *Aeromonas enteropelogenes* (32325051), *Micromonospora aurantiaca* (32162988), *Moritella viscosa* (31933483), *Yersinia aldovae* (31912331), *Leclercia adecarboxylata* (31868528), *Salinivibrio costicola* subsp. *costicola* (31850688), *Aggregatibacter aphrophilus* (31611082), *Photobacterium leiognathi* (31590325), *Streptomyces canus* (31293262), *Pantoea dispersa* (29923491), *Pantoea rwandensis* (29806428), *Paenibacillus borealis* (29548601), *Aliivibrio wodanis* (28541257), *Streptomyces virginiae* (23221817), *Escherichia coli* (7158493), *Mycobacterium tuberculosis* (887973), *Streptococcus mutans* (1028925), *Streptococcus cristatus* (29901602), *Enterococcus hirae* (13176624), *Bacillus licheniformis* (3031413), *Chromobacterium violaceum* (24949178), *Parabacteroides distasonis* (5308542), *Bacteroides vulgatus* (5303840), *Faecalibacterium prausnitzii* (34753201), *Melissococcus plutonius* (34410474), *Streptococcus gallolyticus* subsp. *gallolyticus* (34397064), *Enterococcus malodoratus* (34355146), *Bacteroides oleiciplenus* (32503668), *Listeria monocytogenes* (985766), *Enterococcus faecalis* (1200510), *Campylobacter jejuni* subsp. *jejuni* (905864), *Lactobacillus plantarum* (1063963), *Yersinia enterocolitica* subsp. *enterocolitica* (4713333), *Streptococcus equinus* (33961143), *Macrococcus canis* (35294771), *Streptococcus sanguinis* (4807186), *Lactobacillus salivarius* (3978441), *Lactococcus lactis* subsp. *lactis* (1115478), *Enterococcus faecium* (12999835), *Clostridium botulinum* A (5184387), *Clostridium acetobutylicum* (1117164), *Bacillus thuringiensis* serovar *konkukian* (2857050), *Cryobacterium flavum* (35899117), *Enterovibrio norvegicus* (35871749), *Bacillus acidiceler* (34874556), *Prevotella intermedia* (34516987), *Pseudobutyrivibrio ruminis* (34419801), *Pseudovibrio ascidiaceicola* (34149433), *Corynebacterium coyleae* (34026109), *Lactobacillus curvatus* (33994172), *Cellulosimicrobium cellulans* (33980622), *Lactobacillus agilis* (33975995), *Lactobacillus sakei* (33973512), *Staphylococcus simulans* (32051953), *Obesumbacterium proteus* (29501324), *Salmonella enterica* subsp. *enterica* serovar *Typhi* (1247402), *Streptococcus agalactiae* (1014207), *Streptococcus agalactiae* (1013114), *Legionella pneumophila* subsp. *pneumophila* str. Philadelphia (119832735), *Pyrococcus furiosus* (1468475), *Mannheimia haemolytica* (15340992), *Thalassiosira pseudonana* (7444511), *Thalassiosira pseudonana* (7444510), *Streptococcus thermophilus* (31940129), *Sulfolobus solfataricus*

(1454925), Streptococcus iniae (35765828), Streptococcus iniae (35764800), Bifidobacterium thermophilum (31839084), Bifidobacterium animalis subsp. lactis (29695452), Streptobacillus moniliformis (29673299), Thermogladius calderae (13013001), Streptococcus oralis subsp. tigurinus (31538096), Lactobacillus ruminis (29802671), Streptococcus parauberis (29752557), Bacteroides ovatus (29454036), Streptococcus gordonii str. Challis substr. CH1 (25052319), Clostridium botulinum B str. Eklund 17B (19963260), Thermococcus litoralis (16548368), Archaeoglobus sulfaticallidus (15392443), Ferroglobus placidus (8778929), Archaeoglobus profundus (8739370), Listeria seeligeri serovar 1/2b (32488230), Bacillus thuringiensis (31632063), Rhodobacter capsulatus (31491679), Clostridium botulinum (29749009), Clostridium perfringens (29571530), Lactococcus garvieae (12478921), Proteus mirabilis (6799920), Lactobacillus animalis (32012274), Vibrio alginolyticus (29869205), Bacteroides thetaiotaomicron (31617701), Bacteroides thetaiotaomicron (31617140), Bacteroides cellulosilyticus (29608790), Bacteroides ovatus (29453452), Bacillus mycoides (29402181), Chlamydomonas reinhardtii (5726206), Fusobacterium periodonticum (35833538), Selenomonas flueggei (32477557), Selenomonas noxia (32475880), Anaerococcus hydrogenalis (32462628), Centipeda periodontii (32173931), Centipeda periodontii (32173899), Streptococcus thermophilus (31938326), Enterococcus durans (31916360), Fusobacterium nucleatum (31730399), Anaerostipes hadrus (31625694), Anaerostipes hadrus (31623667), Enterococcus haemoperoxidus (29838940), Gardnerella vaginalis (29692621), Streptococcus salivarius (29397526), Klebsiella oxytoca (29379245), Bifidobacterium breve (29241363), Actinomyces odontolyticus (25045153), Haemophilus ducreyi (24944624), Archaeoglobus fulgidus (24793671), Streptococcus uberis (24161511), Fusobacterium nucleatum subsp. animalis (23369066), Corynebacterium accolens (23249616), Archaeoglobus veneficus (10394332), Prevotella melaninogenica (9497682), Aeromonas salmonicida subsp. salmonicida (4997325), Pyrobaculum islandicum (4616932), Thermofilum pendens (4600420), Bifidobacterium adolescentis (4556560), Listeria monocytogenes (986485), Bifidobacterium thermophilum (35776852), Methanothermobacter sp. CaT2 (24854111), Streptococcus pyogenes (901706), Exiguobacterium sibiricum (31768748), Clostridioides difficile (4916015), Clostridioides difficile (4913022), Vibrio parahaemolyticus (1192264), Yersinia enterocolitica subsp. enterocolitica (4712948), Enterococcus cecorum (29475065), Bifidobacterium pseudolongum (34879480), Methanothermus fervidus (9962832), Methanothermus fervidus (9962056), Corynebacterium simulans (29536891), Thermoproteus uzoniensis (10359872), Vulcanisaeta distributa (9752274), Streptococcus mitis (8799048), Ferroglobus placidus (8778420), Streptococcus suis (8153745), Clostridium novyi (4541619), Streptococcus mutans (1029528), Thermosynechococcus elongatus (1010568), Chlorobium tepidum (1007539), Fusobacterium nucleatum subsp. nucleatum (993139), Streptococcus pneumoniae (933787), Clostridium baratii (31579258), Enterococcus mundtii (31547246), Prevotella ruminicola (31500814), Aeromonas hydrophila subsp. hydrophila (4490168), Aeromonas hydrophila subsp. hydrophila (4487541), Clostridium acetobutylicum (1117604), Chromobacterium subtsugae (31604683), Gilliamella apicola (29849369), Klebsiella pneumoniae subsp. pneumoniae (11846825), Enterobacter cloacae subsp. cloacae (9125235), Escherichia coli (7150298), Salmonella enterica subsp. enterica serovar Typhimurium (1252363), Salmonella enterica subsp. enterica serovar Typhi (1247322), Bacillus cereus (1202845), Bacteroides thetaiotaomicron (1074343), Bacteroides thetaiotaomicron (1071815), Bacillus coagulans (29814250), Bacteroides cellulosilyticus (29610027), Bacillus anthracis (2850719), Monoraphidium neglectum (25735215), Monoraphidium neglectum (25727595), Alloscardovia omnicolens (35868062), Actinomyces neuii subsp. neuii (35867196), Acetoanaerobium sticklandii (35557713), Exiguobacterium undae (32084128), Paenibacillus pabuli (32034589), Paenibacillus etheri (32019864), Actinomyces oris (31655321), Vibrio alginolyticus (31651465), Brochothrix thermosphacta (29820407), Lactobacillus sakei subsp. sakei (29638315), Anoxybacillus gonensis (29574914), variants thereof as well as fragments thereof. In an embodiment, the PFLA protein is derived from the genus Bifidobacterium and in some embodiments from the species Bifidobacterium adolescentis.

Embodiments of PFLB can be derived, without limitation, from the following (the number in brackets correspond to the Gene ID number): Escherichia coli (945514), Shewanella oneidensis (1170601), Actinobacillus suis (34292499), Finegoldia magna (34165044), Streptococcus cristatus (29901775), Enterococcus hirae (13176625), Bacillus (3031414), Providencia alcalifaciens (34345353), Lactococcus garvieae (34203444), Butyrivibrio proteoclasticus (31781354), Teredinibacter turnerae (29651613), Chromobacterium violaceum (24945652), Vibrio campbellii (5554880), Vibrio campbellii (5554796), Rahnella aquatilis HX2 (34351700), Serratia rubidaea (32375076), Kosakonia sacchari SP1 (23845740), Shewanella baltica (11772863), Streptomyces acidiscabies (33082309), Streptomyces davaonensis (31227068), Parabacteroides distasonis (5308541), Bacteroides vulgatus (5303841), Fibrobacter succinogenes subsp. succinogenes (34755392), Photobacterium damselae subsp. Damselae (34512678), Enterococcus gilvus (34361749), Enterococcus gilvus (34360863), Enterococcus malodoratus (34355213), Enterococcus malodoratus (34354022), Akkermansia muciniphila (34174913), Lactobacillus curvatus (33995135), Dickeya zeae (33924934), Bacteroides oleiciplenus (32502326), Micromonospora aurantiaca (32162989), Selenomonas ruminantium subsp. lactilytica (31522408), Fusobacterium necrophorum subsp. funduliforme (31520832), Bacteroides uniformis (31507007), Streptomyces rimosus subsp. Rimosus (29531908), Clostridium innocuum (26150740), Haemophilus] ducreyi (24944556), Clostridium bolteae (23114829), Vibrio tasmaniensis (7160644), Aeromonas salmonicida subsp. salmonicida (4997718), Listeria monocytogenes (986171), Enterococcus faecalis (1200511), Lactobacillus plantarum (1064019), Vibrio fischeri (3278780), Lactobacillus sakei (33973511), Gardnerella vaginalis (9904192), Vibrio vulnificus (33954428), Vibrio toranzoniae (34373229), Anaerostipes hadrus (34240161), Edwardsiella anguillarum (33940299), Edwardsiella anguillarum (33937990), Lonsdalea quercina subsp. Quercina (33074710), Enterococcus faecium (12999834), Aeromonas hydrophila subsp. hydrophila (4489100), Clostridium acetobutylicum (1117163), Escherichia coli (7151395), Shigella dysenteriae (3795966), Bacillus thuringiensis serovar konkukian (2856201), Salmonella enterica subsp. enterica serovar Typhimurium (1252491), Shigella flexneri (1023824), Streptomyces griseoruber (32320336), Cryobacterium flavum (35898977), Ruminococcus gnavus (35895748), Bacillus acidiceler (34874555), Lactococcus piscium (34864362), Vibrio mediterranei (34766270), Faecalibacterium prausnitzii (34753200), Prevotella intermedia (34516966), *Photobacterium damselae* subsp. *Damselae* (34509286), *Pseudobutyrivibrio ruminis* (34419894), *Melissococcus plutonius* (34408953), *Streptococcus gallolyticus* subsp. *gallolyticus* (34398704), *Enterobacter hormaechei* subsp. *Steigerwaltii* (34155981), *Enterobacter hormaechei* subsp. *Steigerwaltii* (34152298), *Streptomyces venezuelae* (34036549), *Shewanella algae* (34009243), *Lactobacillus agilis* (33976013), *Streptococcus equinus* (33961013), *Neisseria sicca* (33952517), *Kitasatospora purpeofusca* (32375782), *Paenibacillus borealis* (29549449), *Vibrio fluvialis* (29387150), *Aliivibrio wodanis* (28542465), *Aliivibrio wodanis* (28541256), *Escherichia coli* (7157421), *Salmonella enterica* subsp. *enterica* serovar *Typhi* (1247405), *Yersinia pestis* (1174224), *Yersinia enterocolitica* subsp. *enterocolitica* (4713334), *Streptococcus suis* (8155093), *Escherichia coli* (947854), *Escherichia coli* (946315), *Escherichia coli* (945513), *Escherichia coli* (948904), *Escherichia coli* (917731), *Yersinia enterocolitica* subsp. *enterocolitica* (4714349), variants thereof as well as fragments thereof. In an embodiment, the PFLB protein is derived from the genus *Bifidobacterium* and in some embodiments from the specifies *Bifidobacterium adolescentis*.

In some embodiments, the yeast cell comprises a genetic modification for expressing a PFLA protein, a PFLB protein or a combination. In a specific embodiment, the yeast cell comprises a genetic modification for expressing a PFLA protein and a PFLB protein which can, in some embodiments, be provided on distinct heterologous nucleic acid molecules. As indicated below, the recombinant yeast host cell can also include additional genetic modifications to provide or increase its ability to transform acetyl-CoA into an alcohol such as ethanol.

Alternatively or in combination, the yeast cell can bear one or more genetic modifications for utilizing acetyl-CoA for example, by providing or increasing acetaldehyde and/or alcohol dehydrogenase activity. Acetyl-CoA can be converted to an alcohol such as ethanol using an acetaldehyde dehydrogenase and then an alcohol dehydrogenase. Acylating acetaldehyde dehydrogenases (E.C. 1.2.1.10) are known to catalyze the conversion of acetyl-CoA into acetaldehyde. Alcohol dehydrogenases (E.C. 1.1.1.1) are known to be able to catalyze the conversion of acetaldehyde into ethanol. The acetaldehyde dehydrogenase and alcohol dehydrogenase activity can be provided by a single protein (e.g., a bifunctional acetaldehyde/alcohol dehydrogenase) or by a combination of more than one protein (e.g., an acetaldehyde dehydrogenase and an alcohol dehydrogenase). In embodiments in which the acetaldehyde/alcohol dehydrogenase activity is provided by more than one protein, it may not be necessary to provide the combination of proteins in a recombinant form in the recombinant yeast host cell as the cell may have some pre-existing acetaldehyde or alcohol dehydrogenase activity. In such embodiments, the genetic modification can include providing one or more heterologous nucleic acid molecule encoding one or more of an heterologous acetaldehyde dehydrogenase (AADH), an heterologous alcohol dehydrogenase (ADH) and/or heterologous bifunctional acetalaldehyde/alcohol dehydrogenases (ADHE). In another embodiment, the genetic modification comprises introducing an heterologous nucleic acid encoding an heterologous bifunctional acetaldehyde/alcohol dehydrogenases (ADHE) such as those described in U.S. Pat. No. 8,956,851 and WO 2015/023989. Heterologous AADHs of the present disclosure include, but are not limited to, the ADHE polypeptides or a polypeptide encoded by an adhe gene ortholog.

The co-cultures described herein can be provided as a combination with the yeast cell described herein. In such combination, co-cultures can be provided in a distinct container from the yeast cell. The co-culture itself can be provided in distinct containers (one for the first recombinant LAB cell, another one for the second recombinant LAB cell) or in the same container (comprising both the first recombinant LAB cell and the second recombinant LAB cell). The LAB cells of the co-cultures can be provided as a cell concentrate. The cell concentrate comprising the LAB cells can be obtained, for example, by propagating the LAB cells in a culture medium and removing at least one components of the medium comprising the propagated LAB cells. This can be done, for example, by dehydrating, filtering (including ultra-filtrating) and/or centrifuging the medium comprising the propagated LAB cells. In an embodiment, the co-cultures can be provided as a frozen concentrate in the combination. The yeast cell can be provided as a cell concentrate. The cell concentrate comprising the yeast cell can be obtained, for example, by propagating the yeast cells in a culture medium and removing at least one components of the medium comprising the propagated yeast host cell. This can be done, for example, by dehydrating, filtering (including ultra-filtrating) and/or centrifuging the medium comprising the propagated yeast cells. In an embodiment, the yeast cell is provided as a cream in the combination.

The co-cultures described herein can be provided as a kit for making a fermented product. The kit comprises the first recombinant LAB cell described herein and the second recombinant LAB cell. In some embodiments, the kit can further include the yeast cell described herein. In the kit, co-cultures can be provided in a distinct container from the yeast cell. The co-culture itself can be provided in distinct containers (one for the first recombinant LAB cell, another one for the second recombinant LAB cell) or in the same container (comprising both the first recombinant LAB cell and the second recombinant LAB cell). The LAB cells of the co-cultures can be provided in the kit as a cell concentrate. The cell concentrate comprising the LAB cells can be obtained, for example, by propagating the LAB cells in a culture medium and removing at least one components of the medium comprising the propagated LAB cells. This can be done, for example, by dehydrating, filtering (including ultra-filtrating) and/or centrifuging the medium comprising the propagated LAB cells. In an embodiment, the co-cultures can be provided as a frozen concentrate in the combination. The yeast cell can be provided in the kit as a cell concentrate. The cell concentrate comprising the yeast cell can be obtained, for example, by propagating the yeast cells in a culture medium and removing at least one components of the medium comprising the propagated yeast host cell. This can be done, for example, by dehydrating, filtering (including ultra-filtrating) and/or centrifuging the medium comprising the propagated yeast cells. In an embodiment, the yeast cell is provided in the kit as a cream in the combination. The kit can, in some embodiments, include the instructions for performing the process for making the fermentation product.

The present disclosure provides a medium comprising the first recombinant LAB cell described herein, the second recombinant LAB cell described herein and optionally the yeast cell described herein. The medium can be a propagation medium, e.g., a medium that was used to propagate the LAB cells. The medium can be a fermentation medium, e.g., a medium that was used to convert a biomass into a fermentation product. In such embodiment, the fermentation medium can also include the fermentation product.

Process for Making a Fermented Product

The co-cultures described herein can be used (alone or in combination with a yeast cell) to make a fermented product from a biomass. In some embodiments, the co-cultures and the combinations are used to limit microbial contamination during fermentation and consequently maintain or improve the fermentation yield (when compared to a fermentation in the absence of the co-cultures or the combinations). It is known in the art that the reduction in fermentation yield is influenced by the type of microbial (bacterial) contamination, the concentration of microbial (bacterial) contamination, the type of fermentation medium (including its solids content), etc. In the context of the present disclosure, a microbial contamination is defined as the presence of a microorganism (that may be a bacteria) that (i) differs from the first and second recombinant LAB cell and the fermenting yeast cell which may optionally be present and (ii) causes a reduction in the yield of the desired end product (ethanol, for example) during fermentation. In some embodiments in which a corn mash is being used as the biomass, the co-cultures described herein can limit the bacterial contamination to a level below about $10^6$, $10^5$, $10^4$, $10^3$, $10^2$ or less CFU/g of corn mash.

The biomass that can be fermented with the co-cultures and combinations described herein includes any type of biomass known in the art and described herein. For example, the biomass can include, but is not limited to, starch, sugar and lignocellulosic materials. Starch materials can include, but are not limited to, mashes such as corn, wheat, rye, barley, rice, or milo. Sugar materials can include, but are not limited to, sugar beets, artichoke tubers, sweet sorghum, molasses or cane. The terms "lignocellulosic material", "lignocellulosic substrate" and "cellulosic biomass" mean any type of biomass comprising cellulose, hemicellulose, lignin, or combinations thereof, such as but not limited to woody biomass, forage grasses, herbaceous energy crops, non-woody-plant biomass, agricultural wastes and/or agricultural residues, forestry residues and/or forestry wastes, paper-production sludge and/or waste paper sludge, wastewater-treatment sludge, municipal solid waste, corn fiber from wet and dry mill corn ethanol plants and sugar-processing residues. The terms "hemicellulosics", "hemicellulosic portions" and "hemicellulosic fractions" mean the non-lignin, non-cellulose elements of lignocellulosic material, such as but not limited to hemicellulose (i.e., comprising xyloglucan, xylan, glucuronoxylan, arabinoxylan, mannan, glucomannan and galactoglucomannan), pectins (e.g., homogalacturonans, rhamnogalacturonan I and II, and xylogalacturonan) and proteoglycans (e.g., arabinogalactan-protein, extensin, and pro line-rich proteins). In some embodiments, the biomass can include and/or be supplemented with citric acid (especially when acetic acid or acetate is the first metabolic product).

In a non-limiting example, the lignocellulosic material can include, but is not limited to, woody biomass, such as recycled wood pulp fiber, sawdust, hardwood, softwood, and combinations thereof; grasses, such as switch grass, cord grass, rye grass, reed canary grass, miscanthus, or a combination thereof; sugar-processing residues, such as but not limited to sugar cane bagasse; agricultural wastes, such as but not limited to rice straw, rice hulls, barley straw, corn cobs, cereal straw, wheat straw, canola straw, oat straw, oat hulls, and corn fiber; stover, such as but not limited to soybean stover, corn stover; succulents, such as but not limited to, agave; and forestry wastes, such as but not limited to, recycled wood pulp fiber, sawdust, hardwood (e.g., poplar, oak, maple, birch, willow), softwood, or any combination thereof. Lignocellulosic material may comprise one species of fiber; alternatively, lignocellulosic material may comprise a mixture of fibers that originate from different lignocellulosic materials. Other lignocellulosic materials are agricultural wastes, such as cereal straws, including wheat straw, barley straw, canola straw and oat straw; corn fiber; stovers, such as corn stover and soybean stover; grasses, such as switch grass, reed canary grass, cord grass, and miscanthus; or combinations thereof.

Substrates for cellulose activity assays can be divided into two categories, soluble and insoluble, based on their solubility in water. Soluble substrates include cellodextrins or derivatives, carboxymethyl cellulose (CMC), or hydroxyethyl cellulose (HEC). Insoluble substrates include crystalline cellulose, microcrystalline cellulose (Avicel), amorphous cellulose, such as phosphoric acid swollen cellulose (PASC), dyed or fluorescent cellulose, and pretreated lignocellulosic biomass. These substrates are generally highly ordered cellulosic material and thus only sparingly soluble.

It will be appreciated that suitable lignocellulosic material may be any feedstock that contains soluble and/or insoluble cellulose, where the insoluble cellulose may be in a crystalline or non-crystalline form. In various embodiments, the lignocellulosic biomass comprises, for example, wood, corn, corn stover, sawdust, bark, molasses, sugarcane, leaves, agricultural and forestry residues, grasses such as switchgrass, ruminant digestion products, municipal wastes, paper mill effluent, newspaper, cardboard or combinations thereof.

Paper sludge is also a viable feedstock for lactate or acetate production. Paper sludge is solid residue arising from pulping and paper-making, and is typically removed from process wastewater in a primary clarifier. The cost of disposing of wet sludge is a significant incentive to convert the material for other uses, such as conversion to ethanol. Processes provided by the present invention are widely applicable. Moreover, the saccharification and/or fermentation products may be used to produce ethanol or higher value added chemicals, such as organic acids, aromatics, esters, acetone and polymer intermediates.

The process of the present disclosure contacting the co-cultures or combinations described herein with a biomass so as to allow the conversion of at least a part of the biomass into the fermentation product. The fermented product can be an alcohol, such as, for example, ethanol, isopropanol, n-propanol, 1-butanol, methanol, acetone and/or 1,2 propanediol. In an embodiment, the biomass or substrate to be hydrolyzed is a lignocellulosic biomass and, in some embodiments, it comprises starch (in a gelatinized or raw form). In the process of the present disclosure, the yeast cells can be first contacted with the biomass. Alternatively, the LAB cells can be first contacted with the biomass. Also, in some embodiments, both the yeast cells and LAB cells can be contacted simultaneously with the biomass.

The fermentation process can be performed at temperatures of at least about 25° C., about 28° C., about 30° C., about 31° C., about 32° C., about 33° C., about 34° C., about 35° C., about 36° C., about 37° C., about 38° C., about 39° C., about 40° C., about 41° C., about 42° C., or about 50° C. In some embodiments, the process can be conducted at temperatures above about 30° C., about 31° C., about 32° C., about 33° C., about 34° C., about 35° C., about 36° C., about 37° C., about 38° C., about 39° C., about 40° C., about 41° C., about 42° C., or about 50° C.

In some embodiments, the yeast and the co-cultures obtained at the end of an initial fermentation cycle can be substantially isolated from the fermented medium and recycled in a further fermentation cycle. In such embodiments, the yeasts and the recombinant LAB cells can be substantially isolated from the fermented medium using, for example, centrifugation. In still another embodiments, the substantially isolated yeasts and recombinant LAB cells can be submitted to an acid wash before being used in a further fermentation cycle.

In some embodiments, the process can be used to produce ethanol at a particular rate. For example, in some embodiments, ethanol is produced at a rate of at least about 0.1 mg per hour per liter, at least about 0.25 mg per hour per liter, at least about 0.5 mg per hour per liter, at least about 0.75 mg per hour per liter, at least about 1.0 mg per hour per liter, at least about 2.0 mg per hour per liter, at least about 5.0 mg per hour per liter, at least about 10 mg per hour per liter, at least about 15 mg per hour per liter, at least about 20.0 mg per hour per liter, at least about 25 mg per hour per liter, at least about 30 mg per hour per liter, at least about 50 mg per hour per liter, at least about 100 mg per hour per liter, at least about 200 mg per hour per liter, or at least about 500 mg per hour per liter.

Ethanol production can be measured using any method known in the art. For example, the quantity of ethanol in fermentation samples can be assessed using HPLC analysis. Many ethanol assay kits are commercially available that use, for example, alcohol oxidase enzyme based assays.

The present invention will be more readily understood by referring to the following examples which are given to illustrate the invention rather than to limit its scope.

Example I—Nisin Production System

The *Lactobacillus paracasei* strain 12A (described in WO2018/013791) was engineered into an ethanologen (*L. paracasei* E3.1) by deleting its native LDH enzymes (ldh1, ldh2, ldh3, ldh4 and dhic) and addition of synthetic genes encoding the PDC (SEQ ID NO: 1, encoded by the nucleic acid sequence of SEQ ID NO: 5) and ADH (SEQ ID NO: 3, encoded by the nucleic acid sequence of SEQ ID NO: 6) enzymes from *Z. mobilis*. Two copies of the *Z. mobilis* genes were integrated into the genome with one cassette driven by the glycolytic phosphoglycerate mutase (pgm) promoter, and the second cassette driven by the promoter of the universal stress protein A (uspA) which has been shown to be up-regulated during late growth stages. In addition, two native genes encoding mannitol-1-phosphate 5-dehydrogenase, mtlD1 and mtlD2, were also deleted to eliminate the conversion of fructose-6-phosphate to mannitol.

The nisin operon of *L. lactis* is complex and consists of 11 distinct genes (nisA, B, T, C, P, R, K, F, E and G). A synthetic operon consisting of only the immunity genes, nisIEFG (encoding respectively the polypeptides of SEQ ID NO: 11 (encoded by the nucleic acid sequence of SEQ ID NO: 56), 13 (encoded by the nucleic acid sequence of SEQ ID NO: 60), 12 (encoded by the nucleic acid sequence of SEQ ID NO: 58), and 14 (encoded by the nucleic acid sequence of SEQ ID NO: 62)), was designed and synthesized. In constructing strains E6.2 and M26400, the nisIFEG gene cluster was integrated into the E3.1 chromosome and expressed by fusing the nisin genes with the synthetic P5 promoter.

The *Lactococcus lactis* strain NP1 was engineered into an ethanologen (e.g., *L. lactis* BAC-1 or M25077) by deletion of the primary L-LDH enzyme and addition of synthetic genes for the PDC (SEQ ID NO: 1, encoded by the nucleic acid sequence of SEQ ID NO: 153) and ADH enzymes (SEQ ID NO: 3, encoded by the nucleic acid sequence of SEQ ID NO: 154) from *Z. mobilis*. The *Z. mobilis* genes were expressed from a high copy plasmid, pNZ8048, driven by the pepN promoter.

Resulting *Lb. paracasei* strains (±the nisin resistance construct) were grown in MRS (no nisin) and MRS supplemented with 500 ppm of nisin. The $OD_{600}$ was monitored. When nisin was absent from the media both strains grew identically, indicating no deleterious effect of NisIEFG expression (FIG. 1). However, when nisin was present, the growth of *Lb. paracasei* E3.1 harboring the empty vector was completely inhibited (FIG. 1). Conversely, the strain expressing the synthetic autoimmunity construct (pDW2-P5-nisIEFG) showed only a minimal decrease in growth rate (FIG. 1).

The nisin producing *L. lactis* strain and a non-nisin producing *L. lactis* control were grown in MRS broth at 30° C. for two transfers. The supernatant was harvested by centrifugation and filter sterilized through a 0.22 μm syringe filter. Eleven ethanol plant isolates, as described in Table 1, were grown for two transfers in MRS and inoculated into a microtiter plate containing MRS media with various dilutions (⅕, ⅒, 1/20, and 1/50) of supernatants from each of the two *L. lactis* strains.

TABLE 1

List of plant isolates tested for nisin sensitivity. The process step from which the strain was isolated is included.
*Lb, Lactobacillus; P., Pediococcus.*

| Identifier | Species | Process Step |
|---|---|---|
| M14628 | *Lb. reuteri* | Fermentation |
| M15054 | *Lb. brevis* | Cooled mash |
| M16690 | *Lb. plantarum* | Cooled mash |
| M16696 | *Lb. helveticus* | Cooled mash |
| M16701 | *Lb. plantarum* | Recycled water |
| M16840 | *Lb. pontis* | Fermentation |
| M16927 | *Lb. amylovorous* | Beer well |
| M17005 | *Lb. paracasei* | Fermentation |
| M17455 | *Lb. plantarum* | Fermentation |
| M17468 | *P. pentosaceus* | Fermentation |
| M17634 | *Lb. fermentum* | Beer well |

Figure 2:
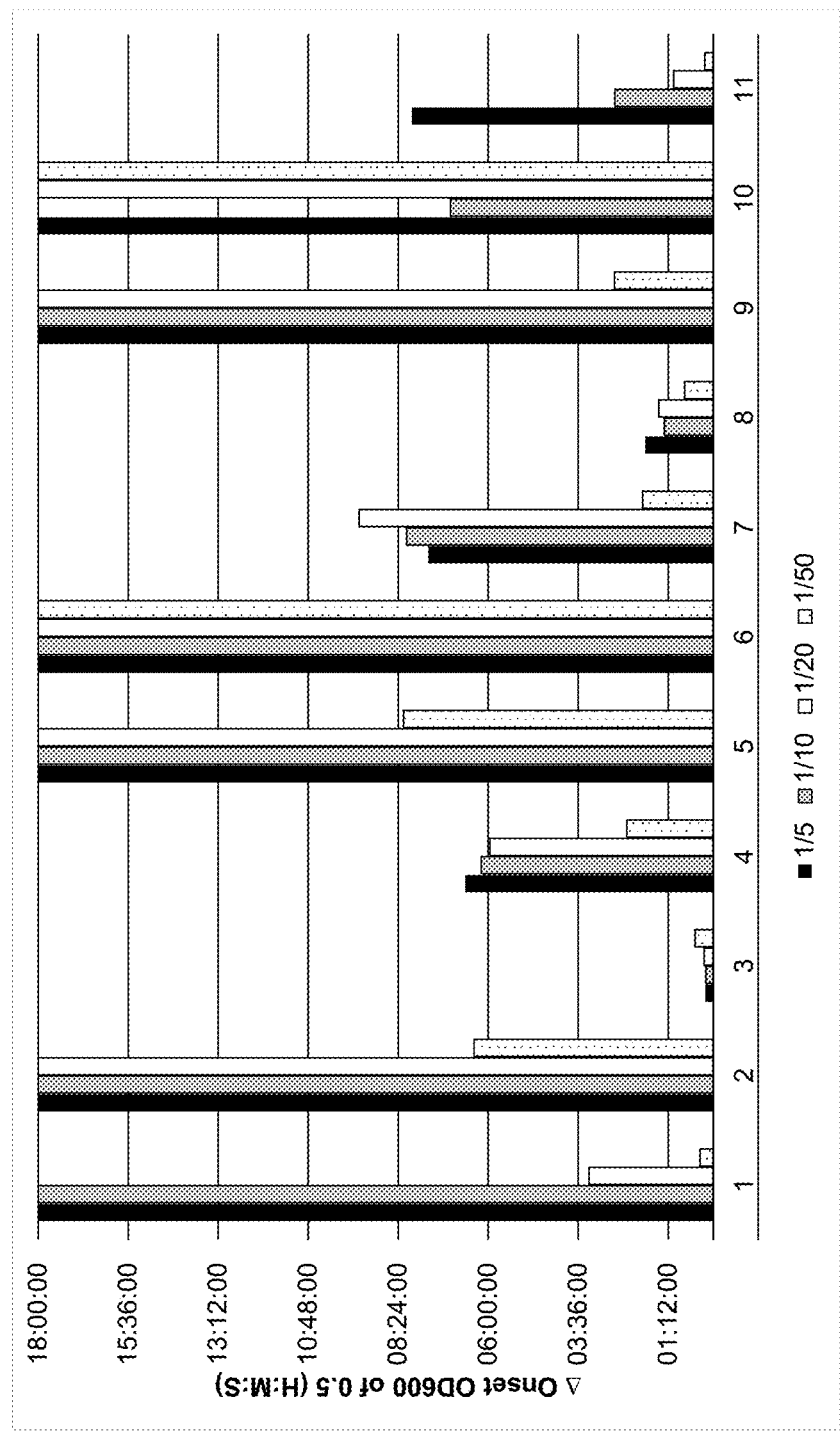
FIG. 2 illustrates the time required for the different isolates to reach an OD of 0.5 in ⅕, ⅒, 1/20 and 1/50 dilutions of *L. lactis* nisin containing supernatant. Results are shown as the onset of $OD_{600}$ of 0.5 in function of the strain as well as supernatant concentration used.

The $OD_{600}$ was monitored for 18 hours and the time to reach an a reading of 0.5 was recorded for each strain. The increase in time observed between the nisin containing supernatant and the non-nisin control was plotted and used as a measure of nisin inhibition. No difference in growth was observed for strains containing the various doses of control supernatant whereas six of the eleven strains tested were completely inhibited by the nisin containing supernatant (FIG. 2). The remaining strains showed various levels of inhibition but were able to reach an $OD_{600}$ of 0.5 within the 18 hour time frame (FIG. 2).

Strains *L. paracasei* E6.2 and *L. lactis* BAC-1 were cultured individually or together in a medium comprising of fermentation backset (e.g., a liquid obtained after the fermentation of corn, the removal of distilled dried grains and ethanol distillation) with 8.5% solids, a pH 5.5, 4% glucose at a temperature of 33° C. The colony-forming units (CFU) were determined at various time intervals and are presented in Table 2.

TABLE 2

CFU per mL of *L. paracasei* E6.2 and *L. lactis* BAC-1 cells at the initiation of culture (0 h) as well as 12 h, 36 h, 42 h and 48 h after the beginning of the culture.

| Time | *L. lactis* BAC-1 | *L. paracasei* E6.2 | *L. lactis* BAC-1 *L. paracasei* E6.2 |
|---|---|---|---|
| 0 h | $1.1 \times 10^6$ | $5.0 \times 10^5$ | $1.0 \times 10^6$ $5.0 \times 10^5$ |
| 12 h | $1.9 \times 10^7$ | $3.7 \times 10^7$ | $5.0 \times 10^6$ $1.9 \times 10^7$ |
| 36 h | $1.8 \times 10^9$ | $5.0 \times 10^9$ | $7.0 \times 10^8$ $3.1 \times 10^9$ |
| 42 h | $2.1 \times 10^9$ | $4.0 \times 10^9$ | $7.0 \times 10^8$ $2.1 \times 10^9$ |
| 48 h | $1.6 \times 10^9$ | $7.0 \times 10^9$ | $7.0 \times 10^8$ $4.0 \times 10^9$ |

Example II—Pediocin Expression System

Figures 3A, 3B, 3C, 3D:
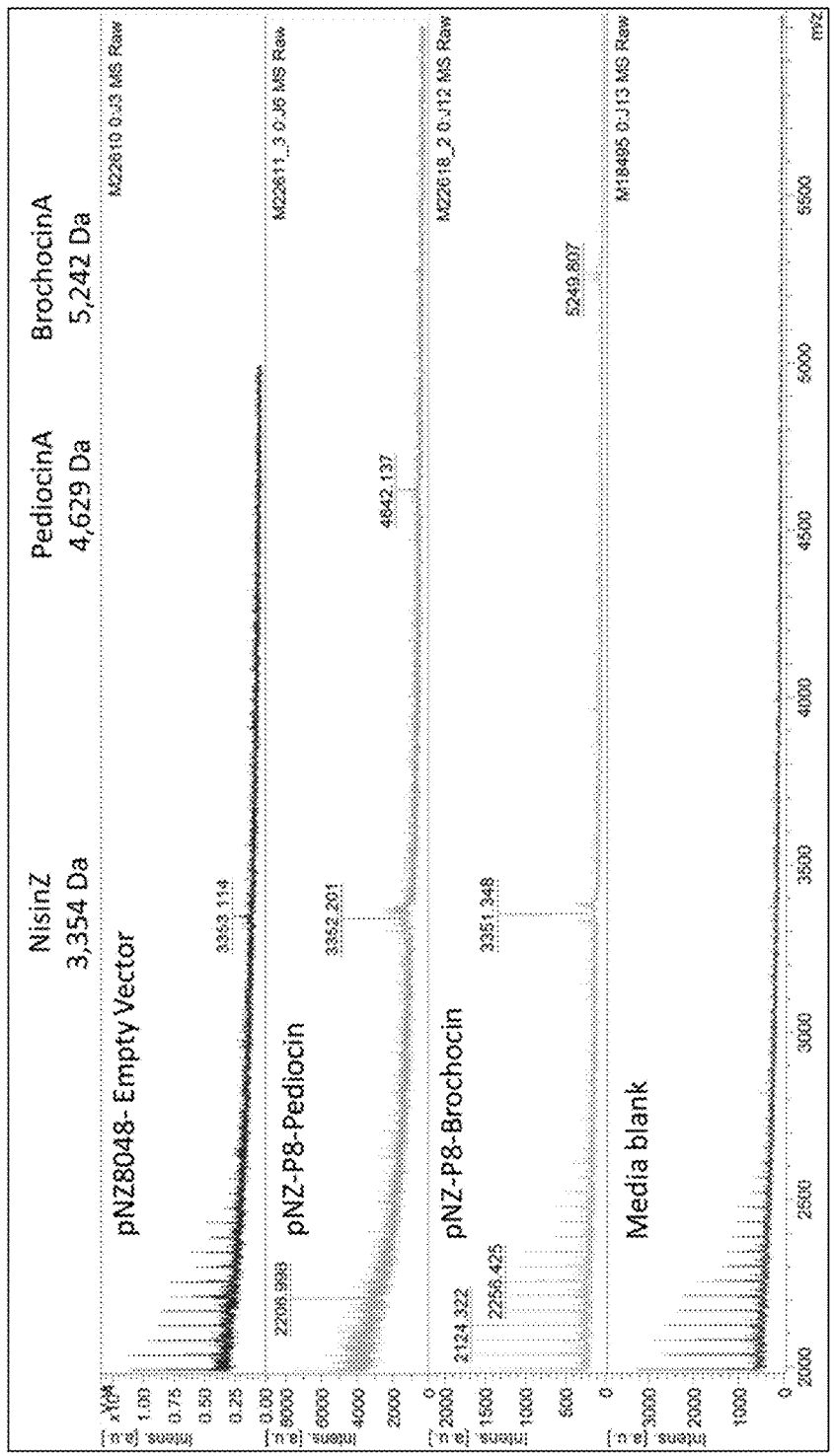
FIGS. 3A to 3D illustrate the detection by mass spectrometry of various bacteriocins produced by various *L. lactis* strains in a culture medium.

The nisin producing *L. lactis* strain NP1 was engineered to secrete pediocin via the high copy vector pNZ8048. The four genes responsible for pediocin production, immunity, and processing, pedABCD, were cloned in a single operon under control of the *L. lactis* phosphopentomutase promoter. The native pediocin secretion signal was maintained on PedA. Resulting *L. lactis* strains were propagated in GM17 substrate and supernatants were analyzed for the presence of pediocin by MALDI-TOF mass spectrometry (see results shown in FIG. 3B).

Example III—Brochocin Expression System

The nisin producing *L. lactis* strain NP1 was engineered to secrete brochocin via the high copy vector pNZ8048. The structural and immunity genes from the pediocin operon described above, PedAB, were replaced with the two structural proteins of brochocin, brcAB as well as the immunity gene brcI. The native pediocin secretion signal was therefore utilized for BrcA secretion as well as the pediocin processing genes pedCD. The resulting strains were propagated in GM17 substrate and the supernatants analyzed for the presence of brochocin by MALDI-TOF mass spectrometry (see results shown in FIG. 3C).

Example IV—Additional Bacteriocin Expression Systems

Additional bacteriocin expression systems have been designed and constructed. The details of these additional bacteriocin expression systems are provided in Table 3.

TABLE 3

Description of the proteins encoded by the various bacteriocin systems as well as the nucleic acid present in the various bacteriocin systems. Each cassette includes coding regions for a bacteriocin, its related immunity protein(s) and, when present its additional related protein(s).

| Bacteriocin system | Bacteriocin | Related immunity protein(s) | Additional related proteins (transport, processing, etc.) |
|---|---|---|---|
| Pediocin 20336A | PedA with native signal sequence (SEQ ID NO: 51); or PedA with usp45TM8 signal sequence (SEQ ID NO: 75 or 144) | PedB (SEQ ID NO: 22) | PedC (SEQ ID NO: 146); and PedD (SEQ ID NO: 149) |
| | pedA (SEQ ID NO: 74) | pedB (SEQ ID NO: 77 or 78) | pedC (SEQ ID NO: 148); and pedD (SEQ ID NO: 151) |
| Lactococcin A | LcnA with native signal sequence (SEQ ID NO: 40) | LciA (SEQ ID NO: 42) | LcmA (SEQ ID NO: 43); and LceA (SEQ ID NO: 44) |
| | lcnA (SEQ ID NO: 121) | lciA (SEQ ID NO: 122) | lcmA (SEQ ID NO: 124) |
| Horediocin | HdrA (SEQ ID NO: 46) | HdrI (SEQ ID NO: 47) | HdrM (SEQ ID NO: 48) |
| | hdrA (SEQ ID NO: 130) | hdrI (SEQ ID NO: 133) | hdrM (SEQ ID NO: 136) |
| Plantaricin 423 | PlaA (SEQ ID NO: 36) | PlaB (SEQ ID NO: 37) | |
| | plaA (SEQ ID NO: 112) | plaB (SEQ ID NO: 115) | |
| Plantaricyclin A | PlcA (SED ID NO: 28) | PlcD (SEQ ID NO: 30); and PlcI (SEQ ID NO: 31) | PlcT (SEQ ID NO: 32); PlcE (SEQ ID NO: 33); and PlcB (SEQ ID NO: 34) |
| | plcA (SEQ ID NO: 94) | plcD (SEQ ID NO: 96); and plcI (SEQ ID NO: 99) | plcT (SEQ ID NO: 102) |

While the invention has been described in connection with specific embodiments thereof, it will be understood that the scope of the claims should not be limited by the preferred embodiments set forth in the examples, but should be given the broadest interpretation consistent with the description as a whole.

REFERENCES

Fukao M, Obita T, Yoneyama F, Kohda D, Zendo T, Nakayama J, Sonomoto K. Complete covalent structure of nisin Q, new natural nisin variant, containing post-translationally modified amino acids. Biosci Biotechnol Biochem. 2008 July; 72(7):1750-5.

O'Connor P M, O'Shea E F, Guinane C M, O'Sullivan O, Cotter P D, Ross R P, Hill C. Nisin H Is a New Nisin Variant Produced by the Gut-Derived Strain *Streptococcus* hyointestinalis DPC6484. Appl Environ Microbiol. 2015 Jun. 15; 81(12):3953-60.

O'Sullivan J N, O'Connor P M, Rea M C, O'Sullivan O, Walsh C J, Healy B, Mathur H, Field D, Hill C, Ross R P. Nisin J, a Novel Natural Nisin Variant, Is Produced by *Staphylococcus capitis* Sourced from the Human Skin Microbiota. J Bacteriol. 2020 Jan. 15; 202(3).

Wirawan R E, Klesse N A, Jack R W, Tagg J R. Molecular and genetic characterization of a novel nisin variant produced by *Streptococcus uberis*. Appl Environ Microbiol. 2006 February; 72(2):1148-56.

What is claimed is:

1. A co-culture of lactic acid bacterial cells for making ethanol from a biomass, the co-culture comprising:
a first recombinant lactic acid bacteria (LAB) cell:
expressing at least one bacteriocin; and
comprising heterologous nucleic acid molecules encoding polypeptides for converting the biomass into ethanol;
and
a second recombinant LAB cell:
capable of converting the biomass into ethanol; comprising heterologous nucleic acid molecules encoding polypeptides for converting the biomass into ethanol;
and comprising one or more heterologous nucleic acid molecules encoding one or more polypeptides for conferring immunity against the at least one bacteriocin expressed by the first recombinant LAB cell
wherein the polypeptides for converting the biomass into ethanol comprise at least:
a pyruvate decarboxylase; and
an alcohol dehydrogenase,
wherein the at least one bacteriocin comprises a lantibiotic, a cyclic bacteriocin, a Class IIA bacteriocin, a Class IIB bacteriocin, or a combination thereof.

2. The co-culture of claim 1, wherein the Lantibiotic is nisin and the heterologous nucleic acid molecule encoding one or more polypeptides for conferring immunity against the at least one bacteriocin encodes NisI; the cyclic bacteriocin is gassericin and the heterologous nucleic acid molecule encoding one or more polypeptides for conferring immunity against the at least one bacteriocin encodes GaaI; the cyclic bacteriocin is plantaricyclin A and the heterologous nucleic acid molecule encoding one or more polypeptides for conferring immunity against the at least one bacteriocin encodes PlcD and/or PlcI; the Class IIA bacteriocin is plantaricin 423 and the heterologous nucleic acid molecule encoding one or more polypeptides for conferring immunity against the at least one bacteriocin encodes PlaB; the Class IIA bacteriocin is pediocin and the heterologous nucleic acid molecule encoding one or more polypeptides for conferring immunity against the at least one bacteriocin encodes PedB; the Class IIA bacteriocin is lactoccin A and the heterologous nucleic acid molecule encoding one or more polypeptides for conferring immunity against the at least one bacteriocin encodes LciA; the Class IIA bacteriocin is horediocin A and the heterologous nucleic acid molecule encoding one or more polypeptides for conferring immunity against the at least one bacteriocin encodes HdrI; or the Class IIB bacteriocin is brochocin and the heterologous nucleic acid molecule encoding one or more polypeptides for conferring immunity against the at least one bacteriocin encodes BrcI.

3. The co-culture of claim 2, wherein nisin has the amino acid sequence of any one of SEQ ID NOS: 7 to 10, is a variant of the amino acid sequence of any one of SEQ ID NOS: 7 to 10 having nisin bacteriocin activity or is a fragment of the amino acid sequence of any one of SEQ ID NOS: 7 to 10 having nisin bacteriocin activity.

4. The co-culture of claim 2, wherein NisI has the amino acid sequence of SEQ ID NO: 11, is a variant of the amino acid sequence of SEQ ID NO: 11 conferring immunity against nisin or is a fragment of the amino acid sequence of SEQ ID NO: 11 conferring immunity against nisin.

5. The co-culture of claim 2, wherein the heterologous nucleic acid molecule encoding one or more polypeptides for conferring immunity against the at least one bacteriocin further encodes NisE, NisF and/or NisG.

6. The co-culture of claim 5, wherein NisE has the amino acid sequence of SEQ ID NO: 13, is a variant of the amino acid sequence of SEQ ID NO: 13 having nisin transporter activity or is a fragment of the amino acid sequence of SEQ ID NO: 13 having nisin transporter activity.

7. The co-culture of claim 5, wherein NisF has the amino acid sequence of SEQ ID NO: 12, is a variant of the amino acid sequence of SEQ ID NO: 12 having nisin transporter activity or is a fragment of the amino acid sequence of SEQ ID NO: 12 having nisin transporter activity.

8. The co-culture of claim 5, wherein NisG has the amino acid sequence of SEQ ID NO: 14, is a variant of the amino acid sequence of SEQ ID NO: 14 having nisin permease activity or is a fragment of the amino acid sequence of SEQ ID NO: 14 having nisin permease activity.

9. The co-culture of claim 1, wherein the first recombinant LAB cell expresses a plurality of bacteriocins.

10. The co-culture of claim 1, wherein the pyruvate decarboxylase has the amino acid sequence of SEQ ID NO: 1, is a variant of the amino acid sequence of SEQ ID NO: 1 having pyruvate decarboxylase activity or is a fragment of the amino acid sequence of SEQ ID NO: 1 having pyruvate decarboxylase activity.

11. The co-culture of claim 1, wherein the alcohol dehydrogenase has the amino acid sequence of SEQ ID NO: 3, is a variant of the amino acid sequence of SEQ ID NO: 3 having alcohol dehydrogenase activity or is a fragment of the amino acid sequence of SEQ ID NO: 3 having alcohol dehydrogenase activity.

12. The co-culture of claim 1, wherein the first recombinant LAB cell and/or the second recombinant LAB cell comprises:
at least one inactivated or deleted native gene coding for a lactate dehydrogenase;
inactivated or deleted native ldh1, ldh2, ldh3, ldh4 and dhic genes;
at least one inactivated or deleted native gene coding for a mannitol-1-phosphate 5-dehydrogenase; and/or
inactivated or deleted native mltD1 and mltD2 genes.

13. The co-culture of claim 1, wherein the first recombinant LAB cell is from the genus *Lactococcus* or from the species *Lactococcus lactis*.

14. The co-culture of claim 1, wherein the second recombinant LAB cell is from the genus *Lactobacillus* or from the species *Lactobacillus paracasei*.

15. A combination comprising the co-culture of claim 1 and a yeast cell.

16. A process for converting a biomass into a fermentation product, wherein the process comprises contacting the biomass with the co-culture of claim 1 under conditions to allow the conversion of the biomass into said fermentation product of claim 1.

17. The process of claim 16, wherein the biomass comprises corn.

18. The process of claim 16, wherein said fermentation product is ethanol.

19. The co-culture of claim 1, wherein the at least one bacteriocin is native to the first recombinant LAB cell.

20. The co-culture of claim 1, wherein the first recombinant LAB cell further comprises a heterologous nucleic acid molecule encoding the at least one bacteriocin and one or more polypeptides for conferring immunity against the at least one bacteriocin.

21. The combination of claim 15 wherein the yeast cell is from the genus *Saccharomyces* sp.

22. The combination of claim 15 wherein the yeast cell is from the species *Saccharomyces cerevisiae*.

* * * * *

SEQUENCE LISTING

```
<160> NUMBER OF SEQ ID NOS: 154

<210> SEQ ID NO 1
<211> LENGTH: 568
<212> TYPE: PRT
<213> ORGANISM: Zymomonas mobilis

<400> SEQUENCE: 1

Met Ser Tyr Thr Val Gly Thr Tyr Leu Ala Glu Arg Leu Val Gln Ile
1               5                   10                  15

Gly Leu Lys His His Phe Ala Val Ala Gly Asp Tyr Asn Leu Val Leu
                20                  25                  30

Leu Asp Asn Leu Leu Leu Asn Lys Asn Met Glu Gln Val Tyr Cys Cys
            35                  40                  45

Asn Glu Leu Asn Cys Gly Phe Ser Ala Glu Gly Tyr Ala Arg Ala Lys
        50                  55                  60

Gly Ala Ala Ala Val Val Thr Tyr Ser Val Gly Ala Leu Ser Ala
65                  70                  75                  80

Phe Asp Ala Ile Gly Gly Ala Tyr Ala Glu Asn Leu Pro Val Ile Leu
                85                  90                  95

Ile Ser Gly Ala Pro Asn Asn Asn Asp His Ala Ala Gly His Val Leu
            100                 105                 110

His His Ala Leu Gly Lys Thr Asp Tyr His Tyr Gln Leu Glu Met Ala
        115                 120                 125

Lys Asn Ile Thr Ala Ala Ala Glu Ala Ile Tyr Thr Pro Glu Glu Ala
    130                 135                 140

Pro Ala Lys Ile Asp His Val Ile Lys Thr Ala Leu Arg Glu Lys Lys
145                 150                 155                 160

Pro Val Tyr Leu Glu Ile Ala Cys Asn Ile Ala Ser Met Pro Cys Ala
                165                 170                 175

Ala Pro Gly Pro Ala Ser Ala Leu Phe Asn Asp Glu Ala Ser Asp Glu
            180                 185                 190

Ala Ser Leu Asn Ala Ala Val Glu Glu Thr Leu Lys Phe Ile Ala Asn
        195                 200                 205

Arg Asp Lys Val Ala Val Leu Val Gly Ser Lys Leu Arg Ala Ala Gly
    210                 215                 220

Ala Glu Ala Ala Val Lys Phe Ala Asp Ala Leu Gly Gly Ala Val
225                 230                 235                 240

Ala Thr Met Ala Ala Lys Ser Phe Phe Pro Glu Glu Asn Pro His
                245                 250                 255

Tyr Ile Gly Thr Ser Trp Gly Glu Val Ser Tyr Pro Gly Val Glu Lys
            260                 265                 270
```

```
Thr Met Lys Glu Ala Asp Ala Val Ile Ala Leu Ala Pro Val Phe Asn
            275                 280                 285

Asp Tyr Ser Thr Thr Gly Trp Thr Asp Ile Pro Asp Pro Lys Lys Leu
            290                 295                 300

Val Leu Ala Glu Pro Arg Ser Val Val Val Asn Gly Val Arg Phe Pro
305                 310                 315                 320

Ser Val His Leu Lys Asp Tyr Leu Thr Arg Leu Ala Gln Lys Val Ser
                325                 330                 335

Lys Lys Thr Gly Ala Leu Asp Phe Phe Lys Ser Leu Asn Ala Gly Glu
            340                 345                 350

Leu Lys Lys Ala Ala Pro Ala Asp Pro Ser Ala Pro Leu Val Asn Ala
            355                 360                 365

Glu Ile Ala Arg Gln Val Glu Ala Leu Leu Thr Pro Asn Thr Thr Val
            370                 375                 380

Ile Ala Glu Thr Gly Asp Ser Trp Phe Asn Ala Gln Arg Met Lys Leu
385                 390                 395                 400

Pro Asn Gly Ala Arg Val Glu Tyr Glu Met Gln Trp Gly His Ile Gly
            405                 410                 415

Trp Ser Val Pro Ala Ala Phe Gly Tyr Ala Val Gly Ala Pro Glu Arg
            420                 425                 430

Arg Asn Ile Leu Met Val Gly Asp Gly Ser Phe Gln Leu Thr Ala Gln
            435                 440                 445

Glu Val Ala Gln Met Val Arg Leu Lys Leu Pro Val Ile Ile Phe Leu
            450                 455                 460

Ile Asn Asn Tyr Gly Tyr Thr Ile Glu Val Met Ile His Asp Gly Pro
465                 470                 475                 480

Tyr Asn Asn Ile Lys Asn Trp Asp Tyr Ala Gly Leu Met Glu Val Phe
            485                 490                 495

Asn Gly Asn Gly Gly Tyr Asp Ser Gly Ala Gly Lys Gly Leu Lys Ala
            500                 505                 510

Lys Thr Gly Gly Glu Leu Ala Glu Ala Ile Lys Val Ala Leu Ala Asn
            515                 520                 525

Thr Asp Gly Pro Thr Leu Ile Glu Cys Phe Ile Gly Arg Glu Asp Cys
530                 535                 540

Thr Glu Glu Leu Val Lys Trp Gly Lys Arg Val Ala Ala Ala Asn Ser
545                 550                 555                 560

Arg Lys Pro Val Asn Lys Leu Leu
                565

<210> SEQ ID NO 2
<211> LENGTH: 1707
<212> TYPE: DNA
<213> ORGANISM: Zymomonas mobilis

<400> SEQUENCE: 2
atgagttata ctgtcggtac ctatttagcg gagcggcttg tccagattgg tctcaagcat     60
cacttcgcag tcgcgggcga ctacaacctc gtccttcttg acaacctgct tttgaacaaa    120
aacatggagc aggtttattg ctgtaacgaa ctgaactgcg gtttcagtgc agaaggttat    180
gctcgtgcca aggcgcagc agcagccgtc gttacctaca cgtcggtgc ctttccgca    240 tttgatgcta tcggtggcgc ctatgcagaa aaccttccgg ttatcctgat ctccggtgct    300
ccgaacaaca atgatcacgc tgctggtcac gtgttgcatc acgctcttgg caaaaccgac    360
tatcactatc agttggaaat ggccaagaac atcacggccg cagctgaagc gatttacacc    420
```

```
ccagaagaag ctccggctaa aatcgatcac gtgattaaaa ctgctcttcg tgagaagaag      480
ccggtttatc tcgaaatcgc ttgcaacatt gcttccatgc cctgcgccgc tcctggaccg      540
gcaagcgcat tgttcaatga cgaagccagc gacgaagctt ctttgaatgc agcggttgaa      600
gaaaccctga aattcatcgc caaccgcgac aaagttgccg tcctcgtcgg cagcaagctg      660
cgcgcagctg gtgctgaaga agctgctgtc aaatttgctg atgctctcgg tggcgcagtt      720
gctaccatgg ctgctgcaaa aagcttcttc ccagaagaaa acccgcatta catcggtacc      780
tcatggggtg aagtcagcta tccgggcgtt gaaaagacga tgaaagaagc cgatgcggtt      840
atcgctctgg ctcctgtctt caacgactac tccaccactg gttggacgga tattcctgat      900
cctaagaaac tggttctcgc tgaaccgcgt tctgtcgtcg ttaacggcgt tcgcttcccc      960
agcgttcatc tgaaagacta tctgacccgt ttggctcaga agtttccaa gaaaaccggt      1020 gctttggact tcttcaaatc cctcaatgca ggtgaactga agaaagccgc tccggctgat     1080
ccgagtgctc cgttggtcaa cgcagaaatc gcccgtcagg tcgaagctct tctgaccccg     1140
aacacgacgg ttattgctga aaccggtgac tcttggttca atgctcagcg catgaagctc     1200
ccgaacggtg ctcgcgttga atatgaaatg cagtggggtc acatcggttg gtccgttcct     1260
gccgccttcg gttatgccgt cggtgctccg gaacgtcgca acatcctcat ggttggtgat     1320
ggttccttcc agctgacggc tcaggaagtc gctcagatgg ttcgcctgaa actgccggtt     1380
atcatcttct tgatcaataa ctatggttac accatcgaag ttatgatcca tgatggtccg     1440
tacaacaaca tcaagaactg ggattatgcc ggtctgatgg aagtgttcaa cggtaacggt     1500
ggttatgaca gcggtgctgg taaaggcctg aaggctaaaa ccggtggcga actggcagaa     1560
gctatcaagg ttgctctggc aaacaccgac ggcccaaccc tgatcgaatg cttcatcggt     1620
cgtgaagact gcactgaaga attggtcaaa tggggtaagc gcgttgctgc cgccaacagc     1680
cgtaagcctg ttaacaagct cctctag                                         1707
```

<210> SEQ ID NO 3
<211> LENGTH: 383
<212> TYPE: PRT
<213> ORGANISM: Zymomonas mobilis

<400> SEQUENCE: 3

```
Met Ala Ser Ser Thr Phe Tyr Ile Pro Phe Val Asn Glu Met Gly Glu
1               5                   10                  15

Gly Ser Leu Glu Lys Ala Ile Lys Asp Leu Asn Gly Ser Gly Phe Lys
                20                  25                  30

Asn Ala Leu Ile Val Ser Asp Ala Phe Met Asn Lys Ser Gly Val Val
            35                  40                  45

Lys Gln Val Ala Asp Leu Leu Lys Ala Gln Gly Ile Asn Ser Ala Val
        50                  55                  60

Tyr Asp Gly Val Met Pro Asn Pro Thr Val Thr Ala Val Leu Glu Gly
65                  70                  75                  80

Leu Lys Ile Leu Lys Asp Asn Asn Ser Asp Phe Val Ile Ser Leu Gly
                85                  90                  95

Gly Gly Ser Pro His Asp Cys Ala Lys Ala Ile Ala Leu Val Ala Thr
            100                 105                 110

Asn Gly Gly Glu Val Lys Asp Tyr Glu Gly Ile Asp Lys Ser Lys Lys
        115                 120                 125

Pro Ala Leu Pro Leu Met Ser Ile Asn Thr Thr Ala Gly Thr Ala Ser
    130                 135                 140
```

Glu Met Thr Arg Phe Cys Ile Ile Thr Asp Glu Val Arg His Val Lys
145                 150                 155                 160

Met Ala Ile Val Asp Arg His Val Thr Pro Met Val Ser Val Asn Asp
            165                 170                 175

Pro Leu Leu Met Val Gly Met Pro Lys Gly Leu Thr Ala Ala Thr Gly
        180                 185                 190

Met Asp Ala Leu Thr His Ala Phe Glu Ala Tyr Ser Ser Thr Ala Ala
    195                 200                 205

Thr Pro Ile Thr Asp Ala Cys Ala Leu Lys Ala Ala Ser Met Ile Ala
210                 215                 220

Lys Asn Leu Lys Thr Ala Cys Asp Asn Gly Lys Asp Met Pro Ala Arg
225                 230                 235                 240

Glu Ala Met Ala Tyr Ala Gln Phe Leu Ala Gly Met Ala Phe Asn Asn
                245                 250                 255

Ala Ser Leu Gly Tyr Val His Ala Met Ala His Gln Leu Gly Gly Tyr
            260                 265                 270

Tyr Asn Leu Pro His Gly Val Cys Asn Ala Val Leu Leu Pro His Val
        275                 280                 285

Leu Ala Tyr Asn Ala Ser Val Val Ala Gly Arg Leu Lys Asp Val Gly
290                 295                 300

Val Ala Met Gly Leu Asp Ile Ala Asn Leu Gly Asp Lys Glu Gly Ala
305                 310                 315                 320

Glu Ala Thr Ile Gln Ala Val Arg Asp Leu Ala Ala Ser Ile Gly Ile
                325                 330                 335

Pro Ala Asn Leu Thr Glu Leu Gly Ala Lys Lys Glu Asp Val Pro Leu
            340                 345                 350

Leu Ala Asp His Ala Leu Lys Asp Ala Cys Ala Leu Thr Asn Pro Arg
        355                 360                 365

Gln Gly Asp Gln Lys Glu Val Glu Glu Leu Phe Leu Ser Ala Phe
    370                 375                 380

<210> SEQ ID NO 4
<211> LENGTH: 1152
<212> TYPE: DNA
<213> ORGANISM: Zymomonas mobilis

<400> SEQUENCE: 4
atggcttctt caactttta tattcctttc gtcaacgaaa tgggcgaagg ttcgcttgaa      60
aaagcaatca aggatcttaa cggcagcggc tttaaaaatg cgctgatcgt ttctgatgct     120
ttcatgaaca atccggtgt tgtgaagcag gttgctgacc tgttgaaagc acagggtatt     180
aattctgctg tttatgatgg cgttatgccg aacccgactg ttaccgcagt tctggaaggc     240
cttaagatcc tgaaggataa caattcagac ttcgtcatct ccctcggtgg tggttctccc     300
catgactgcg ccaaagccat cgctctggtc gcaaccaatg gtggtgaagt caaagactac     360
gaaggtatcg acaaatctaa gaaacctgcc ctgcctttga tgtcaatcaa cacgacggct     420
ggtacggctt ctgaaatgac gcgttctgc atcatcactg atgaagtccg tcacgttaag     480
atggccattg ttgaccgtca cgttaccccg atggtttccg tcaacgatcc tctgttgatg     540
gttggtatgc caaaaggcct gaccgccgcc accggtatgg atgctctgac ccacgcattt     600
gaagcttatt cttcaacggc agctactccg atcaccgatg cttgcgcctt gaaggctgcg     660
tccatgatcg ctaagaatct gaagaccgct tgcgacaacg gtaaggatat gccagctcgt     720
gaagctatgg cttatgccca attcctcgct ggtatggcct tcaacaacgc ttcgcttggt     780

| | |
|---|---|
| tatgtccatg ctatggctca ccagttgggc ggctactaca acctgccgca tggtgtctgc | 840 |
| aacgctgttc tgcttccgca tgttctggct tataacgcct ctgtcgttgc tggtcgtctg | 900 |
| aaagacgttg gtgttgctat gggtctcgat atcgccaatc tcggtgataa agaaggcgca | 960 |
| gaagccacca ttcaggctgt tcgcgatctg gctgcttcca ttggtattcc agcaaatctg | 1020 |
| accgagctgg gtgctaagaa agaagatgtg ccgcttcttg ctgaccacgc tctgaaagat | 1080 |
| gcttgtgctc tgaccaaccc gcgtcagggt gatcagaaag aagttgaaga actcttcctg | 1140 |
| agcgctttct aa | 1152 |

<210> SEQ ID NO 5
<211> LENGTH: 1707
<212> TYPE: DNA
<213> ORGANISM: Artificial Sequence
<220> FEATURE:
<223> OTHER INFORMATION: Codon-optimized version for Lactobacillus paracasei encoding SEQ ID NO: 1

<400> SEQUENCE: 5

| | |
|---|---|
| atgtcatata ccgttggcac ctatttggct gaacgtttgg ttcaaatcgg cttgaagcac | 60 |
| cacttcgctg ttgctggcga ttataacttg gttttgttgg ataacttgtt gttgaacaag | 120 |
| aacatggaac aagtttattg ctgcaacgaa ttgaactgcg gcttctcagc tgaaggctat | 180 |
| gctcgtgcta aggcgctgc tgctgctgtt gttacctatt cagttggcgc tttgtcagct | 240 |
| ttcgatgcta tcggcggcgc ttatgctgaa aacttgccag ttatcttgat ctcaggcgct | 300 |
| ccaaacaaca acgatcacgc tgctggccac gttttgcacc acgctttggg caagaccgat | 360 |
| tatcactatc aattggaaat ggctaagaac atcaccgctg ctgctgaagc tatctatacc | 420 |
| ccagaagaag ctccagctaa gatcgatcac gttatcaaga ccgctttgcg tgaaaagaag | 480 |
| ccagttttatt tggaaatcgc ttgcaacatc gcttcaatgc catgcgctgc tccaggccca | 540 |
| gcttcagctt tgttcaacga tgaagcttca gatgaagctt cattgaacgc tgctgttgaa | 600 |
| gaaaccttga gttcatcgc taaccgtgat aaggttgctg ttttggttgg ctcaaagttg | 660 |
| cgtgctgctg gcgctgaaga gctgctgtt aagttcgctg atgctttggg cggcgctgtt | 720 |
| gctaccatgg ctgctgctaa gtcattcttc ccagaagaaa acccacacta tcggcacc | 780 |
| tcatggggcg aagtttcata tccaggcgtt gaaaagacca tgaaggaagc tgatgctgtt | 840 |
| atcgctttgg ctccagtttt caacgattat tcaaccaccg ctggaccga tatcccagat | 900 |
| ccaaagaagt tggttttggc tgaaccacgt tcagttgttg ttaacggcgt tcgtttccca | 960 |
| tcagttcact tgaaggatta tttgacccgt ttggctcaaa aggtttcaaa gaagaccggc | 1020 |
| gctttggatt tcttcaagtc attgaacgct ggcgaattga agaaggctgc tccagctgat | 1080 |
| ccatcagctc cattggttaa cgctgaaatc gctcgtcaag ttgaagcttt gttgacccca | 1140 |
| aacaccaccg ttatcgctga aaccggcgat tcatggttca cgctcaacg tatgaagttg | 1200 |
| ccaaacggcg ctcgtgttga atatgaaatg caatggggcc acatcggctg gtcagttcca | 1260 |
| gctgctttcg gctatgctgt tggcgctcca gaacgtcgta acatcttgat ggttggcgat | 1320 |
| ggctcattcc aattgaccgc tcaagaagtt gctcaaatgg ttcgtttgaa gttgccagtt | 1380 |
| atcatcttct tgatcaacaa ctatggctat accatcgaag ttatgatcca cgatggccca | 1440 |
| tataacaaca tcaagaactg ggattatgct ggcttgatgg aagttttcaa cggcaacggc | 1500 |
| ggctatgatt caggcgctgg caagggcttg aaggctaaga ccggcggcga attggctgaa | 1560 |
| gctatcaagg ttgctttggc taacaccgat ggcccaacct tgatcgaatg cttcatcggc | 1620 |

```
cgtgaagatt gcaccgaaga attggttaag tggggcaagc gtgttgctgc tgctaactca    1680
cgtaagccag ttaacaagtt gttgtag                                        1707

<210> SEQ ID NO 6
<211> LENGTH: 1152
<212> TYPE: DNA
<213> ORGANISM: Artificial Sequence
<220> FEATURE:
<223> OTHER INFORMATION: Codon-optimized version for Lactobacillus
      paracasei encoding SEQ ID NO: 3

<400> SEQUENCE: 6
atggcttcat caaccttcta tatcccattc gttaacgaaa tgggcgaagg ctcattggaa      60
aaggctatca aggatttgaa cggctcaggc ttcaagaacg ctttgatcgt ttcagatgct     120
ttcatgaaca gtcaggcgt tgttaagcaa gttgctgatt tgttgaaggc tcaaggcatc      180
aactcagctg tttatgatgg cgttatgcca aacccaaccg ttaccgctgt tttggaaggc     240
ttgaagatct tgaaggataa caactcagat ttcgttatct cattgggcgg cggctcacca     300
cacgattgcg ctaaggctat cgctttggtt gctaccaacg gcggcgaagt taaggattat     360
gaaggcatcg ataagtcaaa gaagccagct ttgccattga tgtcaatcaa caccaccgct     420
ggcaccgctt cagaaatgac ccgtttctgc atcatcaccg atgaagttcg tcacgttaag     480
atggctatcg ttgatcgtca cgttacccca atggtttcag ttaacgatcc attgttgatg     540
gttggcatgc caaagggctt gaccgctgct accggcatgg atgctttgac ccacgctttc     600
gaagcttatt catcaaccgc tgctacccca atcaccgatg cttgcgcttt gaaggctgct     660
tcaatgatcg ctaagaactt gaagaccgct tgcgataacg caaggatat gccagctcgt      720 gaagctatgg cttatgctca attcttggct ggcatggctt caacaacgc ttcattgggc      780 tatgttcacg ctatggctca ccaattgggc ggctattata acttgccaca cggcgtttgc     840
aacgctgttt tgttgccaca cgttttggct tataacgctt cagttgttgc tggccgtttg     900
aaggatgttg gcgttgctat gggcttggat atcgctaact gggcgataa ggaaggcgct      960 gaagctacca tccaagctgt tcgtgatttg gctgcttcaa tcggcatccc agctaacttg    1020
accgaattgg gcgctaagaa ggaagatgtt ccattgttgg ctgatcacgc tttgaaggat    1080
gcttgcgctt tgaccaaccc acgtcaaggc gatcaaaagg aagttgaaga attgttcttg    1140 tcagcttttct aa                                                       1152

<210> SEQ ID NO 7
<211> LENGTH: 57
<212> TYPE: PRT
<213> ORGANISM: Lactococcus lactis
<220> FEATURE:
<221> NAME/KEY: SIGNAL
<222> LOCATION: (1)..(23)

<400> SEQUENCE: 7

Met Ser Thr Lys Asp Phe Asn Leu Asp Leu Val Ser Val Ser Lys Lys
1               5                   10                  15

Asp Ser Gly Ala Ser Pro Arg Ile Thr Ser Ile Ser Leu Cys Thr Pro
            20                  25                  30

Gly Cys Lys Thr Gly Ala Leu Met Gly Cys Asn Met Lys Thr Ala Thr
        35                  40                  45

Cys Asn Cys Ser Ile His Val Ser Lys
    50                  55
```

```
<210> SEQ ID NO 8
<211> LENGTH: 34
<212> TYPE: PRT
<213> ORGANISM: Lactococcus lactis

<400> SEQUENCE: 8

Ile Thr Ser Ile Ser Leu Cys Thr Pro Gly Cys Lys Thr Gly Ala Leu
1               5                   10                  15

Met Gly Cys Asn Met Lys Thr Ala Thr Cys Asn Cys Ser Ile His Val
            20                  25                  30

Ser Lys

<210> SEQ ID NO 9
<211> LENGTH: 57
<212> TYPE: PRT
<213> ORGANISM: Lactococcus lactis
<220> FEATURE:
<221> NAME/KEY: SIGNAL
<222> LOCATION: (1)..(23)

<400> SEQUENCE: 9

Met Ser Thr Lys Asp Phe Asn Leu Asp Leu Val Ser Val Ser Lys Lys
1               5                   10                  15

Asp Ser Gly Ala Ser Pro Arg Ile Thr Ser Ile Ser Leu Cys Thr Pro
            20                  25                  30

Gly Cys Lys Thr Gly Ala Leu Met Gly Cys Asn Met Lys Thr Ala Thr
        35                  40                  45

Cys His Cys Ser Ile His Val Ser Lys
    50                  55

<210> SEQ ID NO 10
<211> LENGTH: 34
<212> TYPE: PRT
<213> ORGANISM: Lactococcus lactis

<400> SEQUENCE: 10

Ile Thr Ser Ile Ser Leu Cys Thr Pro Gly Cys Lys Thr Gly Ala Leu
1               5                   10                  15

Met Gly Cys Asn Met Lys Thr Ala Thr Cys His Cys Ser Ile His Val
            20                  25                  30

Ser Lys

<210> SEQ ID NO 11
<211> LENGTH: 245
<212> TYPE: PRT
<213> ORGANISM: Lactococcus lactis

<400> SEQUENCE: 11

Met Arg Arg Tyr Leu Ile Leu Ile Val Ala Leu Ile Gly Ile Thr Gly
1               5                   10                  15

Leu Ser Gly Cys Tyr Gln Thr Ser His Lys Lys Val Arg Phe Asp Glu
            20                  25                  30

Gly Ser Tyr Thr Asn Phe Ile Tyr Asp Asn Lys Ser Tyr Phe Val Thr
        35                  40                  45

Asp Lys Glu Ile Pro Gln Glu Asn Val Asn Ser Lys Ala Lys Phe
    50                  55                  60

Tyr Lys Leu Leu Ile Val Asp Met Lys Ser Glu Lys Leu Leu Ser Ser
65                  70                  75                  80

Ser Asn Lys Asn Ser Val Thr Leu Val Leu Asn Asn Ile Tyr Glu Ala
                85                  90                  95
```

```
Ser Asp Lys Ser Leu Cys Met Gly Ile Asn Asp Arg Tyr Tyr Lys Ile
                100                 105                 110

Leu Pro Glu Ser Asp Lys Gly Ala Val Lys Ala Leu Arg Leu Gln Asn
            115                 120                 125

Phe Asp Val Thr Ser Asp Ile Ser Asp Asn Phe Val Ile Asp Lys
        130                 135                 140

Asn Asp Ser Arg Lys Ile Asp Tyr Met Gly Asn Ile Tyr Ser Ile Ser
145                 150                 155                 160

Asp Ser Thr Val Ser Asp Glu Glu Leu Gly Glu Tyr Gln Asp Val Leu
                165                 170                 175

Ala Glu Val Arg Val Phe Asp Ser Val Ser Gly Lys Ser Ile Pro Arg
            180                 185                 190

Ser Glu Trp Gly Arg Ile Asp Lys Asp Gly Ser Asn Ser Lys Gln Ser
        195                 200                 205

Arg Thr Glu Trp Asp Tyr Gly Glu Ile His Ser Ile Arg Gly Lys Ser
            210                 215                 220

Leu Thr Glu Ala Phe Ala Val Glu Ile Asn Asp Asp Phe Lys Leu Ala
225                 230                 235                 240

Thr Lys Val Gly Asn
                245

<210> SEQ ID NO 12
<211> LENGTH: 225
<212> TYPE: PRT
<213> ORGANISM: Lactococcus lactis

<400> SEQUENCE: 12

Met Gln Val Lys Ile Gln Asn Leu Ser Lys Thr Tyr Lys Glu Lys Gln
1               5                   10                  15

Val Leu Gln Asp Ile Ser Phe Asp Ile Lys Ser Gly Thr Val Cys Gly
            20                  25                  30

Leu Leu Gly Val Asn Gly Ala Gly Lys Ser Thr Leu Met Lys Ile Leu
        35                  40                  45

Phe Gly Leu Ile Ser Ala Asp Thr Gly Lys Ile Phe Phe Asp Gly Gln
    50                  55                  60

Glu Lys Thr Asn Asn Gln Leu Gly Ala Leu Ile Glu Ala Pro Ala Ile
65                  70                  75                  80

Tyr Met Asn Leu Ser Ala Phe Asp Asn Leu Lys Thr Lys Ala Leu Leu
                85                  90                  95

Phe Gly Ile Ser Asp Lys Arg Ile His Glu Thr Leu Glu Val Ile Gly
            100                 105                 110

Leu Ala Glu Thr Gly Lys Lys Arg Ala Gly Lys Phe Ser Leu Gly Met
        115                 120                 125

Lys Gln Arg Leu Gly Ile Gly Met Ala Ile Leu Thr Glu Pro Gln Phe
    130                 135                 140

Leu Ile Leu Asp Glu Pro Thr Asn Gly Leu Asp Pro Asp Gly Ile Ala
145                 150                 155                 160

Glu Leu Leu Asn Leu Ile Leu Lys Leu Lys Ala Lys Gly Val Thr Ile
                165                 170                 175

Leu Ile Ser Ser His Gln Leu His Glu Ile Ser Lys Val Ala Ser Gln
            180                 185                 190

Ile Ile Ile Leu Asn Lys Gly Lys Ile Arg Tyr Asn His Ala Asn Asn
        195                 200                 205

Lys Glu Asp Asp Ile Glu Gln Leu Phe Phe Lys Ile Val His Gly Gly
```

```
            210                 215                 220

Met
225

<210> SEQ ID NO 13
<211> LENGTH: 242
<212> TYPE: PRT
<213> ORGANISM: Lactococcus lactis

<400> SEQUENCE: 13

Met Lys Arg Ile Ile Ala Ser Glu Ala Ile Lys Leu Lys Lys Ser Gly
1               5                   10                  15

Thr Leu Arg Leu Val Leu Ile Ile Pro Phe Val Thr Leu Phe Ile Ala
            20                  25                  30

Phe Leu Met Gly Gly Ile Gln Ile Phe Ser Val Phe Ser Ile Tyr Trp
        35                  40                  45

Trp Glu Thr Gly Phe Leu Phe Leu Leu Met Ser Leu Leu Phe Leu Tyr
50                  55                  60

Asp Ile Lys Ser Glu Glu Gln Ala Gly Asn Phe Gln Asn Val Lys Trp
65                  70                  75                  80

Lys Lys Leu Ser Trp Lys Ile His Leu Ala Lys Met Leu Leu Ile Trp
                85                  90                  95

Leu Arg Gly Ile Leu Ala Ser Ile Val Leu Ile Ile Leu Leu Tyr Leu
            100                 105                 110

Val Ala Phe Val Phe Gln Gly Ile Val Val Asp Phe Met Lys Val
        115                 120                 125

Ser Val Ala Leu Ile Ala Ile Leu Leu Ala Ala Ser Trp Asn Leu Pro
130                 135                 140

Phe Ile Tyr Leu Ile Phe Lys Trp Ile Asn Thr Tyr Val Leu Leu Ala
145                 150                 155                 160

Ala Asn Thr Leu Ile Cys Leu Ile Val Ala Pro Phe Val Ala Gln Thr
                165                 170                 175

Pro Val Trp Phe Leu Leu Pro Tyr Thr Tyr His Tyr Lys Val Thr Glu
            180                 185                 190

Ser Leu Leu Asn Ile Lys Pro Ser Gly Asp Leu Leu Thr Gly Lys Ile
        195                 200                 205

Asn Phe Ser Ile Trp Glu Val Leu Leu Pro Phe Gly Leu Ser Ile Val
    210                 215                 220

Val Thr Ile Gly Val Ser Tyr Leu Leu Lys Gly Val Ile Glu His Asp
225                 230                 235                 240

Lys Lys

<210> SEQ ID NO 14
<211> LENGTH: 214
<212> TYPE: PRT
<213> ORGANISM: Lactococcus lactis

<400> SEQUENCE: 14

Met Ile Arg Ser Glu Cys Leu Lys Leu Lys Asn Ser Leu Gly Phe Tyr
1               5                   10                  15

Leu Val Phe Leu Phe Thr Leu Glu Leu Leu Thr Val Pro Ile Tyr
            20                  25                  30

Leu Ala Phe Gly Arg Ser His Val Ser Met Thr Asp Ser Ser Leu Met
        35                  40                  45

Ile Phe Leu Phe Phe Pro Leu Leu Val Thr Ile Leu Ser Ile Leu Ile
    50                  55                  60
```

```
Phe Glu Gln Glu Ser Leu Ala Asn His Phe Gln Glu Ile Asn Val Asn
 65                  70                  75                  80

Lys Lys Ser Ser Arg Ile Trp Leu Ser Lys Leu Ile Val Val Asp Phe
                 85                  90                  95

Leu Leu Phe Phe Pro Ser Ala Met Ile Trp Ile Ile Thr Gly Val Ser
            100                 105                 110

Gln Ala Val Gly Gln Gln Gly Met Met Ile Ala Thr Ala Ser Trp Leu
        115                 120                 125

Met Ala Ile Phe Leu Asn His Phe His Leu Leu Leu Thr Phe Ile Ile
130                 135                 140

Asn Arg Gly Gly Ser Met Ile Ile Ala Ile Glu Ile Leu Leu Ile
145                 150                 155                 160

Ile Phe Ala Ser Asn Lys Val Leu Leu Ala Ala Tyr Trp Cys Pro Ile
                165                 170                 175

Ala Leu Pro Val Asn Phe Met Ile Thr Gly Arg Cys Ala Tyr Leu Ile
            180                 185                 190

Ala Ala Val Gly Trp Ile Val Leu Ser Thr Ile Ile Leu Val Ala Leu
        195                 200                 205

Ser Lys Lys Lys Ile Arg
    210

<210> SEQ ID NO 15
<211> LENGTH: 91
<212> TYPE: PRT
<213> ORGANISM: Lactobacillus gasseri
<220> FEATURE:
<221> NAME/KEY: SIGNAL
<222> LOCATION: (1)..(33)

<400> SEQUENCE: 15

Met Val Thr Lys Tyr Gly Arg Asn Leu Gly Leu Asn Lys Val Glu Leu
  1               5                  10                  15

Phe Ala Ile Trp Ala Val Leu Val Val Ala Leu Leu Thr Thr Ala
                 20                  25                  30

Asn Ile Tyr Trp Ile Ala Asp Gln Phe Gly Ile His Leu Ala Thr Gly
                 35                  40                  45

Thr Ala Arg Lys Leu Leu Asp Ala Met Ala Ser Gly Ala Ser Leu Gly
 50                  55                  60

Thr Ala Phe Ala Ala Ile Leu Gly Val Thr Leu Pro Ala Trp Ala Leu
 65                  70                  75                  80

Ala Ala Ala Gly Ala Leu Gly Ala Thr Ala Ala
                 85                  90

<210> SEQ ID NO 16
<211> LENGTH: 58
<212> TYPE: PRT
<213> ORGANISM: Lactobacillus gasseri

<400> SEQUENCE: 16

Ile Tyr Trp Ile Ala Asp Gln Phe Gly Ile His Leu Ala Thr Gly Thr
  1               5                  10                  15

Ala Arg Lys Leu Leu Asp Ala Met Ala Ser Gly Ala Ser Leu Gly Thr
                 20                  25                  30

Ala Phe Ala Ala Ile Leu Gly Val Thr Leu Pro Ala Trp Ala Leu Ala
             35                  40                  45

Ala Ala Gly Ala Leu Gly Ala Thr Ala Ala
             50                  55
```

<210> SEQ ID NO 17
<211> LENGTH: 53
<212> TYPE: PRT
<213> ORGANISM: Lactobacillus gasseri

<400> SEQUENCE: 17

Met Gln Lys Leu Leu Arg Ile Ile Ala Leu Ile Ser Leu Ile Ala Ala
1               5                   10                  15

Ile Ile Ser Phe Phe Ile Phe Lys Ile Asn Tyr Ile Thr Tyr Ile Leu
            20                  25                  30

Ile Gly Ile Phe Ile Gly Ser Gly Phe Ile Tyr Gln Ile Arg Ala Gln
        35                  40                  45

Gly Arg Asn Arg Lys
    50

<210> SEQ ID NO 18
<211> LENGTH: 226
<212> TYPE: PRT
<213> ORGANISM: Lactobacillus gasseri

<400> SEQUENCE: 18

Met Thr Arg Asn Met Phe Val Asp Ile Lys Asn Val Ser Lys Asn Leu
1               5                   10                  15

Thr Asp Phe Ser Leu Glu Asn Leu Asn Ile Ser Phe Glu Lys Gly Glu
            20                  25                  30

Ile Ile Gly Leu Val Gly Glu Asn Gly Ala Gly Lys Thr Thr Leu Leu
        35                  40                  45

Asn Leu Ile Ser Gly Ile Leu Lys Pro Asp Lys Gly Gln Ile Leu Leu
    50                  55                  60

Ser Ser Asn Asn Ile Gly Tyr Cys Phe Asp Ala Leu Pro Glu Pro Glu
65                  70                  75                  80

Asn Leu Thr Ile Glu Gln Leu Asn Thr Ile Phe Thr Gly Leu Leu Ala
                85                  90                  95

Val Trp Asp Ser Asp Thr Tyr Phe Ser Phe Val Asp Glu Phe Lys Leu
            100                 105                 110

Pro Lys Gly Lys Pro Ile Gly Val Phe Ser Lys Gly Met Lys Met Gln
        115                 120                 125

Leu Asn Val Ser Ile Thr Leu Ser His Asn Pro Thr Leu Leu Leu Leu
    130                 135                 140

Asp Glu Val Thr Ala Gly Leu Asp Pro Ile Val Arg Arg Thr Val Leu
145                 150                 155                 160

Asn Thr Ile Lys Glu Tyr Ala Ile Ser Ser Glu Cys Ile Val Ile Met
                165                 170                 175

Thr Thr His Asn Leu Glu Asp Ile Ser Asp Ile Cys Asn Arg Leu Ile
            180                 185                 190

Leu Leu Asn Asn Gly Ser Ile Leu Leu Asp Asp Asn Phe Glu Asp Lys
        195                 200                 205

Ser Ser Lys Glu Ile Glu Leu Ile Phe Arg Lys Thr Leu Gly Tyr Gly
    210                 215                 220

Asp Met
225

<210> SEQ ID NO 19
<211> LENGTH: 212
<212> TYPE: PRT
<213> ORGANISM: Lactobacillus gasseri

<400> SEQUENCE: 19

Met Lys Gly Leu Val Gln Lys Asp Ile Tyr Gln Leu Thr Ser Ser Trp
1               5                   10                  15

Phe Arg Pro Val Arg Ile Phe Phe Val Ile Ala Val Leu Ala Ala Gly
                20                  25                  30

Met Ile Phe Leu Lys Gln Asp Ser Ser Ile Ile Leu Val Leu Leu Leu
            35                  40                  45

Leu Leu Met Val Asn Asn Ile Gln Ser Leu Phe Ile Lys Asp Ser Thr
50                  55                  60

Asn Arg Trp Leu Ser Leu Leu Lys Ser Leu Lys Ile Ser Thr Phe Ala
65                  70                  75                  80

Val Ile Gly Ser Arg Tyr Ile Thr Leu Val Val Ile Cys Val Cys Gly
                85                  90                  95

Ala Ile Leu Asn Phe Val Tyr Met Leu Phe Gly Met Leu Leu Phe Asn
                100                 105                 110

Thr Ser Thr Gly Ile Asp Val Leu Val Ile Ser Ser Ile Cys Leu Trp
            115                 120                 125

Val Ser Leu Ile Tyr Gly Leu Val Ile Ile Pro Phe Leu Tyr Ala Phe
130                 135                 140

Lys Gln Asn Gly Leu Thr Leu Ala Ile Ile Ile Met Phe Ser Cys Val
145                 150                 155                 160

Ala Leu Leu Ile Lys Phe Ser Ser Ala Ile Thr Lys Leu Ala Tyr Ile
                165                 170                 175

Ile His Ser Tyr Ser Tyr Val Gln Leu Ile Leu Ile Ala Ile Val Ala
                180                 185                 190

Leu Ile Gly Ile Gly Ile Ile Ser Met Val Val Ser Tyr Leu Ile Val
            195                 200                 205

Glu Lys Glu Lys
        210

<210> SEQ ID NO 20
<211> LENGTH: 62
<212> TYPE: PRT
<213> ORGANISM: Pediococcus sp.
<220> FEATURE:
<221> NAME/KEY: SIGNAL
<222> LOCATION: (1)..(18)

<400> SEQUENCE: 20

Met Lys Lys Ile Glu Lys Leu Thr Glu Lys Met Ala Asn Ile Ile
1               5                   10                  15

Gly Gly Lys Tyr Tyr Gly Asn Gly Val Thr Cys Gly Lys His Ser Cys
                20                  25                  30

Ser Val Asp Trp Gly Lys Ala Thr Thr Cys Ile Ile Asn Asn Gly Ala
            35                  40                  45

Met Ala Trp Ala Thr Gly Gly His Gln Gly Asn His Lys Cys
50                  55                  60

<210> SEQ ID NO 21
<211> LENGTH: 44
<212> TYPE: PRT
<213> ORGANISM: Pediococcus sp.

<400> SEQUENCE: 21

Lys Tyr Tyr Gly Asn Gly Val Thr Cys Gly Lys His Ser Cys Ser Val
1               5                   10                  15

```
Asp Trp Gly Lys Ala Thr Thr Cys Ile Ile Asn Asn Gly Ala Met Ala
            20                  25                  30

Trp Ala Thr Gly Gly His Gln Gly Asn His Lys Cys
        35                  40
```

<210> SEQ ID NO 22
<211> LENGTH: 112
<212> TYPE: PRT
<213> ORGANISM: Pediococcus sp.

<400> SEQUENCE: 22

```
Met Asn Lys Thr Lys Ser Glu His Ile Lys Gln Gln Ala Leu Asp Leu
1               5                   10                  15

Phe Thr Arg Leu Gln Phe Leu Leu Gln Lys His Asp Thr Ile Glu Pro
            20                  25                  30

Tyr Gln Tyr Val Leu Asp Ile Leu Glu Thr Gly Ile Ser Lys Thr Lys
        35                  40                  45

His Asn Gln Gln Thr Pro Glu Arg Gln Ala Arg Val Val Tyr Asn Lys
    50                  55                  60

Ile Ala Ser Gln Ala Leu Val Asp Lys Leu His Phe Thr Ala Glu Glu
65                  70                  75                  80

Asn Lys Val Leu Ala Ala Ile Asn Glu Leu Ala His Ser Gln Lys Gly
                85                  90                  95

Trp Gly Glu Phe Asn Met Leu Asp Thr Thr Asn Thr Trp Pro Ser Gln
            100                 105                 110
```

<210> SEQ ID NO 23
<211> LENGTH: 77
<212> TYPE: PRT
<213> ORGANISM: Artificial Sequence
<220> FEATURE:
<223> OTHER INFORMATION: Brochothrix campestris BrcA pro-protein with
      the pediocin signal sequence
<220> FEATURE:
<221> NAME/KEY: SIGNAL
<222> LOCATION: (1)..(18)

<400> SEQUENCE: 23

```
Met Lys Lys Ile Glu Lys Leu Thr Glu Lys Glu Met Ala Asn Ile Ile
1               5                   10                  15

Gly Gly Tyr Ser Ser Lys Asp Cys Leu Lys Asp Ile Gly Lys Gly Ile
            20                  25                  30

Gly Ala Gly Thr Val Ala Gly Ala Ala Gly Gly Leu Ala Ala Gly
        35                  40                  45

Leu Gly Ala Ile Pro Gly Ala Phe Val Gly Ala His Phe Gly Val Ile
    50                  55                  60

Gly Gly Ser Ala Ala Cys Ile Gly Gly Leu Leu Gly Asn
65                  70                  75
```

<210> SEQ ID NO 24
<211> LENGTH: 59
<212> TYPE: PRT
<213> ORGANISM: Brochothrix campestris

<400> SEQUENCE: 24

```
Tyr Ser Ser Lys Asp Cys Leu Lys Asp Ile Gly Lys Gly Ile Gly Ala
1               5                   10                  15

Gly Thr Val Ala Gly Ala Ala Gly Gly Leu Ala Ala Gly Leu Gly
            20                  25                  30

Ala Ile Pro Gly Ala Phe Val Gly Ala His Phe Gly Val Ile Gly Gly
```

```
                35                  40                  45

Ser Ala Ala Cys Ile Gly Gly Leu Leu Gly Asn
    50                  55
```

<210> SEQ ID NO 25
<211> LENGTH: 61
<212> TYPE: PRT
<213> ORGANISM: Artificial Sequence
<220> FEATURE:
<223> OTHER INFORMATION: Brochothrix campestris BrcB pro-protein with
      the pediocin signal sequence
<220> FEATURE:
<221> NAME/KEY: SIGNAL
<222> LOCATION: (1)..(18)

<400> SEQUENCE: 25

```
Met Lys Lys Ile Glu Lys Leu Thr Glu Lys Glu Met Ala Asn Ile Ile
1               5                   10                  15

Gly Gly Lys Ile Asn Trp Gly Asn Val Gly Gly Ser Cys Val Gly Gly
                20                  25                  30

Ala Val Ile Gly Gly Ala Leu Gly Gly Leu Gly Gly Ala Gly Gly Gly
                35                  40                  45

Cys Ile Thr Gly Ala Ile Gly Ser Ile Trp Asp Gln Trp
    50                  55                  60
```

<210> SEQ ID NO 26
<211> LENGTH: 43
<212> TYPE: PRT
<213> ORGANISM: Brochothrix campestris

<400> SEQUENCE: 26

```
Lys Ile Asn Trp Gly Asn Val Gly Gly Ser Cys Val Gly Gly Ala Val
1               5                   10                  15

Ile Gly Gly Ala Leu Gly Gly Leu Gly Gly Ala Gly Gly Cys Ile
                20                  25                  30

Thr Gly Ala Ile Gly Ser Ile Trp Asp Gln Trp
                35                  40
```

<210> SEQ ID NO 27
<211> LENGTH: 53
<212> TYPE: PRT
<213> ORGANISM: Brochothrix campestris

<400> SEQUENCE: 27

```
Met Val Lys Thr Ile Leu Phe Ser Val Val Ile Ser Phe Val Ala Leu
1               5                   10                  15

Cys Asn Phe Leu Ile Lys Lys Asp Val Ser Ser Lys Lys Lys Leu Phe
                20                  25                  30

Leu Thr Gly Ser Ile Ala Val Phe Leu Ile Ile Tyr Asp Phe Leu Trp
                35                  40                  45

Ile Ile Phe Ser Asn
    50
```

<210> SEQ ID NO 28
<211> LENGTH: 91
<212> TYPE: PRT
<213> ORGANISM: Lactiplantibacillus plantarum
<220> FEATURE:
<221> NAME/KEY: SIGNAL
<222> LOCATION: (1)..(33)

<400> SEQUENCE: 28

```
Met Leu Ser Ala Tyr Arg Ser Lys Leu Gly Leu Asn Lys Phe Glu Val
1               5                  10                 15

Thr Val Leu Met Ile Ile Ser Leu Phe Ile Leu Leu Phe Ala Thr Val
                20                 25                 30

Asn Ile Val Trp Ile Ala Lys Gln Phe Gly Val His Leu Thr Thr Ser
                35                 40                 45

Leu Thr Gln Lys Ala Leu Asp Leu Leu Ser Ala Gly Ser Ser Leu Gly
        50                 55                 60

Thr Val Ala Ala Ala Val Leu Gly Val Thr Leu Pro Ala Trp Ala Val
65                 70                 75                 80

Ala Ala Ala Gly Ala Leu Gly Gly Thr Ala Ala
                85                 90
```

<210> SEQ ID NO 29
<211> LENGTH: 58
<212> TYPE: PRT
<213> ORGANISM: Lactiplantibacillus plantarum

<400> SEQUENCE: 29

```
Ile Val Trp Ile Ala Lys Gln Phe Gly Val His Leu Thr Thr Ser Leu
1               5                  10                 15

Thr Gln Lys Ala Leu Asp Leu Leu Ser Ala Gly Ser Ser Leu Gly Thr
                20                 25                 30

Val Ala Ala Ala Val Leu Gly Val Thr Leu Pro Ala Trp Ala Val Ala
                35                 40                 45

Ala Ala Gly Ala Leu Gly Gly Thr Ala Ala
        50                 55
```

<210> SEQ ID NO 30
<211> LENGTH: 161
<212> TYPE: PRT
<213> ORGANISM: Lactiplantibacillus plantarum

<400> SEQUENCE: 30

```
Met Thr Ile Phe Val Asn Lys Pro Arg Ser Asn Ile Pro Ala Leu Leu
1               5                  10                 15

Ile Val Phe Ile Ile Phe Leu Ile Leu Gly Val Leu Phe Ser Lys Tyr
                20                 25                 30

Phe Ala Thr Ala Ser Ser Gln His Ser Leu Asp Ser Phe Lys Val Ile
                35                 40                 45

His Leu Asn Trp Phe Thr Glu Ile Ile Phe Arg Asn Thr Ile Ala Phe
        50                 55                 60

Leu Val Leu Ser Ser Thr Leu Phe Leu Gly Asn Ile Val Ser Val Ile
65                 70                 75                 80

Phe Phe Cys Val Asn Gly Phe Asn Val Gly Leu Ile Cys Gly Gln Leu
                85                 90                 95

Pro Ile Phe Gln Ser Ile Val Leu Leu Ser Pro His Gly Val Ile Glu
                100                105                110

Ile Thr Ser Tyr Ile Trp Leu Val Tyr Ala Val Thr His Val Asn His
                115                120                125

Met Lys Ile Asn Ile Ile Arg Ser Tyr Cys Leu Leu Phe Leu Ala Ala
        130                135                140

Ile Ile Glu Val Phe Val Thr Pro Gly Leu Ala Leu Trp Leu Leu Gly
145                150                155                160

Asp
```

```
<210> SEQ ID NO 31
<211> LENGTH: 54
<212> TYPE: PRT
<213> ORGANISM: Lactiplantibacillus plantarum

<400> SEQUENCE: 31

Met Lys Asn Leu Asp Met Leu Val Arg Val Ile Thr Ile Ile Leu Leu
1               5                   10                  15

Leu Ala Thr Ile Thr Ala Phe Phe Lys Gly Leu Ser Thr Ile Thr
            20                  25                  30

Tyr Ile Cys Ala Ile Ile Thr Val Val Leu Ala Phe Val Tyr Gln Leu
            35                  40                  45

Ile Lys Arg His Thr Asp
        50

<210> SEQ ID NO 32
<211> LENGTH: 227
<212> TYPE: PRT
<213> ORGANISM: Lactiplantibacillus plantarum

<400> SEQUENCE: 32

Met Cys Met Thr Lys Val Ser Met Ser Gln Val Arg Lys Lys Tyr Asp
1               5                   10                  15

Asn Phe Ile Leu Gly Asp Ile Asn Phe Gln Ala Lys Glu Lys Glu Ile
            20                  25                  30

Ile Gly Leu Ile Gly Glu Asn Gly Ala Gly Lys Thr Thr Leu Leu Lys
            35                  40                  45

Ser Ile Gly Gly Ile Asn Lys Ile Asp Phe Gly Thr Ile Lys Lys Asp
    50                  55                  60

Phe Lys Glu Leu Gly Phe Cys Phe Asp Ser Ile Pro Phe Pro Glu Glu
65                  70                  75                  80

Leu Asn Ile Leu Gln Leu Glu His Ile Phe Gln Asn Ile Gly Ile Asn
                85                  90                  95

Trp Asp Thr Gln Ala Phe Trp Pro Tyr Ile Lys Ala Leu Gln Leu Pro
            100                 105                 110

Ile Lys Ile Pro Ile Ser Asn Phe Ser Lys Gly Met Lys Met Gln Leu
            115                 120                 125

Asn Leu Cys Ile Ser Ile Ser His His Pro Asp Leu Leu Leu Leu Asp
        130                 135                 140

Glu Ile Thr Ser Gly Leu Asp Pro Leu Met Arg Arg Lys Val Leu Arg
145                 150                 155                 160

Leu Ile Lys Lys Tyr Val Asp Gln Asn Asp Cys Ala Val Ile Ile Thr
                165                 170                 175

Thr His Asn Leu Asn Asp Val Val Glu Ile Cys Thr Arg Phe Asp Leu
            180                 185                 190

Leu Asp His Gly Lys Ile Ile Leu Glu Lys Asn Met Gln Lys Phe Gly
        195                 200                 205

Ala Glu Asn Leu Glu Lys Leu Phe Glu Glu Thr Val Lys Lys Ala Asn
    210                 215                 220

Leu Gly Glu
225

<210> SEQ ID NO 33
<211> LENGTH: 214
<212> TYPE: PRT
<213> ORGANISM: Lactiplantibacillus plantarum

<400> SEQUENCE: 33
```

```
Met Leu Gly Leu Met Leu Lys Asp Tyr Tyr Gln Leu Cys Asp Lys Trp
1               5                   10                  15

Phe Lys Lys Ile Tyr Leu Leu Gly Val Ser Phe Ser Leu Ile Ile Ala
            20                  25                  30

Thr Ile Phe Leu Lys Ser Asp Ser Trp Ile Val Ala Thr Leu Ile Ser
        35                  40                  45

Met Ile Met Ile Asn Ser Ile Gln Ser Leu Phe Leu Ser Asp Asn Lys
50                  55                  60

Asn Asn Trp Ile Asn Phe Leu Thr Thr Leu Ser Ile Lys Lys Ser Ile
65                  70                  75                  80

Ser Val Leu Ala Arg Tyr Leu Phe Val Ile Ile Val Cys Ala Val Thr
                85                  90                  95

Ala Ile Leu Asn Gly Leu Phe Phe Leu Val Ile Ser Leu Phe Phe Lys
            100                 105                 110

Gly Ile Thr Ile Glu Ser Ile Met Ile Val Pro Ile Cys Leu Phe Thr
        115                 120                 125

Val Ser Ile Ile Tyr Ile Ser Phe Ile Leu Pro Phe Leu Tyr Ala Phe
    130                 135                 140

Gln Gln Asn Gly Leu Thr Val Gly Val Leu Leu Ile Leu Gly Ile Ala
145                 150                 155                 160

Phe Val Ser Ile Arg Phe Phe Gly Ile Leu Ser Lys Ile Lys Lys Leu
                165                 170                 175

Ile Leu Leu Asp Ser Lys Thr Glu Leu Ile Phe Leu Val Ala Leu Ala
            180                 185                 190

Leu Ile Ile Thr Val Ala Leu Ser Tyr Ser Ile Ala Tyr Val Ile Ser
        195                 200                 205

Leu Ile Arg Gly Glu Glu
    210

<210> SEQ ID NO 34
<211> LENGTH: 173
<212> TYPE: PRT
<213> ORGANISM: Lactiplantibacillus plantarum

<400> SEQUENCE: 34

Met Lys Phe Arg His Thr Ile Leu Tyr Trp Ile Phe Ala Trp Gly Ala
1               5                   10                  15

Leu Phe Val Leu Ala Ile Leu Arg Leu Phe Lys Thr Phe Lys Ile Leu
            20                  25                  30

Pro Asn Ser Asn Arg Ile Leu Lys Gly Ile Pro Val Asp Ile Val Ala
        35                  40                  45

Pro Thr Phe Gly Ile Leu Leu Cys Leu Val Val Phe Ile Ser Ala Leu
50                  55                  60

Gly Ser Tyr Leu Val Phe Val Phe Asn Lys Ile Lys Arg Leu Asn
65                  70                  75                  80

Leu Thr Phe Leu Ser Arg Phe Lys Thr Lys Val Tyr Asp Ile Tyr Leu
                85                  90                  95

Ser Ser Tyr Ile Val Tyr Asn Leu Leu Tyr Val Ile Tyr Ile Tyr Leu
            100                 105                 110

Tyr Lys Lys Thr Ala Thr Asn Phe Gln Ile Asn Ile Phe Ser Leu Leu
        115                 120                 125

Leu Gly Thr Phe Ile Ser Phe Leu Ile Phe Asn Tyr Leu Arg Lys Gln
    130                 135                 140

Lys Ile Ser Leu Lys Asn Asn Met Glu Phe Ser Ser Thr Ile Leu Leu
```

```
                145                 150                 155                 160
Ile Asn Ile Ile Thr Pro Ile Tyr Ser Leu Ile Phe Leu
            165                 170

<210> SEQ ID NO 35
<211> LENGTH: 56
<212> TYPE: PRT
<213> ORGANISM: Lactiplantibacillus plantarum
<220> FEATURE:
<221> NAME/KEY: SIGNAL
<222> LOCATION: (1)..(19)

<400> SEQUENCE: 35

Met Met Lys Lys Ile Glu Lys Leu Thr Glu Lys Glu Met Ala Asn Ile
1               5                   10                  15

Ile Gly Gly Lys Tyr Tyr Gly Asn Gly Val Thr Cys Gly Lys His Ser
            20                  25                  30

Cys Ser Val Asn Trp Gly Gln Ala Phe Ser Cys Ser Val Ser His Leu
        35                  40                  45

Ala Asn Phe Gly His Gly Lys Cys
    50                  55

<210> SEQ ID NO 36
<211> LENGTH: 37
<212> TYPE: PRT
<213> ORGANISM: Lactiplantibacillus plantarum

<400> SEQUENCE: 36

Lys Tyr Tyr Gly Asn Gly Val Thr Cys Gly Lys His Ser Cys Ser Val
1               5                   10                  15

Asn Trp Gly Gln Ala Phe Ser Cys Ser Val Ser His Leu Ala Asn Phe
            20                  25                  30

Gly His Gly Lys Cys
        35

<210> SEQ ID NO 37
<211> LENGTH: 109
<212> TYPE: PRT
<213> ORGANISM: Lactiplantibacillus plantarum

<400> SEQUENCE: 37

Met Ala Glu Gln Tyr Val Thr Glu Leu Tyr Lys Lys Leu Lys Ser Arg
1               5                   10                  15

Asp Ser Lys Thr Ser Gly Leu Leu Asp Ile Leu Asp Val Leu Ile Gln
            20                  25                  30

Val Gln Lys Asn Leu Ser Thr Val Lys Asn Pro Glu Ala Leu Val Asn
        35                  40                  45

Arg Cys Val Gln Tyr Ile Arg Ser Val Ala Ile Lys Asp Lys Leu Tyr
    50                  55                  60

Phe Pro Pro Ala Glu Glu Asn Ile Ile Asn Leu Glu Val Ile Gly
65                  70                  75                  80

Gln Lys Ala Gly Trp Asn Gly Ser Tyr Met Ala Asp Phe Ser Asp Lys
                85                  90                  95

Ser Gln Phe Tyr Lys Leu Ser Glu Ser Ile Pro His His
            100                 105

<210> SEQ ID NO 38
<211> LENGTH: 174
<212> TYPE: PRT
<213> ORGANISM: Lactiplantibacillus plantarum
```

<400> SEQUENCE: 38

```
Met Ser Lys Lys Phe Trp Ser Asn Ile Phe Leu Ala Leu Gly Val Phe
1               5                   10                  15

Leu Ala Phe Ala Gly Val Ala Thr Ile Ser Val Ser Ala Asp Ser Ser
                20                  25                  30

Ala Thr Ile Glu Ser Asn Thr Ser Ser Lys Ile Ile Asp Gly Ala Thr
            35                  40                  45

Tyr Glu Glu Asn Ile Lys Gly Val Ile Pro Ile Thr Leu Thr Gln Tyr
        50                  55                  60

Leu His Lys Ala Gln Thr Gly Glu Lys Phe Ile Val Phe Val Gly Phe
65              70                  75                  80

Lys Glu Cys Val His Cys Arg Lys Phe Ser Pro Val Met Lys Gln Tyr
                85                  90                  95

Leu Gln Gln Ser Gln His Pro Ile Tyr Tyr Leu Asp Tyr Gly Asn Asn
                100                 105                 110

Gly Ser Phe Ser Met Ala Ser Gln Lys Gln Ile Thr Asp Phe Tyr Ser
            115                 120                 125

Thr Phe Ala Thr Pro Met Ser Phe Met Gly Thr Pro Thr Val Ala Leu
130                 135                 140

Leu Asp Asn Gly Lys Val Val Ser Met Thr Ala Gly Asp Asp Thr Thr
145                 150                 155                 160

Leu Ser Asp Leu Gln Gln Ile Thr Ala Asp Tyr Asn Asn Gln
                165                 170
```

<210> SEQ ID NO 39
<211> LENGTH: 724
<212> TYPE: PRT
<213> ORGANISM: Lactiplantibacillus plantarum

<400> SEQUENCE: 39

```
Met Trp Thr Gln Lys Trp His Lys Tyr Tyr Thr Ala Gln Val Asp Glu
1               5                   10                  15

Asn Asp Cys Gly Leu Ala Ala Leu Asn Met Ile Leu Lys Tyr Tyr Gly
                20                  25                  30

Ser Asp Tyr Met Leu Ala His Leu Arg Gln Leu Ala Lys Thr Thr Ala
            35                  40                  45

Asp Gly Thr Thr Val Leu Gly Leu Val Lys Ala Lys His Leu Asn
        50                  55                  60

Leu Asn Ala Glu Ala Val Arg Ala Asp Met Asp Ala Leu Thr Ala Ser
65              70                  75                  80

Gln Leu Pro Leu Pro Val Ile Val His Val Phe Lys Lys Asn Lys Leu
                85                  90                  95

Pro His Tyr Tyr Val Val Tyr Gln Val Thr Glu Asn Asp Leu Ile Ile
                100                 105                 110

Gly Asp Pro Asp Pro Thr Val Lys Thr Thr Lys Ile Ser Lys Ser Gln
            115                 120                 125

Phe Ala Lys Glu Trp Thr Gln Ile Ala Ile Ile Ala Pro Thr Val
130                 135                 140

Lys Tyr Lys Pro Ile Lys Glu Ser Arg His Thr Leu Ile Asp Leu Val
145                 150                 155                 160

Pro Leu Leu Ile Lys Gln Lys Arg Leu Ile Gly Leu Ile Ile Thr Ala
                165                 170                 175

Ala Ala Ile Thr Thr Leu Ile Ser Ile Ala Gly Ala Tyr Phe Phe Gln
                180                 185                 190
```

```
Leu Ile Ile Asp Thr Tyr Leu Pro His Leu Met Thr Asn Arg Leu Ser
        195                 200                 205

Leu Val Ala Ile Gly Leu Ile Val Ala Tyr Ala Phe Gln Ala Ile Ile
210                 215                 220

Asn Tyr Ile Gln Ser Phe Phe Thr Ile Val Leu Gly Gln Arg Leu Met
225                 230                 235                 240

Ile Asp Ile Val Leu Lys Tyr Val His His Leu Phe Asp Leu Pro Met
                245                 250                 255

Asn Phe Phe Thr Thr Arg His Val Gly Glu Met Thr Ser Arg Phe Ser
                260                 265                 270

Asp Ala Ser Lys Ile Ile Asp Ala Leu Gly Ser Thr Thr Leu Thr Leu
                275                 280                 285

Phe Leu Asp Met Trp Ile Leu Leu Ala Val Gly Leu Phe Leu Ala Tyr
                290                 295                 300

Gln Asn Ile Asn Leu Phe Leu Cys Ser Leu Val Val Pro Ile Tyr
305                 310                 315                 320

Ile Ser Ile Val Trp Leu Phe Lys Lys Thr Phe Asn Arg Leu Asn Gln
                325                 330                 335

Asp Thr Met Glu Ser Asn Ala Val Leu Asn Ser Ala Ile Ile Glu Ser
                340                 345                 350

Leu Ser Gly Ile Glu Thr Ile Lys Ser Leu Thr Gly Glu Ala Thr Thr
        355                 360                 365

Lys Lys Lys Ile Asp Thr Leu Phe Ser Asp Leu Leu His Lys Asn Leu
        370                 375                 380

Ala Tyr Gln Lys Ala Asp Gln Gly Gln Gln Ala Ile Lys Ala Ala Thr
385                 390                 395                 400

Lys Leu Ile Leu Thr Ile Val Ile Leu Trp Trp Gly Thr Phe Phe Val
                405                 410                 415

Met Arg His Gln Leu Ser Leu Gly Gln Leu Leu Thr Tyr Asn Ala Leu
                420                 425                 430

Leu Ala Tyr Phe Leu Thr Pro Leu Glu Asn Ile Ile Asn Leu Gln Pro
                435                 440                 445

Lys Leu Gln Ala Ala Arg Val Ala Asn Asn Arg Leu Asn Glu Val Tyr
        450                 455                 460

Leu Val Glu Ser Glu Phe Ser Lys Ser Arg Glu Ile Thr Ala Leu Glu
465                 470                 475                 480

Gln Leu Asn Gly Asp Ile Glu Val Asn His Val Ser Phe Asn Tyr Gly
                485                 490                 495

Tyr Cys Ser Asn Ile Leu Glu Asp Val Ser Leu Thr Ile Pro His His
                500                 505                 510

Gln Lys Ile Thr Ile Val Gly Met Ser Gly Ser Gly Lys Thr Thr Leu
                515                 520                 525

Ala Lys Leu Leu Val Gly Phe Phe Glu Pro Gln Glu Gln His Gly Glu
        530                 535                 540

Ile Gln Ile Asn His His Asn Ile Ser Asp Ile Ser Arg Thr Ile Leu
545                 550                 555                 560

Arg Gln Tyr Ile Asn Tyr Val Pro Gln Glu Pro Phe Ile Phe Ser Gly
                565                 570                 575

Ser Val Leu Glu Asn Leu Leu Leu Gly Ser Arg Pro Gly Val Thr Gln
                580                 585                 590

Gln Met Ile Asp Gln Ala Cys Ser Phe Ala Glu Ile Lys Thr Asp Ile
                595                 600                 605
```

-continued

Glu Asn Leu Pro Gln Gly Tyr His Thr Arg Leu Ser Glu Ser Gly Phe
610                 615                 620

Asn Leu Ser Gly Gly Gln Lys Gln Arg Leu Ser Ile Ala Arg Ala Leu
625                 630                 635                 640

Leu Ser Pro Ala Gln Cys Phe Ile Phe Asp Glu Ser Thr Ser Asn Leu
            645                 650                 655

Asp Thr Ile Thr Glu His Lys Ile Val Ser Lys Leu Leu Phe Met Lys
            660                 665                 670

Asp Lys Thr Ile Ile Phe Val Ala His Arg Leu Asn Ile Ala Ser Gln
            675                 680                 685

Thr Asp Lys Val Val Val Leu Asp His Gly Lys Ile Val Glu Gln Gly
690                 695                 700

Ser His Arg Gln Leu Leu Asn Tyr Asn Gly Tyr Tyr Ala Arg Leu Ile
705                 710                 715                 720

His Asn Gln Glu

<210> SEQ ID NO 40
<211> LENGTH: 75
<212> TYPE: PRT
<213> ORGANISM: Lactococcus lactis subsp. cremoris
<220> FEATURE:
<221> NAME/KEY: SIGNAL
<222> LOCATION: (1)..(21)

<400> SEQUENCE: 40

Met Lys Asn Gln Leu Asn Phe Asn Ile Val Ser Asp Glu Glu Leu Ser
1               5                   10                  15

Glu Ala Asn Gly Gly Lys Leu Thr Phe Ile Gln Ser Thr Ala Ala Gly
            20                  25                  30

Asp Leu Tyr Tyr Asn Thr Asn Thr His Lys Tyr Val Tyr Gln Gln Thr
        35                  40                  45

Gln Asn Ala Phe Gly Ala Ala Ala Asn Thr Ile Val Asn Gly Trp Met
    50                  55                  60

Gly Gly Ala Ala Gly Gly Phe Gly Leu His His
65                  70                  75

<210> SEQ ID NO 41
<211> LENGTH: 54
<212> TYPE: PRT
<213> ORGANISM: Lactococcus lactis subsp. cremoris

<400> SEQUENCE: 41

Lys Leu Thr Phe Ile Gln Ser Thr Ala Ala Gly Asp Leu Tyr Tyr Asn
1               5                   10                  15

Thr Asn Thr His Lys Tyr Val Tyr Gln Gln Thr Gln Asn Ala Phe Gly
            20                  25                  30

Ala Ala Ala Asn Thr Ile Val Asn Gly Trp Met Gly Gly Ala Ala Gly
        35                  40                  45

Gly Phe Gly Leu His His
    50

<210> SEQ ID NO 42
<211> LENGTH: 98
<212> TYPE: PRT
<213> ORGANISM: Lactococcus lactis subsp. cremoris

<400> SEQUENCE: 42

Met Lys Lys Lys Gln Ile Glu Phe Glu Asn Glu Leu Arg Ser Met Leu
1               5                   10                  15

```
Ala Thr Ala Leu Glu Lys Asp Ile Ser Gln Glu Arg Asn Ala Leu
             20                  25                  30

Asn Ile Ala Glu Lys Ala Leu Asp Asn Ser Glu Tyr Leu Pro Lys Ile
         35                  40                  45

Ile Leu Asn Leu Arg Lys Ala Leu Thr Pro Leu Ala Ile Asn Arg Thr
 50                  55                  60

Leu Asn His Asp Leu Ser Glu Leu Tyr Lys Phe Ile Thr Ser Ser Lys
 65                  70                  75                  80

Ala Ser Asn Lys Asn Leu Gly Gly Gly Leu Ile Met Ser Trp Gly Arg
                 85                  90                  95

Leu Phe

<210> SEQ ID NO 43
<211> LENGTH: 715
<212> TYPE: PRT
<213> ORGANISM: Lactococcus lactis subsp. cremoris

<400> SEQUENCE: 43

Met Lys Phe Lys Lys Lys Asn Tyr Thr Ser Gln Val Asp Glu Met Asp
 1               5                  10                  15

Cys Gly Cys Ala Ala Leu Ser Met Ile Leu Lys Ser Tyr Gly Thr Glu
             20                  25                  30

Lys Ser Leu Ala Ser Leu Arg Leu Leu Ala Gly Thr Thr Ile Glu Gly
         35                  40                  45

Thr Ser Ala Leu Gly Ile Lys Lys Ala Ala Glu Ile Leu Glu Phe Ser
 50                  55                  60

Val Gln Ala Leu Arg Thr Asp Ala Ser Leu Phe Glu Met Lys Asn Ala
 65                  70                  75                  80

Pro Tyr Pro Phe Ile Ala His Val Ile Lys Asp Gln Lys Tyr Pro His
                 85                  90                  95

Tyr Tyr Val Ile Thr Gly Ala Asn Lys Asn Ser Val Phe Ile Ala Asp
            100                 105                 110

Pro Asp Pro Thr Ile Lys Met Thr Lys Leu Ser Lys Glu Ala Phe Leu
        115                 120                 125

Ser Glu Trp Thr Gly Ile Ser Leu Phe Leu Ser Thr Thr Pro Ser Tyr
    130                 135                 140

His Pro Thr Lys Glu Lys Ala Ser Ser Leu Leu Ser Phe Ile Pro Ile
145                 150                 155                 160

Ile Thr Arg Gln Lys Lys Val Ile Leu Asn Ile Val Ile Ala Ser Phe
                165                 170                 175

Ile Val Thr Leu Ile Asn Ile Leu Gly Ser Tyr Tyr Leu Gln Ser Met
            180                 185                 190

Ile Asp Ser Tyr Ile Pro Asn Ala Leu Met Gly Thr Leu Gly Ile Ile
        195                 200                 205

Ser Val Gly Leu Leu Leu Thr Tyr Ile Ile Gln Gln Val Leu Glu Phe
    210                 215                 220

Ala Lys Ala Phe Leu Leu Asn Val Leu Ser Gln Arg Leu Ala Ile Asp
225                 230                 235                 240

Val Ile Leu Ser Tyr Ile Arg His Ile Phe Gln Leu Pro Met Ser Phe
                245                 250                 255

Phe Ser Thr Arg Arg Thr Gly Glu Ile Thr Ser Arg Phe Ser Asp Ala
            260                 265                 270

Ser Ser Ile Leu Asp Ala Ile Ala Ser Thr Ile Leu Ser Leu Phe Leu
        275                 280                 285
```

```
Asp Leu Thr Ile Val Val Met Thr Gly Leu Ile Leu Gly Leu Gln Asn
    290                 295                 300

Met Gln Leu Phe Leu Leu Val Leu Leu Ala Ile Pro Leu Tyr Ile Val
305                 310                 315                 320

Val Ile Ile Ile Phe Thr Pro Leu Phe Glu Lys Gln Asn His Glu Val
                325                 330                 335

Met Gln Thr Asn Ala Val Leu Asn Ser Ser Ile Ile Glu Asp Ile Asn
            340                 345                 350

Gly Ile Glu Thr Ile Lys Ala Leu Ala Ser Glu Gln Glu Arg Tyr Gln
        355                 360                 365

Lys Ile Asp Tyr Glu Phe Ala Ser Tyr Leu Lys Lys Ala Phe Thr Leu
370                 375                 380

Gln Lys Ser Glu Ala Ile Gln Gly Leu Ile Lys Ala Ile Ile Gln Leu
385                 390                 395                 400

Thr Leu Ser Val Thr Ile Leu Trp Phe Gly Ala Thr Leu Val Ile Ser
                405                 410                 415

Gln Lys Ile Thr Leu Gly Gln Leu Ile Thr Phe Asn Ala Leu Leu Ser
            420                 425                 430

Tyr Phe Thr Asn Pro Ile Thr Asn Ile Ile Asn Leu Gln Thr Lys Leu
        435                 440                 445

Gln Lys Ala Arg Val Ala Asn Glu Arg Leu Asn Glu Val Tyr Leu Val
450                 455                 460

Pro Ser Glu Phe Glu Glu Lys Lys Thr Glu Leu Ser Leu Ser His Phe
465                 470                 475                 480

Asn Leu Asn Met Ser Asp Ile Ser Tyr Gln Tyr Gly Phe Gly Arg Lys
                485                 490                 495

Val Leu Ser Glu Ile Glu Leu Ser Ile Lys Glu Asn Glu Lys Leu Thr
            500                 505                 510

Ile Val Gly Met Ser Gly Ser Gly Lys Ser Thr Leu Val Lys Leu Leu
        515                 520                 525

Val Asn Phe Phe Gln Pro Thr Ser Gly Thr Ile Thr Leu Gly Gly Ile
530                 535                 540

Asp Leu Gln Gln Phe Asp Lys His Gln Leu Arg Arg Leu Ile Asn Tyr
545                 550                 555                 560

Leu Pro Gln Gln Pro Tyr Ile Phe Thr Gly Ser Ile Leu Asp Asn Leu
                565                 570                 575

Leu Leu Gly Ala Asn Glu Asn Ala Ser Gln Glu Glu Ile Leu Lys Ala
            580                 585                 590

Val Glu Leu Ala Glu Ile Arg Ala Asp Ile Glu Gln Met Gln Leu Gly
        595                 600                 605

Tyr Gln Thr Glu Leu Ser Ser Asp Ala Ser Ser Leu Ser Gly Gly Gln
610                 615                 620

Lys Gln Arg Ile Ala Leu Ala Arg Ala Leu Leu Ser Pro Ala Lys Ile
625                 630                 635                 640

Leu Ile Leu Asp Glu Ala Thr Ser Asn Leu Asp Met Ile Thr Glu Lys
                645                 650                 655

Lys Ile Leu Lys Asn Leu Leu Pro Leu Asp Lys Thr Ile Ile Phe Ile
            660                 665                 670

Ala His Arg Leu Ser Val Ala Glu Met Ser His Arg Ile Ile Val Val
        675                 680                 685

Asp Gln Gly Lys Val Ile Glu Ser Gly Ser His Val Asp Leu Leu Ala
690                 695                 700
```

```
Gln Asn Gly Phe Tyr Glu Gln Leu Tyr His Asn
705                 710                 715
```

<210> SEQ ID NO 44
<211> LENGTH: 474
<212> TYPE: PRT
<213> ORGANISM: Lactococcus lactis subsp. cremoris

<400> SEQUENCE: 44

```
Met Phe Asp Lys Lys Leu Leu Glu Ser Glu Leu Tyr Asp Lys Arg
1               5                   10                  15

Tyr Arg Asn Phe Ser Thr Leu Ile Ile Leu Pro Leu Phe Ile Leu Leu
                20                  25                  30

Val Gly Gly Val Ile Phe Thr Phe Phe Ala His Lys Glu Leu Thr Val
            35                  40                  45

Ile Ser Thr Gly Ser Ile Glu Pro Thr Lys Ile Val Ala Lys Ile Gln
    50                  55                  60

Ser Thr Asn Ala Asn Pro Ile Ile Glu Asn Asn Leu Lys Glu Gly Glu
65                  70                  75                  80

Ala Val Lys Glu Asn Ser Leu Leu Lys Tyr Asn Gly Thr Pro Glu
                85                  90                  95

Gln Thr Gln Leu Ser Glu Leu Leu Thr Gln Lys Lys Gln Ala Leu Asp
                100                 105                 110

Lys Lys Val Gln Leu Asp Leu Leu Gln Arg Ser Leu Thr Asn Glu Lys
            115                 120                 125

Asn Glu Phe Pro Thr Ala Asp Ser Phe Gly Tyr Glu Lys Ser Phe Glu
    130                 135                 140

Asn Tyr Glu Ala Gln Val Lys Ser Leu Glu Ala Thr Ile Gln Lys Ser
145                 150                 155                 160

Asn Gln Ala Val Glu Asp Gln Asn Lys Ser Thr Glu Ser Gln Lys Gln
                165                 170                 175

Ala Ile Gln Asn Gln Val Ala Thr Leu Gln Gln Ala Ile Gln Asn Tyr
                180                 185                 190

Ser Glu Ile Glu Asn Ala Val Ser Ser Gly Gly Val Ser Gln Asp
                195                 200                 205

Asn Pro Tyr Leu Ser Gln Tyr Asn Ser Tyr Gln Ala Gln Gln Ala Thr
    210                 215                 220

Leu Glu Ala Asp Leu Lys Asn Gln Lys Asn Pro Asp Glu Thr Ala Lys
225                 230                 235                 240

Gln Ala Ala Lys Ser Gln Glu Glu Ser Leu Lys Ser Gln Phe Leu Ser
                245                 250                 255

Gly Leu Ala Ser Ser Lys Asp Ser Leu Lys Ser Gln Ile Gln Ser Phe
                260                 265                 270

Asn Val Gln Glu Ser Ser Leu Thr Gly Ser Asn Ala Tyr Asp Asn Ser
                275                 280                 285

Gln Ser Ser Gln Ile Leu Thr Leu Lys Ser Gln Ala Leu Ser Ala Ser
                290                 295                 300

Asn Lys Glu Met Thr Asp Leu Asn Ser Thr Leu Thr Asp Leu Glu Thr
305                 310                 315                 320

Lys Ile Ser Leu Gln Lys Gln Asp Asp Gln Tyr Ser Gln Val Phe Ala
                325                 330                 335

Glu Gln Ala Gly Val Leu His Val Leu Pro Asp Ile Leu Gly Met Lys
                340                 345                 350

Lys Ile Pro Ile Gly Thr Pro Ile Ala Glu Ile Tyr Pro Leu Leu Lys
                355                 360                 365
```

-continued

```
Ser Glu Thr Gln Val Asn Leu Thr Ser Tyr Ile Pro Ser Thr Gln Ile
        370                 375                 380

Ser Gly Met Lys Val Gly Gln Lys Val Arg Phe Thr Val Gln Gln Asn
385                 390                 395                 400

Leu Pro Gln Pro Glu Ile Leu Thr Gly Ile Ile Asn Gln Ile Asp Ser
                    405                 410                 415

Ala Pro Thr Ala Phe Lys Glu Gly Asn Ala Tyr Lys Val Ser Ala Thr
                420                 425                 430

Thr Thr Ile Asn Ala Lys Asp Leu Pro Asn Ile Arg Tyr Gly Leu Gln
            435                 440                 445

Gly Lys Thr Val Thr Ile Ile Gly Lys Lys Thr Tyr Phe Asn Tyr Phe
        450                 455                 460

Leu Asp Lys Ile Met Gly Arg Gly Asn Gln
465                 470

<210> SEQ ID NO 45
<211> LENGTH: 56
<212> TYPE: PRT
<213> ORGANISM: Liquorilactobacillus hordei
<220> FEATURE:
<221> NAME/KEY: SIGNAL
<222> LOCATION: (1)..(18)

<400> SEQUENCE: 45

Met Lys Lys Glu Ile Glu Leu Ser Glu Lys Glu Leu Val Arg Ile Ile
1               5                   10                  15

Gly Gly Lys Tyr Tyr Gly Asn Gly Val Ser Cys Thr Lys Lys His Gly
            20                  25                  30

Cys Lys Val Asn Trp Gly Gln Ala Phe Thr Cys Ser Val Asn Arg Phe
        35                  40                  45

Ala Asn Phe Gly His Gly Asn Cys
    50                  55

<210> SEQ ID NO 46
<211> LENGTH: 38
<212> TYPE: PRT
<213> ORGANISM: Liquorilactobacillus hordei

<400> SEQUENCE: 46

Lys Tyr Tyr Gly Asn Gly Val Ser Cys Thr Lys Lys His Gly Cys Lys
1               5                   10                  15

Val Asn Trp Gly Gln Ala Phe Thr Cys Ser Val Asn Arg Phe Ala Asn
            20                  25                  30

Phe Gly His Gly Asn Cys
        35

<210> SEQ ID NO 47
<211> LENGTH: 126
<212> TYPE: PRT
<213> ORGANISM: Liquorilactobacillus hordei

<400> SEQUENCE: 47

Met Gln Ile Arg Lys Glu Val Tyr Phe Leu Lys Asp Thr Lys Lys
1               5                   10                  15

Glu Ala Ile Arg Glu Ile Ser Leu Leu Val Asn Tyr Leu Glu Ser Arg
            20                  25                  30

Asp Asp Lys Ser Ser Gly Leu Leu Asp Ile Ile Asp Val Leu Lys Gln
        35                  40                  45
```

-continued

```
Val Tyr Lys Asn Leu Glu Asp Ala Lys Asn Pro Glu Ala Leu Leu Asn
         50                  55                  60

Lys Leu Ile Asn Tyr Ile Arg Ser Val Ala Met Gln Tyr Lys Ile His
 65                  70                  75                  80

Phe Pro Ser Lys Glu Glu Lys Leu Ile Ile Asp Leu Glu Val Leu Gly
                 85                  90                  95

Gln Arg Ala Gly Leu Asn Gly Arg Tyr Met Ala Asp Phe Ser Asp Lys
                100                 105                 110

Ser Gln Phe Tyr Ser Leu Leu Glu Asn Ile Pro Arg His Asn
                115                 120                 125

<210> SEQ ID NO 48
<211> LENGTH: 177
<212> TYPE: PRT
<213> ORGANISM: Liquorilactobacillus hordei

<400> SEQUENCE: 48

Met Met Asn Leu Glu Lys His Lys Thr Tyr Phe Phe Leu Phe Ile Ser
 1               5                  10                  15

Leu Phe Ile Gly Thr Ile Val Leu Phe Leu Gln Thr Ala Glu Ile Gln
                20                  25                  30

Ala Ser Thr Asn Asn Gln Leu Thr Ser Gln Gln Asn Asp Thr Gln Val
                35                  40                  45

Gln His Leu Val Ser Gln Asp Glu Tyr Glu Glu Asn Ile Lys Lys Thr
         50                  55                  60

Ile Pro Ile Ser Thr Thr Glu Leu Ile Thr Lys Phe Asn Ser Gly Glu
 65                  70                  75                  80

Thr Phe Val Leu Phe Ile Gly Tyr Lys Glu Cys Lys Tyr Cys Arg Ala
                 85                  90                  95

Phe Ser Pro Thr Leu Asn Val Phe Met Asn Thr Ser Thr Val Pro Val
                100                 105                 110

Tyr Tyr Leu Asp Val Asp Ser Val Ser Gln Ser Glu Leu Thr Gln Asn
                115                 120                 125

Phe Val Asp Ile Met Tyr Asn Lys Ile Lys Leu Gln Gly Thr Pro Thr
                130                 135                 140

Ile Ala Leu Ile Lys His Gly Lys Val Ile His Glu Tyr Ile Gly Ser
145                 150                 155                 160

Asn Thr Ser Leu Asn Gln Leu Gln Thr Leu Lys Lys Tyr Lys Tyr Ala
                165                 170                 175

Asn

<210> SEQ ID NO 49
<211> LENGTH: 718
<212> TYPE: PRT
<213> ORGANISM: Liquorilactobacillus hordei

<400> SEQUENCE: 49

Met Phe Phe Glu Arg Asn Ile Tyr Thr Met Gln Val Asp Glu Ser Asp
 1               5                  10                  15

Cys Gly Val Ala Cys Leu Ala Met Ile Leu Lys His Phe Gly Ser Ser
                20                  25                  30

Ile Ser Leu Ala Tyr Leu Arg Asn Leu Ala Lys Thr Asn Thr Glu Gly
                35                  40                  45

Thr Thr Ala Leu Gly Leu Val Lys Thr Ala Glu Lys Leu Lys Phe Glu
         50                  55                  60

Thr Lys Ala Ile Lys Ala Asp Met Thr Leu Phe Asp Ile Met Asp Leu
```

-continued

```
                65                  70                  75                  80
Pro Leu Pro Phe Ile Ala His Val Val Lys Pro Gly Gly Leu Leu His
                    85                  90                  95
Tyr Tyr Val Val Leu Lys Val Lys Lys Asp Gln Leu Ile Ile Ala Asp
                    100                 105                 110
Pro Asp Pro Thr Val Gly Val Ile Lys Met Arg Lys Lys Gln Phe Ser
                    115                 120                 125
Gln Glu Trp Ser Gly Val Ala Leu Phe Met Ala Pro Lys Pro Thr Tyr
                    130                 135                 140
Gln Pro Ile Lys Gln Glu Lys Ser Ser Leu Phe Ser Phe Pro Ser
145                 150                 155                 160
Met Ile Lys Gln Lys Lys Leu Val Gly Asn Ile Ile Leu Ala Ala Leu
                    165                 170                 175
Leu Ile Thr Ile Ile Ser Ile Ala Gly Ser Tyr Phe Leu Gln Thr Ile
                    180                 185                 190
Ile Asp Thr Tyr Ile Pro Asn Asn Met His Ser Thr Leu Ala Ile Ile
                    195                 200                 205
Ala Leu Gly Leu Ile Ile Phe Tyr Ile Phe Gln Ser Ile Phe Thr Tyr
                    210                 215                 220
Ala Gln Asn Phe Leu Leu Ala Val Leu Gly Gln Arg Leu Ser Ile Glu
225                 230                 235                 240
Ile Ile Leu Gly Tyr Ile Arg His Ile Phe Glu Leu Pro Met Glu Phe
                    245                 250                 255
Phe Thr Thr Arg Lys Thr Gly Glu Ile Val Ser Arg Phe Thr Asp Ala
                    260                 265                 270
Ser Lys Ile Ile Asp Ala Leu Ala Ser Thr Val Val Ser Met Phe Leu
                    275                 280                 285
Asp Val Gly Ile Val Ile Val Met Gly Ile Ile Leu Ala Leu Gln Ser
                    290                 295                 300
Ser Gln Leu Phe Trp Ile Thr Leu Ile Ser Leu Pro Ile Tyr Ile Ala
305                 310                 315                 320
Ile Ile Leu Ile Phe Ser Lys Ala Phe Glu Lys Leu Asn Gln Lys Glu
                    325                 330                 335
Met Glu Ser Asn Ala Ile Leu Ser Ser Ser Ile Ile Glu Asp Ile His
                    340                 345                 350
Gly Ile Glu Thr Ile Lys Ala Leu Asn Ser Glu Pro Gln Arg Tyr Gln
                    355                 360                 365
Lys Ile Asp Thr Glu Phe Val Asp Phe Leu Lys Lys Ser Leu Ala Tyr
                    370                 375                 380
Thr Lys Ala Asp Thr Leu Gln Gln Ala Leu Lys Leu Phe Val Gln Leu
385                 390                 395                 400
Ser Leu Asn Val Leu Ile Leu Trp Ile Gly Ala Leu Leu Val Ile His
                    405                 410                 415
Asn Arg Leu Ser Val Gly Gln Leu Met Thr Tyr Asn Ala Leu Leu Ala
                    420                 425                 430
Tyr Phe Val Asn Pro Leu Gln Ser Ile Ile Asn Leu Gln Pro Lys Leu
                    435                 440                 445
Gln Ser Ala Arg Val Ala Asn Asn Arg Leu Asn Glu Val Phe Leu Val
                    450                 455                 460
Glu Ser Glu Phe Ala Asp Ser Arg Pro Ile Lys Lys Val Glu Gln Leu
465                 470                 475                 480
Gln Gly Pro Ile Val Phe Lys Gln Val Ser Tyr His Tyr Gly Tyr Gly
                    485                 490                 495
```

```
Gln Asp Val Leu Lys Asn Ile Asn Leu Gln Phe Asn Leu Gly Asp Lys
                500                 505                 510

Ile Thr Ile Val Gly Met Ser Gly Ser Gly Lys Ser Thr Leu Val Lys
            515                 520                 525

Leu Leu Ile Asp Phe Phe Glu Pro Ser Ser Gly Glu Ile Leu Ile Asn
        530                 535                 540

Gln His Pro Leu Lys Leu Val Asp Lys His Ile Ile Arg Ser Phe Ile
545                 550                 555                 560

Asn Tyr Ile Pro Gln Glu Pro Tyr Ile Phe Ser Gly Ser Ile Glu Asp
                565                 570                 575

Asn Leu Arg Leu Gly Asn Arg Ala Asn Ile Thr Leu Ala Glu Ile Glu
            580                 585                 590

Lys Ala Cys Lys Thr Ala Met Ile Ala Ala Asp Ile Glu Lys Met Pro
        595                 600                 605

Leu Gln Phe Asn Thr Asn Leu Asp Glu Asn Gly Asn Thr Leu Ser Gly
        610                 615                 620

Gly Gln Lys Gln Arg Leu Thr Ile Ala Arg Ala Leu Leu Ser Pro Ala
625                 630                 635                 640

Lys Ile Leu Ile Phe Asp Glu Ser Thr Ser Gly Leu Asp Thr Ile Thr
                645                 650                 655

Glu Lys Lys Leu Ile Asp Asn Leu Thr Lys Leu Ser Asp Lys Thr Ile
            660                 665                 670

Ile Phe Ile Ala His Arg Leu Ala Val Ala Gln Arg Thr Asp Lys Ile
        675                 680                 685

Leu Val Leu His Glu Gly Lys Leu Val Glu Gln Gly Ser His Ala Glu
        690                 695                 700

Leu Met Arg Lys Gln Gly Tyr Tyr Asn Leu Val Asn Ser
705                 710                 715

<210> SEQ ID NO 50
<211> LENGTH: 458
<212> TYPE: PRT
<213> ORGANISM: Liquorilactobacillus hordei

<400> SEQUENCE: 50

Met Asp Lys Arg Phe Leu Glu Ser Ser Glu Phe Tyr Asn Gly Arg Tyr
1               5                   10                  15

Asn Asn Phe Ser Thr Ile Leu Ile Pro Met Ser Leu Leu Leu Ile
            20                  25                  30

Gly Ile Val Gly Phe Ser Leu Phe Ala Lys Arg Glu Ile Thr Val Thr
        35                  40                  45

Gly Val Gly Thr Leu Glu Ala Thr Gln Leu Ala Thr Thr Val Gln Ala
    50                  55                  60

Thr Thr Asn Ser Ala Ile Glu Lys Asn Tyr Leu Ser Glu Gly Lys Tyr
65                  70                  75                  80

Val Lys Lys Gly Gln Thr Leu Leu Ile Tyr Asn Asn Val Leu Asn Arg
                85                  90                  95

Asn Lys Leu Lys Leu Tyr Gln Gln Gln Leu Lys Gln Leu Gln Gln Gln
            100                 105                 110

Lys Thr Ala Leu Lys Thr Leu Arg Gln Gly Ile Ile Asn Gln Asp
        115                 120                 125

Ser Phe Lys Gln Asp Asp Ala Phe Gly Tyr Arg Ala Met Leu Gln Ser
130                 135                 140

Tyr Leu Lys Gln Arg Gln Ile Tyr Gln Thr Glu Asn Gln Met Leu Ala
```

```
                145                 150                 155                 160
        Gln Lys Ala Asn Ser Thr Lys Ser Lys Gln Ala Ser Leu Ile Gln Thr
                        165                 170                 175
        Glu Gln Gln Val Val Asp Arg Asn Asp Ser Asn Leu Gln Ala Tyr Gln
                    180                 185                 190
        Asn Leu Tyr Thr Ala Ile Asn Gln Asp Lys Gly Tyr Ala Ser Asn Ala
                195                 200                 205
        Lys Tyr Ser Tyr Ile Tyr Gln Glu Tyr Lys Ser Lys Leu Ser Asn Leu
            210                 215                 220
        Gly Ser Ser Asp Asp Lys Ser Glu Leu Lys Asp Asp Thr Leu Ala Ser
        225                 230                 235                 240
        Val Gln Gln Gln Ile Asp Ser Leu Gln Asp Ser Val Ala Ser Ala Lys
                        245                 250                 255
        Val Gln Val Glu Glu Leu Gln Asp Phe Asp Ser Thr Asn Phe Ser Val
                    260                 265                 270
        Thr Thr Asn Asn Gln Lys Met Gln Thr Leu Gln Ser Asp Gln Leu Asn
                275                 280                 285
        Thr Val Ala Gln Asp Leu Ile Lys Val Gln Gln Ser Leu Lys Glu Val
            290                 295                 300
        Gly Asn Asn Ile Val Ala Leu Lys Ser Glu Asn His Glu Tyr Thr Ile
        305                 310                 315                 320
        Thr Ala Pro Lys Thr Gly Val Leu His Val Asn Asn Asp Tyr Gln Gly
                        325                 330                 335
        Ile Lys Tyr Ile Ser Ser Gly Thr Ala Ile Ala Thr Ile Tyr Pro Ile
                    340                 345                 350
        Leu Lys Lys Gln Lys Phe Leu Glu Ile Lys Ala Tyr Ile Ser Thr Thr
                355                 360                 365
        Asp Ile Ser Glu Ile Lys Ile Gly Gln Asn Val Arg Phe Lys Val Ser
            370                 375                 380
        Arg Asn Val Pro Lys Ser Ile Val Ile Asn Gly Lys Ile Asn Lys Ile
        385                 390                 395                 400
        Ser Val Ser Pro Ile Thr Val Asn His Gly Ser Tyr Tyr Val Ile Thr
                        405                 410                 415
        Ser Lys Ala Lys Ile Thr Asn Gln Gln Lys Ser Leu Leu Lys Tyr Gly
                    420                 425                 430
        Met Ser Gly Lys Ile Ser Val Ile Thr Gly Lys Lys Thr Phe Phe Asn
                435                 440                 445
        Tyr Tyr Lys Asp Lys Leu Leu Asn Lys Ser
            450                 455

<210> SEQ ID NO 51
<211> LENGTH: 63
<212> TYPE: PRT
<213> ORGANISM: Pediococcus pentosaceus
<220> FEATURE:
<221> NAME/KEY: SIGNAL
<222> LOCATION: (1)..(19)

<400> SEQUENCE: 51

Met Met Lys Lys Ile Glu Lys Leu Thr Glu Lys Glu Met Ala Asn Ile
1               5                   10                  15

Ile Gly Gly Lys Tyr Tyr Gly Asn Gly Leu Tyr Cys Gly Lys His Ser
            20                  25                  30

Cys Ser Val Asp Trp Gly Lys Ala Thr Thr Cys Ile Ile Asn Asn Gly
        35                  40                  45
```

Ala Met Ala Trp Ala Thr Gly Gly His Gln Gly Thr His Lys Cys
            50                  55                  60

<210> SEQ ID NO 52
<211> LENGTH: 44
<212> TYPE: PRT
<213> ORGANISM: Pediococcus pentosaceus

<400> SEQUENCE: 52

Lys Tyr Tyr Gly Asn Gly Leu Tyr Cys Gly Lys His Ser Cys Ser Val
1               5                   10                  15

Asp Trp Gly Lys Ala Thr Thr Cys Ile Ile Asn Asn Gly Ala Met Ala
            20                  25                  30

Trp Ala Thr Gly Gly His Gln Gly Thr His Lys Cys
            35                  40

<210> SEQ ID NO 53
<211> LENGTH: 174
<212> TYPE: DNA
<213> ORGANISM: Lactococcus lactis

<400> SEQUENCE: 53
atgagtacaa aagattttaa cttggatttg gtatctgttt cgaagaaaga ttcaggtgca      60
tcaccacgca ttacaagtat ttcgctatgt acacccggtt gtaaaacagg agctctgatg     120
ggttgtaaca tgaaaacagc aacttgtaat tgtagtattc acgtaagcaa ataa           174

<210> SEQ ID NO 54
<211> LENGTH: 174
<212> TYPE: DNA
<213> ORGANISM: Lactococcus lactis

<400> SEQUENCE: 54
atgagtacaa aagattttaa cttggatttg gtatctgttt cgaagaaaga ttcaggtgca      60
tcaccacgca ttacaagtat ttcgctatgt acacccggtt gtaaaacagg agctctgatg     120
ggttgtaaca tgaaaacagc aacttgtcat tgtagtattc acgtaagcaa ataa           174

<210> SEQ ID NO 55
<211> LENGTH: 738
<212> TYPE: DNA
<213> ORGANISM: Lactococcus lactis

<400> SEQUENCE: 55
atgagaagat atttaatact tattgtggcc ttaataggga taacaggttt atcagggtgt      60
tatcaaacaa gtcataaaaa ggtgaggttt gacgaaggaa gttatactaa tttatttat     120 gataataaat cgtatttcgt aactgataag gagattcctc aggagaacgt taacaattcc     180
aaagcaaaat tttataagct gttgattgtt gacatgaaaa gtgagaaact tttatcaagt     240
agcaacaaaa atagtgtgac tttggtctta aataatattt tgaggcttc tgacaagtcg     300 ctatgtatgg gtattaacga cagatactat aagatacttc cagaaagtga taaggggcg     360 gtcaaagctt tgagattaca aaactttgat gtgacaagcg atatttctga tgataatttt     420
gttattgata aaaatgattc acgaaaaatt gactatatgg gaaatatta cagtatatcg     480 gacagcaccg tatctgatga agaattggga gaatatcagg atgttttagc tgaagtacgt     540
gtgtttgatt cagttagtgg caaaagtatc ccgaggtctg aatgggggag aattgataag     600
gatggttcaa attccaaaca gagtaggacg gaatgggatt atggcgaaat ccattctatt     660
agaggaaaat ctcttactga agcatttgcc gttgagataa atgatgattt taagcttgca     720

```
acgaaggtag gaaactag                                                 738

<210> SEQ ID NO 56
<211> LENGTH: 738
<212> TYPE: DNA
<213> ORGANISM: Lactococcus lactis

<400> SEQUENCE: 56
atgcgtcgtt acttaatctt gatcgttgca ttgattggca tcaccggctt aagtggttgc    60
tatcaaacgt cacataagaa agttcgcttc gatgaaggtt catatactaa tttcatctac   120
gataataaga gctactttgt tacagacaaa gaaattcctc aagaaaatgt caacaactcc   180
aaggcaaagt tctataagct attgattgtt gatatgaaga gtgaaaaact gttgagctca   240
tccaataaga actctgttac gctggttctt aataacattt acgaagcaag tgataaatct   300 cttttgtatgg gtattaacga tcggtattat aagatttttgc ctgagtcaga taagggtgcc   360
gttaaggctc tgcgtcttca aaacttcgac gttaccagcg atatctctga cgacaacttc   420
gttattgata agaacgatag tcggaaaatc gattacatgg caacatctta ttctatcagc   480
gactcaaccg tctcggacga agaactaggc gaataccaag acgttttggc ggaagttcgt   540
gttttcgact cagtctccgg gaagtccatt ccgcgtagcg aatggggccg tatcgataag   600
gatggtagca actctaaaca gtctcgtacc gaatgggatt atggcgaaat tcacagtatc   660
cgtggcaagt ctctgacaga agcttttgca gtggaaatta cgatgatttt caagttggct   720
accaaggttg gcaactag                                                 738

<210> SEQ ID NO 57
<211> LENGTH: 678
<212> TYPE: DNA
<213> ORGANISM: Lactococcus lactis

<400> SEQUENCE: 57
atgcaggtaa aaattcaaaa tctttctaaa acatataaag aaaagcaggt gctacaagat    60
atcagttttg atattaaatc tggaacagtc tgtggtttat taggagttaa cggtgcagga   120
aaatcaactt tgatgaaaat tttgtttggt ttaatttctg cagatactgg aaaaattttt   180
tttgatggac aagaaaagac aaataatcaa cttggagcct taatcgaggc tccagcaata   240
tatatgaatt tatctgcttt cgataatctt aaaactaagg ctttgctttt tggaatttca   300
gataagagaa ttcatgaaac tctagaagtg attggtttgg ctgaaacagg aagagaaaga   360
gcaggaaaat tctctcttagg gatgaaacaa cgtttgggaa ttggtatggc tattcttaca   420
gaacctcaat tttaattct tgatgaacct actaatggtt tggatcctga tggtattgcg   480
gagttgttaa acttaatctt aaaacttaaa gctaaaggtg tgacaatctt gatttctagt   540
catcagttgc acgaaataag taaagtagct agtcaaatta ttattttgaa caaaggtaag   600
attcgttata atcatgcgaa caataagaa gacgacattg aacagttatt ctttaagatt   660
gtgcatggag gaatgtga                                                 678

<210> SEQ ID NO 58
<211> LENGTH: 678
<212> TYPE: DNA
<213> ORGANISM: Artificial Sequence
<220> FEATURE:
<223> OTHER INFORMATION: Codon-optimized version for Lactobacillus
      paracasei encoding SEQ ID NO: 12

<400> SEQUENCE: 58
```

```
atgcaagtta agattcaaaa cctgtctaaa acctataagg agaagcaggt tctccaagat    60
atttcatttg atatcaagag cggtacggtt tgtggtctct gggtgttaa cggcgctggc   120 aagtccactc ttatgaagat tctgttcggc ttgatctccg ccgacactgg taagattttt   180
tttgatggcc aggaaaagac gaacaatcaa ttgggcgcct tgatcgaagc tccggccatc   240
tacatgaatc tgtccgcttt tgataacttg aagacaaagg ctcttctttt cggcattagc   300
gacaagcgca ttcatgaaac gttggaggtt attggcttgg ccgaaacagg caagaaacgt   360
gcagggaaat tctctctggg tatgaagcaa cgcctgggca ttggtatggc cattttgacc   420
gaaccacaat tcttgatcct tgacgagccg accaacgggc ttgatcctga tggtatcgca   480
gaacttctga atttaatctt gaagctgaag gctaagggtg ttaccatctt gatttcatca   540
catcagttgc atgaaatttc taaggttgcg agtcagatca tcatccttaa caaaggtaag   600
atccgttata atcatgccaa caacaaggaa gatgacattg aacagctttt cttcaagatt   660
gtccatggtg gtatgtga                                                 678
```

<210> SEQ ID NO 59
<211> LENGTH: 729
<212> TYPE: DNA
<213> ORGANISM: Lactococcus lactis

<400> SEQUENCE: 59

```
atgaaaagaa taatagcatc agaagcaata aaattaaaaa aatcaggaac tcttagattg    60
gtattaatta tcccttttgt gactctattt atagcatttc ttatgggtgg aatacagatt   120
tttagtgttt tttcaattta ttggtgggaa actggttttt tattcctttt gatgagtttg   180
ctttttcttt atgatataaa atcagaggag caagctggaa attttcaaaa tgtgaaatgg   240
aaaaagctga gttggaaaat tcatttggcc aaaatgttgt tgatttggct aagaggtata   300
ctagcgagca tagtcttgat tattttgctt tatttggttg cttttgtgtt tcaaggtatt   360
gtagtggtgg atttttatga agtaagtgtg gcattgattg ctatattact agcagcttct   420
tggaatttac cctttatata cttgattttc aagtggatta atacttacgt attgttagct   480
gcgaatacct tgatttgttt aattgttgcc ccttttgttg cacaaactcc agtatggttc   540
ttgctaccat acacttatca ctataaagtt acagaaagtt tgttaaatat caaaccatca   600
ggagatttgt taacagggaa gataaatttc agtatttggg aagttttatt accatttgga   660
ctttccatag ttgtaacgat aggagtttcg tatttactta aggagtgat agaacatgat   720 aagaagtga                                                           729
```

<210> SEQ ID NO 60
<211> LENGTH: 729
<212> TYPE: DNA
<213> ORGANISM: Artificial Sequence
<220> FEATURE:
<223> OTHER INFORMATION: Codon-optimized version for Lactobacillus paracasei encoding SEQ ID NO: 13

<400> SEQUENCE: 60

```
atgaagcgga ttattgcaag cgaggctatt aagttgaaga agagtggaac cttacgtctg    60
gtcttgatta ttccgttcgt cacattattc atcgcattct tgatgggcgg tatccagatc   120
ttttcagttt tctctatcta ctggtgggag acaggctttc tgttcctgtt gatgagtttg   180
ttgttcttgt atgacattaa gtctgaagaa caggctggca acttccaaaa cgttaagtgg   240
aagaagcttt catggaagat tcacttggct aagatgcttc tcatctggtt acgtggcatt   300
```

```
ctcgcttcca tcgttttgat cattcttttg tacctggttg ctttcgtttt ccagggcatc    360
gttgtagttg acttcatgaa agtctcagtg gcattgattg ctatcttgtt ggccgcaagt    420
tggaatctcc cgttcattta tttgatttc aaatggatca acacatatgt tttactggca    480
gcgaacactt tgatctgctt gatcgttgct ccatttgttg ctcagacacc agtttggttc    540
ttgctgccgt acacctacca ttacaaggtt accgaaagcc tccttaacat caaaccaagt    600
ggtgatctgt tgaccggcaa aattaatttt agtatctggg aagttttgtt accgtttggc    660
ttaagtattg tggttacaat cggggtgtct tacttattga agggcgtcat tgaacacgat    720
aagaagtga                                                            729

<210> SEQ ID NO 61
<211> LENGTH: 645
<212> TYPE: DNA
<213> ORGANISM: Lactococcus lactis

<400> SEQUENCE: 61
atgataagaa gtgaatgtct caaattaaaa aatagcttag ggttttattt agttttctc     60 tttactttat tagagctttt aacggttcct atttatttag cttttggaag aagtcatgtt    120
tcaatgactg attcgtcgct catgattttt ttgttttttc cgttactggt tacaattttg    180
tctattctaa tctttgaaca ggagagtctg gccaatcatt tccaagaaat aaatgtaaat    240
aaaaaaagta gcagaatttg gttatcaaag ctaatagtag tggatttcct tttgttcttt    300
ccatcagcaa tgatctggat aattacggga gtttcacagg cagtagggca acaaggaatg    360
atgatcgcaa cagctagctg gttgatggca atttttctta atcattttca tctttttattg    420 accttataa tcaatcgagg agggagcatg attatcgcga ttattgaaat attactcatt    480 attttgcca gtaataaagt tttattagca gcttattggt gtcctattgc tttacctgtt    540
aattttatga taactgggcg gtgtgcttat ctgatagctg ccgtagggtg gattgtttta    600
tccacaataa ttcttgtagc attatctaaa aaaagatta gataa                    645

<210> SEQ ID NO 62
<211> LENGTH: 645
<212> TYPE: DNA
<213> ORGANISM: Artificial Sequence
<220> FEATURE:
<223> OTHER INFORMATION: Codon-optimized version for Lactobacillus
      paracasei encoding SEQ ID NO: 14

<400> SEQUENCE: 62
atgattcgct ctgaatgcct taagcttaaa aactccttgg gtttctattt agttttcttg    60
ttcacattac tggaattgtt aacggttcca atttatcttg cgtttggccg cagtcatgtt    120
agcatgaccg attcatcact catgatcttc ctattcttcc cgcttctggt tacaatcttg    180
tccattttga tctttgaaca agaatctctg gctaatcatt tccaagaaat taatgttaac    240
aagaaatcgt cacggatttg gttaagcaaa ttgattgttg ttgacttctt attgttttt    300 ccatcagcta tgatttggat tatcactggt gtctctcaag ctgttggtca acagggtatg    360
atgatcgcca ccgcttcatg gttgatggcc atctttctga accactttca cttattactt    420
accttcatca tcaatcgtgg tggcagcatg attatcgcta tcattgaaat tttgctcatt    480
atctttgcca gcaataaggt tctttttggct gcttactggt gcccaattgc actgccagtc    540
aacttcatga tcaccgggcg ttgcgcttac ttaattgctg ccgttggttg gattgtcttg    600
tcaacgatta ttctcgtggc cttgagcaaa aaaagattc gctaa                    645
```

<210> SEQ ID NO 63
<211> LENGTH: 276
<212> TYPE: DNA
<213> ORGANISM: Lactobacillus gasseri

<400> SEQUENCE: 63
atggttacta agtacggacg taatttaggt ttgaacaagg tagagttgtt tgcaatttgg      60
gcggttttag tagttgctct tttattgacc acagcgaaca tttattggat tgctgatcaa     120
ttcgggattc atttagcgac tggaacagcc cgtaagttat tagatgcaat ggcttctggt     180
gcctcattgg gaactgcctt tgctgctatt tgggcgtga cattacctgc atgggctttg      240
gcagctgcag gagcattggg agcgactgca gcctag                               276

<210> SEQ ID NO 64
<211> LENGTH: 276
<212> TYPE: DNA
<213> ORGANISM: Artificial Sequence
<220> FEATURE:
<223> OTHER INFORMATION: Codon-optimized version for Lactococcus lactis
      encoding SEQ ID NO: 15

<400> SEQUENCE: 64
atggttacaa atatggacg taatctaggg ttgaacaaag tagaattatt cgctatatgg       60
gctgttcttg tagttgctct tttgcttaca actgcaaata tttattggat cgcagatcaa     120
ttcggtattc atttggcgac aggtactgca cgtaaactat ggatgcaat ggcttctggt      180 gcatctttgg gtaccgcttt cgccgcgatt cttggggtaa ctttaccggc ctgggctctt    240
gctgcggcag gtgcattggg cgcaacagca gcataa                               276

<210> SEQ ID NO 65
<211> LENGTH: 162
<212> TYPE: DNA
<213> ORGANISM: Lactobacillus gasseri

<400> SEQUENCE: 65
atgcaaaaac tattacggat tattgctttg attagtttaa tagctgctat aatatcattc      60
tttatattta aaattaatta taacatat atccttatag gaatatttat tggttctggc       120
ttcatttatc aaattagagc acaaggcaga atagaaagt aa                         162

<210> SEQ ID NO 66
<211> LENGTH: 162
<212> TYPE: DNA
<213> ORGANISM: Artificial Sequence
<220> FEATURE:
<223> OTHER INFORMATION: Codon-optimized version for Lactococcus lactis
      encoding SEQ ID NO: 17

<400> SEQUENCE: 66
atgcaaaaac ttcttcgtat tattgctctt atctcattaa ttgcagcgat tatttctttc      60 tttatttta aaattaacta catcacttat atcttaattg gaatctttat aggatcaggt      120
tttatttatc aaatccgggc ccaaggtcgt aatcgtaaat aa                        162

<210> SEQ ID NO 67
<211> LENGTH: 162
<212> TYPE: DNA
<213> ORGANISM: Artificial Sequence
<220> FEATURE:
<223> OTHER INFORMATION: Codon-optimized version for Lactobacillus
      paracasei encoding SEQ ID NO: 17

<400> SEQUENCE: 67

```
atgcaaaagt tacttcgaat tatcgcctta atttcgttga ttgccgcaat tatcagtttc      60
tttatcttca aaatcaatta tattacctat atcttaatcg gtatcttcat tggctcaggc     120
ttcatctacc aaatccgtgc tcaaggtcgt aaccgcaagt ag                        162
```

<210> SEQ ID NO 68
<211> LENGTH: 681
<212> TYPE: DNA
<213> ORGANISM: Lactobacillus gasseri

<400> SEQUENCE: 68

```
atgacaagaa atatgtttgt agacattaaa atgttagca aaaccttac tgattttca         60
ttggaaaatc taaacatcag ctttgaaaaa ggtgaaatta ttggattagt tggtgaaaat    120
ggagccggaa agactacttt gttaaactta atatctggaa tattaaaacc ggataaggga    180
cagatacttc ttagttctaa taatattgga tattgttttg atgcattacc tgagccagaa    240
aatttaacaa tagagcaact taatacgata tttactggat tactagcagt atgggatagt    300
gatacttatt tttcttttcgt ggatgaattt aaattaccta aggaaagcc atcggggtc     360
ttttctaaag gaatgaaaat gcaattaaat gtatcaataa cgttatccca taatcctaca    420
cttttgctct tagatgaagt cacggcggga ttagatccaa tagtgcgaag aactgtacta    480
aatacaataa aagaatacgc aatttcatca gagtgtatcg ttattatgac aacacacaac    540
ctagaggata tttctgatat atgtaaccga ttaattcttt tgaataacgg cagcatattg    600
ttagatgata attttgagga taaaagttca aaagaaatag aattaatctt tcgaaagact    660
ttaggatatg gagatatgta g                                              681
```

<210> SEQ ID NO 69
<211> LENGTH: 681
<212> TYPE: DNA
<213> ORGANISM: Artificial Sequence
<220> FEATURE:
<223> OTHER INFORMATION: Codon-optimized version for Lactococcus lactis
      encoding SEQ ID NO: 18

<400> SEQUENCE: 69

```
atgacccgta atatgtttgt tgatatcaaa atgttagta agaatttgac agattttagc       60
ttagaaaatt taaatattag tttcgaaaag ggcgaaataa ttggattggt tggtgaaaat    120
ggagctggga aaactaccct acttaaccta attagcggaa ttttaaaacc agataaaggt    180
caaatttgt tatcatctaa taacattggt tattgttttg atgcattgcc ggaacctgaa     240
aatttaacaa tagaacaatt aaataccatt tttactggtc ttctcgcagt ctgggacagt    300
gatacttatt tttcttttgt cgatgaattc aaattaccaa aggaaaaacc cattggagta    360
tttagtaagg gtatgaaaat gcaattaaat gtttcaatta ctttaagcca taatcctaca    420
ttgcttttat tggatgaagt cacagctgga ttagacccaa ttgttcgacg tacggtgcta    480
aataccatca agaatatgc tatatcatct gaatgtattg ttattatgac tacacacaat    540
ttagaggata tttctgacat ttgtaacaga ttgattttgc ttaataacgg tagtattctc    600
cttgacgata attttgaaga caaatcaagt aaagaaattg agcttatttt tagaaaaacg    660
cttgggtacg gagatatgta g                                              681
```

<210> SEQ ID NO 70
<211> LENGTH: 639

<212> TYPE: DNA
<213> ORGANISM: Lactobacillus gasseri

<400> SEQUENCE: 70

```
atgaaaggat tagtacaaaa agatatttac cagttaacca gtagctggtt tcgtcctgta      60
aggatatttt ttgtaatagc tgtattggct gcgggtatga ttttttttaaa acaagatagt    120
tcaattattt tagttttatt gctgttgttg atggtgaata atattcaatc attgtttata    180
aaagatagta cgaacagatg gttatctcta cttaaatcgt tgaaaatcag tacatttgct    240
gttataggt cacgctatat tacattagta gttatctgcg tatgtggtgc aatactcaat    300
tttgtataca tgcttttgg tatgctttta ttcaacacca gcactggtat tgatgtatta    360
gtaatcagta gcatatgttt atgggtatct ttaatttatg gattagtaat aattccattt    420
ttatatgctt taagcaaaaa tgggttgact ttggccataa tcattatgtt tagctgtgtc    480
gctttactga taaagttttc ttcagcaata actaaattag cttatatcat acattcgtat    540
agttatgtac agttaatttt gatcgcaatt gttgcactga ttggcatagg aataatttca    600
atggtagtgt catacttaat tgtcgaaaaa gaaaagtga                           639
```

<210> SEQ ID NO 71
<211> LENGTH: 638
<212> TYPE: DNA
<213> ORGANISM: Artificial Sequence
<220> FEATURE:
<223> OTHER INFORMATION: Codon-optimized version for Lactococcus lactis encoding SEQ ID NO: 19

<400> SEQUENCE: 71

```
atgaaaggtc ttgtacaaaa agatatttat caattaacct catcttggtt tcgccctgtc      60
cgtatttct ttgtaattgc tgtgttggcg gccggaatga tttttcttaaa acaagacagc    120
tcaataattt tggttctctt gcttttactt atggtcaaca atatccaatc tttatttatt    180
aaagatagta ctaatcgttg gttgagcttg cttaaatcat taaaaattag tacatttgcc    240
gtaataggct ctagatatat tacacttgtt gtaatttgtg tttgtggagc tatttttaaat    300
tttgtctata tgcttttgg tatgttgctt ttcaacacga gtacgggtat agacgtactt    360
gtcatcagtt ctatctgctt gtgggtcagc ctcatatatg gcctcgttat tatcccgttc    420
ttgtatgcat ttaaacaaaa tgggctaaca ttagccataa ttataatgtt ctcatgtgtc    480
gcgcttctca ttaaatttag ttctgcgatt acgaaacttg catacatcat tcatagctat    540
tcatatgttc aattgatttt aattgctatc gttgcactta ttggtatagg tatcatttct    600
atggttgtaa gctatttaat tgttgaaaaa gaaaaata                             638
```

<210> SEQ ID NO 72
<211> LENGTH: 189
<212> TYPE: DNA
<213> ORGANISM: Pediococcus sp.

<400> SEQUENCE: 72

```
atgaaaaaaa ttgaaaaatt aactgaaaaa gaaatggcca atatcattgg tggtaaatac      60
tacggtaatg gggttacttg tggcaaacat tcctgctctg ttgactgggg taaggctacc    120
acttgcataa tcaataatgg agctatggca tgggctactg gtggacatca aggtaatcat    180
aaatgctag                                                             189
```

<210> SEQ ID NO 73
<211> LENGTH: 189

```
<212> TYPE: DNA
<213> ORGANISM: Artificial Sequence
<220> FEATURE:
<223> OTHER INFORMATION: Codon-optimized version for Lactococcus lactis
      encoding SEQ ID NO: 20

<400> SEQUENCE: 73
atgaaaaaaa ttgaaaaatt aactgaaaaa gaaatggcca atatcattgg tggtaaatat      60
tacggtaacg gtgtgacttg tggcaaacac agttgttcag ttgactgggg caaagcaaca     120
acttgtatca tcaacaatgg agctatggct tgggccacag gaggacacca aggaaatcac     180
aaatgttaa                                                             189

<210> SEQ ID NO 74
<211> LENGTH: 216
<212> TYPE: DNA
<213> ORGANISM: Artificial Sequence
<220> FEATURE:
<223> OTHER INFORMATION: Codon-optimized version for Lactococcus lactis
      encoding Pediococcus sp. pedA gene with the usp45TM8 signal
      sequence
<220> FEATURE:
<221> NAME/KEY: CDS
<222> LOCATION: (1)..(216)

<400> SEQUENCE: 74 atg aaa aaa aag gtg ctg aag gct cat tta gct gtg gtt gtg atg ctt       48
Met Lys Lys Lys Val Leu Lys Ala His Leu Ala Val Val Val Met Leu
1               5                   10                  15 acg acg gca gcc ccg att tcc aat gtt aag gcc aaa tat tac ggt aac       96
Thr Thr Ala Ala Pro Ile Ser Asn Val Lys Ala Lys Tyr Tyr Gly Asn
            20                  25                  30 ggt gtg act tgt ggc aaa cac agt tgt tca gtt gac tgg ggc aaa gca      144
Gly Val Thr Cys Gly Lys His Ser Cys Ser Val Asp Trp Gly Lys Ala
        35                  40                  45 aca act tgt atc atc aac aat gga gct atg gct tgg gcc aca gga gga      192
Thr Thr Cys Ile Ile Asn Asn Gly Ala Met Ala Trp Ala Thr Gly Gly
    50                  55                  60 cac caa gga aat cac aaa tgt taa                                      216
His Gln Gly Asn His Lys Cys
65                  70

<210> SEQ ID NO 75
<211> LENGTH: 71
<212> TYPE: PRT
<213> ORGANISM: Artificial Sequence
<220> FEATURE:
<223> OTHER INFORMATION: Synthetic Construct

<400> SEQUENCE: 75

Met Lys Lys Lys Val Leu Lys Ala His Leu Ala Val Val Val Met Leu
1               5                   10                  15

Thr Thr Ala Ala Pro Ile Ser Asn Val Lys Ala Lys Tyr Tyr Gly Asn
            20                  25                  30

Gly Val Thr Cys Gly Lys His Ser Cys Ser Val Asp Trp Gly Lys Ala
        35                  40                  45

Thr Thr Cys Ile Ile Asn Asn Gly Ala Met Ala Trp Ala Thr Gly Gly
    50                  55                  60

His Gln Gly Asn His Lys Cys
65                  70

<210> SEQ ID NO 76
<211> LENGTH: 336
```

```
<212> TYPE: DNA
<213> ORGANISM: Pediococcus sp.

<400> SEQUENCE: 76
atgaataaga ctaagtcgga acatattaaa caacaagctt tggacttatt tactaggcta      60 cagttttac tacagaagca cgatactatc gaaccttacc agtacgtttt agatattctg      120
gagactggta tcagtaaaac taaacataac cagcaaacgc ctgaacgaca agctcgtgta      180
gtctacaaca agattgccag ccaagcgtta gtagataagt tacattttac tgccgaagaa      240
aacaaagttc tagcagccat caatgaattg gcgcattctc aaaaagggtg gggcgagttt      300
aacatgctag atactaccaa tacgtggcct agccaa                              336

<210> SEQ ID NO 77
<211> LENGTH: 339
<212> TYPE: DNA
<213> ORGANISM: Artificial Sequence
<220> FEATURE:
<223> OTHER INFORMATION: Codon-optimized version for Lactococcus lactis
      encoding SEQ ID NO: 22

<400> SEQUENCE: 77
atgaacaaaa caaaatcaga acatattaaa caacaagctc ttgatttgtt cacacgtctt      60
caatttcttc ttcaaaaaca tgatacaatc gaaccttacc aatacgtttt ggacattctt      120
gaaactggca tttcaaaaac aaaacacaac caacaaactc cggaacgtca agctcgtgtt      180
gtttacaata aaattgcttc tcaagcgctt gttgacaaat tacattttac agctgaagaa      240
aacaaagttc ttgctgcaat taatgagctt gcccattcac aaaaaggttg gggcgaattc      300
aatatgcttg acacaactaa tacctggcct tctcaataa                           339

<210> SEQ ID NO 78
<211> LENGTH: 336
<212> TYPE: DNA
<213> ORGANISM: Artificial Sequence
<220> FEATURE:
<223> OTHER INFORMATION: Codon-optimized version for Lactobacillus
      paracasei encoding SEQ ID NO: 22

<400> SEQUENCE: 78
atgaataaga ccaaaagcga gcacattaaa cagcaagctc ttgaccttt tactcgcctt      60 caattttac tccagaagca cgatacaatt gaaccatatc aatacgtcct tgatatcttg      120
gaaactggta ttagtaaaac gaaacacaat cagcaaactc ctgaacggca ggcccgtgtt      180
gtctataata agattgccag tcaagccttg gttgacaaat tacatttcac agcggaggaa      240
aataaagtct tggctgcaat taacgaactg gcccacagtc aaaagggttg gggtgaattc      300
aacatgttgg atacgactaa cacctggccg agccaa                             336

<210> SEQ ID NO 79
<211> LENGTH: 234
<212> TYPE: DNA
<213> ORGANISM: Brochothrix campestris

<400> SEQUENCE: 79
atgcacaagg taaaaaaatt aaacaatcaa gagttacaac agatcgtggg aggttacagt      60
tcaaaagatt gtctaaaaga tattggtaaa ggaattggtg ctggtacagt agctggggca      120
gccggcggtg cctagctgc aggattaggt gctatcccag gagcattcgt tggagcacat      180
tttggagtaa tcggcggatc tgccgcatgc attggtggat tattaggtaa ctag          234
```

<210> SEQ ID NO 80
<211> LENGTH: 234
<212> TYPE: DNA
<213> ORGANISM: Artificial Sequence
<220> FEATURE:
<223> OTHER INFORMATION: Codon-optimized version for Lactococcus lactis
      encoding SEQ ID NO: 23

<400> SEQUENCE: 80

```
atgcataaag ttaagaaatt aaacaatcaa gaactacagc aaattgtcgg tgggtattca    60
tctaaagatt gccttaaaga tattggtaaa ggtattggag cgggaacagt tgcaggagca   120
gctggtggag gttagcagc tgggttagga gctattccag gtgcttttgt tggggcccat    180
tttggtgtta taggaggttc agcagcttgc attggtggcc ttttaggtaa ttaa         234
```

<210> SEQ ID NO 81
<211> LENGTH: 234
<212> TYPE: DNA
<213> ORGANISM: Artificial Sequence
<220> FEATURE:
<223> OTHER INFORMATION: Codon-optimized version for Lactococcus lactis
      encoding Brochothrix campestris brcA gene with the pediocin signal
      sequence

<400> SEQUENCE: 81

```
atgaaaaaaa ttgaaaaatt aactgaaaaa gaaatggcca atatcattgg tggttattct    60
tctaaagatt gtctcaaaga tattggtaaa ggtattggtg ctggaactgt tgctggtgct   120
gctgggggtg gtcttgcagc tgg

```
atg aaa aaa aag gtg ctg aag gct cat tta gct gtg gtt gtg atg ctt    48
Met Lys Lys Lys Val Leu Lys Ala His Leu Ala Val Val Val Met Leu
 1               5                  10                  15 acg acg gca gcc ccg att tcc aat gtt aag gcc tat tct tct aaa gat    96
Thr Thr Ala Ala Pro Ile Ser Asn Val Lys Ala Tyr Ser Ser Lys Asp
                20                  25                  30 tgt ctc aaa gat att ggt aaa ggt att ggt gct gga act gtt gct ggt   144
Cys Leu Lys Asp Ile Gly Lys Gly Ile Gly Ala Gly Thr Val Ala Gly
            35                  40                  45 gct gct ggg ggt ggt ctt gca gct gga tta ggt gct att cca ggt gcc   192
Ala Ala Gly Gly Gly Leu Ala Ala Gly Leu Gly Ala Ile Pro Gly Ala
        50                  55                  60 ttc gtt ggt gct cat ttc gga gtc atc gga ggc tct gca gca tgt att   240
Phe Val Gly Ala His Phe Gly Val Ile Gly Gly Ser Ala Ala Cys Ile
65                  70                  75                  80 ggt ggc ctt ctt ggt aat tag                                        261
Gly Gly Leu Leu Gly Asn
                85
```

<210> SEQ ID NO 84
<211> LENGTH: 86
<212> TYPE: PRT
<213> ORGANISM: Artificial Sequence
<220> FEATURE:
<223> OTHER INFORMATION: Synthetic Construct

<400> SEQUENCE: 84

```
Met Lys Lys Lys Val Leu Lys Ala His Leu Ala Val Val Val Met Leu
 1               5                  10                  15

Thr Thr Ala Ala Pro Ile Ser Asn Val Lys Ala Tyr Ser Ser Lys Asp
                20                  25                  30

Cys Leu Lys Asp Ile Gly Lys Gly Ile Gly Ala Gly Thr Val Ala Gly
            35                  40                  45

Ala Ala Gly Gly Gly Leu Ala Ala Gly Leu Gly Ala Ile Pro Gly Ala
        50                  55                  60

Phe Val Gly Ala His Phe Gly Val Ile Gly Gly Ser Ala Ala Cys Ile
65                  70                  75                  80

Gly Gly Leu Leu Gly Asn
                85
```

<210> SEQ ID NO 85
<211> LENGTH: 183
<212> TYPE: DNA
<213> ORGANISM: Brochothrix campestris

<400> SEQUENCE: 85

```
atgaaaaaag aactattgaa taaaaatgaa atgagtagaa ttatcggcgg caaaataaat    60
tggggaaatg ttggcggttc ttgtgttgga ggtgcagtaa ttggaggcgc cctcggtgga   120
ctaggtggag ctggcggagg ttgcattaca ggagctatcg gaagtatttg ggatcaatgg   180
taa                                                                 183
```

<210> SEQ ID NO 86
<211> LENGTH: 183
<212> TYPE: DNA
<213> ORGANISM: Artificial Sequence
<220> FEATURE:
<223> OTHER INFORMATION: Codon-optimized version for Lactococcus lactis
      encoding SEQ ID NO: 25

<400> SEQUENCE: 86

```
atgaagaaag aacttttaaa taaaaacgaa atgtcacgaa tcattggtgg aaaaattaat      60
tggggtaatg tgggcgggag ttgtgttggg ggagctgtta taggtggagc tttaggaggg     120
ttaggagggg caggtggagg ttgtattaca ggcgctattg gtagtatttg ggaccaatgg     180
taa                                                                   183
```

<210> SEQ ID NO 87
<211> LENGTH: 186
<212> TYPE: DNA
<213> ORGANISM: Artificial Sequence
<220> FEATURE:
<223> OTHER INFORMATION: Codon-optimized version for Lactococcus lactis
      encoding Brochothrix campestris brcB gene with the pediocin signal
      sequence
<220> FEATURE:
<221> NAME/KEY: CDS
<222> LOCATION: (1)..(186)

<400> SEQUENCE: 87

```
atg aaa aaa att gaa aaa tta act gaa aaa gaa atg gcc aat atc att       48
Met Lys Lys Ile Glu Lys Leu Thr Glu Lys Glu Met Ala Asn Ile Ile
1               5                   10                  15 ggt ggt aaa att aat tgg ggt aat gtg ggt ggt tct tgt gtg ggt ggt       96
Gly Gly Lys Ile Asn Trp Gly Asn Val Gly Gly Ser Cys Val Gly Gly
            20                  25                  30 gcc gtt att gga ggc gcg ctt ggt ggt ttg ggt ggg gct ggt ggt gga      144
Ala Val Ile Gly Gly Ala Leu Gly Gly Leu Gly Gly Ala Gly Gly Gly
        35                  40                  45 tgc att act ggt gct att ggt tcc att tgg gat caa tgg taa              186
Cys Ile Thr Gly Ala Ile Gly Ser Ile Trp Asp Gln Trp
    50                  55                  60
```

<210> SEQ ID NO 88
<211> LENGTH: 61
<212> TYPE: PRT
<213> ORGANISM: Artificial Sequence
<220> FEATURE:
<223> OTHER INFORMATION: Synthetic Construct

<400> SEQUENCE: 88

```
Met Lys Lys Ile Glu Lys Leu Thr Glu Lys Glu Met Ala Asn Ile Ile
1               5                   10                  15

Gly Gly Lys Ile Asn Trp Gly Asn Val Gly Gly Ser Cys Val Gly Gly
            20                  25                  30

Ala Val Ile Gly Gly Ala Leu Gly Gly Leu Gly Gly Ala Gly Gly Gly
        35                  40                  45

Cys Ile Thr Gly Ala Ile Gly Ser Ile Trp Asp Gln Trp
    50                  55                  60
```

<210> SEQ ID NO 89
<211> LENGTH: 213
<212> TYPE: DNA
<213> ORGANISM: Artificial Sequence
<220> FEATURE:
<223> OTHER INFORMATION: Codon-optimized version for Lactococcus lactis
      encoding Brochothrix campestris brcB gene with the usp45TM8 signal
      sequence
<220> FEATURE:
<221> NAME/KEY: CDS
<222> LOCATION: (1)..(213)

<400> SEQUENCE: 89

```
atg aaa aaa aag g

```
                1               5                   10                  15
acg acg gca gcc ccg att tcc aat gtt aag gcc aaa att aat tgg ggt         96
Thr Thr Ala Ala Pro Ile Ser Asn Val Lys Ala Lys Ile Asn Trp Gly
            20                  25                  30 aat gtg ggt ggt tct tgt gtg ggt ggt gcc gtt att gga ggc gcg ctt         144
Asn Val Gly Gly Ser Cys Val Gly Gly Ala Val Ile Gly Gly Ala Leu
            35                  40                  45 ggt ggt ttg ggt ggg gct ggt ggt gga tgc att act ggt gct att ggt         192
Gly Gly Leu Gly Gly Ala Gly Gly Gly Cys Ile Thr Gly Ala Ile Gly
    50                  55                  60 tcc att tgg gat caa tgg taa                                             213
Ser Ile Trp Asp Gln Trp
65                  70

<210> SEQ ID NO 90
<211> LENGTH: 70
<212> TYPE: PRT
<213> ORGANISM: Artificial Sequence
<220> FEATURE:
<223> OTHER INFORMATION: Synthetic Construct

<400> SEQUENCE: 90

Met Lys Lys Lys Val Leu Lys Ala His Leu Ala Val Val Val Met Leu
1               5                   10                  15

Thr Thr Ala Ala Pro Ile Ser Asn Val Lys Ala Lys Ile Asn Trp Gly
            20                  25                  30

Asn Val Gly Gly Ser Cys Val Gly Gly Ala Val Ile Gly Gly Ala Leu
            35                  40                  45

Gly Gly Leu Gly Gly Ala Gly Gly Gly Cys Ile Thr Gly Ala Ile Gly
    50                  55                  60

Ser Ile Trp Asp Gln Trp
65                  70

<210> SEQ ID NO 91
<211> LENGTH: 162
<212> TYPE: DNA
<213> ORGANISM: Brochothrix campestris

<400> SEQUENCE: 91
atggtaaaaa ctatactatt ttcggttgta atttcattcg ttgcattatg taacttttta      60
ataaaaaaag atgtgtcttc aaaaaaaaaa ttatttttaa caggttctat tgctgtcttt     120
ctaattatct atgattttct atggattata ttctctaact ag                        162

<210> SEQ ID NO 92
<211> LENGTH: 162
<212> TYPE: DNA
<213> ORGANISM: Artificial Sequence
<220> FEATURE:
<223> OTHER INFORMATION: Codon-optimized version for Lactococcus lactis
      encoding SEQ ID NO: 27

<400> SEQUENCE: 92
atggttaaaa cgattttgtt ttcagtcgtt atctcatttg ttgctttatg caattttctt      60
attaaaaaag atgtttcatc aaaaaaaaaa ctcttcctta ctggatcaat tgcagttttt     120
ttgatcatct atgattttctt gtggattatt ttctcaaact ag                       162

<210> SEQ ID NO 93
<211> LENGTH: 162
<212> TYPE: DNA
<213> ORGANISM: Artificial Sequence
```

```
<220> FEATURE:
<223> OTHER INFORMATION: Codon-optimized version for Lactobacillus
      paracasei encoding SEQ ID NO: 27

<400> SEQUENCE: 93
atggttaaga caattttgtt ctctgtcgtg atcagttttg tcgctctctg caatttctc      60 attaaaaagg acgtcagcag taagaaaaag ttgtttttaa ctggttcgat tgccgttttt     120
ttaatcattt acgatttcct ttggatcatt ttttctaatt aa                        162

<210> SEQ ID NO 94
<211> LENGTH: 276
<212> TYPE: DNA
<213> ORGANISM: Lactobacillus plantarum

<400> SEQUENCE: 94
atgctttcag catatcgtag taaattagga ttgaacaaat ttgaggttac tgttttaatg      60
atcatctctc tttttatttt attatttgcc acagttaata ttgtatggat tgcaaaacaa     120
tttggtgtgc atttgacaac tagtcttaca caaaaagctt tagatctatt atctgctgga    180
tcatctttgg gcaccgtggc agctgctgtc ttaggtgtta cattgccagc atgggcagtt    240
gcagcagctg gggctctcgg gggtactgca gcttaa                              276

<210> SEQ ID NO 95
<211> LENGTH: 276
<212> TYPE: DNA
<213> ORGANISM: Artificial Sequence
<220> FEATURE:
<223> OTHER INFORMATION: Codon-optimized version for Lactococcus lactis
      encoding SEQ ID NO: 28

<400> SEQUENCE: 95
atgttaagtg catacccgcag taaattagga cttaataagt ttgaagtcac agttcttatg     60
ataatttcac ttttcatctt acttttttgct actgttaata ttgtttggat tgcaaaacaa    120
tttggcgtac atttaaccac tagccttact caaaaagcgc tagatttatt gtctgctgga    180
tcaagtttag ggacagtagc tgcagctgtt ttgggagtta ctcttcctgc ctgggcagtt    240
gcagctgcag gggcgttggg aggcactgct gcatag                              276

<210> SEQ ID NO 96
<211> LENGTH: 486
<212> TYPE: DNA
<213> ORGANISM: Lactobacillus plantarum

<400> SEQUENCE: 96
atgaccatct ttgtgaataa accgcggagt aatatccctg ctttattgat agtatttata     60 attttttttaa ttttgggtgt cttgtttagc aaatattttg caactgcaag ctctcaacat   120
tcattagatt catttaaagt aattcattta aactggttta ctgaaattat ctttagaaat    180
acaatagcat tttttagtatt aagctctact cttttttttgg gaaatatagt aagtgtcata   240 ttctttttgcg ttaatggctt taacgttggt ctaatatgcg gtcaattacc aatatttcaa   300
agtatcgttc ttctctcacc acatggtgtt attgaaataa cttcgtatat atggttagta   360
tatgctgtaa cacatgttaa tcacatgaaa attaatataa taagatccta ctgtctttttg    420 tttcttgcag caataattga agttttttgtt accccaggat tagccttatg gttgttagga    480
gattaa                                                              486

<210> SEQ ID NO 97
```

<211> LENGTH: 486
<212> TYPE: DNA
<213> ORGANISM: Artificial Sequence
<220> FEATURE:
<223> OTHER INFORMATION: Codon-optimized version for Lactococcus lactis encoding SEQ ID NO: 30

<400> SEQUENCE: 97

```
atgaccatct tgttaataa gccacgtagt aatattccag ctctattaat cgtattcata      60
atttttttaa ttcttggcgt gttgttctct aaatatttcg ccaccgctag ctcacaacat    120
agtttagata gttttaaagt cattcattta aattggttta ctgaaattat atttcgcaat    180
actatcgcat ttctcgtatt atcttcaaca ttattccttg ggaatattgt ttctgttatc    240
tttttctgtg ttaatggatt taatgtgggt cttatctgtg gtcaattacc tatttttcaa    300
tcaattgttc tcctttctcc acatggagtc atcgaaatta catcatatat ttggcttgtt    360
tacgcagtca cacatgtaaa ccacatgaaa atcaatatca ttcgttctta tgcctatta    420
tttttagcag ccatcattga agttttgtt actcctgggc tagcactatg gttactagga    480
gactaa                                                              486
```

<210> SEQ ID NO 98
<211> LENGTH: 486
<212> TYPE: DNA
<213> ORGANISM: Artificial Sequence
<220> FEATURE:
<223> OTHER INFORMATION: Codon-optimized version for Lactobacillus paracasei encoding SEQ ID NO: 30

<400> SEQUENCE: 98

```
atgactattt tcgtgaacaa gccacgaagt aatatccccg cgttactaat tgtgtttatt      60
atctttttga tccttggagt gcttttttagt aaatatttg cgaccgcgtc aagccaacac    120
agtctggata gctttaaagt tattcatctt aattggttta ccgaaatcat tttccggaac    180
accatcgctt tctagtgct gtccagtacc ttgttttttgg gaaacattgt ctcggtaatt    240
ttctttttgtg ttaatggttt caacgtcggt ttaatctgcg gccaattacc gatcttccaa    300
tcaattgtac tgttgtcgcc acatggagtc atcgaaatca gtcgtacat ctggctggtt    360
tacgctgtga cccatgttaa tcatatgaaa attaatatca ttcggtcgta ctgtcttttg    420
ttcctggctg caattatcga ggttttttgtc acacctgggt tagcccttttg gttgctgggc    480
gactga                                                              486
```

<210> SEQ ID NO 99
<211> LENGTH: 165
<212> TYPE: DNA
<213> ORGANISM: Lactobacillus plantarum

<400> SEQUENCE: 99

```
atgaagaatt tagatatgtt agtacgtgtc attacaatta ttttattgtt agcgacaata      60
actgccttt tctttaaggg tctcagtact ataacttata tatgtgcaat aattacagtg    120
gtattggctt tgtatatca gctaattaaa cggcatacag attaa                    165
```

<210> SEQ ID NO 100
<211> LENGTH: 165
<212> TYPE: DNA
<213> ORGANISM: Artificial Sequence
<220> FEATURE:
<223> OTHER INFORMATION: Codon-optimized version for Lactococcus lactis encoding SEQ ID NO: 31

<400> SEQUENCE: 100

```
atgaagaatc ttgatatgct tgttcgtgtt attacgataa ttcttttact agcaacaatc    60
actgctttct ttttcaaggg tttgagtact atcacttata tttgtgctat aattacggtc   120
gttcttgcat tcgtctatca acttataaaa cgtcatacag attga                   165
```

<210> SEQ ID NO 101
<211> LENGTH: 165
<212> TYPE: DNA
<213> ORGANISM: Artificial Sequence
<220> FEATURE:
<223> OTHER INFORMATION: Codon-optimized version for Lactobacillus
      paracasei encoding SEQ ID NO: 31

<400> SEQUENCE: 101

```
atgaaaaatc tcgatatgct agttcgggtc attacaatca ttctcttgct ggctaccatt    60
acggctttct ttttcaaagg tctctctact atcacgtata tttgcgcaat cattactgtg   120
gtcctggcgt tcgtgtatca gctgattaaa cgacatacgg actga                   165
```

<210> SEQ ID NO 102
<211> LENGTH: 684
<212> TYPE: DNA
<213> ORGANISM: Lactobacillus plantarum

<400> SEQUENCE: 102

```
atgtgtatga ctaaggtgag tatgagtcaa gtcaggaaaa aatatgacaa tttatattg     60
ggcgacataa attttcaagc aaaagaaaaa gaaatcattg gtttaattgg cgagaatggt   120
gctggaaaaa ccacactatt aaaatctatt ggaggaatca ataagataga ttttggaact   180
attaaaaaag attttaaaga attagggttt gctttgaca gcattccatt ccctgaagaa    240
ctaaacatac ttcagttgga acatatattt caaaacattg gaataaactg ggatactcaa   300
gcttttttggc cttatattaa agcacttcag ttacctatta aaataccgat atctaatttt   360
tccaaaggaa tgaaaatgca actaaactta tgcatttcta tttcacatca tccggactta   420
ttgttgttag atgaaataac tagtggcctt gatccactta tgcgacgaaa agtattgcga   480
ctaatcaaaa aatatgtaga tcaaaatgac tgtgcagtaa taattaccac tcataatttg   540
aatgatgttg tagaaatctg tactcgtttt gacttgctag atcatggaaa aatcattttg   600
gaaaaaaca tgcaaaaatt tggggcagaa aaccttgaga aactatttga agagacagta   660
aaaaaagcga atttaggtga ataa                                          684
```

<210> SEQ ID NO 103
<211> LENGTH: 684
<212> TYPE: DNA
<213> ORGANISM: Artificial Sequence
<220> FEATURE:
<223> OTHER INFORMATION: Codon-optimized version for Lactococcus lactis
      encoding SEQ ID NO: 32

<400> SEQUENCE: 103

```
atgtgtatga caaagttc aatgagtcaa gtacgtaaaa agtatgacaa ttttatccta      60
ggagacatta actttcaagc caaagagaaa gaaatcatag gtttaatcgg agaaaatggt   120
gcaggtaaaa ctacccttt aaaatctatt ggaggtatca ataagattga ctttggaacg   180
ataaagaaag attttaaaga actcggattt tgttttgatt ctatccctt tccagaggaa    240
ttaaatattc tccaattaga acacattttt cagaacattg gtattaattg ggataccaa    300
gctttctggc cttacatcaa agcccttcaa cttccaatta agattccaat ctcaaatttt   360
```

```
tctaaaggta tgaaaatgca actaaactta tgtatctcaa tttctcacca tcctgatttg    420
ttattgcttg atgaaattac aagcggtttg gatccattaa tgcgacgtaa ggtattacga    480
ttaattaaaa agtatgttga tcagaatgac tgcgctgtta tcattaccac acataacttg    540
aatgatgttg tagaaatatg tacaagattt gatttacttg atcatgggaa aatcattctt    600
gaaaagaata tgcaaaaatt tggtgctgag aatttagaaa aacttttga ggaaaccgtt     660 aagaaagcca acttagggga ataa                                           684
```

<210> SEQ ID NO 104
<211> LENGTH: 645
<212> TYPE: DNA
<213> ORGANISM: Lactobacillus plantarum

<400> SEQUENCE: 104

```
atgcttggat tgatgttaaa agattattat cagctgtgtg ataagtggtt caaaaaaata    60
tatttgttag gtgtatcttt ttctttaatt atagccacaa tttttctaaa aagtgatagt    120
tggatagtag caacattgat atcaatgata atgattaata gcattcaatc actctttcta    180
tccgataata aaaacaactg gataaatttt ttaacaactt tatctataaa aaaatctata    240
agtgttcttg caaggtatct atttgttatc attgtctgtg ctgtaactgc tatactgaat    300
gggctatttt ttctagtgat atcattattt ttcaaaggta ttactattga agtataatg    360 attgttccta tttgcttgtt tacagtttca ataatttata tatcctttat tctcccttt     420 ttatatgctt ttcagcaaaa cggattaact gttggtgtgt tactgatttt agggatagct    480
tttgtaagta tacgtttttt tggtattctg tctaaaataa aaaaattaat tttactagat    540
tctaaaactg aattaatatt tcttgtcgct cttgctttaa ttataactgt tgctttgtca    600
tacagtattg cctatgtaat tagtttaatt agaggagaag aataa                    645
```

<210> SEQ ID NO 105
<211> LENGTH: 645
<212> TYPE: DNA
<213> ORGANISM: Artificial Sequence
<220> FEATURE:
<223> OTHER INFORMATION: Codon-optimized version for Lactococcus lactis
      encoding SEQ ID NO: 33

<400> SEQUENCE: 105

```
atgttaggat tgatgcttaa agactactat caattatgtg ataaatggtt caagaaaatt    60
tatttattgg gggtaagttt tagcttgata attgctacaa ttttcttgaa gtcagacagt    120
tggattgtag ctactttaat ttctatgatt atgattaatt caatccaatc attatttctt    180
tctgataata aaaacaattg gattaatttt ttaactacac tttctatcaa gaaatcaatc    240
agtgttttag ctagatattt atttgtcatc attgtatgcg cagttactgc tatttttaaat   300 ggattgtttt tccttgttat cagcttattt ttcaaaggga ttacaattga gagcattatg    360
attgttccta tatgtttatt tacagttagt ataatttata tctctttcat cttgccattt    420
ttgtacgctt ttcagcaaaa tggtcttact gtcggtgttt tacttatttt gggaattgct    480
tttgtctcaa ttagattctt tggtattta tctaagatta gaaacttat tttgttagac      540 tctaaaacag aattaatttt tcttgtcgct ttggctctta taattaccgt tgcattatct    600
tatagtattg cctatgtaat tagtcttatt cgtggagaag aataa                    645
```

<210> SEQ ID NO 106
<211> LENGTH: 522

<212> TYPE: DNA
<213> ORGANISM: Lactobacillus plantarum

<400> SEQUENCE: 106

```
atgaaattta gacatacaat actatattgg attttcgcat gggggggcatt gtttgtatta      60
gcgatcttaa gattatttaa aacattcaaa attctgccta attctaatcg cattttaaaa     120
gggattcctg ttgatatagt agcacctacc tttggaatct tgctatgttt ggtagttttt     180
atatcagctt taggaagtta cctagtattc tttgtattta ataaaatcaa acggttgaac     240
cttacattct tatctcgctt taaaacaaag gtatatgaca tttatctatc ttcatacatt     300
gtatataatt tactatatgt catttatatc tacttatata aaaaaacagc aaccaacttt     360
caaataaata tttttagctt actgcttgga acttttatca gctttctaat atttaactat     420
cttagaaagc aaaaaatatc tttaaaaaat aatatgaat tttcaagtac cattcttta      480
ataaatatta tcacacctat atatagcttg atttttttat ag                        522
```

<210> SEQ ID NO 107
<211> LENGTH: 522
<212> TYPE: DNA
<213> ORGANISM: Artificial Sequence
<220> FEATURE:
<223> OTHER INFORMATION: Codon-optimized version for Lactococcus lactis
      encoding SEQ ID NO: 34

<400> SEQUENCE: 107

```
atgaaatttc gacacactat tctttattgg attttttgcgt ggggagccct atttgttcta      60
gcaatccttc gattatttaa aacattcaaa atccttccaa attctaatag aattttgaag     120
ggtattccag ttgatattgt ggctccaact tttgggattt tgttatgttt agtggtattt     180
atttcagctt tgggctctta cttagttttt ttcgtattta ataaaattaa aagacttaat     240
ttaacatttc ttagtagatt taaaaccaaa gtttacgaca tttatttatc ttcatatatt     300
gtttacaatt tactctatgt tatttatatt tacctataca agaaaactgc aactaatttc     360
caaattaaca tttttagtct attgctcggg accttcattt cattccttat ttttaattac     420
cttagaaaac aaaaaatttc tcttaaaaac aatatgaat tttcaagtac tattctattg     480
attaatataa ttacgccaat ttatagcctt attttccttt aa                        522
```

<210> SEQ ID NO 108
<211> LENGTH: 171
<212> TYPE: DNA
<213> ORGANISM: Lactobacillus plantarum

<400> SEQUENCE: 108

```
atgatgaaaa aaattgaaaa attaactgaa aaagaaatgg ccaatatcat tggtggtaaa      60
tactatggta atggggttac ttgtggtaaa cattcctgct ctgttaactg gggccaagca     120
ttttcttgta gtgtgtcaca tttagctaac ttcggtcatg gaaagtgcta a              171
```

<210> SEQ ID NO 109
<211> LENGTH: 171
<212> TYPE: DNA
<213> ORGANISM: Artificial Sequence
<220> FEATURE:
<223> OTHER INFORMATION: Codon-optimized version for Lactococcus lactis
      encoding SEQ ID NO: 35

<400> SEQUENCE: 109

```
atgatgaaga aaatcgaaaa attaacagaa aaagaaatgg caaacatcat tggtggaaaa      60
```

```
tactatggca atggcgttac ttgcggcaag cattcatgtt cagtcaattg gggtcaggct        120
ttctcatgtt ctgtttctca tctagctaat ttcggtcatg gaaaatgcta a                171
```

<210> SEQ ID NO 110
<211> LENGTH: 165
<212> TYPE: DNA
<213> ORGANISM: Artificial Sequence
<220> FEATURE:
<223> OTHER INFORMATION: Codon-optimized version for Lactococcus lactis
      encoding Lactobacillus plantarum plaA gene with the pediocin
      signal sequence
<220> FEATURE:
<221> NAME/KEY: CDS
<222> LOCATION: (1)..(165)

<400> SEQUENCE: 110

```
atg aaa aaa att gaa aaa tta act gaa aaa gaa atg gcc aat atc att          48
Met Lys Lys Ile Glu Lys Leu Thr Glu Lys Glu Met Ala Asn Ile Ile
1               5                   10                  15 ggt ggt aaa tat tac ggt aac ggt gtt aca tgt ggt aaa cat tca tgc          96
Gly Gly Lys Tyr Tyr Gly Asn Gly Val Thr Cys Gly Lys His Ser Cys
            20                  25                  30 tct gtg aat tgg ggt caa gcg ttc tca tgc tca gtt tca cat ctt gct        144
Ser Val Asn Trp Gly Gln Ala Phe Ser Cys Ser Val Ser His Leu Ala
        35                  40                  45 aat ttc ggt cac gga aaa tgt                                            165
Asn Phe Gly His Gly Lys Cys
    50                  55
```

<210> SEQ ID NO 111
<211> LENGTH: 55
<212> TYPE: PRT
<213> ORGANISM: Artificial Sequence
<220> FEATURE:
<223> OTHER INFORMATION: Synthetic Construct

<400> SEQUENCE: 111

```
Met Lys Lys Ile Glu Lys Leu Thr Glu Lys Glu Met Ala Asn Ile Ile
1               5                   10                  15

Gly Gly Lys Tyr Tyr Gly Asn Gly Val Thr Cys Gly Lys His Ser Cys
            20                  25                  30

Ser Val Asn Trp Gly Gln Ala Phe Ser Cys Ser Val Ser His Leu Ala
        35                  40                  45

Asn Phe Gly His Gly Lys Cys
    50                  55
```

<210> SEQ ID NO 112
<211> LENGTH: 192
<212> TYPE: DNA
<213> ORGANISM: Artificial Sequence
<220> FEATURE:
<223> OTHER INFORMATION: Codon-optimized version for Lactococcus lactis
      encoding Lactobacillus plantarum plaA gene with the usp45TM8
      signal sequence
<220> FEATURE:
<221> NAME/KEY: CDS
<222> LOCATION: (1)..(192)

<400> SEQUENCE: 112

```
atg aaa aaa aag gtg ctg aag gct cat tta gct gtg gtt gtg atg ctt          48
Met Lys Lys Lys Val Leu Lys Ala His Leu Ala Val Val Val Met Leu
1               5                   10                  15 acg acg gca gcc ccg att tcc aat gtt aag gcc aaa tat tac ggt aac          96
Thr Thr Ala Ala Pro Ile Ser Asn Val Lys Ala Lys Tyr Tyr Gly Asn
            20                  25                  30
```

```
ggt gtt aca tgt ggt aaa cat tca tgc tct gtg aat tgg ggt caa gcg    144
Gly Val Thr Cys Gly Lys His Ser Cys Ser Val Asn Trp Gly Gln Ala
         35                  40                  45 ttc tca tgc tca gtt tca cat ctt gct aat ttc ggt cac gga aaa tgt    192
Phe Ser Cys Ser Val Ser His Leu Ala Asn Phe Gly His Gly Lys Cys
 50                  55                  60
```

<210> SEQ ID NO 113
<211> LENGTH: 64
<212> TYPE: PRT
<213> ORGANISM: Artificial Sequence
<220> FEATURE:
<223> OTHER INFORMATION: Synthetic Construct

<400> SEQUENCE: 113

```
Met Lys Lys Lys Val Leu Lys Ala His Leu Ala Val Val Met Leu
 1               5                  10                  15

Thr Thr Ala Ala Pro Ile Ser Asn Val Lys Ala Lys Tyr Tyr Gly Asn
             20                  25                  30

Gly Val Thr Cys Gly Lys His Ser Cys Ser Val Asn Trp Gly Gln Ala
         35                  40                  45

Phe Ser Cys Ser Val Ser His Leu Ala Asn Phe Gly His Gly Lys Cys
 50                  55                  60
```

<210> SEQ ID NO 114
<211> LENGTH: 330
<212> TYPE: DNA
<213> ORGANISM: Lactobacillus plantarum

<400> SEQUENCE: 114

```
atggctgagc agtacgtaac tgaactatat aaaaaattaa agtctcgaga ttcaaaaaca     60
tctggccttt tagatatttt agatgttctt atccaagttc aaaaaaactt atcaacggtg    120
aaaaaccctg aggcattagt aaatcgttgc gttcaatata tacgtagtgt tgccatcaaa    180
gacaaattat attttcctcc agcagaagaa aatataatta ttaatttaga agttattggc    240
caaaaagcag gttggaacgg tagctatatg gctgatttta gtgataaatc acagttttat    300
aaactttcag aatcaatccc acaccattag                                     330
```

<210> SEQ ID NO 115
<211> LENGTH: 327
<212> TYPE: DNA
<213> ORGANISM: Artificial Sequence
<220> FEATURE:
<223> OTHER INFORMATION: Codon-optimized version for Lactococcus lactis
      encoding SEQ ID NO: 37

<400> SEQUENCE: 115

```
atggctgaac aatacgtcac tgaattgtat aaaaaaactca agtcacgtga tagcaaaacc     60
tctggtcttc ttgacatact tgatgtcctt atccaagttc aaaaaaattt gtcaactgtt    120
aaaaatccag aagctttggt taatcgttgt gtccaatata ttcgtagcgt tgccattaaa    180
gataaactct atttccctcc agcagaagag aatattatta tcaatttaga agttattggt    240
caaaaggcag gttggaatgg ttcatacatg gctgattttt ctgacaaatc acaatttat    300 aaactttcag aatcaatccc acaccat                                        327
```

<210> SEQ ID NO 116
<211> LENGTH: 330
<212> TYPE: DNA
<213> ORGANISM: Artificial Sequence
<220> FEATURE:
<223> OTHER INFORMATION: Codon-optimized version for Lactobacillus
      paracasei encoding SEQ ID NO: 37

<400> SEQUENCE: 116

| | | |
|---|---|---|
| atggcggaac agtatgttac tgagctttat aaaaagctga atctcgcga ttcaaagacg | 60 |
| tctggttat tggatattct agatgtattg atccaagtgc aaaaaaactt gagtacagtt | 120 |
| aagaaccctg aagcgctagt aaatcgctgc gttcaatata ttcgaagcgt ggcgattaag | 180 |
| gataaattgt acttcccacc tgctgaggaa aatatcatta tcaatcttga agtgattggg | 240 |
| caaaaggcgg gttggaatgg ctcgtatatg gcagatttct ccgataagag ccagttctac | 300 |
| aaactatcgg aaagcatccc acaccactaa | 330 |

<210> SEQ ID NO 117
<211> LENGTH: 525
<212> TYPE: DNA
<213> ORGANISM: Lactobacillus plantarum

<400> SEQUENCE: 117

| | | |
|---|---|---|
| atgtctaaga aattttggtc aaatatcttt ttagcattag gcgtctttct tgcttttgca | 60 |
| ggagttgcta ccatatcggt gagtgctgac agttccgcta ctatagaatc aaatactagc | 120 |
| tcgaaaatca tcgatggtgc aacttatgaa gaaaacatca agggcgttat tcctattacg | 180 |
| ctaactcaat atttgcataa agctcaaact ggagaaaaat ttattgtctt tgtcgggttc | 240 |
| aaggagtgtg tgcattgtcg taaattttct ccagtcatga acagtactt acaacaaagt | 300 |
| cagcatccca tttattactt agactatggg aacaacgggt ctttcagcat ggcttctcaa | 360 |
| aaacaaataa ctgatttcta ttcaactttt gcaaccccca tgagttttat gggaacgcca | 420 |
| actgttgcct tgctcgataa tggtaaggtg gtatcaatga ccgctggtga tgataccact | 480 |
| ttatctgatt tacaacagat tactgctgat tacaataatc agtag | 525 |

<210> SEQ ID NO 118
<211> LENGTH: 522
<212> TYPE: DNA
<213> ORGANISM: Artificial Sequence
<220> FEATURE:
<223> OTHER INFORMATION: Codon-optimized version for Lactococcus lactis
      encoding SEQ ID NO: 38

<400> SEQUENCE: 118

| | | |
|---|---|---|
| atgtcaaaaa aattttggtc taacattttt cttgcattgg gcgtattttt ggcttttgca | 60 |
| ggtgtcgcta ctatcagcgt ttcagcagat tcttcagcta caattgaatc aaacacaagt | 120 |
| tcaaaaatta tcgatggtgc gacttacgaa gaaaatatca aggtgtaat ccaattacg | 180 |
| ttgactcaat atttacataa agcacaaact ggtgaaaaat tcattgtgtt tgttggtttt | 240 |
| aaagaatgtg tccactgccg taaattttca cctgtcatga acaatatttt gcaacaatct | 300 |
| caacatccaa tttattactt ggattatgga aacaatggtt cattctctat ggcttctcaa | 360 |
| aaacaaatca ctgattttta ttctacattt gctactccaa tgtcattcat gggtactcct | 420 |
| actgtagctt tgcttgacaa tggtaaagtt gtttcaatga cagcaggaga tgatacgact | 480 |
| ttgtctgatc ttcaacaaat tacagccgat tacaataatc aa | 522 |

<210> SEQ ID NO 119
<211> LENGTH: 2175
<212> TYPE: DNA
<213> ORGANISM: Lactobacillus plantarum

<400> SEQUENCE: 119

```
atgtggactc aaaaatggca caaatattat acagcacaag ttgatgaaaa tgactgtggt      60
ttagctgcac taaatatgat cctaaaatac tatggctccg attacatgtt ggcccatctt     120
cgacagcttg ccaaaacaac tgctgacggt acaactgttt tggggcttgt aaaagcagca     180
aaacacttaa atttaaatgc cgaagctgtg cgtgctgata tggatgcttt gacagcctca     240
caattgccat taccagtcat tgttcatgta ttcaagaaaa ataagttacc acactactat     300
gttgtctatc aggtaactga aaacgattta attattggtg atcctgatcc aaccgttaaa     360
accactaaaa tatcgaaatc acaatttgct aaagaatgga cccagattgc aattatcata     420
gccccaacag ttaaatataa acccataaaa gaatcacggc acacattaat tgatctagtg     480
cctttattga ttaaacaaaa aagattaatt ggactaatta ttaccgcagc agctataaca     540
acattaatca gtattgctgg tgcatatttc tttcagttaa ttatcgatac ttatttgccg     600
cacttgatga ctaataggct ttcactagtt gccattggtc tgattgtagc ttatgctttc     660
caagcaatta tcaactatat acaaagtttt tttacgattg tattaggaca acgtctcatg     720
atcgacatcg ttttaaaata cgttcaccat ctttttgatt taccaatgaa tttttttact     780
acccgtcatg tcggtgaaat gacctcacgc ttttctgatg caagcaaaat tattgatgca     840
cttggaagta caacgctcac ccttttttta gacatgtgga ttttattagc agtagggtta     900
tttttggcct atcaaaacat caattttttt ttatgctcgt tagttgtggt tccaatttac     960
atctcgattg tttggctatt taaaaaaact tttaatcgtt taaatcaaga tacaatggaa    1020
agcaatgcag ttcttaattc tgctattatt gaaagtctca gtggcataga accattaaa    1080
tcactaactg gtgaagcaac tacaaaaaaa aagattgaca cactattttc tgacttattg    1140
cataaaaact tggcttatca aaaagctgat caaggacaac aagctatcaa agcagctact    1200
aaattaatcc taactattgt tatcctttgg tggggtactt ttttttgttat gcgacaccaa    1260
ctgtctttag gtcagctgtt aacttataat gctttgctcg cttacttctt gaccccatta    1320
gaaaatatta ttaatttaca gcctaaacta caagctgcca gagtggctaa taatcgatta    1380
aatgaggttt atctagtaga gtctgaattt tctaaatcta gggaaataac tgctctagag    1440
caactaaatg gtgatattga ggttaatcat gttagtttta actatggcta tgttctaat    1500
atacttgagg atgtttctct aacaattcca catcatcaga agattactat tgtaggcatg    1560
agtggttcgg ggaaaacgac cctagccaag ttgctagttg ttttttttga gcctcaagaa    1620
cagcacggtg aaattcagat taatcatcac aatatatctg atattagtcg cacaattta    1680
cgccaatata ttaattatgt tcctcaagaa cctttcattt tttcgggctc tgtattagaa    1740
aatttattgt taggtagccg tcctggagta actcaacaaa tgattgatca agcttgttcc    1800
tttgctgaaa tcaaaactga tatagaaaat ttgcctcaag gttatcatac tagattaagt    1860
gaaagtggat tcaacttatc tggtgggcaa aaacagcggt tatcaatagc tagagcatta    1920
ttgtctccgg cacaatgttt cattttttgac gaatcaacca gtaatttaga caccattact    1980
gaacataaaa tagtctctaa gctattattc atgaaagaca aaacgataat ttttgtagca    2040
catcgtctca atattgcgtc tcaaaccgat aaagttgtcg ttcttgatca tggaaagatt    2100
gttgaacagg gatcacatcg acaattgtta aattataatg ggtattatgc acggttaatt    2160
cataatcaag aataa                                                      2175
```

<210> SEQ ID NO 120
<211> LENGTH: 2175

```
<212> TYPE: DNA
<213> ORGANISM: Artificial Sequence
<220> FEATURE:
<223> OTHER INFORMATION: Codon-optimized version for Lactococcus lactis
      encoding SEQ ID NO: 39

<400> SEQUENCE: 120
atgtggactc aaaaatggca caaatactat acagcacaag ttgatgaaaa tgattgtggt      60
ttagctgcct aaatatgat cttaaaatac tatggttcag attatatgtt agcccatctt     120
cgtcaattgg ctaaaactac agcagatggc acaactgttt taggacttgt gaaggcagcc     180
aaacatctaa atttgaatgc agaggcggtt agagcggata tggatgcgct acagcctct      240
caattaccat tacctgtaat agttcatgtt tttaagaaaa ataaattacc acattactat     300
gtcgtttatc aagtcacaga aaatgatttg atcattggtg atcctgatcc aacagttaaa     360
acgactaaaa tttctaaatc tcaatttgca aaagaatgga cccaaatcgc tattatcatt     420
gctcctacag tgaaatataa accaattaaa gaaagccgac acacattaat tgacttagtt     480
ccactcttga tcaaacaaaa gagactcatc ggacttatca ttactgccgc ggcaattacc     540
acattgattt caattgctgg tgcatacttt ttccaattga taattgacac ttatttacca     600
catcttatga caaatcgttt gtcacttgtc gcaattggac tcattgttgc atacgcgttt     660
caagcaatca ttaattacat tcaaagcttc tttacaattg tacttggcca acgtcttatg     720
attgatattg ttttaaaata cgtgcatcac ttgttcgact accaatgaa tttctttacc      780
actagacacg tgggtgaaat gacgagtcgt ttctctgatg cttctaagat aattgatgca     840
ttgggatcaa caactttaac gcttttcttg gatatgtgga ttttactcgc agtaggattg     900
ttcttggctt accaaaatat taatctttc ttgtgtagtt tagtggttgt acctatatat      960
atctcaattg tttggctttt taagaaaacc tttaatagac ttaatcaaga tactatggaa    1020
agtaatgcag tacttaatag tgcaatcatt gaatctttga gcggtattga aacaattaaa    1080
tctttgacag gagaggccac aactaaaaag aaaatcgaca ctttgttttc tgatctttta    1140
cataagaatt tagcatacca aaaagcagac caaggtcagc aagcaattaa agctgcgact    1200
aagttaattt taactattgt aatcttgtgg tggggaacat tctttgtaat gcgtcatcag    1260
ttatcacttg gacaactttt gacatacaat gcattactcg catatttcct tactccattg    1320
gaaaatataa tcaaccttca acctaaatta caagccgcaa gagtggccaa taccgccttt    1380
aatgaagttt acctagtaga gtcagagttt agtaagagtc gagaaattac agctcttgag    1440
caactcaatg gagatatcga agtcaatcat gttagcttca attatgggta ttgctcaaat    1500
attcttgaag atgtgtcatt gactatccca catcaccaaa aaattaccat tgtcggtatg    1560
tcaggaagtg gtaagactac attagctaag ttacttgttg gcttctttga acctcaagaa    1620
caacatggtg aaatccaaat taatcaccat aatattagtg atatctctcg cactattctt    1680
cgtcaatata ttaattatgt accccaggaa ccttttattt tcagtggctc tgtgttagag    1740
aatctttat ggggtcacg tccagggtt actcagcaaa tgatagatca agcatgttca       1800
tttgctgaaa tcaagactga cattgaaaat cttcctcaag atatcatac acgtctcagt    1860
gaatcagggt tcaatttaag cggcggtcaa aaacaaagat tatctattgc ccgcgctctc    1920
ttatcaccag cacaatgctt tattttcgat gaatctacct caaatttaga tacgattacg    1980
gaacacaaaa ttgttttcaaa attactttt atgaaggata aaacaataat ttttgttgca    2040
catagattaa acatcgcatc acaaacagac aaagtcgtgg tcttagatca tggaaagatt    2100
gttgaacaag ggtcacatag acaattgtta aattataatg ggtactatgc acgattgatt    2160
```

```
cataaccaag aatga                                              2175
```

<210> SEQ ID NO 121
<211> LENGTH: 228
<212> TYPE: DNA
<213> ORGANISM: Lactococcus lactis

<400> SEQUENCE: 121

```
atgaaaaatc aattaaattt taatattgtt tcagatgaag aactttcaga agctaacgga    60
ggaaaattaa catttattca atcgacagcg gctggagatt tatattacaa tactaataca   120
cacaaatatg tttaccaaca aactcaaaac gcttttgggg ctgctgctaa taccattgtt   180
aatggatgga tgggtggcgc tgctggaggt ttcgggttgc accattga               228
```

<210> SEQ ID NO 122
<211> LENGTH: 297
<212> TYPE: DNA
<213> ORGANISM: Lactococcus lactis

<400> SEQUENCE: 122

```
atgaaaaaaa aacaaataga atttgaaaac gagctaagaa gtatgttggc taccgccctt    60 gaaaagaca ttagtcaaga ggaaagaaat gctctgaata ttgcagaaaa ggcgcttgac    120
aattctgaat atttaccaaa aattatttta aacctcagaa aagccctaac tccattagct   180
ataaatcgaa cacttaacca tgatttatct gaactgtata aattcattac aagttccaaa   240
gcatcaaaca aaaatttagg tggtggttta attatgtcgt ggggacgact attctaa      297
```

<210> SEQ ID NO 123
<211> LENGTH: 297
<212> TYPE: DNA
<213> ORGANISM: Artificial Sequence
<220> FEATURE:
<223> OTHER INFORMATION: Codon-optimized version for Lactobacillus
      paracasei encoding SEQ ID NO: 42

<400> SEQUENCE: 123

```
atgaaaaaga acagatcga gtttgaaaat gagctccgct cgatgttggc cacggcatta    60
gaaaaggata tctcacagga ggaacggaat gcgcttaata ttgcggagaa ggcattagac   120
aattcggaat acttgccaaa gatcattcta aatttgcgta aggcccttac tccattggcg   180
atcaatcgaa ctcttaacca cgatttgagc gaactctaca gtttattac atccagtaaa   240 gcttcgaata agaatctggg cggggggtcta attatgagtt ggggacgctt gttttag     297
```

<210> SEQ ID NO 124
<211> LENGTH: 2148
<212> TYPE: DNA
<213> ORGANISM: Lactococcus lactis

<400> SEQUENCE: 124

```
atgaaattta aaagaaaaa ttatacctca caagtagatg aaatggactg tggctgtgct    60
gccttatcaa tgattttaaa gtcttatggc acagaaaaat ctctcgcttc attgcgctta   120
cttgcaggta caacaatcga aggaacctcc gctttaggga taaaaaggc agctgaaata   180 ttagagtttt cagttcaggc cctaagaaca gatgcaagcc ttttttgaaat gaaaaacgct   240 ccttacccat ttattgctca tgtcattaaa gaccaaaaat acccacatta ttatgtgatc   300
actggcgcaa ataaaaattc ggtattcatt gctgatcctg acccaaccat taaaatgaca   360
aaattatcaa agaagctttt ttatcggaa tggactggga ttagtttatt tctttcgact   420
```

```
acaccatctt atcatcccac taaagaaaaa gcttcctcat tattatcttt tatcccaatt    480
atcacccgtc aaaagaaagt cattctcaat attgttattg cctcattcat tgtaacactg    540
attaatattc taggctctta ctacctccag agcatgattg acagctatat tccaaatgcc    600
ttaatgggaa ctttagggat tatctcagta gggctattgt taacctatat tatccaacag    660
gtcttagaat ttgctaaggc cttcttattg aacgttcttt ctcaaagatt agctattgat    720
gtcattcttt cttatattag acacattttc caacttccca tgtctttctt ttcgacccga    780
agaacaggag aaattaccag tcggttttcc gatgcgagtt ctattttaga tgctattgcc    840
tcaacgattc tttcgctctt tttagatttg acgattgtcg tcatgacagg actaatttta    900
ggccttcaaa atatgcaact cttcttctc gttcttttgg caatcccact ctatattgtt    960
gttattatta tttttacgcc cctttttgaa aaacaaaacc atgaagtcat gcagaccaat   1020
gccgtcttaa actcctcaat tattgaagat atcaatggga ttgaaactat aaaggcactt   1080
gccagtgaac aagaaagata tcaaaaaatt gactacgaat ttgcaagtta tctaaaaaag   1140
gctttcactt tacaaaaatc agaagctatt caaggcttaa ttaaagcaat tatacaacta   1200
acattgagtg tcaccatttt atggtttggt gccacattag taataagtca aaaaattacg   1260
ctcggacaat tgattacttt taatgccctg ctttcttact ttacaaatcc aattaccaat   1320
atcattaacc ttcaaacaaa actccaaaag gcaagggtag ccaatgaacg attaaatgag   1380
gtctatcttg tacccagtga atttgaggaa aagaaaacag aactgtccct ctcacatttt   1440
aacttaaaca tgtccgatat ttcatatcaa tatggttttg gcagaaaagt cttatctgag   1500
atagaactct ctattaaaga aaatgaaaaa ttgactattg tgggcatgag tggttcagga   1560
aagagtaccc ttgttaaatt attggtcaac ttctttcaac ccacttctgg caccatcact   1620
ttaggtggaa ttgacctgca acagtttgat aaacaccaac tccgaagatt aatcaactat   1680
cttccccaac aaccttatat ttttactggt tcaattttag ataatctact tctaggagct   1740
aatgagaatg catcacaaga agagattctt aaagcggtgg aattggcaga atccgtgca    1800 gatattgaac aaatgcagtt gggctatcag accgaacttt caagtgatgc aagtagtcta   1860 tcgggggggac aaaaacaacg cattgcttta gctcgtgcgc tcctttcccc tgccaaaatc   1920
ctcattttag atgaagcaac cagtaacctt gatatgatta cagagaagaa aatattaaag   1980
aacttgttgc ccttggataa aaccattatt ttcattgctc accgcctctc tgtggcggaa   2040
atgagtcatc gaattattgt tgtcgatcaa ggaaaagtga tagagagtgg ctcacatgtt   2100
gacctgcttg cacaaaatgg cttttatgaa caactttacc ataactga               2148
```

<210> SEQ ID NO 125
<211> LENGTH: 1425
<212> TYPE: DNA
<213> ORGANISM: Lactococcus lactis

<400> SEQUENCE: 125

```
atgtttgata aaaaattact ggaaagttca gagctttatg ataaacgcta tcgaaatttc     60
tcgaccttaa ttattcttcc acttttatc cttcttgttg gaggagtaat ttttacttc    120 tttgcccata aggagttgac cgtaataagt acaggaagta ttgaacccac aaaaatagtt    180
gctaaaattc aatcaacgaa tgccaatcca atcattgaga taacctcaa agaaggcgaa    240 gcggttaaag aaaatagctt acttctcaaa tataacggga caccagaaca gacccaactc    300
agtgagctac tgactcaaaa gaaacaagcg ttagacaaaa agtacaact cgaccttctc    360
```

```
caaagaagtt tgaccaacga aaaaaatgaa tttcccactg ccgatagttt tggctatgag      420
aaaagttttg aaaactatga ggcacaagta aagagtcttg aagcaaccat acaaaagtca      480
aatcaagccg tagaagatca aaataaaagt accgagagtc aaaagcaagc cattcaaaat      540
caggtggcaa cactccagca agctattcag aattactctg aaatcgaaaa tgcggtatcg      600
agtggtggtg gagtttcaca agataatccc tacctctctc aatataacag ttaccaagcc      660
caacaagcga ctttagaggc cgatttaaaa aatcaaaaaa atccagatga aactgctaag      720
caagcggcta aaagtcaaga ggagtcttta aaaagtcaat ttttatcagg tttagcttcg      780
agtaaagaca gcttaaaaag ccaaattcaa tcctttaatg tgcaagaaag tagcttaaca      840
ggaagtaatg cttatgataa tagccaatct agtcaaatct taactttaaa aagtcaagca      900
ctttcagctt caaataaaga aatgacagac ctaaatagta cccttactga tttagaaaca      960
aaaattagct tgcaaaaaca agatgaccaa tacagtcaag ttttttgcgga acaggctgga     1020 gtcctgcatg tgctcccaga tattttagga atgaaaaaga ttccgattgg aacacctatc     1080
gcagaaatct atcctttatt aaagtcagaa acacaagtta atctgacaag ttatatccca     1140
agtactcaaa tttctggaat gaaagtcggt caaaaagtga gatttacagt acagcaaaat     1200
ttacctcaac ctgaaatttt aactggaata atcaaccaaa tagatagtgc tcccacagct     1260
tttaaagagg gaaatgctta taagtttct gcgacaacca ctatcaatgc aaaagacctc     1320
ccaaatatcc gatatggtct tcaagggaaa acagtaacca ttataggaaa gaaaacttat     1380
ttcaattact ttttagataa ataatgggaa gaggcaatc agtag                      1425

<210> SEQ ID NO 126
<211> LENGTH: 171
<212> TYPE: DNA
<213> ORGANISM: Lactobacillus hordei

<400> SEQUENCE: 126
atgaagaaag aaatagaatt gtcagaaaaa gagctggtaa gaataattgg agggaaatac       60
tatggaaatg gagttagctg tacaaagaaa catggttgca aagtaaattg gggacaagct      120
ttcacttgca gcgttaatcg ttttgcaaat tttggccatg gtaattgtta g               171

<210> SEQ ID NO 127
<211> LENGTH: 171
<212> TYPE: DNA
<213> ORGANISM: Artificial Sequence
<220> FEATURE:
<223> OTHER INFORMATION: Codon-optimized version for Lactococcus lactis
      encoding SEQ ID NO: 45

<400> SEQUENCE: 127
atgaagaaag aaattgaact ttctgaaaaa gaacttgttc gaattatcgg aggtaaatac       60
tatggtaacg gtgtgagctg tactaagaaa cacggttgta aggtaaattg gggccaagca      120
ttcacatgta gtgtaaaccg ctttgcgaac tttgggcacg gaaattgtta a               171

<210> SEQ ID NO 128
<211> LENGTH: 168
<212> TYPE: DNA
<213> ORGANISM: Artificial Sequence
<220> FEATURE:
<223> OTHER INFORMATION: Codon-optimized version for Lactococcus lactis
      encoding Lactobacillus hordei hdrA gene with the pediocin signal
      sequence
<220> FEATURE:
<221> NAME/KEY: CDS
<222> LOCATION: (1)..(168)
```

<400> SEQUENCE: 128

```
atg aaa aaa att gaa aaa tta act gaa aaa gaa atg gcc aat atc att      48
Met Lys Lys Ile Glu Lys Leu Thr Glu Lys Glu Met Ala Asn Ile Ile
1               5                   10                  15 ggt ggt aaa tat tac ggc aat ggc gtt tca tgt act aaa aaa cat ggt      96
Gly Gly Lys Tyr Tyr Gly Asn Gly Val Ser Cys Thr Lys Lys His Gly
            20                  25                  30 tgt aaa gtc aat tgg ggt caa gct ttt aca tgt tca gtt aat cgt ttc     144
Cys Lys Val Asn Trp Gly Gln Ala Phe Thr Cys Ser Val Asn Arg Phe
        35                  40                  45 gct aat ttt gga cac ggt aat tgc                                     168
Ala Asn Phe Gly His Gly Asn Cys
    50                  55
```

<210> SEQ ID NO 129
<211> LENGTH: 56
<212> TYPE: PRT
<213> ORGANISM: Artificial Sequence
<220> FEATURE:
<223> OTHER INFORMATION: Synthetic Construct

<400> SEQUENCE: 129

```
Met Lys Lys Ile Glu Lys Leu Thr Glu Lys Glu Met Ala Asn Ile Ile
1               5                   10                  15

Gly Gly Lys Tyr Tyr Gly Asn Gly Val Ser Cys Thr Lys Lys His Gly
            20                  25                  30

Cys Lys Val Asn Trp Gly Gln Ala Phe Thr Cys Ser Val Asn Arg Phe
        35                  40                  45

Ala Asn Phe Gly His Gly Asn Cys
    50                  55
```

<210> SEQ ID NO 130
<211> LENGTH: 195
<212> TYPE: DNA
<213> ORGANISM: Artificial Sequence
<220> FEATURE:
<223> OTHER INFORMATION: Codon-optimized version for Lactococcus lactis
      Lactobacillus hordei hdrA gene with the usp45TM8 signal sequence
<220> FEATURE:
<221> NAME/KEY: CDS
<222> LOCATION: (1)..(195)

<400> SEQUENCE: 130

```
atg aaa aaa aag gtg ctg aag gct cat tta gct gtg gtt gtg atg ctt      48
Met Lys Lys Lys Val Leu Lys Ala His Leu Ala Val Val Val Met Leu
1               5                   10                  15 acg acg gca gcc ccg att tcc aat gtt aag gcc aaa tat tac ggc aat      96
Thr Thr Ala Ala Pro Ile Ser Asn Val Lys Ala Lys Tyr Tyr Gly Asn
            20                  25                  30 ggc gtt tca tgt act aaa aaa cat ggt tgt aaa gtc aat tgg ggt caa     144
Gly Val Ser Cys Thr Lys Lys His Gly Cys Lys Val Asn Trp Gly Gln
        35                  40                  45 gct ttt aca tgt tca gtt aat cgt ttc gct aat ttt gga cac ggt aat     192
Ala Phe Thr Cys Ser Val Asn Arg Phe Ala Asn Phe Gly His Gly Asn
    50                  55                  60 tgc                                                                 195
Cys
65
```

<210> SEQ ID NO 131
<211> LENGTH: 65
<212> TYPE: PRT

<210> ORGANISM: Artificial Sequence
<220> FEATURE:
<223> OTHER INFORMATION: Synthetic Construct

<400> SEQUENCE: 131

| Met | Lys | Lys | Lys | Val | Leu | Lys | Ala | His | Leu | Ala | Val | Val | Met | Leu |
|-----|-----|-----|-----|-----|-----|-----|-----|-----|-----|-----|-----|-----|-----|-----|
| 1   |     |     |     | 5   |     |     |     |     | 10  |     |     |     |     | 15  |

| Thr | Thr | Ala | Ala | Pro | Ile | Ser | Asn | Val | Lys | Ala | Lys | Tyr | Tyr | Gly | Asn |
|-----|-----|-----|-----|-----|-----|-----|-----|-----|-----|-----|-----|-----|-----|-----|-----|
|     |     |     | 20  |     |     |     |     | 25  |     |     |     |     | 30  |     |     |

| Gly | Val | Ser | Cys | Thr | Lys | Lys | His | Gly | Cys | Lys | Val | Asn | Trp | Gly | Gln |
|-----|-----|-----|-----|-----|-----|-----|-----|-----|-----|-----|-----|-----|-----|-----|-----|
|     |     | 35  |     |     |     |     | 40  |     |     |     |     | 45  |     |     |     |

| Ala | Phe | Thr | Cys | Ser | Val | Asn | Arg | Phe | Ala | Asn | Phe | Gly | His | Gly | Asn |
|-----|-----|-----|-----|-----|-----|-----|-----|-----|-----|-----|-----|-----|-----|-----|-----|
|     | 50  |     |     |     |     | 55  |     |     |     |     | 60  |     |     |     |     |

Cys
65

<210> SEQ ID NO 132
<211> LENGTH: 381
<212> TYPE: DNA
<213> ORGANISM: Lactobacillus hordei

<400> SEQUENCE: 132

```
atgcaaatta gaaaggaggt gtattttttg aaagatacta aaaaaaaaga ggctataagg      60
gaaatctctt tattggttaa ttacttagaa agccgtgacg ataagagttc tggccttttta    120
gatataattg acgttttgaa acaagtgtac aaaaatttgg aagatgctaa aaatccagaa    180
gctttactaa ataagttaat taactacatt agaagtgtag ctatgcagta taaaattcac    240
tttccaagta agaagaaaaa actaataatt gatttagaag tattaggcca gcgagcagga    300
ttaaatggta gatatatggc agattttca gataaatctc aattttatag tttgctagaa    360
aatataccac gtcataatta a                                              381
```

<210> SEQ ID NO 133
<211> LENGTH: 378
<212> TYPE: DNA
<213> ORGANISM: Artificial Sequence
<220> FEATURE:
<223> OTHER INFORMATION: Codon-optimized version for Lactococcus lactis encoding SEQ ID NO: 47

<400> SEQUENCE: 133

```
atgcaaattc gtaaagaagt ttacttcctt aaagatacaa agaagaagga agccattcgc      60
gaaatttcat tattggttaa ttatttggag tcacgtgatg ataaatcttc tggtctttttg   120
gacatcatcg atgttttgaa gcaagtatat aaaaaccttg aagacgcaaa aaatcctgaa    180
gctcttttaa ataaacttat taattacatc cgttcagttg ctatgcaata taaaatccat    240
ttccctagca agaggaaaa attgatcatt gaccttgaag tattaggaca acgtgctggt    300
ttgaatggtc gttacatggc agacttctct gataaatcac aattttatag tttgcttgaa    360
aacattccac gtcataac                                                  378
```

<210> SEQ ID NO 134
<211> LENGTH: 381
<212> TYPE: DNA
<213> ORGANISM: Artificial Sequence
<220> FEATURE:
<223> OTHER INFORMATION: Codon-optimized version for Lactobacillus paracasei encoding SEQ ID NO: 47

<400> SEQUENCE: 134

```
atgcagattc gcaaggaagt ctactttctt aaggatacta aaagaaaga agccattcgg        60 gaaattagct tacttgtcaa ctatcttgaa tcgcgagatg acaaatcatc tggtttgcta      120
gatatcattg acgtcttaaa acaggtttat aaaaacctgg aagatgcaaa gaatccggaa      180
gcactcttga ataaactcat taattatatt cgcagtgttg cgatgcagta taaaatccac      240
tttccgagca aggaggaaaa actgatcatt gatctggaag tgctcggcca gcgcgccggc      300
ttgaacggac gttatatggc cgatttcagc gacaaaagcc aattttactc actgttagaa      360
aatattcctc gccataattg a                                                381
```

<210> SEQ ID NO 135
<211> LENGTH: 534
<212> TYPE: DNA
<213> ORGANISM: Lactobacillus hordei
<400> SEQUENCE: 135

```
atgatgaact tagaaaagca caaaacatat tttttcttat ttatttcact ttttataggg       60
actatcgtct tattcttaca aacagctgag attcaggcta gtaccaataa tcaactgacc      120
tctcaacaaa atgatacaca ggtccaacat ttggtatctc aagatgaata tgaagaaaac      180
attaaaaaga ctattccaat ttctaccacg gagctgataa caaaatttaa cagcggggaa      240 accttttgttc tatttattgg ttataaagaa tgcaaatatt gcagggcgtt ttctcctact      300
ttaaatgtgt tcatgaatac aagtaccgtt cctgtttatt atttagacgt tgatagcgtt      360
tcacaaagtg aattaacaca aaattttgtt gatattatgt ataacaaaat taagttacaa      420
ggaactccta ccattgcact tataaagcac ggtaaagtaa ttcatgagta tatagggtcg      480
aatacatcat taaatcaatt gcagacatta aaaaaatata atatgcaaa ttag            534
```

<210> SEQ ID NO 136
<211> LENGTH: 531
<212> TYPE: DNA
<213> ORGANISM: Artificial Sequence
<220> FEATURE:
<223> OTHER INFORMATION: Codon-optimized version for Lactococcus lactis
      encoding SEQ ID NO: 48

<400> SEQUENCE: 136

```
atgatgaatc tcgaaaaaca taaaacatac ttttttttgt tcatttcatt gttcattggg       60
acaattgtgc ttttccttca aactgcagaa atccaagctt caactaataa ccaacttact      120
tcacaacaaa acgatactca agttcaacat cttgtatcac aagatgaata cgaagaaaac      180
attaaaaaaa caatcccaat ctcaacaact gaattgatca caaatttaa ctcaggagaa       240 acatttgttc tttttatcgg atataaggaa tgtaaatact gccgcgcatt ctcacctact      300
ttaaatgttt tcatgaatac ttcaactgtg cctgtttatt accttgatgt tgattctgtt      360
tcccaatcag aattgactca aaactttgtt gatattatgt ataataaaat caaacttcaa      420
ggtactccta ctatcgcatt aattaaacat ggtaaagtca tccatgaata tattgggtca      480
aatacttcac ttaaccaact tcaaactctt aaaaaatata atacgctaa t                531
```

<210> SEQ ID NO 137
<211> LENGTH: 2157
<212> TYPE: DNA
<213> ORGANISM: Lactobacillus hordei
<400> SEQUENCE: 137

```
atgttttttg aaagaaacat ttacacaatg caagtagatg aatcagattg tggtgttgct       60
```

```
tgtttggcaa tgatcctaaa acatttcggg tctagtatct ccttagccta tctaagaaat    120
cttgctaaaa ctaatacaga aggaactact gcgctaggtt tagtgaagac agctgaaaag    180
ctcaagttcg aaactaaagc cattaaagcc gatatgacct tatttgatat tatggacttg    240
cctttaccat ttatcgctca tgtcgtaaaa cctggaggct tgttgcatta ctatgtcgtg    300
ttaaaagtta aaaaggatca attaatcatt gctgatcctg atccaactgt gggcgttatt    360
aaaatgcgta aaaacaatt ttctcaggaa tggtctggtg ttgctttatt catggctcct    420
aagcccactt atcaaccaat aaaacaagag aaaagttctt tattttcttt ttccccagc    480
atgattaaac aaaaaaaact ggttggaaat attattttag ccgctttact aattacaatc    540
attagtattg ccggttctta tttttacaa acaatcattg atacttatat tcctaacaat    600
atgcatagta ccctagcaat aattgcccta ggcttaatta tctttacat attccaatca    660
atctttactt atgctcaaaa cttttttacta gccgttctag gccaacgatt atcaattgaa    720
attattttag gctacattcg tcatattttt gagttaccaa tggaattttt tacaactcgc    780
aaaacaggag aaattgtttc ccgttttact gatgccagta aaatcattga tgctttggca    840
agtactgtag tttcaatgtt tttagacgtt ggaattgtca ttgtaatggg cattattta     900
gccttgcaaa gtagtcaatt attttggata acgctgattt cgctcccaat atatattgcc    960
attatcttaa tcttttcaaa agcttttgaa aaactaaacc aaaagagat ggaaagtaat     1020
gccattttaa gctcatcaat tattgaagac attcatggga ttgagaccat taaagctctc    1080
aatagtgaac cacaacgtta tcaaaaaatt gatactgagt tgttgattt cttaaagaaa     1140
agtcttgcct acactaaggc cgatactttg cagcaagcac ttaaattatt tgttcaattg    1200
agtttaaatg ttttgattct ctggatcggg gctttactgg ttattcataa tcgactatca    1260
gttgggcaat taatgaccta taatgctttg ttggcctact tgtcaatcc attacaaagt     1320
attatcaatc tccagcctaa actccaaagt gcccgtgtag ctaataatcg tcttaatgaa    1380
gtcttttag tagaaagtga attcgctgac tcacgtccta ttaaaaagt tgagcagtta      1440
caaggaccaa ttgttttta acaagttagc taccattacg gttatggtca agacgtttta     1500
aaaaacatta atttgcagtt caaccttggc gacaaaataa caatcgttgg catgagtggt    1560
tcaggaaaat caactttggt taagttgtta attgatttt ttgaacctag tagcggtgaa     1620
atattaatta accaacatcc attaaaatta gttgataaac atataatcag gagctttatt    1680
aattatattc ctcaagagcc atatatattt tctggatcaa ttgaagataa tcttagacta    1740
ggtaatcgag caaatataac cttagcggag attgaaaaag cttgtaaaac cgccatgatt    1800
gctgctgaca ttgaaaaaat gccattacag ttcaacacta acttagacga aaatggtaat    1860
actctttctg gtgggcaaaa gcaacgtcta actattgctc gagcgctatt atcgcccgcc    1920
aaaattctaa tctttgatga atcaaccagt ggtctagata ctatcactga aagaaacta     1980
attgataact tgactaaact ctcggataaa acaattattt tcattgccca tcgcttagct    2040
gttgcccaac gaactgacaa aattttagtt ttacatgaag gcaaactcgt tgaacaggga    2100
agtcatgcag aattaatgag aaaacaaggt tattactaca accttgttaa tagttag       2157
```

<210> SEQ ID NO 138
<211> LENGTH: 2157
<212> TYPE: DNA
<213> ORGANISM: Artificial Sequence
<220> FEATURE:
<223> OTHER INFORMATION: Codon-optimized version for Lactococcus lactis encoding SEQ ID NO: 49

<400> SEQUENCE: 138

```
atgttttcg agcgtaatat ttacacaatg caagttgatg agtcagattg tggtgtagct    60
tgtcttgcaa tgattttaaa acatttggga tcttcaatct cattagcgta tttacgtaat   120
cttgctaaaa ctaatactga aggaacaact gctttaggtc ttgttaaaac agcagaaaaa   180
ttaaaatttg aaacaaaagc aattaaagcc gatatgacat tgttcgatat catggactta   240
cctctaccat tcattgcaca tgtagttaaa cctggaggtt tactacacta ctatgtagtt   300
cttaaagtta agaaagacca actaattatc gcagatccag atccaactgt tggcgttatt   360
aaaatgcgta agaacaatt ctcacaagaa tggtcaggtg tagctctatt catggcacca   420
aaacctacct atcaaccaat taaacaagaa aaatcttcac tattttcatt ctttcctagc   480
atgatcaagc aaaagaaatt ggttggtaat ataattttag cggctctttt aatcactatc   540
atttcaattg caggatcata cttttttacaa actataattg atacatatat tccgaacaat   600
atgcactcaa ctcttgcaat aattgcctta ggcttgatca ttttctatat atttcaatca   660
atttttactt acgctcaaaa ttttttgcta gcagttttag gtcaaagatt gtctattgaa   720
ataattttag gttatattcg acatattttt gaacttccaa tggaattttt cacaactcgt   780
aaaacggggg aaattgtttc tcgatttact gatgctagca aaattatcga tgcacttgct   840
agcactgtag tctctatgtt tctcgatgtg gggattgtaa ttgtcatggg aatcattctt   900
gctttgcaaa gctcacagct tttctggata actctcatta gtttgccaat ttatattgct   960
attatactca ttttttctaa ggcatttgaa aagttaaatc aaaagaaat ggagtcaaat   1020
gccattttga gcagttcaat aatcgaagat attcatggga ttgaaaccat caaagctttg   1080
aattctgaac cacagcgata ccagaagatt gatactgaat tgttgactt tttgaagaaa   1140
tcattggctt atacgaaagc agatactcta cagcaagcac ttaaattgtt cgttcaatta   1200
tcattaaatg tattaatcct ttggattggc gcacttttag taattcataa tagactcagt   1260
gtggggcaat taatgacata taacgcattg cttgcatatt tcgtgaatcc attacaatct   1320
atcattaatc tacaacccaa gttacaatct gctcgagttg ccaataacag actaaatgaa   1380
gttttttctag ttgaatcaga atttgcagat tcacgtccta tcaaaaaggt ggagcaactt   1440
caaggtccaa tcgtatttaa acaagtcagt taccattacg gttacggaca agacgttctc   1500
aaaaatatta atcttcaatt taatcttgga gacaaaatta ctatcgtggg aatgtcaggc   1560
tcaggtaagt caacgttagt taagttactc attgactttt tcgagccaag ttcaggagaa   1620
attttgatta tcaacaccc tttaaagtta gttgataaac atattatcag aagtttcatc   1680
aattatattc cccaagaacc atacattttt tctggatcta ttgaagataa cttgcgttta   1740
ggaaatcgtg caaatattac tttagcgag attgaaaaag cctgtaaaac agctatgatc   1800
gctgcagata tcgaaaaaat gcctctacaa ttcaatacta atctcgatga aaacggtaat   1860
actttaagtg gaggtcaaaa acaacgattg acaatagcta gagctctttt aagcccagca   1920
aagattctta ttttttgatga atcaacatct ggtcttgaca caattacaga aaagaaattg   1980
atcgacaatc ttactaaact tagcgataaa actatcattt ttattgcaca tcgcctcgca   2040
gtggctcaac gtacagataa aatacttgtt ttgcatgaag gtaaattagt agaacaaggc   2100
tctcatgctg aattgatgag aaaacaaggc tattactata atctagtgaa ctcttaa     2157
```

<210> SEQ ID NO 139
<211> LENGTH: 1377
<212> TYPE: DNA
<213> ORGANISM: Lactobacillus hordei

<400> SEQUENCE: 139

```
atggataaac gcttttttaga aagcagtgag ttttataatg gccgctacaa taatttttca     60
actatcttga ttattccaat gagtcttttg ttaattggaa ttgttggttt ttctttattt    120
gccaaaagag aaataaccgt cacaggcgtt ggaacattag aagctacaca gctagctaca    180
actgttcaag ctactactaa tagtgctatt gaaaaaaatt atttaagtga aggtaagtat    240
gtaaaaaagg ggcagacatt gctgatttat aataatgttt aaatcgaaa taaactaaaa     300
ctctatcagc aacaacttaa gcaacttcaa caacaaaaaa cagctttaaa gactttaaga    360
caaggaatta taattaacca agatagtttt aaacaagacg atgcatttgg ttaccgcgct    420
atgctccaaa gttacttaaa acagcgtcaa atttatcaaa cagaaaacca atgctagca     480
caaaaagcaa acagtactaa aagcaaacaa gctagtttaa tccaaaccga gcaacaagtt    540
gttgatcgaa atgacagcaa tctacaagct taccaaaatt tgtataccgc cattaaccaa    600
gataagggtt acgccagcaa tgctaaatac agctatatat atcaagaata taaaagcaaa    660
ctaagtaatt taggttcatc tgacgataag tcagaactca agatgacac tttagccagt    720
gtgcaacaac aaaattgatag tttacaggac tcagtcgcct cagctaaagt tcaggtagag    780
gagttgcaag actttgattc aacaaatttc agtgtcacaa ctaataatca aaagatgcaa    840
actctacaaa gtgatcaatt aaataccgtg gctcaagatc taataaaagt tcagcaaagc    900
ctcaaagaag tcggcaataa cattgttgct ttaaaatcag aaaatcatga atacaccatt    960
actgcaccta aaacaggtgt cctacatgtt aataacgatt atcaaggaat aaaatatatt   1020
agctctggga cagctattgc gactatctat cccattttaa aaaaacaaaa attttagaa    1080
attaaagcct atatttcaac aactgacatt tcagaaatta aaatcggtca aatgttcgt    1140
tttaaggttt ctcgaaacgt gcctaaatct attgttatta acggaaagat taacaaaatt   1200
agcgtttcac caataactgt aaatcatggt agctattatg taattacttc aaaagcaaaa   1260
ataaccaatc aacaaaaaag ccttttgaaa tatggcatga gtggaaaaat atcagtgata   1320
accggtaaaa aaacattctt taattattac aaagataagt tgttaaataa gagttaa     1377
```

<210> SEQ ID NO 140
<211> LENGTH: 1377
<212> TYPE: DNA
<213> ORGANISM: Artificial Sequence
<220> FEATURE:
<223> OTHER INFORMATION: Codon-optimized version for Lactococcus lactis encoding SEQ ID NO: 50

<400> SEQUENCE: 140

```
atggataaac gcttcttgga atcttcagaa ttttataatg ggcgttataa caatttttagt     60
acaattctta taattccaat gagcctctta ctcatcggca ttgttgggtt ttctctttttc    120
gccaaaagag aaattactgt gaccggggtg ggtaccttag aagcaactca attagcaact    180
acagttcaag caacaactaa ttctgcaatt gaaaaaaatt acttatcaga gggcaaatat    240
gtcaagaaag gacaaactct cctaatttat aacaatgttc taaacagaaa taaattgaaa    300
ctctatcaac agcaattgaa acaacttcaa cagcaaaaaa cagcgcttaa acactacgt     360
caaggaataa tcattaacca agattcattt aaacaagatg acgcatttgg ttatcgtgcc    420
atgttacaat catacttaaa acaacgccaa atttatcaaa ccgaaaacca atgttggct     480
caaaaagcta actctactaa atctaaacag gctagtttaa tacaaacaga acagcaagtc    540
gtggatagaa atgatagtaa cttacaagct taccagaact tatacacagc aataaatcaa    600
```

```
gataagggat atgcgtcaaa tgcgaaatat agctatattt atcaagaata taaatcaaaa    660
ctaagtaatt tgggttcaag cgacgataaa tcagaattga aagacgatac acttgcttca    720
gttcaacagc aaattgattc attgcaagat agtgttgctt cagccaaagt acaagtggaa    780
gagcttcaag actttgattc tacaaatttc tcagtgacta caaacaatca gaaaatgcaa    840
actttgcagt ctgatcaact taataccgtg gctcaggatc ttataaaagt ccagcaatca    900
ttgaaagaag ttggtaacaa tattgtggca cttaaaagtg aaaatcatga atatactata    960
acagctccaa aaactggtgt cttacatgtt aacaatgatt atcaaggtat aaatatatt    1020 agctcaggaa cggccattgc gactatttac ccaattctca agaaacaaaa atttcttgaa    1080
atcaaagctt atataagtac taccgatatt tctgaaataa aaattggaca gaatgtgcgt    1140
tttaaagtta gtcgtaatgt tccaaagtca attgttatca atggcaagat taataaaatc    1200
agtgtgtctc cgataactgt taaccatggt tcatactatg ttataacaag caaagcgaaa    1260
atcactaatc aacagaaatc actactcaaa tatggaatga gcggtaaaat atcagtgatt    1320
accggaaaga aaactttctt taattactat aaagacaaat tgttaaataa atcttaa      1377

<210> SEQ ID NO 141
<211> LENGTH: 192
<212> TYPE: DNA
<213> ORGANISM: Pediococcus pentosaceus

<400> SEQUENCE: 141
atgatgaaaa aaattgaaaa attaactgaa aaagaaatgg ccaatatcat tggtggtaaa     60
tactacggta atgggcttta ttgtggcaaa cattcctgct ctgttgactg gggtaaggct    120
accacttgca taatcaataa tggagctatg gcatgggcta ctggtggaca tcaaggtact    180
cataaatgct ag                                                       192

<210> SEQ ID NO 142
<211> LENGTH: 189
<212> TYPE: DNA
<213> ORGANISM: Artificial Sequence
<220> FEATURE:
<223> OTHER INFORMATION: Codon-optimized version for Lactococcus lactis
      encoding SEQ ID NO: 50

<400> SEQUENCE: 142
atgatgaaaa aaatcgaaaa attgactgaa aaagaaatgg caaacatcat tggtggtaaa     60
tactatggca atggtttgta ttgcggaaaa catagctgtt cagtcgactg ggtaaagca    120 acaacatgta tcatcaacaa cggtgctatg gcatgggcaa ctggtgggca tcaaggaact    180
cacaaatgt                                                           189

<210> SEQ ID NO 143
<211> LENGTH: 213
<212> TYPE: DNA
<213> ORGANISM: Artificial Sequence
<220> FEATURE:
<223> OTHER INFORMATION: Codon-optimized version for Lactococcus lactis
      encoding Pediococcus pentosaceus pedA20336a gene with the usp45TM8
      signal sequence
<220> FEATURE:
<221> NAME/KEY: CDS
<222> LOCATION: (1)..(213)

<400> SEQUENCE: 143 atg aaa aaa aag gtg ctg aag gct cat tta gct gtg gtt gtg atg ctt     48
Met Lys Lys Lys Val Leu Lys Ala His Leu Ala Val Val Val Met Leu
```

```
                1               5                   10                  15
    acg acg gca gcc ccg att tcc aat gtt aag gcc aaa tac tat ggc aat        96
    Thr Thr Ala Ala Pro Ile Ser Asn Val Lys Ala Lys Tyr Tyr Gly Asn
                    20                  25                  30 ggt ttg tat tgc gga aaa cat agc tgt tca gtc gac tgg ggt aaa gca       144
    Gly Leu Tyr Cys Gly Lys His Ser Cys Ser Val Asp Trp Gly Lys Ala
                35                  40                  45 aca aca tgt atc atc aac aac ggt gct atg gca tgg gca act ggt ggg       192
    Thr Thr Cys Ile Ile Asn Asn Gly Ala Met Ala Trp Ala Thr Gly Gly
        50                  55                  60 cat caa gga act cac aaa tgt                                           213
    His Gln Gly Thr His Lys Cys
    65                  70
```

<210> SEQ ID NO 144
<211> LENGTH: 71
<212> TYPE: PRT
<213> ORGANISM: Artificial Sequence
<220> FEATURE:
<223> OTHER INFORMATION: Synthetic Construct

<400> SEQUENCE: 144

```
Met Lys Lys Val Leu Lys Ala His Leu Ala Val Val Val Met Leu
1               5                   10                  15

Thr Thr Ala Ala Pro Ile Ser Asn Val Lys Ala Lys Tyr Tyr Gly Asn
                20                  25                  30

Gly Leu Tyr Cys Gly Lys His Ser Cys Ser Val Asp Trp Gly Lys Ala
            35                  40                  45

Thr Thr Cys Ile Ile Asn Asn Gly Ala Met Ala Trp Ala Thr Gly Gly
    50                  55                  60

His Gln Gly Thr His Lys Cys
65                  70
```

<210> SEQ ID NO 145
<211> LENGTH: 27
<212> TYPE: PRT
<213> ORGANISM: Lactococcus lactis

<400> SEQUENCE: 145

```
Met Lys Lys Lys Val Leu Lys Ala His Leu Ala Val Val Val Met Leu
1               5                   10                  15

Thr Thr Ala Ala Pro Ile Ser Asn Val Lys Ala
                20                  25
```

<210> SEQ ID NO 146
<211> LENGTH: 174
<212> TYPE: PRT
<213> ORGANISM: Pediococcus sp.

<400> SEQUENCE: 146

```
Met Ser Lys Lys Phe Trp Ser Asn Ile Phe Leu Ala Leu Gly Val Phe
1               5                   10                  15

Leu Ala Phe Ala Gly Val Ala Thr Ile Ser Val Ser Ala Asp Ser Ser
                20                  25                  30

Ala Thr Ile Glu Ser Asn Thr Ser Ser Lys Ile Ile Asp Gly Ala Thr
            35                  40                  45

Tyr Glu Glu Asn Ile Lys Gly Val Ile Pro Ile Thr Leu Thr Gln Tyr
        50                  55                  60

Leu His Lys Ala Gln Thr Gly Glu Lys Phe Ile Val Phe Val Gly Phe
65                  70                  75                  80
```

Lys Glu Cys Val His Cys Arg Lys Phe Ser Pro Val Met Lys Gln Tyr
                85                  90                  95

Leu Gln Gln Ser Gln His Pro Ile Tyr Tyr Leu Asp Tyr Gly Asn Asn
            100                 105                 110

Gly Ser Phe Ser Met Ala Ser Gln Lys Gln Ile Thr Asp Phe Tyr Ser
        115                 120                 125

Thr Phe Ala Thr Pro Met Ser Phe Met Gly Thr Pro Thr Val Ala Leu
    130                 135                 140

Leu Asp Asn Gly Lys Val Val Ser Met Thr Ala Gly Asp Asp Thr Thr
145                 150                 155                 160

Leu Ser Asp Leu Gln Gln Ile Thr Ala Asp Tyr Asn Asn Gln
                165                 170

<210> SEQ ID NO 147
<211> LENGTH: 525
<212> TYPE: DNA
<213> ORGANISM: Pediococcus sp.

<400> SEQUENCE: 147
atgtctaaga aattttggtc aaatatcttt ttagcattag gcgtctttct tgcttttgca      60
ggagttgcta ccatatcggt gagtgctgac agttccgcta ctatagaatc aaatactagc     120
tcgaaaatca tcgatggtgc aacttatgaa gaaaacatca agggcgttat tcctattacg     180
ctaactcaat atttgcataa agctcaaact ggagaaaaat ttattgtctt tgtcgggttc     240
aaggagtgtg tgcattgtcg taaatttttct ccagtcatga acagtactt acaacaaagt     300 cagcatccca tttattactt agactatggg aacaacgggt ctttcagcat ggcttctcaa     360
aaacaaataa ctgatttcta ttcaactttt gcaaccccca tgagttttat gggaacgcca     420
actgttgcct tgctcgataa tggtaaggtg gtatcaatga ccgctggtga tgataccact     480
ttatctgatt tacaacagat tactgctgat tacaataatc agtag                     525

<210> SEQ ID NO 148
<211> LENGTH: 525
<212> TYPE: DNA
<213> ORGANISM: Artificial Sequence
<220> FEATURE:
<223> OTHER INFORMATION: Codon-optimized version for Lactococcus lactis
      encoding SEQ ID NO: 148

<400> SEQUENCE: 148
atgagcaaaa aattctggtc taatattttt cttgccttgg gagtttttct cgctttcgct      60
ggtgttgcga ctattagtgt cagtgcagac tcatcagcaa ctatcgaatc aaatacatca     120
tcaaaaatca ttgatggtgc gacttacgaa gaaaacatcc gtggggttat tccaattact     180
ttgacgcaat acttgcataa agctcaaacg ggagaaaaat tcattgtctt tgttggattc     240
aaagaatgtg ttcattgtcg taaatttagt ccagttatga acaatatttt gcaacaatca     300
caacatccta tttactacct tgactacggt aacaacggct ctttcagcat ggcttcacaa     360
aaacaaatta ctgacttcta tagcactttc gccacaccaa tgtctttcat gggaacacct     420
actgttgctt tacttgataa cggtaaagtt gtttcaatga cagcaggtga tgacacgacc     480
ctttcagatt tgcaacaaat tacagctgac tataacaatc aataa                     525

<210> SEQ ID NO 149
<211> LENGTH: 724
<212> TYPE: PRT
<213> ORGANISM: Pediococcus sp.

<400> SEQUENCE: 149

Met Trp Thr Gln Lys Trp His Lys Tyr Tyr Thr Ala Gln Val Asp Glu
1               5                   10                  15

Asn Asp Cys Gly Leu Ala Ala Leu Asn Met Ile Leu Lys Tyr Tyr Gly
            20                  25                  30

Ser Asp Tyr Met Leu Ala His Leu Arg Gln Leu Ala Lys Thr Thr Ala
        35                  40                  45

Asp Gly Thr Thr Val Leu Gly Leu Val Lys Ala Ala Lys His Leu Asn
    50                  55                  60

Leu Asn Ala Glu Ala Val Arg Ala Asp Met Asp Ala Leu Thr Ala Ser
65                  70                  75                  80

Gln Leu Pro Leu Pro Val Ile Val His Val Phe Lys Lys Asn Lys Leu
                85                  90                  95

Pro His Tyr Tyr Val Val Tyr Gln Val Thr Glu Asn Asp Leu Ile Ile
            100                 105                 110

Gly Asp Pro Asp Pro Thr Val Lys Thr Thr Lys Ile Ser Lys Ser Gln
        115                 120                 125

Phe Ala Lys Glu Trp Thr Gln Ile Ala Ile Ile Ala Pro Thr Val
    130                 135                 140

Lys Tyr Lys Pro Ile Lys Glu Ser Arg His Thr Leu Ile Asp Leu Val
145                 150                 155                 160

Pro Leu Leu Ile Lys Gln Lys Arg Leu Ile Gly Leu Ile Ile Thr Ala
                165                 170                 175

Ala Ala Ile Thr Thr Leu Ile Ser Ile Ala Gly Ala Tyr Phe Phe Gln
            180                 185                 190

Leu Ile Ile Asp Thr Tyr Leu Pro His Leu Met Thr Asn Arg Leu Ser
        195                 200                 205

Leu Val Ala Ile Gly Leu Ile Val Ala Tyr Ala Phe Gln Ala Ile Ile
    210                 215                 220

Asn Tyr Ile Gln Ser Phe Phe Thr Ile Val Leu Gly Gln Arg Leu Met
225                 230                 235                 240

Ile Asp Ile Val Leu Lys Tyr Val His His Leu Phe Asp Leu Pro Met
                245                 250                 255

Asn Phe Phe Thr Thr Arg His Val Gly Glu Met Thr Ser Arg Phe Ser
            260                 265                 270

Asp Ala Ser Lys Ile Ile Asp Ala Leu Gly Ser Thr Thr Leu Thr Leu
        275                 280                 285

Phe Leu Asp Met Trp Ile Leu Leu Ala Val Gly Leu Phe Leu Ala Tyr
    290                 295                 300

Gln Asn Ile Asn Leu Phe Leu Cys Ser Leu Val Val Val Pro Ile Tyr
305                 310                 315                 320

Ile Ser Ile Val Trp Leu Phe Lys Lys Thr Phe Asn Arg Leu Asn Gln
                325                 330                 335

Asp Thr Met Glu Ser Asn Ala Val Leu Asn Ser Ala Ile Ile Glu Ser
            340                 345                 350

Leu Ser Gly Ile Glu Thr Ile Lys Ser Leu Thr Gly Glu Ala Thr Thr
        355                 360                 365

Lys Lys Lys Ile Asp Thr Leu Phe Ser Asp Leu Leu His Lys Asn Leu
    370                 375                 380

Ala Tyr Gln Lys Ala Asp Gln Gly Gln Gln Ala Ile Lys Ala Ala Thr
385                 390                 395                 400

Lys Leu Ile Leu Thr Ile Val Ile Leu Trp Trp Gly Thr Phe Phe Val

```
            405                 410                 415
Met Arg His Gln Leu Ser Leu Gly Gln Leu Leu Thr Tyr Asn Ala Leu
            420                 425                 430

Leu Ala Tyr Phe Leu Thr Pro Leu Glu Asn Ile Ile Asn Leu Gln Pro
            435                 440                 445

Lys Leu Gln Ala Ala Arg Val Ala Asn Asn Arg Leu Asn Glu Val Tyr
            450                 455                 460

Leu Val Glu Ser Glu Phe Ser Lys Ser Arg Glu Ile Thr Ala Leu Glu
465                 470                 475                 480

Gln Leu Asn Gly Asp Ile Glu Val Asn His Val Ser Phe Asn Tyr Gly
                485                 490                 495

Tyr Cys Ser Asn Ile Leu Glu Asp Val Ser Leu Thr Ile Pro His His
                500                 505                 510

Gln Lys Ile Thr Ile Val Gly Met Ser Gly Ser Gly Lys Thr Thr Leu
            515                 520                 525

Ala Lys Leu Leu Val Gly Phe Phe Glu Pro Gln Glu Gln His Gly Glu
        530                 535                 540

Ile Gln Ile Asn His His Asn Ile Ser Asp Ile Ser Arg Thr Ile Leu
545                 550                 555                 560

Arg Gln Tyr Ile Asn Tyr Val Pro Gln Glu Pro Phe Ile Phe Ser Gly
                565                 570                 575

Ser Val Leu Glu Asn Leu Leu Gly Ser Arg Pro Gly Val Thr Gln
            580                 585                 590

Gln Met Ile Asp Gln Ala Cys Ser Phe Ala Glu Ile Lys Thr Asp Ile
            595                 600                 605

Glu Asn Leu Pro Gln Gly Tyr His Thr Arg Leu Ser Glu Ser Gly Phe
610                 615                 620

Asn Leu Ser Gly Gly Gln Lys Gln Arg Leu Ser Ile Ala Arg Ala Leu
625                 630                 635                 640

Leu Ser Pro Ala Gln Cys Phe Ile Phe Asp Glu Ser Thr Ser Asn Leu
                645                 650                 655

Asp Thr Ile Thr Glu His Lys Ile Val Ser Lys Leu Leu Phe Met Lys
                660                 665                 670

Asp Lys Thr Ile Ile Phe Val Ala His Arg Leu Asn Ile Ala Ser Gln
            675                 680                 685

Thr Asp Lys Val Val Val Leu Asp His Gly Lys Ile Val Glu Gln Gly
            690                 695                 700

Ser His Arg Gln Leu Leu Asn Tyr Asn Gly Tyr Tyr Ala Arg Leu Ile
705                 710                 715                 720

His Asn Gln Glu

<210> SEQ ID NO 150
<211> LENGTH: 2175
<212> TYPE: DNA
<213> ORGANISM: Pediococcus sp.

<400> SEQUENCE: 150
atgtggactc aaaaatggca caaatattat acagcacaag ttgatgaaaa tgactgtggt     60
ttagctgcac taaatatgat cctaaaatac tatggctctg attacatgtt ggcccatctt    120
cgacagcttg ccaaaacaac tgctgacggt acaactgttt ggggcttgt taaagcagca    180 aaacacttaa atttaaatgc cgaagctgtg cgtgctgata tggatgcttt gacagcctca    240
caattgccat taccagtcat tgttcatgta ttcaagaaaa ataagttacc acactactat    300
```

```
gttgtctatc aggtaactga aaacgattta attattggtg atcctgatcc aaccgttaaa      360
accactaaaa tatcgaaatc acaatttgct aaagaatgga cccagattgc aattatcata      420
gccccaacag ttaaatataa acccataaaa gaatcacggc acacattaat tgatctagtg      480
cctttattga ttaaacaaaa aagattaatt ggactaatta ttaccgcagc agctataaca      540
acattaatca gtattgctgg tgcatatttc tttcagttaa ttatcgatac ttatttgccg      600
cacttgatga ctaataggct ttcactagtt gccattggtc tgattgtagc ttatgctttc      660
caagcaatta tcaactatat acaaagtttt tttacgattg tattaggaca acgtctcatg      720
atcgacatcg ttttaaaata cgttcaccat cttttttgatt taccaatgaa ttttttttact    780 acccgtcatg tcggtgaaat gacctcacgc ttttctgatg caagcaaaat tattgatgca     840
cttggaagta caacgctcac ccttttttta gacatgtgga ttttattagc agtagggtta     900
tttttggcct atcaaaacat caatttattt ttatgctcgt tagttgtggt tccaatttac     960
atctcgattg tttggctatt taaaaaaact tttaatcgtt taaatcaaga tacaatggaa    1020
agcaatgcag ttcttaattc tgctattatt gaaagtctca gtggcataga aaccattaaa    1080
tcactaactg gtgaagcaac tacaaaaaaa aagattgaca cactattttc tgacttattg    1140
cataaaaact tggcttatca aaaagctgat caaggacaac aggctatcaa agcagctact    1200
aaattaatcc taactattgt tatcctttgg tggggtactt ttttttgttat gcgacaccaa    1260 ctgtctttag gtcagctgtt aacttataat gctttgctcg cttacttctt gaccccatta    1320
gaaaatatta ttaatttaca acctaaacta caagctgcca gagtggctaa taatcgatta    1380
aatgaggttt atctagtaga gtctgaattt tctaaatcta gggaaataac tgctctagag    1440
caactaaatg gtgatattga ggttaatcat gttagtttta actatggcta ttgttctaat    1500
atacttgagg atgtttctct aacaattcca catcatcaga agattactat tgtaggcatg    1560
agtggttcgg ggaaaacgac cctagccaag ttgctagttg gtttttttga gcctcaagaa    1620
cagcacggtg aaattcagat taatcatcac aatatatctg atattagtcg cacaattttta   1680 cgccaatata ttaattatgt tcctcaagaa cctttcattt tttcgggctc tgtattagaa     1740
aatttattgt taggtagccg tcctggagta actcaacaaa tgattgatca agcttgttcc    1800
tttgctgaaa tcaaaactga tatagaaaat ttgcctcaag gttatcatac tagattaagt    1860
gaaagtggat tcaacttatc tggtgggcaa aaacagcgct tatcaatagc tagagcatta    1920
ttgtctccgg cacaatgttt cattttttgac gaatcaacca gtaatttaga caccattact    1980
gaacataaaa tagtctctaa gctattattc atgaaagaca aaacgataat ttttgtagca    2040
catcgtctca atattgcgtc tcaaaccgat aaagttgtcg ttcttgatca tggaaagatt    2100
gttgaacagg gatcacatcg acaattgtta aattataatg ggtattatgc acggttaatt    2160
cataatcaag aatag                                                      2175
```

<210> SEQ ID NO 151
<211> LENGTH: 2175
<212> TYPE: DNA
<213> ORGANISM: Artificial Sequence
<220> FEATURE:
<223> OTHER INFORMATION: Codon-optimized version for Lactococcus lactis
      encoding SEQ ID NO: 149

<400> SEQUENCE: 151

```
atgtggacac aaaaatggca caagtattac acagcacaag ttgatgaaaa cgattgtggt       60
ttggctgctt taaatatgat tttaaaatac tatgggtctg attatatgct cgcacacttg     120
```

```
cgtcaattag ctaaaactac tgcagatggt acaacagttt tgggattggt taaagctgct      180
aaacatttaa atcttaatgc tgaagcagtt cgcgctgaca tggacgcatt gactgcttca      240
caattgccac tcccagttat tgttcacgtt tttaaaaaaa ataaacttcc acactattat      300
gtagtttacc aagttacaga aaatgatttg atcatcggtg atccagaccc tacagttaaa      360
actacaaaaa tctctaaatc acaattcgcc aaagaatgga cacaaattgc aattatcatc      420
gcaccaacag ttaaatataa acctattaaa gaatacgtc atactcttat tgacttggtt       480
cctttgctca tcaaacaaaa acgccttatt ggtttgatca ttacagcagc tgcaattaca      540
actttgatct caattgctgg agcctacttt ttccaactta tcatcgacac atatcttcca      600
catttaatga caaatcgtct ttcattggta gctattggtt taatcgttgc ttacgcgttt      660
caagcaatta ttaactatat tcaatcattc tttacaatcg ttttgggaca acgtttgatg      720
attgatattg ttttgaaata cgtccaccac cttttgatt tgccaatgaa cttcttcaca       780
actcgtcacg ttggagagat gacttctcgt ttttctgatg cttcaaaaat tattgatgca      840
cttggttcta ctacacttac tttgttcctt gatatgtgga tcttgttggc agttggactt      900
ttccttgcgt atcaaaatat taacttgttc ctttgcagcc ttgtggtcgt tcctatctat      960
atctctattg tttggctttt caaaaaaact tttaaccgtt tgaaccagga tacaatggaa     1020
tcaaatgcag ttttgaactc tgcaatcatc gaatcattat ctgggatcga tacaattaaa     1080
agccttacag gggaagccac gactaaaaaa aaaatcgata ctttgttcag tgatttgctt     1140
cataaaaatt tggcctatca aaaagctgat caaggtcaac aagctattaa agctgcaact     1200
aaattaattt tgactattgt tatcctttgg tggggaacat tttttgttat gcgtcaccaa     1260
ctttcactcg gtcaactcct cacctacaac gcactccttg catatttctt gactccactt     1320
gaaaacatca ttaaccttca accaaaactt caagccgcac gtgtggctaa caaccgactt     1380
aacgaagttt accttgtaga atcagaattt tcaaaaagtc gtgaaatcac agctcttgag     1440
caattgaacg gtgacattga agtcaatcac gtttcattca actacggtta ctgtagtaac     1500
atcttggagg atgtttcatt gactatccca catcaccaaa agattactat tgttggaatg     1560
tctggttcag gaaaaactac tcttgccaaa ttgttggttg gtttcttcga accacaagaa     1620
caacacggtg aaatccaaat taatcatcat aatatttctg atatttctcg tactatcttg     1680
cgtcaatata ttaattatgt tcctcaagaa ccattcattt ttagtggatc agttctcgaa     1740
aatttattgc ttggctcacg tcctggagtt acacaacaaa tgatcgacca agcttgtagc     1800
ttcgcagaaa tcaagacaga tattgaaaat ttacctcaag gttaccatac acgtttgtca     1860
gaaagcgggt ttaatcttag cggtggacaa aaacaacgcc tttctatcgc ccgtgctttg     1920
ttatctccag cccaatgttt cattttcgat gaatcaactt ctaacttaga cacaattaca     1980
gaacataaaa ttgtttctaa acttcttttt atgaaagata aaactatcat ctttgttgct     2040
catcgtctca atattgcatc tcaaactgat aaagtagttg ttttggatca cggcaaaatt     2100
gtggaacaag ttctcatcg tcaacttctt aattacaacg ttactacgc acgcctcatt      2160 cataatcaag aataa                                                       2175
```

<210> SEQ ID NO 152
<211> LENGTH: 81
<212> TYPE: DNA
<213> ORGANISM: Lactococcus lactis

<400> SEQUENCE: 152

```
atgaaaaaaa aggtgctgaa ggctcattta gctgtggttg tgatgcttac gacggcagcc       60
```

<210> SEQ ID NO 153
<211> LENGTH: 1707
<212> TYPE: DNA
<213> ORGANISM: Artificial Sequence
<220> FEATURE:
<223> OTHER INFORMATION: Codon-optimized version for Lactococcus lactis encoding SEQ ID NO: 1

<400> SEQUENCE: 153

```
atgtcataca ctgttggtac ttaccttgct gaacgtcttg ttcaaatcgg tcttaaacac      60
cacttcgctg ttgctggtga ttacaacctt gttcttcttg ataaccttct tcttaacaaa     120
aacatggaac aagtttactg ttgtaacgaa cttaactgtg gtttctcagc tgaaggttac     180
gctcgtgcta aggtgctgc tgctgctgtt gttacttact cagttggtgc tctttcagct      240
ttcgatgcta tcggtggtgc ttacgctgaa aaccttccag ttatccttat ctcaggtgct     300
ccaaacaaca cgatcacgc tgctggtcac gttcttcacc acgctcttgg taaaactgat      360
taccactacc aacttgaaat ggctaaaaac atcactgctg ctgctgaagc tatctacact     420
ccagaagaag ctccagctaa aatcgatcac gttatcaaaa ctgctcttcg tgaaaaaaaa     480
ccagtttacc ttgaaatcgc ttgtaacatc gcttcaatgc catgtgctgc tccaggtcca     540
gcttcagctc ttttcaacga tgaagcttca gatgaagctt cacttaacgc tgctgttgaa     600
gaaactctta aattcatcgc taaccgtgat aaagttgctg ttcttgttgg ttcaaaactt     660
cgtgctgctg gtgctgaaga agctgctgtt aaattcgctg atgctcttgg tggtgctgtt     720
gctactatgg ctgctgctaa atcattcttc ccagaagaaa acccacacta catcggtact     780
tcatggggcg aagtgagcta cccaggtgtt gaaaaaacta tgaaagaagc tgatgctgtt     840
atcgctcttg ctccagtttt caacgattac tcaactactg gttggactga tatcccagat     900
ccaaaaaaac ttgttcttgc tgaaccacgt tcagttgttg ttaacggtgt tcgtttccca     960
tcagttcacc ttaaagatta ccttactcgt cttgctcaaa agttccaaa aaaaactggt    1020
gctcttgatt tcttcaaatc acttaacgct ggtgaactta aaaaagctgc tccagctgat    1080
ccatcagctc cacttgttaa cgctgaaatc gctcgtcaag ttgaagctct tcttactcca    1140
aacactactg ttatcgctga aactggtgat tcatggttca acgctcaacg tatgaaactt    1200
ccaaacggtg ctcgtgttga atacgaaatg caatggggtc acatcgggtg gtcagttcca    1260
gctgcgttcg gttacgctgt tggtgctcca gaacgtcgta acatccttat ggttggtgat    1320
ggttcattcc aacttactgc tcaagaagtt gctcaaatgg ttcgtcttaa acttccagtt    1380
atcatcttcc ttatcaacaa ctacggttac actatcgaag ttatgatcca cgatggtcca    1440
tacaacaaca tcaaaaactg ggattacgct ggtcttatgg aagttttcaa cggtaacggt    1500
ggttacgatt caggtgctgg taaggtctt aaagctaaaa ctggtggtga acttgctgaa    1560
gctatcaaag ttgctcttgc taacactgat ggtccaactc ttatcgaatg tttcatcggt    1620
cgtgaagatt gtactgaaga acttgttaaa tggggtaaac gtgttgctgc tgctaactca    1680
cgtaaaccag ttaacaaact tctttaa                                       1707
```

<210> SEQ ID NO 154
<211> LENGTH: 1152
<212> TYPE: DNA
<213> ORGANISM: Artificial Sequence
<220> FEATURE:
<223> OTHER INFORMATION: Codon-optimized version for Lactococcus lactis encoding SEQ ID NO: 3

<400> SEQUENCE: 154

```
atggcttcat caactttcta catcccattc gttaacgaaa tgggtgaagg ttcacttgaa      60
aaagctatca aagatcttaa cggttcaggt ttcaaaaacg ctcttatcgt ttcagatgct     120
ttcatgaaca aatcaggtgt tgttaaacaa gttgctgatc ttcttaaagc tcaaggtatc     180
aactcagctg tttacgatgg tgttatgcca aacccaactg ttactgctgt tcttgaaggt     240
cttaaaatcc ttaaagataa caactcagat ttcgttatct cacttggtgg tggttcacca     300
cacgattgtg ctaaagctat cgctcttgtt gctactaacg gtggtgaagt taaagattac     360
gaaggtatcg ataaatcaaa aaaaccagct cttccactta tgtcaatcaa cactactgct     420
ggtactgctt cagaaatgac tcgtttctgt atcatcactg atgaagttcg tcacgttaaa     480
atggctatcg ttgatcgtca cgttactcca atggtttcag ttaacgatcc acttcttatg     540
gttggtatgc caaaaggtct tactgctgct actggtatgg atgctcttac tcacgctttc     600
gaagcttact catcaactgc tgctactcca atcactgatg cttgtgctct taaagctgct     660
tcaatgatcg ctaaaaacct taaaactgct tgtgataacg gtaaagatat gccagctcgt     720
gaagctatgg cttacgctca attccttgct ggtatggctt tcaacaacgc ttcacttggt     780
tacgttcacg ctatggctca ccaacttggt ggttactaca accttccaca cggtgtttgt     840
aacgctgttc ttcttccaca cgttcttgct tacaacgctt cagttgttgc tggtcgtctt     900
aaagatgttg gtgttgctat gggtcttgat atcgctaacc ttggtgataa agaaggtgct     960
gaagctacta tccaagctgt tcgtgatctt gctgcttcaa tcggtatccc agctaacctt    1020
actgaacttg gtgctaaaaa agaagatgtt ccacttcttg ctgatcacgc tcttaaagat    1080
gcttgtgctc ttactaaccc acgtcaaggt gatcaaaaag aagttgaaga acttttcctt    1140
tcagctttct aa                                                        1152
```